United States Patent
Cho et al.

(10) Patent No.: US 10,336,834 B2
(45) Date of Patent: Jul. 2, 2019

(54) METHODS OF USING ANTI-PHOSPHOLIPASE D4 ANTIBODIES

(71) Applicant: SBI Biotech Co., Ltd., Tokyo (JP)

(72) Inventors: Minkwon Cho, Tokyo (JP); Tomohide Yamazaki, Tokyo (JP); Mayuki Endo, Tokyo (JP); Koji Ishida, Tokyo (JP)

(73) Assignee: SBI Biotech Co., Ltd., Tokyo (JP)

( * ) Notice: Subject to any disclaimer, the term of this patent is extended or adjusted under 35 U.S.C. 154(b) by 0 days.

(21) Appl. No.: 15/910,206

(22) Filed: Mar. 2, 2018

(65) Prior Publication Data

US 2018/0258185 A1  Sep. 13, 2018

Related U.S. Application Data

(62) Division of application No. 14/375,266, filed as application No. PCT/JP2013/052781 on Jan. 31, 2013, now Pat. No. 9,944,715.

(30) Foreign Application Priority Data

Jan. 31, 2012 (JP) .................. 2012-018266

(51) Int. Cl.
C07K 16/40 (2006.01)

(52) U.S. Cl.
CPC .......... *C07K 16/40* (2013.01); *C07K 2317/33* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 7,098,015 B2 | 8/2006 | MacBeth et al. |
| 2005/0058649 A1 | 3/2005 | Landes et al. |

OTHER PUBLICATIONS

Lloyd et al. (Protein Engineering, Design & Selection 2009, 22:159-168).*
Asselin-Paturel et al., "Mouse Strain Differences in Plasmacytoid Dendritic Cell Frequency and Function Revealed by a Novel Monoclonal Antibody", J. Immunol. 171:6466-6477 (2003).
Blasius et al., "A cell-surface molecule selectively expressed on murine natural interferon-producing cells that blocks secretion of interferon-alpha", Blood, 103(11):4201-4206 (2004).
Campbell, Monoclonal Antibody Technology, Chapter 1, (1984), pp. 1-32.
Catalog of mouse PLD4 polyclonal antibody against full length human PLD4 protein (Abnova, catalog No. H00122618-B01P) (Aug. 29, 2012).
Clark et al., "The Secreted Protein Discovery Initiative (SPDI), a Large-Scale Effort to Identify Novel Human Secreted and Transmembrane Proteins: A Bioinformatics Assessment", Genome Res. 13(10):2265-2270 (2003).
Dzionek et al., "BDCA-2, a Novel Plasmacytoid Dendritic Cell-specific Type II C-type Lectin, Mediates Antigen Capture and Is a Potent Inhibitor of Interferon α/β Induction", J. Exp. Med. 194:1823-1834 (2001).
Dzionek et al., "BDCA-2, BDCA-3, and BDCA-4: Three Markers for Distinct Subsets of Dendritic Cells in Human Peripheral Blood", J. Immunol. 165:6037-6046 (2000).
Human Phospholipase D4, Accession No. Q96BZ4 dated Nov. 28, 2012; URL: https://www.ncbi.nlm.nih.gov/protein/121944492?sat=17&satkey=725971.
International Search Report for PCT/JP2013/052781 dated May 14, 2013.
Kamogawa-Schifter et al., "Ly49Q defines 2pDC subsets in mice", Blood, 105(7):2787-2792, (2005).
Mishima, N. et al., "Insertion of Stabilizing Loci in Vectors of T7 RNA Polymerase-Mediated *Escherichia coli* Expression Systems: A Case Study on the Plasmids Involving Foreign Phospholipase D Gene", *Biotechnology Prog.* (1997), 13(6):864-868.
Office Action issued in Chinese Application No. 201380018285.5, dated Jul. 4, 2016, 14 pages (with English Translation).
Office Action issued Japanese Application No. 2014-554166, dated Nov. 18, 2016, 4 pages (with English translation).
Otani et al., "PLD4 Is Involved in Phagocytosis of Microglia: Expression and Localization Changes of PLD4 Are Correlated with Activation State of Microglia", Plos One www.plosone.org, vol. 6, Issue 11, e27544, pp. 1-10 (Nov. 2011).
Tao et al., "Quantitative phosphoproteome analysis using a dendrimer conjugation chemistry and tandem mass spectrometry", Nat. Methods 2(8):591-598 (2005).
Yoshikawa et al., "Phospholipase D Family Member 4, a Transmembrane Glycoprotein with No Phospholipase D Activity, Expression in Spleen and Early Postnatal Microglia", Plos ONE www.plosone.org. vol. 5, Issue 11, e13932 pp. 1-13 (Nov. 2010).
Office Action in Chinese Application No. 201380018285.5, dated Jul. 3, 2018, 25 pages (with English Translation).
Abnova.com [online], "PLD4 (Human) Recombinant Protein (P01) Datasheet," Dec. 2011, [retrieved on Jun. 13, 2016], retrieved from: URL<http://www.abnova.com/protocol_pdf/DS_H00122618-P01.pdf>, 1 page.
Abnova.com [online], "PLD4 purified MaxPab mouse polyclonal antibody (B01P) Datasheet," Dec. 2011, [retrieved on Jun. 13, 2016], retrieved from: URL<http://www.abnova.com/protocol_pdf/DS_H00122618-B01P.pdf>, 1 page.
European Extended Search Report in European Application No. 18188036.0, dated Jan. 4, 2019, 8 pages.
GenBank Accession No. ABV55809.1, "immunoglobulin kappa light chain, partial [Mus musculus]," Jul. 26, 2016, 1 page.
Office Action in Indian Patent Application No. 6365/DELNP/2014, dated Mar. 7, 2019, 8 pages (with English Translation).
Office Action in Korean Patent Application No. 10-2014-7023620, dated Mar. 20, 2019, 4 pages (English Translation only).

\* cited by examiner

*Primary Examiner* — Sharon X Wen

(74) *Attorney, Agent, or Firm* — Fish & Richardson P.C.

(57) ABSTRACT

A monoclonal antibody that binds to a phospholipase D4 (PLD4) protein, or a fragment containing an antigen-binding region thereof.

7 Claims, 27 Drawing Sheets

Specification includes a Sequence Listing.

FIG. 1

Transmembrane domain

Outer 2PLD domain (HKD motif)

```
         10         20         30         40         50         60
MLKPLWKAAV APTWPCSMPP RRPWDREAGT LQVLGALAVL WLGSVALICL LWQVPRPPTW 70         80         90        100        110        120
GQVQPKDVPR SWEHGSSPAW EPLEAEARQQ RDSCQLVLVE SIPQDLPSAA GSPSAQPLGQ 130        140        150        160        170        180
AWLQLLDTAQ ESVHVASYYW SLTGPDIGVN DSSSQLGEAL LQKLQQLLGR NISLAVATSS 190        200        210        220        230        240
PTLARTSTDL QVLAARGAHV RQVPMGRLTR GVLHSKFWVV DGRHIYMGSA NMDWRSLTQV 250        260        270        280        290        300
KELGAVIYNC SHLAQDLEKT FQTYWVLGVP KAVLPKTWPQ NFSSHFNRFQ PFHGLFDGVP 310        320        330        340        350        360
TTAYFSASPP ALCPQGRTRD LEALLAVMGS AQEFIYASVM EYFPTTRFSH PPRYWPVLDN 370        380        390        400        410        420
ALRAAAFGKG VRVRLLVGCG LNTDPTMFPY LRSLQALSNP AANVSVDVKV FIVPVGNHSN 430        440        450        460        470        480
IPFSRVNHSK FMVTEKAAYI GTSNWSEDYF SSTAGVGLVV TQSPGAQPAG ATVQEQLRQL 490        500
FERDWSSRYA VGLDGQAPGQ DCVWQG
```

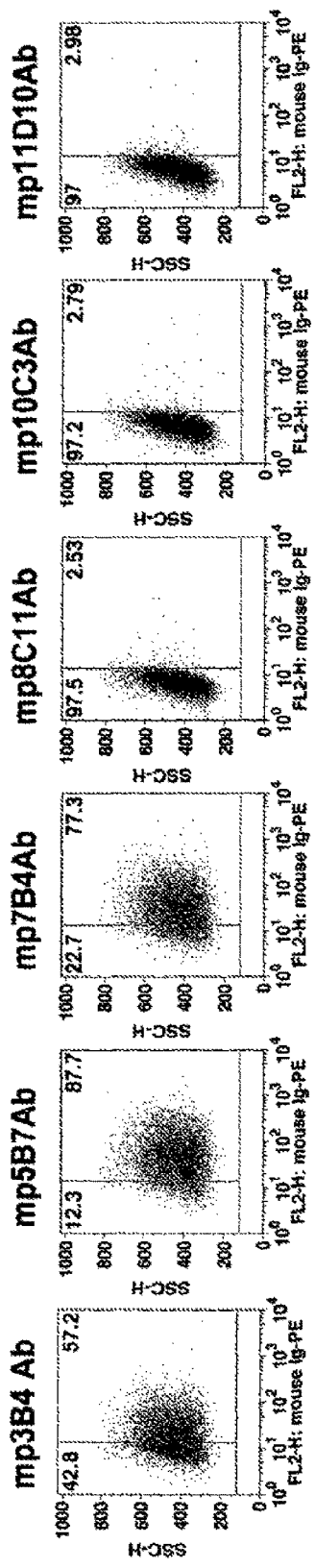
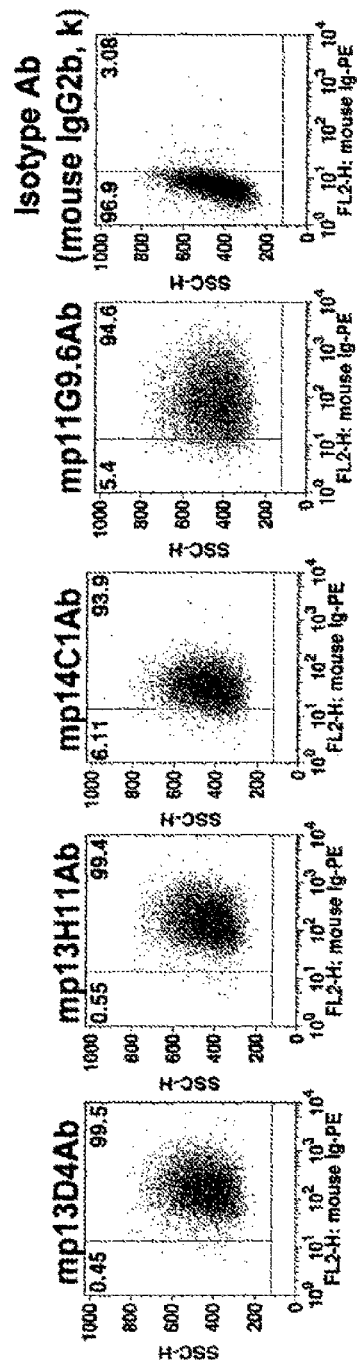
FIG. 16

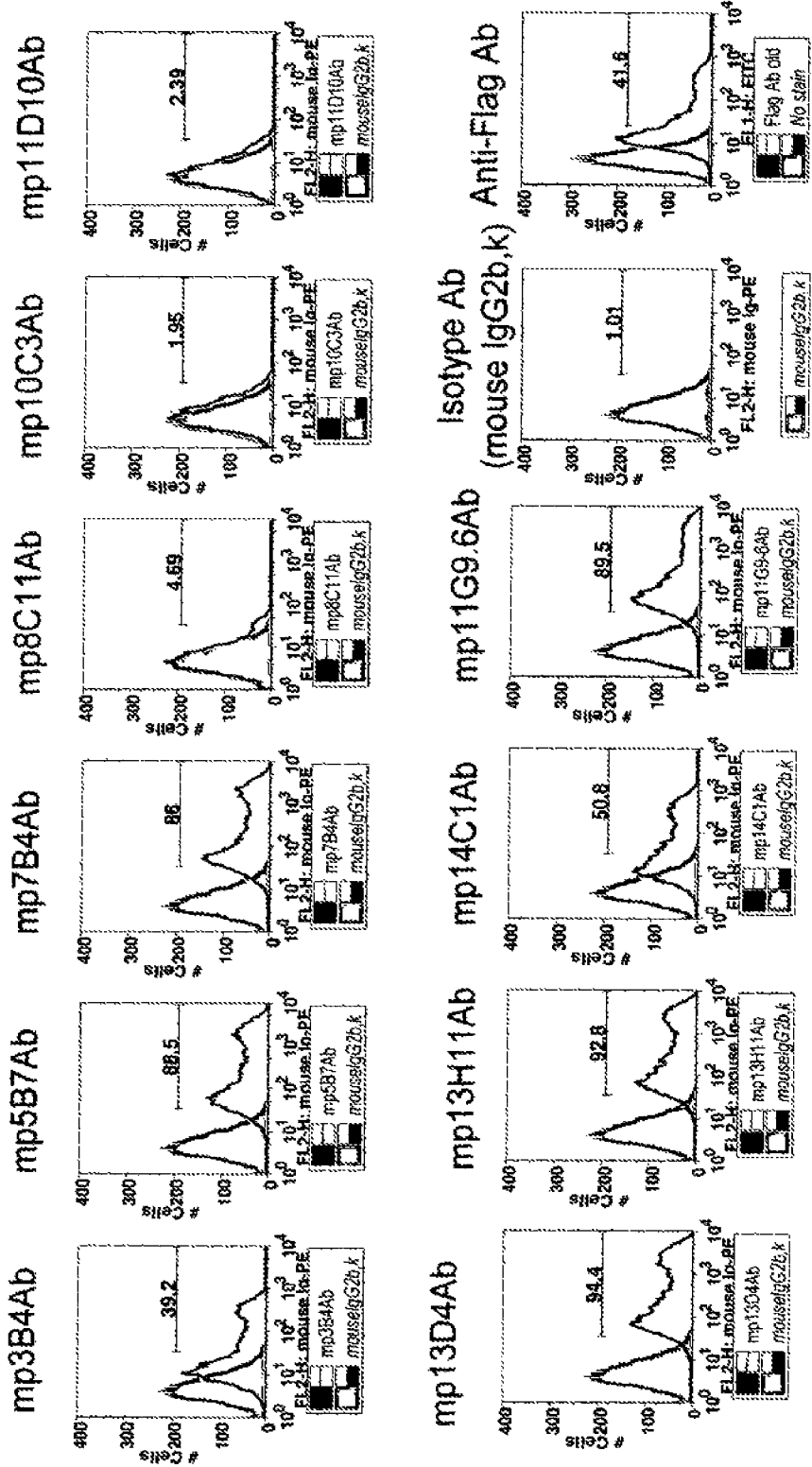

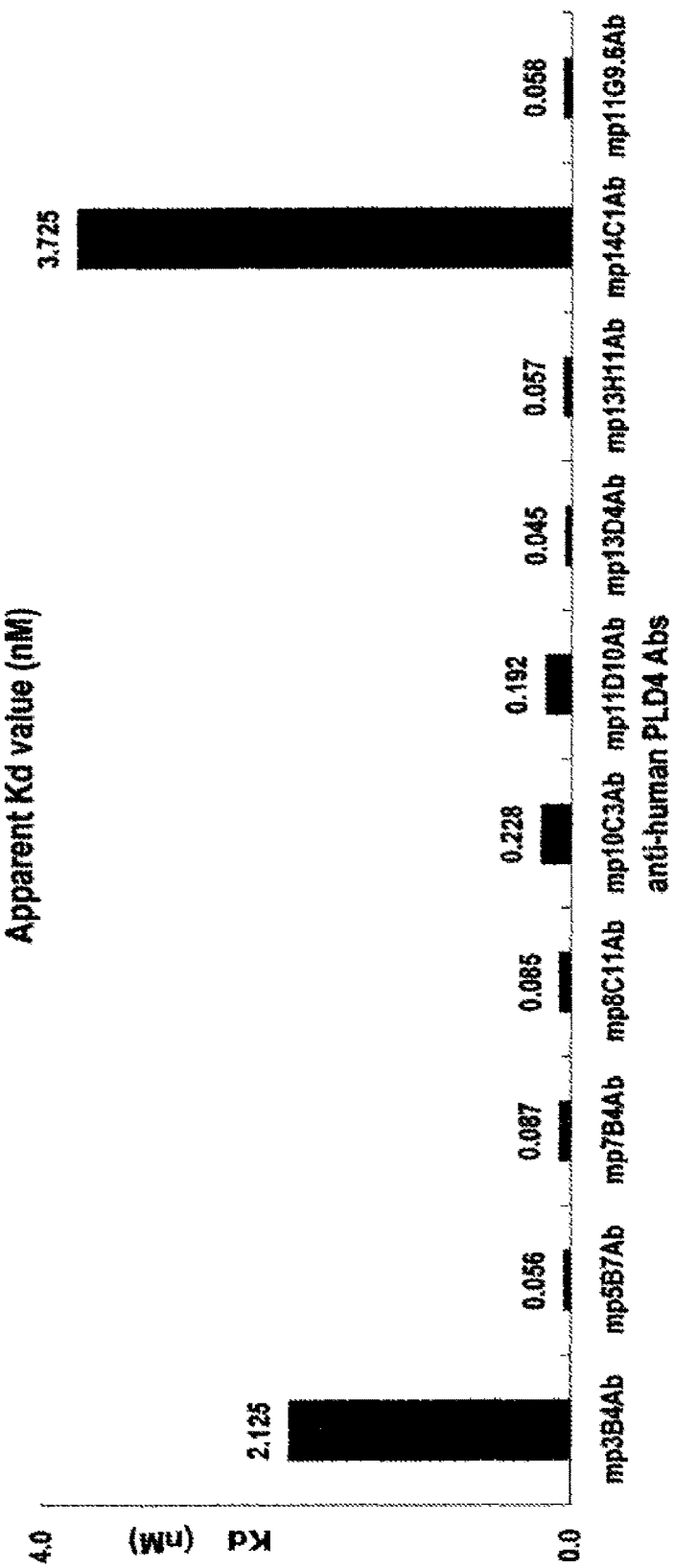

FIG. 23
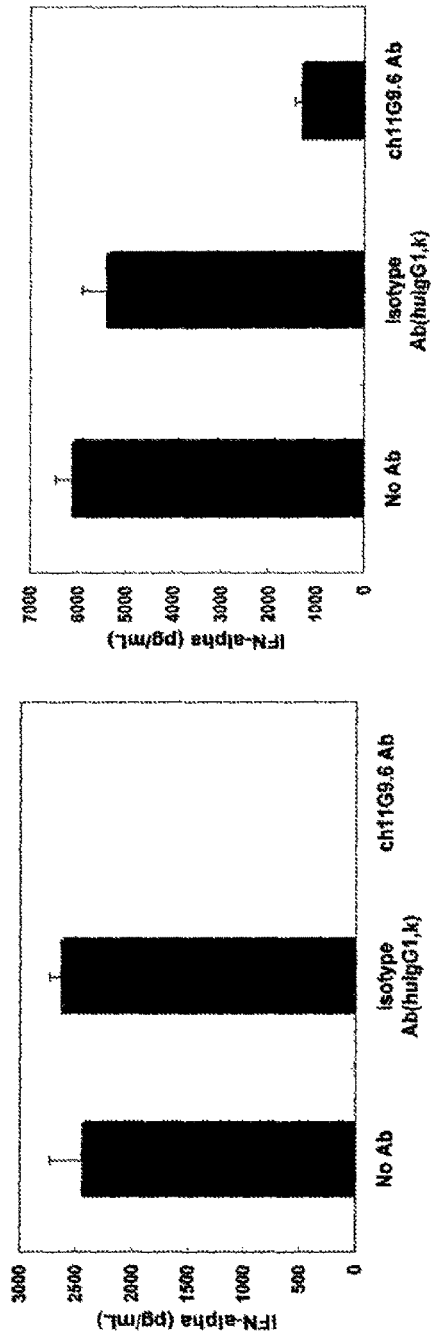
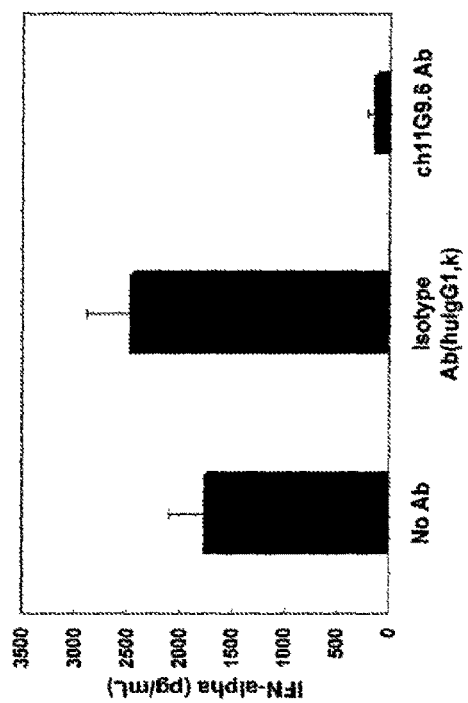

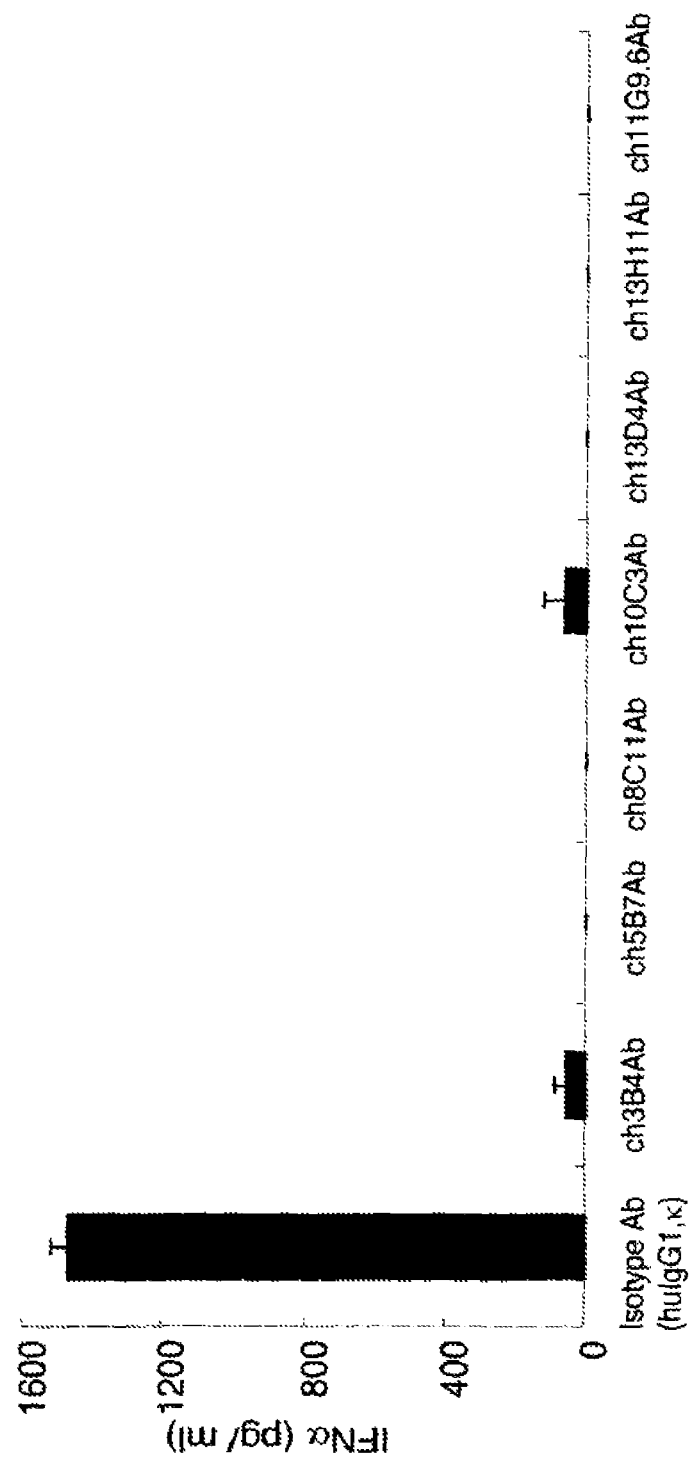

METHODS OF USING ANTI-PHOSPHOLIPASE D4 ANTIBODIES

TECHNICAL FIELD

The present invention relates to an antibody that binds to phospholipase D4. Hereinafter, "phospholipase D" may be abbreviated as PLD, and "phospholipase D4" and the like may be abbreviated as PLD4 and the like.

BACKGROUND ART

Interferon (hereinafter, the "interferon" may be abbreviated as IFN) is the most important cytokine in the anti-virus immune response. Interferon producing cell in human blood (IPC: IPC is an undifferentiated lymphocyte-based dendritic cell positioned as a precursor cell of the dendritic cell (DC). The IPC may be also called plasmacytoid dendritic cell or plasmacytoid dendritic cell (pDC). Hereinafter, in the present specification, IPC and pDC are synonymous, and uniformly referred to as a term of pDC in principle below.) expresses CD4 and major histocompatible complex class II protein. However, isolation or particular characterization of the cells has not been performed until now due to an insufficient number of such cells, rapid apoptosis, and further lack of lineage (system) marker. It has been revealed that pDC is $CD4^+CD11c^-2$ type precursor cell of the dendritic cell, and found out that pDC produces IFN more by 200 to 1000 folds than other blood cells after stimulation by a microorganism. Accordingly, pDC is a conclusive immune system effector cell in an anti-virus/anti-tumor immune response.

IFNα and IFNβ are known as type I IFN having anti-virus activity or anti-tumor activity. On the other hand, it has been revealed that IFNα is associated with autoimmune diseases. For example, abnormal production of IFNα has been reported in patients of autoimmune diseases such as systemic lupus erythematosus and chronic rheumatoid arthritis. Furthermore, it has been reported a case where autoimmune disease symptoms are expressed or aggravated upon administration of a recombinant IFNα2 or IFN. It has been also suggested that autoimmune symptoms are likely to be alleviated by neutralization of IFNα.

In addition, it has been also revealed that IFNα induces differentiation of dendritic cell (DC). It has been contemplated that induction of differentiation of a dendritic cell constitutes an important mechanism in an autoimmune disease since a dendritic cell is an antigen presenting cell. In fact, it has been suggested that induction of differentiation of a dendritic cell of IFNα is deeply associated with development of systemic lupus erythematosus. As described above, close relationship of IFNα with autoimmune diseases as well as anti-tumor activity has been pointed out. In addition, IFNα is also deeply associated with development of psoriasis.

Only a few pDC exists in the blood. It is contemplated that the ratio of pDC occupying the peripheral blood lymphocyte is 1% or less. However, pDC has very high IFN-production ability. The IFN-production ability of pDC reaches, for example, 3000 pg/mL/$10^4$ cells. That is to say, it can be said that most of IFNα or IFNβ in the blood produced at the time of virus infection is caused by pDC, although the number of the cells is small.

pDC is differentiated into a dendritic cell by virus stimulation, and induces production of IFN-γ or interleukin (IL)-10 by T cell. In addition, pDC is also differentiated into a dendritic cell by IL-3 stimulation. The dendritic cell differentiated upon IL-3 stimulation induces production of Th2 cytokine (IL-4, IL-5, IL-10) by T cell. As described above, pDC has a property that it is differentiated into different dendritic cells depending on the difference of stimulations.

Accordingly, pDC is a cell that has two sides, i.e., one side as an IFN producing cell, and the other side as a precursor cell of a dendritic cell. Either one of the cells plays an important role in the immune system. That is to say, pDC is one of the important cells that support the immune system in various aspects.

In regulation of the activity of a humoral factor such as IFN, administration of an antibody that recognizes the factor is effective. For example, an attempt to treat autoimmune diseases with an antibody against IL-1 or IL-4 was in practical use. In addition, also for IFN similarly, neutralization antibody is regarded as a therapeutic agent for autoimmune diseases. It can be expected that similar approach is effective for IFN producing pDC. However, such approach is based on inhibition of the action of a humoral factor after being produced. If production of an intended humoral factor can be directly controlled, further essential therapeutic effects can be achieved.

Antibodies that recognize human pDC have been reported. For example, anti-BDCA-2 monoclonal antibody is a human pDC-specific monoclonal antibody (Dzionek, A. et al. J. Immunol, 165: 6037-6046, 2000). It has been revealed that the anti-BDCA-2 monoclonal antibody has an action of suppressing IFN production of human pDC (J. Exp. Med. 194: 1823-1834, 2001). Additionally, it has been also reported that a monoclonal antibody that recognizes mouse interferon-producing cell suppresses the production of interferon (Blood 2004 Jun. 1; 103/11: 4201-4206. Epub 2003 December). It has been also reported that the number of dendritic cells decreases by a monoclonal antibody for mouse pDC (J. Immunol. 2003, 171: 6466-6477).

Similarly, it would be useful if an antibody that can recognize human pDC and regulate the activity thereof is provided. For example, the present inventors revealed already that an antibody recognizing Ly49Q specifically binds to mouse pDC. However, the antibody for Ly49Q did not interfere with the activity of mouse pDC (Blood, 1 Apr. 2005, Vol. 105, No. 7, pp. 2787-2792).

PLD is an enzyme that catalyzes a reaction of hydrolysis of phosphatidyl choline to produce phosphatidic acid and choline, and causes signaling in various cells. It is contemplated that the produced phosphatidic acid functions as a lipid signal molecule.

PLD1 and PLD2 are conventionally known as two kinds of mammal PLDs, and contain Phox homology domain (PX domain), which is bondable to phosphatidyl inositide, and pleckstrin homology domain (PH domain) at the N terminal region thereof. Both of the domains are involved in PLD membrane targeting.

PLD1 and PLD2 further contain two His-x-Lys-x-x-x-x-Asp sequences (HKD motif). This HKD motif is an essential domain in PLD activity.

It has been contemplated that phosphatidic acid produced by PLD1 and PLD2 is involved in re-constitution of cellular skeleton, exocytosis, phagocytosis, canceration, cell adhesion, chemotaxis, and the like, and acts centrally in the nerve system, the immune system, and the like.

Although human Hu-K4 and mouse SAM9 are officially named as PLD3 until now, they are lack of PX and PH domains, and exhibit no PLD activity though they have two HKD motifs. Furthermore, although there are three PLD family members, i.e., PLD4, PLD5, and PLD6, these non-classical PLDs are scarcely known.

The cerebellar development transcriptome database (CDT-DB) for gene expression pattern in development of mouse cerebellum was searched, and as a result thereof, PLD4, which was a transcription product that was controlled at the time of development, was identified (see Tao et al., Nat. Methods 2(8), 591-598(2005)). Basic characteristics of PLD4 have not been reported. It is regarded that it should be determined from now whether PLD4 exhibits enzymatic activity or not, and whether a de-glycosylated form of PLD4 has PLD activity or not.

PLD4 is a 506 amino acid sequence represented by SEQ ID NO: 1 (Tao et al., Nat. Methods 2(8), 591-598(2005) and Clark et al., Genome Res. 13(10), 2265-2270(2003)). The PLD4 protein has two tentative PDE regions (phosphodiesterase motif), which are constituted with two HKD motifs (amino acid sequence of His-x-Lys-x-x-x-x-Asp, wherein x is the other amino acids) conserved in the C terminal region, and a presumptive phosphorylation site (Thr 472). The structure of the PLD4 protein is predicted as a type II monotropic transmembrane protein. In addition, the N terminal region of the PLD4 protein does not have PX region and PH region, which are possessed by PLD1 and PLD2 that are classical PLD family (FIGS. 1 and 2).

On the other hand, although PLD4 belongs to the PLD family from the fact that it has two HKD motifs, PLD4 is lack of PX domain and PH domain, but has a putative transmembrane domain instead.

mRNA expression of PLD4, which was characteristically at from a low level to a medium level, was found in a cell subpopulation that was preferentially localized at the corpus callosum and the periphery of the white matter region including cerebellar white matter of a mouse 1 week after birth. These cells expressing the PLD4 mRNA have been identified as Ibal positive microglia (see Tao et al., Nat. Methods 2(8), 591-598(2005)).

The period of 1 week after birth is a period when activation of myelin formation starts in the corpus callosum and the cerebellar white matter of a mouse. In this period, PLD4 is highly expressed at the amoeboid (activated state) microglia that exists in the white matter. From these facts, a possibility is contemplated that PLD4 expression cell in the white matter is involved in myelin formation in this period. Particularly, accumulation PLD4 in the phagocytic vesicle becomes evident, and a possibility is suggested that PLD4 expression cell is involved in phagocytosis. From the amoeboid microglia in the activated state, various cytokines or growth factors are secreted, and phagocytosis is activated as well. It is contemplated that extra oligodendrocyte (glia cell in the central nervous system, which forms myelin as rolled and attached to the axon) causes apoptosis in the white matter of the brain at the development stage. A possibility has been contemplated that the extra oligodendrocyte is degraded and removed from the amoeboid microglia to secret a signal molecule, whereby to arrange the environment for myelin formation in the white matter. It is suggested that PLD4 is involved in these processes including the myelin formation.

PLD4 mRNA expression is universally seen also in non-nerve tissues, but is mainly distributed in the spleen. Strong PLD4 expression is detected at the periphery of the border zone of red pulp of the spleen, and splenic PLD4 protein collected from the membrane fraction in the cell is highly N-glycosylated. When PLD4 was expressed in a heterogeneous cell system, they were localized in the endoplasmic reticulum and the Golgi body. Heterologously-expressed PLD4 showed no PLD enzymatic activity (Plos ONE www.plosone.org, November 2010, Volume 5, Issue 11, e13932).

From the pattern of the PLD4 expression limited in terms of time and location, it is suggested that PLD4 plays a role in common functions in the microglia or the cell in the spleen border region at the time of brain development at the initial stage after birth.

The PLD4 mRNA expression and PLD4 distribution in the nerve tissue and non-nerve tissue have been overviewed above. However, the present inventors found out that PLD4 mRNA is specifically highly expressed in a pDC cell at the resting stage (resting pDC) in the level of a cell species described below.

Mouse anti-human PLD4 polyclonal antibody against total length human PLD4 protein is commercially available (PLD4 purified MaxPab mouse polyclonal antibody (B01P), catalog No. H00122618-B01P, manufactured by Abnova Corporation). However, a monoclonal antibody that binds only to a certain site of PLD4, or a monoclonal antibody that can specifically bind to PLD4, has not been obtained.

CITATION LIST

Non-Patent Literature (1) Tao et al., Nat. Methods 2(8), 591-598 (2005)
(2) Clark et al., Genome Res. 13(10), 2265-2270 (2003)
(3) Plos ONE www.plosone.org, November 2010, Volume 5, Issue 11, e13932
(4) Catalog of mouse PLD4 polyclonal antibody against full length human PLD4 protein (Abnova, catalog No. H00122618-B01P)
(5) Dzionek, A. et al. J. Immunol. 165: 6037-6046, 2000 (6) J. Exp. Med. 194:1823-1834, 2001
(7) Blood 2004 Jun. 1; 103/11:4201-4206. Epub 2003 December
(8) J. Immunol. 2003, 171:6466-6477
(9) Blood, 1 Apr. 2005, Vol. 105, No. 7, pp. 2787-2792
(10) Nat. Methods 2(8), 591-598(2005)

SUMMARY OF INVENTION

Technical Problem

A problem to be solved by the invention is to provide an antibody that binds to PLD4, and to detect, identify, or isolate pDC. In addition, a problem to be solved by the invention is to regulate activity of pDC.

Solution to Problem

The present inventors confirmed through a research for PLD4 that expression of PLD4 specifically rises in pDC, particularly pDC at the resting stage in addition to pDC at the active stage. Consequently, the present inventors tried the preparation of PLD4 antibody and the elucidation of its action.

In order to obtain an antibody that recognizes a slight amount of a protein derived from a living organism, a protein prepared by gene recombinant technology is generally used as an immunogen. The present inventors tried expression of PLD4 based on the information of the base sequence of PLD4 cDNA, and an amino acid sequence (GenBank Accession No. NM_138790.2) encoded by it, which has been already revealed (Nat. Methods 2(8), 591-598 (2005)).

In order to obtain an antibody of a protein, use of a partial amino acid sequence of a natural protein as an immunogen is often tried. However, in order for an antibody to recognize a molecule on the cell surface, it is necessary to select a region that constitutes a part recognized by the antibody as an epitope on the cell surface. Accordingly, it has been contemplated that it is not realistic to use a fragment amino acid sequence as an immunogen to obtain an antibody specific to PLD4.

Under such circumstances, the present inventors revealed that use of a special immunogen allows obtaining an antibody that binds to pDC. Furthermore, the present inventors confirmed that thus-obtained antibody specifically recognizes human pDC, and further has an action of regulating its activity, and completed the invention. That is to say, the invention relates to an anti-PLD4 antibody, a preparation method thereof, and use thereof described below.

The invention is as follows:

(1) A monoclonal antibody that binds to a phospholipase D4 (PLD4) protein, or a fragment containing an antigen-binding region thereof.

(2) The monoclonal antibody, or a fragment containing an antigen-binding region thereof as described in the above-mentioned (1), which has the sequence SYWMH (SEQ ID NO: 2) as CDR1, the sequence DIYPGSDSTNYNEKFKS (SEQ ID NO: 3) as CDR2, and the sequence GGWLDAMDY (SEQ ID NO: 4) as CDR3 in the heavy chain variable region.

(3) The monoclonal antibody, or a fragment containing an antigen-binding region thereof as described in the above-mentioned (1), which has the sequence RASQDISNYLN (SEQ ID NO: 5) as CDR1, the sequence YTSRLHS (SEQ ID NO: 6) as CDR2, and sequence QQGNTLPW (SEQ ID NO: 7) as CDR3 in the light chain variable region.

(4) The monoclonal antibody, or a fragment containing an antigen-binding region thereof as described in the above-mentioned (1), which has the sequence SYWMH (SEQ ID NO:2) as CDR1, the sequence DIYPGSDSTNYNEKFKS (SEQ ID NO:3) as CDR2 and the sequence GGWLDAMDY (SEQ ID NO:4) as CDR3 in the heavy chain variable region, and has the sequence RASQDISNYLN (SEQ ID NO:5) as CDR1, the sequence YTSRLHS (SEQ ID NO:6) as CDR2, and the sequence QQGNTLPW (SEQ ID NO:7) as CDR3 in the light chain variable regio.

(5) The monoclonal antibody (3B4 antibody), or a fragment containing an antigen-binding region thereof as described in the above-mentioned (1), which has the sequence TYWMH (SEQ ID NO: 8) as CDR1, the sequence AIYPGNSETSYNQKFKG (SEQ ID NO: 9) as CDR2, and the sequence GYSDFDY (SEQ ID NO: 10) as CDR3 in the heavy chain variable region.

(6) The monoclonal antibody, or a fragment containing an antigen-binding region thereof as described in the above-mentioned (1), which has the sequence HASQGIRSNIG (SEQ ID NO: 11) as CDR1, the sequence HGTNLED (SEQ ID NO: 12) as CDR2, and the sequence VQYVQFP (SEQ ID NO: 13) as CDR3 in the light chain variable region.

(7) The monoclonal antibody, or a fragment containing an antigen-binding region thereof as described in the above-mentioned (1), which has the sequence TYWMH (SEQ ID NO:8) as CDR1, the sequence AIYPGNSETSYNQKFKG (SEQ ID NO:9) as CDR2, and the sequence GYSDFDY (SEQ ID NO: 10) as CDR3 in the heavy chain variable region, and has the sequence HASQGIRSNIG (SEQ ID NO: 11) as CDR1, the sequence HGTNLED (SEQ ID NO:12) as CDR2, and the sequence VQYVQFP (SEQ ID NO:13) as CDR3 in the light chain variable region.

(8) The monoclonal antibody (5B7 antibody), or a fragment containing an antigen-binding region thereof as described in the above-mentioned (1), which has the sequence DYNLH (SEQ ID NO: 14) as CDR1, the sequence YIYPYNGNTGYNQKFKR (SEQ ID NO: 15) as CDR2, and the sequence GGIYDDYYDYAIDY (SEQ ID NO: 16) as CDR3 in the heavy chain variable region.

(9) The monoclonal antibody, or a fragment containing an antigen-binding region thereof as described in the above-mentioned (1), which has the sequence RASENIYSHIA (SEQ ID NO: 17) as CDR1, the sequence GATNLAH (SEQ ID NO: 18) as CDR2, and the sequence QHFWGTP (SEQ ID NO: 19) as CDR3 in the light chain variable region.

(10) The monoclonal antibody, or a fragment containing an antigen-binding region thereof as described in the above-mentioned (1), which has the sequence DYNLH (SEQ ID NO:14) as CDR1, the sequence YIYPYNGNTGYNQKFKR (SEQ ID NO:15) as CDR2, and the sequence GGIYDDYYDYAIDY (SEQ ID NO: 16) as CDR3 in the heavy chain variable region, and has the sequence RASENIYSHIA (SEQ ID NO: 17) as CDR1, the sequence GATNLAH (SEQ ID NO: 18) as CDR2, and the sequence QHFWGTP (SEQ ID NO: 19) as CDR3 in the light chain variable region.

(11) The monoclonal antibody (8C11 antibody), or a fragment containing an antigen-binding region thereof as described in the above-mentioned (1), which has the sequence SYYLY (SEQ ID NO: 20) as CDR1, the sequence LINPTNSDTIFNEKFKS (SEQ ID NO: 21) as CDR2, and the sequence EGGYGYGPFAY (SEQ ID NO: 22) as CDR3 in the heavy chain variable region.

(12) The monoclonal antibody, or a fragment containing an antigen-binding region thereof as described in the above-mentioned (1), which has the sequence TSSQTLVHSNGNTYLH (SEQ ID NO: 23) as CDR1, the sequence KVSNRFS (SEQ ID NO: 24) as CDR2, and the sequence HSTHVP (SEQ ID NO: 25) as CDR3 in the light chain variable region.

(13) The monoclonal antibody, or a fragment containing an antigen-binding region thereof as described in the above-mentioned (1), which has the sequence SYYLY (SEQ ID NO:20) as CDR1, the sequence LINPTNSDTIFNEKFKS (SEQ ID NO:21) as CDR2, and the sequence EGGYGYGPFAY (SEQ ID NO:22) as CDR3 in the heavy chain variable region, and has the sequence TSSQTLVHSNGNTYLH (SEQ ID NO:23) as CDR1, the sequence KVSNRFS (SEQ ID NO:24) as CDR2, and the sequence HSTHVP (SEQ ID NO:25) as CDR3 in the light chain variable region.

(14) The monoclonal antibody (10C3 antibody), or a fragment containing an antigen-binding region thereof as described in the above-mentioned (1), which has the sequence SYGMS (SEQ ID NO: 26) as CDR1, the sequence TISSGGSYIYYPESVKG (SEQ ID NO: 27) as CDR2, and the sequence LYGGRRGYGLDY (SEQ ID NO: 28) as CDR3 in the heavy chain variable region.

(15) The monoclonal antibody, or a fragment containing an antigen-binding region thereof as described in the above-mentioned (1), which has the sequence RSSKSLLHSDGITYLY (SEQ ID NO: 29) as CDR1, the sequence QMSNLAS (SEQ ID NO: 30) as CDR2, and the sequence AQNLEL (SEQ ID NO: 31) as CDR3 in the light chain variable region.

(16) The monoclonal antibody, or a fragment containing an antigen-binding region thereof as described in the above-mentioned (1), which has the sequence SYGMS (SEQ ID NO:26) as CDR1, the sequence TISSGGSYIYYPESVKG (SEQ ID NO:27) as CDR2, and the sequence LYGGRRGYGLDY (SEQ ID NO:28) as CDR3 in the heavy chain variable region, and has the sequence RSSKSLLHSDGITYLY (SEQ ID NO:29) as CDR1, the sequence QMSNLAS (SEQ ID NO:30) as CDR2, and the sequence AQNLEL (SEQ ID NO:31) as CDR3 in the light chain variable region.

(17) The monoclonal antibody (13D4 antibody), or a fragment containing an antigen-binding region thereof as described in the above-mentioned (1), which has the sequence SHYYWT (SEQ ID NO: 32) as CDR1, the sequence YISYDGSNNYNPSLKN (SEQ ID NO: 33) as CDR2, and the sequence EGPLYYGNPYWYFDV (SEQ ID NO: 34) as CDR3 in the heavy chain variable region.

(18) The monoclonal antibody, or a fragment containing an antigen-binding region thereof as described in the above-mentioned (1), which has the sequence RASQDIDNYLN (SEQ ID NO: 35) as CDR1, the sequence YTSRLHS (SEQ ID NO: 36) as CDR2, and the sequence QQFNTLP (SEQ ID NO: 37) as CDR3 in the light chain variable region.

(19) The monoclonal antibody, or a fragment containing an antigen-binding region thereof as described in the above-mentioned (1), which has the sequence SHYYWT (SEQ ID NO:32) as CDR1, the sequence YISYDGSNNYNPSLKN (SEQ ID NO:33) as CDR2, and the sequence EGPLYYGNPYWYFDV (SEQ ID NO:34) as CDR3 in the heavy chain variable region, and has the sequence RASQDIDNYLN (SEQ ID NO:35) as CDR1, the sequence YTSRLHS (SEQ ID NO:36) as CDR2, and the sequence QQFNTLP (SEQ ID NO:37) as CDR3 in the light chain variable region.

(20) The monoclonal antibody (13H11), or a fragment containing an antigen-binding region thereof as described in the above-mentioned (1), which has the sequence SHYYWS (SEQ ID NO: 38) as CDR1, the sequence YISYDGSNNYNPSLKN (SEQ ID NO: 39) as CDR2, and the sequence EGPLYYGNPYWYFDV (SEQ ID NO: 40) as CDR3 in the heavy chain variable region.

(21) The monoclonal antibody, or a fragment containing an antigen-binding region thereof as described in the above-mentioned (1), which has the sequence RASQDIDNYLN (SEQ ID NO: 41) as CDR1, the sequence YTSRLHS (SEQ ID NO: 42) as CDR2, and the sequence QQFNTLP (SEQ ID NO: 43) as CDR3 in the light chain variable region.

(22) The monoclonal antibody, or a fragment containing an antigen-binding region thereof as described in the above-mentioned (1), which has the sequence SHYYWS (SEQ ID NO:38) as CDR1, the sequence YISYDGSNNYNPSLKN (SEQ ID NO:39) as CDR2, and the sequence EGPLYYGNPYWYFDV (SEQ ID NO:40) as CDR3 in the heavy chain variable region, and has the sequence RASQDIDNYLN (SEQ ID NO:41) as CDR1, the sequence YTSRLHS (SEQ ID NO:42) as CDR2, and the sequence QQFNTLP (SEQ ID NO:43) as CDR3 in the light chain variable region.

(23) A monoclonal antibody, or a fragment containing an antigen-binding region thereof, which is produced by any one of hybridomas mp5B7, mp7B4, mp13D4, and mp13H11 that are deposited under Accession Numbers: NITE BP-1211, NITE BP-1212, NITE BP-1213, and NITE BP-1214.

(24) A hybridoma that produces any one of the monoclonal antibodies as described in the above-mentioned (1) or (2).

(25) A hybridoma mp5B7, mp7B4, mp13D4 or mp13H11 that is deposited under Accession Numbers: NITE BP-1211, NITE BP-1212, NITE BP-1213 or NITE BP-1214.

(26) A method of preparing a monoclonal antibody, containing a process of culturing the hybridoma as described in the above-mentioned (25), and collecting a monoclonal antibody from the culture.

(27) A method of preparing a cell that produces a monoclonal antibody that binds to PLD4, containing the following processes;

1) a process of administering recombinant PLD4-Ig fusion protein that encodes an amino acid sequence containing a PLD4 extracellular domain, to an immune animal, and 2) a process of selecting an antibody-producing cell that produces an antibody that binds to PLD4 from antibody-producing cells of the immune animal.

(28) The method as described in the above-mentioned (27), wherein the cell that expresses PLD4 is a cell that retains an extrinsic polynucleotide that encodes an amino acid sequence containing the PLD4 extracellular domain in an expressible way.

(29) The method as described in the above-mentioned (28), wherein the cell is an animal cell.

(30) The method as described in the above-mentioned (29), wherein the cell is a human-derived cell.

(31) The method as described in the above-mentioned (30), wherein the human-derived cell is a HEK-293T cell.

(32) The method as described in any one of the above-mentioned (27) to (31), containing a process of cloning the obtained antibody-producing cells incrementally.

(33) A method of preparing a monoclonal antibody that binds to a PLD4 extracellular domain, containing a process of culturing the antibody-producing cells obtained by the method as described in the above-mentioned (29), and collecting a monoclonal antibody from the culture.

(34) A monoclonal antibody that recognizes PLD4, or a fragment containing an antigen-binding region thereof, which can be obtained by the following processes;

1) a process of administering a recombinant PLD4-Ig fusion protein that encodes an amino acid sequence containing a PLD4 extracellular domain, to an immune animal, 2) a process of selecting an antibody-producing cell that produces an antibody that binds to PLD4 from antibody-producing cells of the immune animal, and 3) a process of culturing the antibody-producing cells selected in the process 2), and collecting an antibody that recognizes PLD4 from the culture.

(35) An immunogen for preparing an antibody that binds to PLD4, containing (a) an animal cell that retains a polynucleotide that encodes an amino acid sequence containing a PLD4 extracellular domain extrinsically in an expressible way, or a cell membrane fraction thereof.

(36) The immunogen as described in the above-mentioned (35), wherein the animal cell is a human-derived cell.

(37) A method of detecting a plasmacytoid dendritic cell, containing a process of bringing a monoclonal antibody that binds to a PLD4 extracellular domain, or a fragment containing an antigen-binding region thereof into contact with a test cell, and detecting a monoclonal antibody, or a fragment containing an antigen-binding region thereof that binds to the cell.

(38) A reagent for detection of a plasmacytoid dendritic cell, containing a monoclonal antibody that binds to a PLD4 extracellular domain, or a fragment containing an antigen-binding region thereof.

(39) A method of suppressing an activity of a plasmacytoid dendritic cell, containing a process of bring any one of the components described below into contact with the plasmacytoid dendritic cell:

(a) a monoclonal antibody that binds to PLD4 and suppresses an activity of the plasmacytoid dendritic cell, or a fragment containing an antigen-binding region thereof, and (b) an immunoglobulin in which a complementarity-determining region of the monoclonal antibody (a) is transplanted, or a fragment containing an antigen-binding region thereof.

(40) A method of suppressing an activity of a plasmacytoid dendritic cell in a living organism, containing a process of administering any one of the components described below to the living organism:

(a) a monoclonal antibody that binds to PLD4, and suppresses an activity of the plasmacytoid dendritic cell, or a fragment containing an antigen-binding region thereof, and (b) an immunoglobulin in which a complementarity-determining region of the monoclonal antibody (a) is transplanted, or a fragment containing an antigen-binding region thereof.

(41) The method as described in the above-mentioned (39) or (40), wherein the activity of a plasmacytoid dendritic cell is either one of interferon producing activity and survival of an interferon producing cell, or both of them.

(42) An agent for suppressing an activity of a plasmacytoid dendritic cell, containing any one of the components described below as an active component:

(a) a monoclonal antibody that binds to PLD4, and suppresses an activity of the plasmacytoid dendritic cell, or a fragment containing an antigen-binding region thereof, and (b) an immunoglobulin in which a complementarity-determining region of the monoclonal antibody (a) is transplanted, or a fragment containing an antigen-binding region thereof.

(43) The agent for suppressing an activity of an interferon producing cell as described in the above-mentioned (42), wherein the activity of a plasmacytoid dendritic cell is either one of interferon producing activity and survival of an interferon producing cell, or both of them.

Effects of Invention

The invention provides an antibody that specifically recognizes PLD4, immunity that is useful in preparation of the antibody, and a method of preparing an anti-PLD4 antibody using the immunogen. PLD4 is a membrane protein that belongs to PLD4 family. The present inventors revealed that an antibody that specifically recognizes PLD4 can be easily obtained. The anti-PLD4 antibody that can be obtained by the invention is an antibody having high specificity, which distinguishes human pDC from a cell that expresses other PLD families.

In a preferred aspect, the anti-PLD4 antibody provided by the invention binds to human pDC. In addition, the antibody of the invention specifically recognizes human pDC. Accordingly, the antibody of the invention is useful for detection or isolation of pDC. pDC is a cell that produces most of type 1 IFN. Accordingly, such detection or isolation is important in diagnosis or research of diseases associated with pDC such as autoimmune diseases.

Furthermore, in a preferred aspect, the anti-PLD4 antibody provided by the invention has an action of regulating human pDC activity. Accordingly, the anti-PLD4 antibody of the invention can be used for suppressing pDC activity. Accordingly, if suppression of pDC activity is employed using the antibody of the invention, therapeutic effects can be expected for a patient of an autoimmune disease in which IFNα expression has risen.

pDC produces a large amount of IFN in a small number of cells. In neutralization of IFN, an antibody is necessary, which depends on the number of IFN molecules. However, in the invention, the activity of the production cell is directly suppressed. As a result thereof, potent IFN suppression effect can be expected with less amount of the antibody in comparison with neutralization of an anti-IFN antibody. Furthermore, in a case where IFN is produced continuously, it is expected that neutralization by IFN antibody will remain as transient suppression. However, in the invention, pDC activity is suppressed, and from this, IFN-producing suppression effect can be expected over a long time.

BRIEF DESCRIPTION OF DRAWINGS

FIG. 1 is a diagram that illustrates the amino acid sequence of human PLD4 (C14orf175) protein (506 residues). It is contemplated that the 31 to 53 residues from the N terminal are a transmembrane domain as analyzed using "SOSUI program (http://bp.nuap.nagoya-u.ac.jp/sosui/sosui_submit.html)", which is prediction system for a transmembrane region. The 54 to 506 residues contain two phosphodiesterase motifs, and this protein is predicted to be type II transmembrane protein;

FIG. 16 is a FACS measurement diagram that illustrates staining in anti-PLD4 antibody of cynomolgus monkey PLD4-CT125 cell. Among the anti-PLD4 antibodies, seven (3B4, 5B7, 7B4, 13D4, 13H11, 14C1, and 11G9.6) antibodies can binds to cynomolgus monkey PLD4-CT125 stable transfectant;

FIG. 17 is a FACS analysis diagram that illustrates staining in anti-PLD4 antibody, with transient gene introduction of Flag tagged rhesus monkey PLD4 expression vector into human PLD4-293T cell. Cell surface expression of the rhesus monkey PLD4 protein was confirmed in the anti-Flag antibody;

FIG. 19 is a graph that illustrates dissociation constant molar concentration (nM unit, Kd value) of anti-PLD4 antibody against human PLD4-CT125 stable cell strain;

FIG. 23 is a graph that illustrates measurement with ELISA of IFN-α secretion inhibition by treatment with anti-PLD4 chimeric antibody (ch11G9.6) in human PBMC isolated from three healthy individuals.

FIG. 26 is IFNα production from PBMCs by CpG2216 in the presence of chimeric anti-PLD4 Abs.

MODE FOR CARRYING OUT THE INVENTION

The present inventors found that PLD4 is a molecule that is specifically expressed in the mRNA level and protein level in a plasmacytoid dendritic cell at the resting stage (resting pDC). A method of preparing an antibody that recognizes PLD4 is not established.

There is a report that mouse PLD4 is a molecule that is expressed in amoeboid (activated state) microglia at development stage in the cerebellum or the corpus callosum at the initial stage after birth. However, expression of human PLD4 is not known until now. Particularly, expression in the immune system, intracellular location, structure, function, and the like of human PLD4 have not been reported until now. It was confirmed by the invention that human PLD4, which was contemplated until now to be expressed only in the cytoplasm, is a cell surface marker that is expressed in human plasmacytoid dendritic cell (pDC) as type II transmembrane protein. Accordingly, binding of PLD4 antibody to pDC becomes possible, and it has been proved that PLD4 antibody is useful as a molecular target of a therapeutic antibody intended to regulate functions of B cell and pDC cell.

Figure 4:
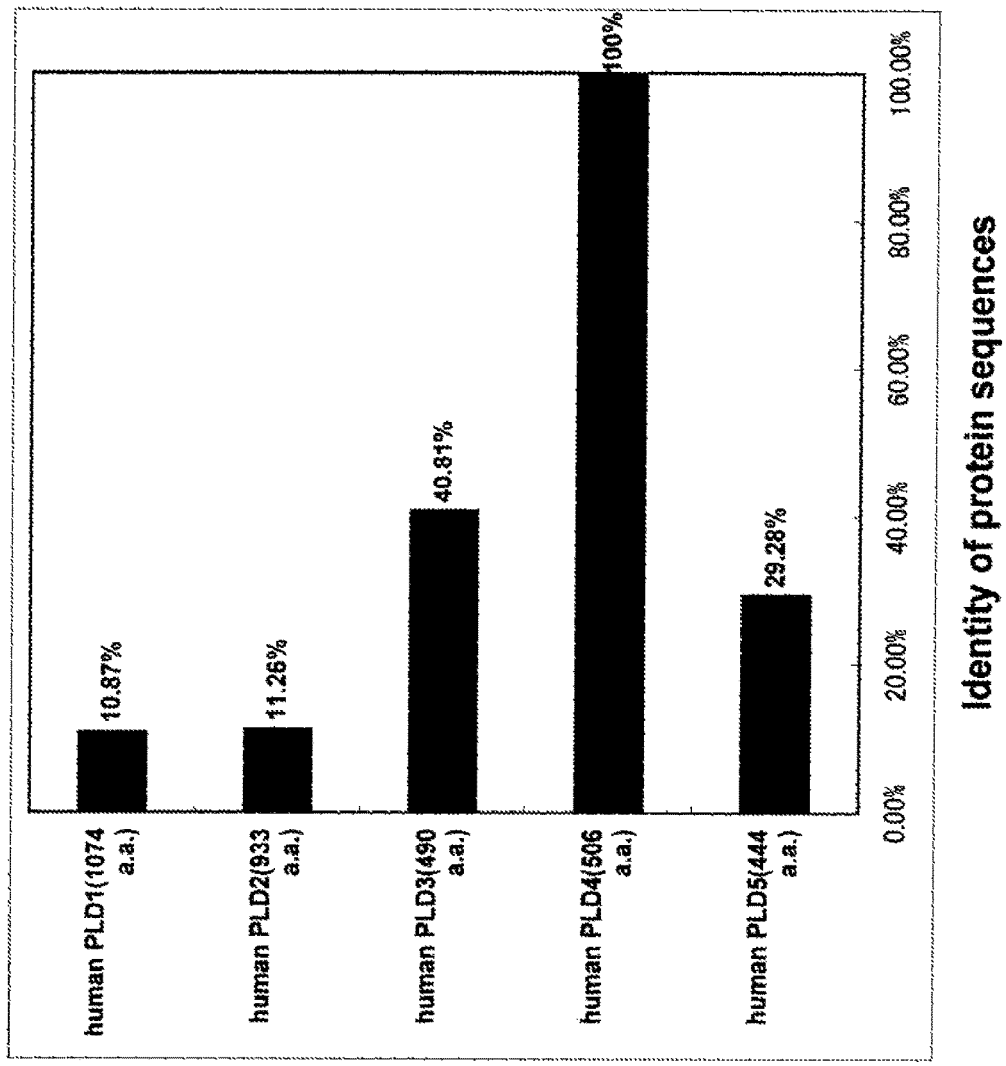
FIG. 4 is a graph that illustrates the homology with human PLD4 protein family (paralogous)

The present inventors confirmed by gene expression analysis that PLD4 is specifically expressed in human pDC. It was contemplated that if an antibody that can distinguish PLD4 immunologically from other molecules, is obtained, it would be useful for pDC research. However, there are many molecules in the PLD family including PLD4, which are very similar in the structure to each other. Molecules such as PLD1, PLD2, PLD3, and PLD5, including PLD that is PLD4, encompass an amino acid sequence having particularly high homology (FIG. 4). Accordingly, it was contemplated that it is difficult to obtain an antibody that distinguish these molecules mutually using an immunogen of a peptide that employs an amino acid sequence (a partial sequence) that constitutes PLD4 (or extracellular domain). Consequently, the present inventors tried acquisition of an antibody against PLD4 using a recombinant PLD4-Ig fusion protein as an immunogen, which encodes an amino acid sequence encompassing PLD4 extracellular domain.

The present inventors repeated researches in order to acquire an antibody that recognizes PLD4 and revealed that the intended antibody is obtained using a recombinant PLD4-Ig fusion protein as an immunogen, and completed the invention. That is to say, the invention relates to a monoclonal antibody that binds to a PLD4 extracellular domain, or a fragment containing an antigen-binding region thereof.

In the invention, PLD4 is a natural molecule that is expressed in human pDC, or an immunologically equivalent molecule to PLD4 that is expressed in human pDC. In the invention, binding of an antibody to PLD4 can be confirmed, for example, as described below.

Confirmation Based on Reactivity with Human Cell:

According to the findings obtained by the present inventors, it is contemplated that PLD4 can be used as a pDC marker, from the fact that it exhibits specific expression in human pDC.

Based on such expression profile of PLD4, binding activity with at least partial subset of pDC is one of the important characteristics of the antibody that binds to PLD4 in the invention. The fact that some cell is pDC can be confirmed by a cell surface marker inherent in each cell family. For example, binding to an intended cell is confirmed by double staining of an antibody that binds to a cell surface marker, and an antibody to be confirmed for the binding activity. That is to say, pDC in the invention encompasses cells that express, for example, BDCA2.

Confirmation Based on Reactivity with Transformed Cell that Expresses PLD4 Gene:

The present inventors confirmed that immunological characteristics of PLD4 that is expressed in human pDC is re-constituted when PLD4 gene is expressed under certain conditions. Accordingly, reactivity with PLD4 can be also confirmed based on the reactivity of an antibody for a cell into which a gene that encodes PLD4 is artificially introduced. That is to say, the invention relates to a monoclonal antibody that binds to a molecule that contains an amino acid sequence that constitutes PLD4 extracellular domain as an extracellular domain, or a fragment containing an antigen-binding region thereof. Meanwhile, the extracellular domain is constituted by an amino acid sequence that corresponds to 54 to 506 from the N terminal in SEQ ID NO 1 (FIG. 1) of the amino acid sequence represented by SEQ ID NO 1.

For example, in a cell that is transformed with an expression vector encompassing DNA that encodes PLD4, immunological characteristics of PLD4 that are expressed in human pDC are maintained. Accordingly, a transformed cell that expresses PLD4 is preferable as a cell for confirming binding property of an antibody to the extracellular domain of PLD4 in the invention. When the reactivity of an antibody by a transformed cell is confirmed in the invention, a non-transformed cell is desirably used as a control.

Next, the antibody that binds to PLD4 in the invention may be an antibody that shows cross property with a cell family that is known to express PLD family other than PLD4, or may be an antibody that does not show such cross property. The antibody showing no cross property is preferable as the antibody that binds to PLD4 in the invention. Specifically, the antibody that binds to PLD4 in the invention is preferably an antibody that may not be confirmed for the binding with a cell family that is known to express PLD family other than PLD4, under the same conditions to the conditions where binding to pDC is confirmed.

That is to say, the monoclonal antibody that binds to a PLD4 extracellular domain in the invention preferably encompasses a monoclonal antibody that has the immunological characteristics described below.

a) Binding to human pDC, b) May not be confirmed for binding to one or multiple species of cells selected from a group consisting of monocyte, macrophage, CD34 positive cell, and dendritic cells derived from these cells, under conditions allowing binding to human pDC.

Particularly, the monoclonal antibody of the invention is preferably an antibody that may not be confirmed for binding to monocyte, macrophage, B cell, CD34 positive cell, and dendritic cells derived from these cells, under conditions allowing binding to human pDC.

Alternatively, the monoclonal antibody that binds to a PLD4 extracellular domain in the invention preferably encompasses a monoclonal antibody that has immunological characteristics described below.

c) Binding to a transformed cell that is transformed with an expression vector that retains DNA encoding PLD4 in an expressible way, d) May not be confirmed for binding with the host cell of c) before being transformed, under conditions allowing binding to the transformed cell c).

The fact that the anti-PLD4 monoclonal antibody is not crossed with other molecules of PLD family in the invention, can be confirmed by employing a cell in which each PLD family was mandatorily expressed. That is to say, mandatory expression is performed by introducing cDNA that encodes the amino acid sequence of each PLD family into an appropriate host cell. The obtained transformed cell is brought into contact with anti-PLD4 monoclonal antibody to be confirmed for the cross property. If binding to a cell that expresses PLD family molecules other than PLD4 is not exhibited, it can be confirmed that the antibody can immunologically distinguish PLD4 from other PLD family molecules. For example, it is confirmed in Examples described below that most of the anti-PLD4 monoclonal antibodies obtained by the invention does not cross with PLD3 and PLD5 having particularly high homology to PLD4, and further PLD1 and PLD2. Accordingly, the monoclonal antibody in the invention is preferably a monoclonal antibody that binds to PLD4, but may not be detected for binding to PLD3, PLD5, PLD1, or PLD2 under the same conditions. If an antibody that can immunologically distinguish these PLD family molecules from PLD4 is used, change of PLD4 expression can be specifically detected.

Binding of a monoclonal antibody to be confirmed for binding activity, to each species of a cell, can be confirmed, for example, in flow cytometry principle. In order to confirm reactivity of an antibody by flow cytometry principle, it is advantageous to label the antibody with a molecule or atom group that produces a detectable signal. Generally, a fluorescent label or a luminescent label is used. In order to analyze binding of a fluorescent-labeled antibody to a cell by the principle of flow cytometry, a fluorescence-activated cell sorter (FACS) can be used. By using FACS, multiple bindings of an antibody to a cell can be confirmed effectively.

Specifically, for example, an antibody A that is preliminarily known to be able to identify pDC, and an antibody B to be analyzed for binding characteristics with pDC, are reacted at the same time with a cell family encompassing pDC. The antibody A and the antibody B are on label with a fluorescent signal that can distinguish them from each other. If both of the signals are detected from the same cell family, it can be confirmed that such antibodies bind to the same cell family. That is to say, it is found out that the antibody A and the antibody B have the same binding characteristics. If the antibody A and the antibody B bind to a different cell family, it is evident that the binding characteristics of them are different from each other.

Examples of preferable monoclonal antibody in the invention include, for example, monoclonal antibodies produced by hybridomas mp5B7, mp7B4, mp13D4, and mp13H11.

The hybridomas mp5B7, mp7B4, mp13D4 and mp13H1 were deposited under Accession Numbers: NITE BP-1211, NITE BP-1212, NITE BP-1213, and NITE BP-1214 at National Institute of Technology and Evaluation (NITE) Patent Microorganisms Depositary on Jan. 27, 2012. Contents to specify the deposition will be described below.

(1) Name And Address of Deposit Authority

Name: National Institute of Technology and Evaluation (NITE), Patent Microorganisms Depositary Address: 2-5-8 Kazusakamatari, Kisarazu-shi, Chiba-ken, 292-0818 JAPAN (2) Deposit date: Jan. 27, 2012

(3) Accession Numbers NITE BP-1211 (hybridoma mp5B7)

NITE BP-1212 (hybridoma mp7B4)

NITE BP-1213 (hybridoma mp13D4)

NITE BP-1214 (hybridoma mp13H11)

The monoclonal antibody of the invention may be a fragment containing an antigen-binding region thereof. For example, an antibody fragment encompassing an antigen binding site that is produced by IgG enzymatic digestion, may be used as the antibody in the invention. Specifically, by digestion with papain or pepsin, an antibody fragment such as Fab or F(ab')2 may be obtained. In addition, an immunoglobulin fragment encompassing a variable region in which complementarily-determining region (CDR) of some monoclonal antibody is transplanted, is encompassed in the fragment containing antigen binding region. It is widely known that these antibody fragments can be used as an antibody molecule that has binding affinity to an antigen. Alternatively, an antibody constructed by gene recombination may be used as long as it maintains the activity necessary for antigen binding. Examples of the antibody constructed by gene recombination include, for example, a chimeric antibody, a CDR transplant antibody, a single chain Fv, a diabody (diabodies), a linear antibody, and a polyspecific antibody formed by antibody fragments, and the like. A method of obtaining such antibodies based on a monoclonal antibody, or an antibody-producing cell that produces it, is known.

The monoclonal antibody of the invention can be obtained by using recombinant PLD4-Ig fusion protein, or a transformed cell that expresses human PLD4 as an immunogen. That is to say, the present invention relates to a method of preparing a cell that produces a monoclonal antibody that binds to a PLD4 extracellular domain, which contains the processes below.

(1) Process of administering an extrinsic protein containing PLD4 extracellular domain, to an immune animal, and (2) process of selecting an antibody-producing cell that produces an antibody that binds to PLD4, from antibody-producing cells of the immune animal.

Thus-obtained antibody-producing cell, or immortalized cell of the antibody-producing cell may be cultured, and an intended monoclonal antibody may be collected from the culture. Various methods are known as a method for immortalizing the antibody-producing cell.

The transformed cell used as an immunogen in the invention can be obtained, for example, by preparing a cell in which an extrinsic polynucleotide (a) that encodes the amino acid sequence containing the PLD4 extracellular domain described below is retained in an expressible way.

The extrinsic polynucleotide in the present invention refers to a polynucleotide that is artificially introduced into a host cell. In a case where a human cell is used as the cell, a human gene is introduced into the human cell. In such combination, artificially introduced polynucleotide is also referred to as the extrinsic polynucleotide. Accordingly, ectopic expression of PLD4 is encompassed in extrinsic polynucleotide expression.

The PLD4 extracellular domain in the invention refers to an amino acid sequence of 54-506 positions that corresponds to the extracellular domain in the amino acid sequence described in SEQ ID NO 1. For example, amino acid sequences containing each of the regions in the order below from the N terminal side are preferable as the amino acid sequence containing the PLD4 extracellular domain in the invention.
[Intracellular Region+Transmembrane Domain+Extracellular Domain]

Alternatively, an amino acid sequence that is partially lack of the intracellular region as described below is also encompassed in the amino acid sequence containing the PLD4 extracellular domain in the present invention.
[Partial Intracellular Region+Transmembrane Domain+Extracellular Domain]

Furthermore, a structure that is lack of the intracellular region as described below is encompassed in the amino acid sequence containing the PLD4 extracellular domain in the present invention.
[Transmembrane Domain+Extracellular Domain]

Other regions than the extracellular domain in the above-mentioned structure may be a sequence selected from the amino acid sequence represented by SEQ ID NO 1, or may be a combination with another homologous amino acid sequence. For example, an amino acid sequence that constitutes a signal sequence, a transmembrane domain, and an intracellular region can be used as an amino acid sequence of PLD family molecules other than PLD4. Alternatively, the amino acid sequence of PLD family of other species than human can be also combined. Furthermore, the amino acid sequence that constitutes other regions than the extracellular domain may contain mutation within a range where each of the functions of the regions can be maintained. In addition, other regions can be interposed between each of the regions. For example, between the signal sequence and the extracellular domain, an epitope tag such as FLAG can be also inserted. Particularly, the signal sequence is a region that is subjected to processing in the step of transport to the cell membrane surface after translation of the protein, and is removed. Accordingly, an arbitrary amino acid sequence that induces passage of the translated protein through the cell membrane can be used as a signal sequence. More specifically, an amino acid sequence of PLD4 (SEQ ID NO 1) is preferable as an amino acid sequence containing the PLD4 extracellular domain.

Accordingly, the above-mentioned polynucleotide (a) in the invention may be an arbitrary base sequence that encodes the amino acid sequence that constitutes the above-mentioned structure [Intracellular region+transmembrane domain+extracellular domain]. For example, the amino acid sequence of SEQ ID NO 1 is encoded by the cDNA base sequence described in SEQ ID NO 44.

The recombinant PLD4-Ig fusion protein as an immunogen in the invention may be obtained by introducing an expression vector which retains the aforementioned polynucleotide in an expressible way, into an appropriate host cell. The cDNA base sequence of the recombinant PLD4-Ig fusion protein is represented by SEQ ID NO 125, and the amino acid sequence is represented by SEQ ID NO 126.

The host cell in the invention is preferably a mammalian cell. Specifically, a cell derived from a human, a monkey, a mouse, or a rat may be used as the host cell. Particularly, human-derived cell is preferable as the host cell. For example, HEK-293T cell is a human embryo-derived renal cell strain that may be preferably used as the host cell in the invention. The HEK-293T cell is available as ATCC CRL-11268. In addition to that, a cell derived from an immune animal may be used as the host cell. If a cell derived from an immune animal is used as an immunogen, immune response against the host cell is small. Therefore, an antibody against the PLD4 extracellular domain, which is expressed extrinsically, can be obtained effectively. Accordingly, for example, when a mouse is used as the immune animal, a cell derived from the mouse can be also used as the host cell.

The above-mentioned polynucleotide can be loaded to a vector that can induce expression in a host cell to transform the cell. A commercially available vector that can induce expression in a mammalian cell may be used. For example, an expression vector such as pCMV-Script® Vector, pSG5 Vector (manufactured by Stratagene), pcDNA3.1 (manufactured by Invitrogen), pMXs-IP retroviral vector (manufactured by Cell BioLabs), and the like can be used for the invention.

Thus-obtained transformed cell is administered to an immune animal, with an additional component such as an adjuvant if necessary. As the adjuvant, Freund's complete adjuvant and the like may be used. In a case where a mouse is used as the immune animal, purified recombinant PLD4-Ig fusion protein is administered to BALB/c mouse. As the adjuvant, Freund's Adjuvant, Complete and Incomplete (manufactured by SIGMA) were used, and administered in 200 μg/mouse at the first time, and 50 μg/mouse at the second time to fourth time. Generally, an immunogen is administered multiple times intervally until the antibody titer increases. For example, in a case of short time immunization method, a transformed cell is administered at an interval of 2 to 4 days, more specifically 3 days, and after 2 to 3 times of the administration, antibody-producing cells can be collected. In addition, the antibody-producing cells can be also collected after the administration 5 to 6 times at an interval of once or so a week.

In order to obtain the monoclonal antibody in the invention, the collected antibody-producing cell is cloned. For the cloning, the antibody-producing cell is preferably immortalized. For example, a cell fusion method represented by hybridoma method, or transformation by Epstein-Barr virus (EBV) may be used as a method for immortalizing the antibody-producing cell.

An antibody-producing cell produces one kind of antibody per one cell. Accordingly, if a cell population derived from one cell can be established (that is to say, cloning), a monoclonal antibody can be obtained. The hybridoma method refers to a method in which an antibody-producing cell is fused with an appropriate cell strain, immortalized, and then cloned. The immortalized antibody-producing cell can be cloned by a method such as limiting dilution method. Many cell strains that are useful in the hybridoma method are known. These cell strains are excellent in immortalization efficiency of a lymphocyte-based cell, and have various gene markers that are necessary for selecting cells that have succeeded in the cell fusion. Furthermore, in a case where acquisition of the antibody-producing cell is intended, a cell strain that is lack of antibody production ability may be also used.

For example, mouse myeloma P3x63Ag8.653 (ATCC CRL-1580) or P3x63Ag8U.1 (ATCC CRL-1597) is universally used as a useful cell strain for a cell fusion method of a mouse or a rat. Generally, a hybridoma is prepared by fusion of homogeneous cells. However, a monoclonal antibody may be also acquired from a heterohybridoma between close heterogeneous species.

A specific protocol of the cell fusion is known. That is to say, an antibody-producing cell of an immune animal is mixed with an appropriate fusion partner, and subjected to cell fusion. As the antibody-producing cell, a splenic cell, a lymphocyte cell collected from the lymph node, peripheral blood B cell, or the like may be used. As the fusion partner, various cell strains described above may be used. For the cell fusion, a polyethylene glycol method or an electric fusion method is used.

Next, cells that have succeeded in the cell fusion are selected based on a selection marker possessed by the fusion cell. For example, in a case where HAT sensitive cell strain is used in the cell fusion, cells that have succeeded in the cell fusion are selected by selecting cells that grow in the HAT medium. Furthermore, an antibody produced by the selected cells is confirmed whether it has intended reactivity.

Each of the hybridoma is screened based on the reactivity of the antibody. That is to say, a hybridoma that produces an antibody that binds to PLD4 is selected by the method as described above. Preferably, in a case where selected hybridoma is subcloned, and production of intended antibody is finally confirmed, the hybridoma is selected as a hybridoma that produces the monoclonal antibody of the invention.

Specifically, intended hybridoma can be selected based on reactivity with a human cell, or reactivity with a transformed cell that expresses PLD4 gene. An antibody that binds to a cell can be detected on the principle of an immunoassay. For example, ELISA, in which a cell is used as an antigen, can be used in detection of intended antibody. Specifically, a culture supernatant of the hybridoma is brought into contact with a carrier that immobilizes human pDC, or a transformed cell used as an immunogen. In a case where the culture supernatant contains the intended antibody, the antibody is captured by the cell immobilized on the carrier. Then, the solid phase is isolated from the culture supernatant, washed if necessary, and then the antibody captured on the solid phase can be detected. In detection of the antibody, an antibody that recognizes the antibody may be used. For example, an antibody of a mouse can be detected by anti-mouse immunoglobulin antibody. If the antibody that recognizes an antibody is on label, the detection thereof is ease. As the label, an enzyme, a fluorescent pigment, a luminescent pigment, or the like may be used.

On the other hand, as the carrier that immobilizes the cell, a particle, or the internal wall of a microtiter plate may be used. The surface of a particle or a container made of plastic, can immobilize the cell by physical adsorption. For example, beads or a reaction container made of polystyrene may be used as a carrier for immobilizing the cell.

In selecting the hybridoma, there may be a case where predicted is not production of an antibody against PLD4, but production of an antibody against a host cell of a transformed cell used as an immunogen. For example, when a human cell is used as an immunogen and a mouse is used as an immune animal as shown in Examples, the human cell is recognized as a foreign substance, and it is predicted that an antibody that binds to it is produced. In the invention, acquisition of an antibody that recognizes PLD4 is intended. Accordingly, acquisition of an antibody that recognizes other human cell antigens than PLD4 is not necessary. In order to exclude a hybridoma that produces such antibody by screening, an antibody not intended may be preliminarily absorbed before confirmation of the antibody reactivity.

Antibodies that are not intended can be absorbed by an antigen that binds to an antibody predicted to exist. Specifically, for example, an antibody against other human cell antigens other than PLD4 can be absorbed by a cell for which expression of PLD4 may not be detected. In the invention, the host cell used for the immunogen is preferable as an antigen for absorbing antibodies not intended.

A monoclonal antibody confirmed to have binding activity to an antigen, is confirmed for practical influence on the activity of pDC, if necessary. The influence on pDC can be confirmed, for example, by a method described below.

The monoclonal antibody of the invention can be collected from a culture that is obtained by culturing a hybridoma that produces the monoclonal antibody. The hybridoma may be cultured in vitro or in vivo. In the culture in vitro, the hybridoma may be cultured using a known medium such as RPMI 1640. Immunoglobulins secreted by the hybridoma are accumulated in the culture supernatant. Accordingly, the monoclonal antibody of the invention may be obtained by collecting the culture supernatant, and purifying it if necessary. Purification of immunoglobulin is ease in a medium that is not added with the serum. However, for the purpose of rapid growth of the hybridoma and promotion of antibody production, 10% or so of bovine fetal serum may be also added to the medium.

The hybridoma may be also cultured in vivo. Specifically, the hybridoma may be cultured in the abdominal cavity by inoculating the hybridoma into the abdominal cavity of a nude mouse. The monoclonal antibody is accumulated in the ascites. Accordingly, ascites is collected, and purified if necessary, to obtain necessary monoclonal antibody. The obtained monoclonal antibody may be suitably modified, or processed depending on the purpose.

The monoclonal antibody of the invention can be expressed by acquiring cDNA that encodes the antigen binding region of the antibody from the hybridoma, and inserting it into an appropriate expression vector. A technology for acquiring cDNA that encodes a variable region of an antibody and express it in an appropriate host cell is known. In addition, an approach is known in which a variable region containing an antigen binding region is bound to a constant region to give a chimeric antibody. For example, a gene of a variable region may give a chimeric antibody by binding to genes that encode a human IgG1 heavy chain constant region and human Ig kappa light chain constant region, respectively. Furthermore, it is known that antigen binding activity of a monoclonal antibody can be transplanted to another immunoglobulin by incorporating CDR that constitutes a variable region into a frame region of another immunoglobulin molecule. Using this, a method is established of transplanting antigen binding activity possessed by a heterogeneous immunoglobulin to a human immunoglobulin. For example, there may be a case where a partial amino acid sequence of a frame region supporting CDR is transplanted to a human variable region from a variable region of a mouse antibody. Next, these humanized, re-constituted variable regions of a human antibody may be linked to a constant region of a human antibody, to obtain a humanized antibody.

Examples of preferable monoclonal antibody in the invention include, for example, monoclonal antibodies produced by hybridomas mp5B7, mp7B4, mp13D4, mp13H11, and the like, which have been deposited under Accession Numbers: NITE BP-1211, NITE BP-1212, NITE BP-1213, and NITE BP-1214, respectively.

As the chimeric antibody containing the variable region, or the humanized antibody in which CDR that constitutes the variable region is transplanted, an antibody having a constant region derived from IgG or IgM is contained preferably in the antibody of the invention.

Particularly, the antibody of the invention is more preferably an antibody that has a combination of:

```
heavy chain
CDR1:
                                           (SEQ ID NO: 14)
DYNLH, CDR2:
                                           (SEQ ID NO: 15)
YIYPYNGNTGYNQKFKR, CDR3:
                                           (SEQ ID NO: 16)
GGIYDDYYDYAIDY
and light chain
CDR1:
                                           (SEQ ID NO: 17)
RASENIYSHIA,

CDR2:
                                           (SEQ ID NO: 18)
GATNLAH,

CDR3:
                                           (SEQ ID NO: 19)
QHFWGTP,
``` as a sequence of CDR that constitutes the variable region of the antibody, an antibody that has a combination of:

```
heavy chain
CDR1:
                                           (SEQ ID NO: 32)
SHYYWT, CDR2:
                                           (SEQ ID NO: 33)
YISYDGSNNYNPSLKN, CDR3:
                                           (SEQ ID NO: 34)
EGPLYYGNPYWYFDV
and light chain
CDR1:
                                           (SEQ ID NO: 35)
RASQDIDNYLN,

CDR2:
                                           (SEQ ID NO: 36)
YTSRLHS,

CDR3:
                                           (SEQ ID NO: 37)
QQFNTLP,
``` as a sequence of CDR that constitutes the variable region, or an antibody that has a combination of:

```
heavy chain
                                           CDR1:
(SEQ ID NO: 38)
SHYYWS, CDR2:
                                           (SEQ ID NO: 39)
YISYDGSNNYNPSLKN, CDR3:
                                           (SEQ ID NO: 40)
EGPLYYGNPYWYFDV
and light chain
CDR1:
                                           (SEQ ID NO: 41)
RASQDIDNYLN,

CDR2:
                                           (SEQ ID NO: 42)
YTSRLHS,

CDR3:
                                           (SEQ ID NO: 43)
QQFNTLP,
``` as a sequence of CDR that constitutes the variable region.

The present inventors have confirmed that the monoclonal antibody against PLD4 has CDC action for a PLD4 expression cell. Accordingly, the antibody that has IgG- or IgM-derived constant region, has an action of cytotoxicity for PLD4 expression cell by CDC action. Such antibody is useful for suppressing the cell number of a PLD4 expression cell such as pDC.

A chimeric antibody, or a humanized antibody that recognizes PLD4 can be prepared by genetic engineering using a polynucleotide that encodes them.

An antibody that can specifically recognize PLD4 was not obtained. An antibody that recognizes PLD4 has been provided for the first time by the immunogen of the invention. That is to say, the invention provides an antibody that recognizes PLD4, which can be obtained by the processes described below.

(1) Process of administering a protein containing a PLD4 extracellular domain, to an immune animal, (2) process of selecting an antibody-producing cell that produces an antibody that binds to PLD4, from antibody-producing cells of the immune animal, and (3) process of culturing the antibody-producing cell selected in (2), and collecting an antibody that recognizes PLD4 from the culture.

It has been revealed that PLD4 is specifically expressed in human pDC. The specific expression in human pDC was also confirmed by gene expression analysis with SAGE by the present inventors. However, PLD4 expression level was all analyzed based on mRNA in a report of the past. In addition, the PLD4 protein is known to be expressed only in the cytoplasm. It has been revealed by the invention that PLD4 is also expressed on the cell surface. Since an antibody that can detect PLD4 was not provided, analysis for the state of protein expression was not conventionally performed. The antibody that binds to a PLD4 extracellular domain provided by the invention has realized analysis of the PLD4 protein.

As confirmed practically by the present inventors, the monoclonal antibody that binds to a PLD4 extracellular domain based on the invention has specifically detected human pDC. That is to say, the invention relates to a method of detecting a plasmacytoid dendritic cell, which contains steps of bringing a monoclonal antibody that binds to a PLD4 extracellular domain, or a fragment containing an antigen-binding region thereof into contact with a test cell, and detecting a monoclonal antibody that binds to the cell, or a fragment containing an antigen-binding region thereof.

By detection of PLD4 based on the invention, it can be confirmed whether some cell is pDC or not. That is to say, the invention provides a method of identifying pDC using PLD4 as an index. Alternatively, a cell for which PLD4 is detected may be isolated based on the invention, whereby to isolate human pDC. That is to say, the invention provides a method of isolating pDC using PLD4 as an index.

In the invention, a monoclonal antibody that binds to a PLD4 extracellular domain, or a fragment containing an antigen-binding region thereof may be on label. For example, the antibody can be easily detected by labeling it with a luminescent pigment or fluorescent pigment. More specifically, fluorescent pigment-labeled antibody is brought into contact with a cell population that possibly contains pDC, and a cell that binds to the antibody of the invention can be detected using the fluorescent pigment as an index. Furthermore, if a cell detected with the fluorescent pigment is isolated, pDC can be isolated. A series of steps can be easily implemented in the principle of FACS.

Alternatively, the antibody of the invention may be also as bound to a solid phase carrier such as a magnetic particle. The antibody that is bound to the solid phase carrier recognizes PLD4, and pDC is captured on the solid phase carrier. As a result thereof, pDC can be detected or isolated.

The antibody that is necessary in the pDC detection method based on the invention may be supplied as a reagent for detection of pDC. That is to say, the invention provides a reagent for detection of pDC containing a monoclonal antibody that binds to a PLD4 extracellular domain, or a fragment containing an antigen-binding region thereof. In the reagent for detection of pDC of the invention, a positive control, or a negative control may be combined in addition to the antibody. For example, a transformed cell that expresses PLD4 extracellular domain used as an immunogen, or pDC collected from a human, or the like may be used as a positive control. Usually, only little human pDC can be obtained from the peripheral blood. Accordingly, a transformed cell is particularly preferable as a positive control in the reagent of the invention. On the other hand, as the negative control, an arbitrary cell that does not express PLD4 may be used.

That is to say, the invention provides a kit for detection of human pDC containing a monoclonal antibody that binds to a PLD4 extracellular domain, or a fragment containing an antigen-binding region thereof.

Furthermore, the inventors analyzed the influence of the antibody that binds to a PLD4 extracellular domain on pDC. As a result thereof, it was confirmed that the antibody that binds to a PLD4 extracellular domain suppresses pDC activity. That is to say, the invention relates to a method of suppressing the activity of an interferon-producing cell, which contains a step of bringing any one of the components below into contact with pDC:

(a) a monoclonal antibody that binds to PLD4 and suppresses pDC activity, or a fragment containing an antigen-binding region thereof, and (b) an immunoglobulin in which a complementarity-determining region of the monoclonal antibody (a) is transplanted, or a fragment containing an antigen-binding region thereof.

Alternatively, the invention relates to a method of suppressing pDC activity in a living organism, which contains a step of administering any one of the components below to a living organism:

(a) a monoclonal antibody that binds to PLD4 and suppresses pDC activity, or a fragment containing an antigen-binding region thereof, (b) an immunoglobulin in which a complementarity-determining region of the monoclonal antibody (a) is transplanted, or a fragment containing an antigen-binding region thereof, and (c) a polynucleotide that encodes the component described in (a) or (b).

The pDC in the invention refers to a cell that has IFN production ability, and expresses PLD4 on the cell surface. Hereinafter, unless otherwise stated particularly, pDC is not only a cell that is a precursor cell of a dendritic cell, but contains a cell that has IFN production ability, and expresses PLD4 on the cell surface. A method of identifying such pDC is known. For example, pDC can be distinguished from other blood cells using several cell surface markers as an index. Specifically, the profile of a human pDC cell surface marker is as described below (Shortman, K. and Liu, Y J. Nature Reviews 2: 151-161, 2002). In recent years, there is also a report which positioned BDCA-2 positive cell as pDC (Dzione k, A. et al. J. Immunol. 165: 6037-6046, 2000).

[Profile of Cell Surface Antigen of Human pDC]
CD4 positive and CDl23 positive,
Lineage (CD3, CD14, CD16, CD19, CD20, and CD56) negative, CD11c negative Accordingly, a cell that has the expression profile of these known markers, and has IFN production ability may be also referred to as pDC. Furthermore, a cell that belongs to a cell family having a different profile from the expression pattern of the expression profile of these markers, but having IFN production ability in a living organism is encompassed in pDC.

Furthermore, examples of common characteristics exhibited by human pDC include the characteristics as described below.

[Morphological Characteristic of Cell]
Similar to plasma cell
Round cell having smooth cell surface
Relatively large nucleus

[Functional Characteristic of Cell]

Production of a large amount of type I IFN in a short time at the time of virus infection Differentiation into dendritic cell after virus infection Suppression of the pDC activity in the invention refers to suppression of at least one of the functions of pDC. Examples of the pDC functions include IFN production and cell survival. The cell survival can be referred to as the cell number in other words. Accordingly, suppression of either one or both of these functions is referred to as the suppression of pDC activity. It has been revealed that type I IFN produced by pDC is a cause for various diseases. Accordingly, suppression of the pDC cell number or IFN production is useful as a strategy for treating such diseases.

For example, the relation of pathological conditions of an autoimmune disease with IFNα has been pointed out. Most of IFNα is produced by pDC. Accordingly, if the production thereof is suppressed, pathological conditions caused by IFNα can be alleviated. Meanwhile, in the invention, suppression of IFN production by pDC refers to suppression of production of at least one kind of IFN produced by pDC. The IFN in the invention is preferably type I IFN. Among them, IFNα is important.

That is to say, the invention relates to a suppressor for IFN production, which contains the antibody that binds to a PLD4 extracellular domain as an active component. Alternatively, the invention provides a method of suppressing IFN production, which contains a process of administering an antibody that binds to a PLD4 extracellular domain. Furthermore, the invention relates to use of an antibody that binds to a PLD4 extracellular domain in preparation of a pharmaceutical composition that suppresses IFN production.

A cell that produces a large amount of IFN in a small number of the cells is encompassed in the pDC. For example, a precursor cell of a dendritic cell that is received with stimulation by a virus or the like produces most of IFN produced by a living organism. Suppression of the cell number of pDC that produces a large amount of IFN leads to suppression of IFN production as results. Accordingly, suppression of the pDC cell number can also alleviate pathological conditions caused by IFNα.

In a preferred aspect of the invention, it was confirmed that the anti-PLD4 monoclonal antibody binds to a PLD4 expression cell, and imparts cytotoxicity by Complement Dependent Cytotoxicity (CDC) action. The CDC action is one of the important action mechanisms of an antibody drug. The anti-PLD4 monoclonal antibody of the invention also has potent cytotoxicity action for a PLD4 expression cell such as pDC by the CDC action. That is to say, the anti-PLD4 monoclonal antibody in a preferred aspect, can be expected for effects of suppressing IFN production not only by a mechanism of suppressing IFN production, but also by cytotoxicity for pDC.

The antibody that recognizes a PLD4 extracellular domain used in the invention can be obtained based on the method as described above. The antibody in the invention may be any class. In addition, a biological species from which the antibody is derived is not limited. Furthermore, a fragment containing a antigen binding region of the antibody can be used as the antibody. For example, an antibody fragment containing an antigen binding site produced by enzymatic digestion of IgG may be used as the antibody in the invention. Specifically, an antibody fragment such as Fab or F(ab')2 may be obtained by digestion by papain or pepsin. It is widely known that these antibody fragments can be used as an antibody molecule that has binding affinity to an antigen. Alternatively, an antibody constructed by gene recombination may be also used as long as it maintains necessary antigen binding activity. Examples of the antibody constructed by gene recombination include a chimeric antibody, a CDR transplantation antibody, a single chain Fv, a diabody (diabodies), a linear antibody, and a polyspecific antibody formed by an antibody fragment, and the like. A method of obtaining these antibodies based on a monoclonal antibody is known.

The antibody in the invention may be modified, if necessary. According to the invention, the antibody that recognizes a PLD4 extracellular domain has an action of suppressing pDC activity. That is to say, a possibility has been contemplated that the antibody itself has cytotoxicity for pDC. A subclass of the antibody exhibiting strong effector action is known. Alternatively, effects of suppressing pDC activity can be further increased by modifying the antibody with a cytotoxic agent. Examples of the cytotoxic agent include the agents described below.

Toxins: *Pseudomonas* Endotoxin (PE), diphtheria toxin, and ricin

Radioactive isotope: Tc99m, Sr89, I131, and Y90

Anti-cancer agent: calicheamicin, mitomycin, and paclitaxel

Toxins containing a protein can binds to an antibody, a fragment thereof, or the like by a bifunctional reagent. Alternatively, a gene that encodes the toxins may be also conjugated with a gene that encodes the antibody, to give a fusion protein of them. A method of binding a radioactive isotope to an antibody is also known. For example, a method of labeling an antibody with a radioactive isotope using a chelate agent is known. Furthermore, an anti-cancer agent can bind to an antibody by using a sugar chain, a bifunctional reagent, or the like.

In the invention, artificially structure-modified antibody may be also used as an active component. For example, various modifications are known to improve cytotoxicity or stability of an antibody. Specifically, an immunoglobulin is known, in which the sugar chain of the heavy chain is modified (Shinkawa, T. et al. J. Biol. Chem. 278: 3466-3473. 2003). Modification of the sugar chain increased Antibody Dependent Cell-mediated Cytotoxicity (ADCC) activity of the immunoglobulin.

The antibody that binds to a PLD4 extracellular domain suppresses the activity of pDC when the antibody is brought into contact with the pDC. Accordingly, such antibody can be used as an agent for suppressing pDC activity, or in a method of suppressing pDC. That is to say, the invention provides an agent for suppressing pDC activity, which contains at least one kind of a component selected from a group consisting of (a) to (c) described below as an active component. Alternatively, the invention relates to a method of suppressing pDC activity, which contains a step of administering at least one kind of a component selected from a group consisting of (a) to (c) described below. Furthermore, the invention relates to use of at least one kind of a component selected from a group consisting of (a) to (c) described below in preparation of an agent for regulating pDC activity.

(a) Antibody that binds to a PLD4 extracellular domain, or a fragment containing an antigen-binding region thereof, (b) an immunoglobulin in which a complementarity-determining region of the monoclonal antibody (a) is transplanted, or a fragment containing an antigen-binding region thereof.

As the monoclonal antibody that suppresses pDC activity in the invention, a monoclonal antibody that recognizes a PLD4 extracellular domain may be used. One kind or multiple kinds of the monoclonal antibodies may be used in the invention. For example, multiple species of the monoclonal antibodies that recognize a PLD4 extracellular domain may be blended, and used in the invention.

The fact that the antibody has an action of suppressing IFN production activity of pDC, can be confirmed in the manner as described below. pDC produces a large amount of IFN upon viral stimulation. The antibody is given to pDC before, after, or at the same time of viral stimulation, and IFN production ability is compared with a control in which the antibody is not given to pDC. The IFN production ability can be evaluated by measuring IFN-α or IFN-β contained in the supernatant of a pDC culture. As a result of the comparison, if the amount of IFN in the supernatant is significantly lowered by addition of the antibody, it can be confirmed that the tested antibody has an action of suppressing the IFN production ability. A method of measuring these IFNs is known. pDC is a cell that produces most of IFN in a living organism. Accordingly, suppression of IFN production ability of pDC can regulate IFN production state in a living organism.

The activity of pDC in the invention encompasses maintenance of the pDC cell number. Accordingly, suppression of pDC activity in the invention encompasses suppression of the pDC cell number. If the pDC cell number is confirmed to be suppressed in the presence of the antibody, the antibody is found out to suppress the pDC activity. Similarly to the IFN production, an inactive immunoglobulin that is derived from the same animal species as the species of the antibody to be confirmed for the activity, may be used as a control for comparison. The pDC cell number can be compared quantitatively by cell counting. The cell number can be counted with FACS or a microscope.

Furthermore, pDC is also assumed to be differentiated into a cell that induces Th2 called Dendritic Cell 2 (DC2) as a result of infection by virus and the like. If pDC of IFN production upon virus stimulation is suppressed, there is a possibility that differentiation to Th2 can be also suppressed. Accordingly, the monoclonal antibody of the invention that suppresses IFN production can be also expected to have therapeutic effects for various allergy diseases.

In a case where the antibody that recognizes a PLD4 extracellular domain is administered to a host that is different from the biological species from which the antibody is derived, it is desirable to process the antibody into a form that is hardly recognized as a foreign substance by the host. For example, immunoglobulin may be rendered to be hardly recognized as a foreign substance by processing the molecule as described below. A method of processing an immunoglobulin molecule as described below is known.

Fragment containing antigen binding region, from which the constant region is deleted (Monoclonal Antibodies: Principles and Practice, third edition, Academic Press Limited. 1995; Antibody Engineering, A Practical Approach, IRL PRESS, 1996)

Chimeric antibody constituted with an antigen binding region of a monoclonal antibody and a constant region of host immunoglobulin (Gene Expression Experiment Manual, Kodansha Ltd. 1994 (edited by Isao ISHIDA and Tamie ANDO))

CDR-substituted antibody in which the complementarity-determining region (CDR) in a host immunoglobulin is substituted with CDR of a monoclonal antibody (Gene Expression Experiment Manual, Kodansha Ltd. 1994 (edited by Isao ISHIDA and Tamie ANDO))

Alternatively, the gene of a human immunoglobulin variable region can be also acquired by phage display method (McCafferty J et al., Nature 348:552-554, 1990; Kretzschmar T et. al., Curr Opin Biotechnol. 2002 December; 13(6): 598-602.). In the phage display method, the gene that encodes the human immunoglobulin variable region is incorporated into the phage gene. Using various immunoglobulin genes as a source, a phage library can be also prepared. A phage expresses the variable region as a fusion protein of the protein that constitutes itself. The variable region expressed on the phage surface by the phage maintains binding activity to antigen. Accordingly, selection of a phage that binds to an antigen or a cell in which the antigen is expressed, or the like, can screen a phage in which a variable region having intended binding activity is expressed from a phage library. Furthermore, a particle of thus-selected phage retains a gene that encodes the variable region having intended binding activity. That is to say, a gene that encodes a variable region having intended binding activity can be acquired using the binding activity of the variable region as an index in the phage display method.

The antibody that recognizes a PLD4 extracellular domain, or an antibody fragment containing at least antigen binding region thereof in the agent for suppressing pDC activity, or the method of suppressing pDC activity according to the invention, can be administered as a protein, or a polynucleotide that encodes the protein. In administering the polynucleotide, it is desirable to use a vector in which a polynucleotide that encodes intended protein, is disposed under control of an appropriate promoter so as to express the intended protein. In the vector, an enhancer or a terminator may be also disposed. A vector is known that retains genes of a heavy chain and a light chain that constitute an immunoglobulin, and can express the immunoglobulin molecule. The vector that can express an immunoglobulin can be administered by being introduced into a cell. In administration to a living organism, a vector that can infect a cell by being administered into a living organism, can be administered as it is. Alternatively, a vector may be also first introduced into a lymphocyte isolated from a living organism, and returned again into the living organism (ex vivo).

The amount of the monoclonal antibody that is administered to a living organism in the agent for suppressing pDC activity, or the method of suppressing pDC activity based on the invention, is usually 0.5 mg to 100 mg, for example 1 mg to 50 mg, preferably 2 mg to 10 mg per 1 kg of the body weight as an immunoglobulin. The administration interval of the antibody to a living organism can be suitably regulated such that an effective concentration of the immunoglobulin in the organism can be maintained during the treatment period. Specifically, administration may be performed, for example, at an interval of 1 to 2 weeks. The administration route is arbitrary. One of ordinary skill in the art can suitably select an effective administration route in the treatment. Specifically, examples of the administration route include oral or non-oral administration. For example, the antibody can be administered systemically or locally by intravenous injection, intramuscular injection, intraperitoneal injection, subcutaneous injection, or the like. Examples of an appropriate formulation for non-oral administration in the invention include an injection, a suppository, a spray, and the like. In addition, in a case where an immunoglobulin is administered to a cell, the immunoglobulin is administered to a culture liquid in usually 1 μg/mL, preferably 10 μg/mL or more, more preferably 50 μg/mL or more, and further preferably 0.5 mg/mL or more.

In the agent for suppressing pDC activity or the method of suppressing pDC activity of the invention, the monoclonal antibody may be administered by any method to a living organism. Usually, the monoclonal antibody is blended with a pharmaceutically acceptable carrier. Along with the monoclonal antibody, additives such as a thickening agent, a stabilizer, a preservative, and a solubilizing agent may be blended if necessary. Examples of such carrier or additives include lactose, citric acid, stearic acid, magnesium stearate, sucrose, starch, talc, gelatin, agar, vegetable oil, ethylene glycol, and the like. The terms called "pharmaceutically acceptable" refers to those approved by government supervisory of each country, or those listed in a pharmacopoeia of each country or a pharmacopoeia generally acknowledged for use in an animal, a mammalian animal, and particularly human. The agent for suppressing pDC activity of the invention may be also supplied in a form of a lyophilized powder or tablet in a single dose or multiple doses. The lyophilized powder or tablet may be further combined with sterilized water, physiological saline, or a buffer solution for injection for dissolving the composition to a desired concentration before administration.

Furthermore, in a case where the agent for suppressing pDC activity of the invention is administered as an immunoglobulin expression vector, the heavy chain and the light chain are co-transfected with a separate plasmid, and each of the plasmids can be administered in 0.1 to 10 mg, for example, 1 to 5 mg per 1 kg of the body weight. In addition, a vector of 1 to 5 µg/$10^6$ cells is used for introduction into a cell in vitro. Hereinafter, the invention will be further specifically explained based on Examples.

Meanwhile, the entire prior art documents cited in the present specification are incorporated into the present specification by reference.

Although the invention will be further specifically described with Examples below, the invention is not limited to such Examples at all.

EXAMPLES

Example 1

A. Analysis of PLD4 Expression
A-1) Analysis Using SAGE Library

Gene expressions in resting pDC, human monocyte, and activated pDCs treated with inactive herpes virus (HSV-1), were compared by SAGE™ (Serial Analysis of Gene Expression) method. The analysis method is as described below.

Figure 2:
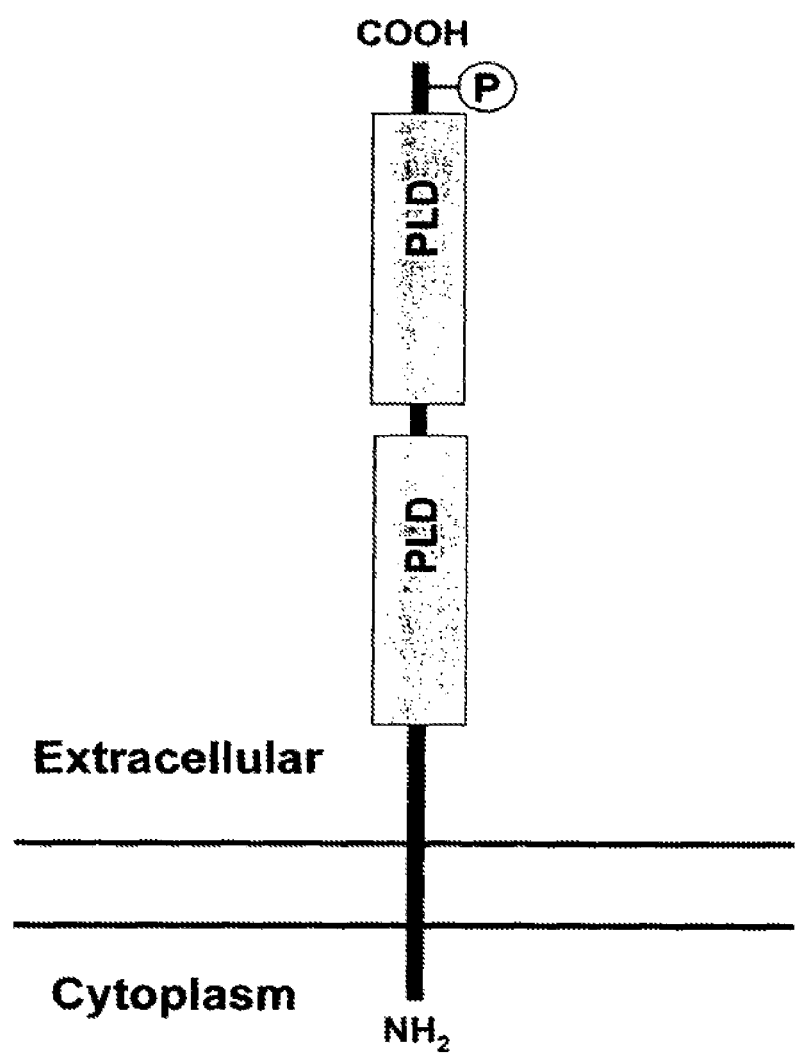
FIG. 2 is a schematic diagram that represents a predicted structure of the human PLD4 protein. The structure has two HKD (HxKxxxxD) motifs in the amino acid 506 residues, and the residue of threonine 472 is possibly a phosphorylation site.
Figure 3:
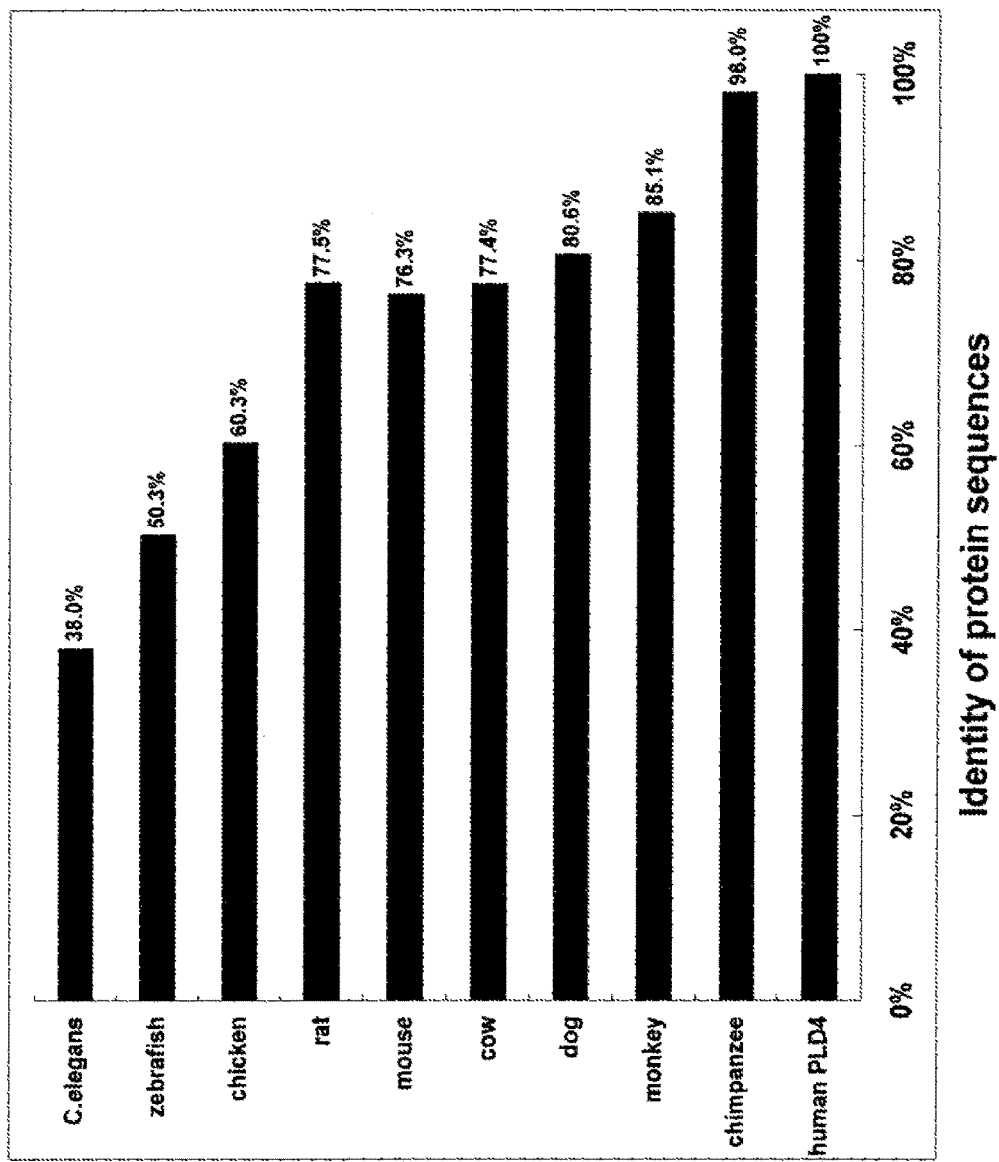
FIG. 3 is a graph that illustrates the homology of human PLD4 protein with homologous molecular species in a heterogeneous animal. The PLD4 protein has been conserved in the evolution process from a mouse to a human.

From the human peripheral blood, the monocyte was isolated as CD14 positive cell and the human pDC cell was isolated as BDCA-4 positive cell with BDCA-4+ isolation kit (Miltenyi Biotec company) and MACS system (Miltenyi Biotec company). Furthermore, the human pDC cell was cultured for 12 hours in the presence of inactive HSV-1, whereby to prepare activated pDC (pDC+HSV). Total RNA was extracted from each of the cells, and the SAGE library was prepared using I-SAGE™ kit (Invitrogen company). The obtained data of about 100,000 tagged base sequences were analyzed with SAGE2000 Analysis Software (Invitrogen company). As a result thereof, the score value of monocyte/pDC/pDC+HSV was 0/9/0 gene, that is to say, PLD4 (Phospholipase D family, member 4, C14orf75; GenBank Accession Number: NM_138790.2) was found, which is a known gene as a gene exhibiting resting pDC cell specific expression (FIG. 1, Tao et al., Nat. Methods 2(8), 591-598(2005); Clark et al., Genome Res. 13(10), 2265-2270(2003)). PLD4 is a 506 amino acid sequence (SEQ ID NO: 1) encoded by a base sequence represented by SEQ ID NO: 44. The PLD4 protein has two tentative PDE regions (Phosphodiesterase motif) constituted with two HKD motifs (His-x-Lys-x-x-x-x-Asp amino acid sequence, the x is the other amino acids) conserved in the C terminal region, and a tentative phosphorylation site (Thr 472). The structure of the PLD4 protein is predicted as type II monotropic transmembrane protein. In addition, the PLD4 protein does not have PX region (Phox homology domain) and PH region (Pleckstrin homology domain) in the N terminal region, which are possessed by PLD1 and PLD2 that are of classical PLD family (FIGS. 1 and 2).

A-2) Expression Analysis of PLD4 mRNA in Human Various Cells Responsible for Immunity by Quantitative Real Time PCR Expression of PLD4 mRNA in a blood cell was specifically reviewed. From the human peripheral blood, each of the cells was isolated and taken by a cell sorter. From each of the cell family isolated and taken, RNA was extracted, and cDNA was synthesized. Using the obtained cDNA as a template, quantitative real time PCR was performed, and expression level of PLD4 mRNA was analyzed.

For the quantitative real time PCR reaction, quantitative PCR was performed with ABI PRISM 7000 using Platinum SYBR Green qPCR Super Mix-UDG kit (Invitrogen company). Sequence Detection System Software (Applied Biosystem company) was used in the data analysis. The PCR reaction conditions and the base sequence of the used primers are as follows.

```
Forward primer for PLD4:
                                        (SEQ ID NO: 45)
5' ATG GAC TGG CGG TCT CTG 3'

Reverse primer for PLD4:
                                        (SEQ ID NO: 46)
5' TGG AAG GTC TTC TCC AGG TC 3'

Forward primer for GAPDH:
                                        (SEQ ID NO: 47)
5' AGC CAC ATC GCT CAG ACA C 3'

Reverse primer for GAPBH:
                                        (SEQ ID NO: 48)
5' GCC CAA TAC GAC CAAATC C 3'
```

Figure 5:
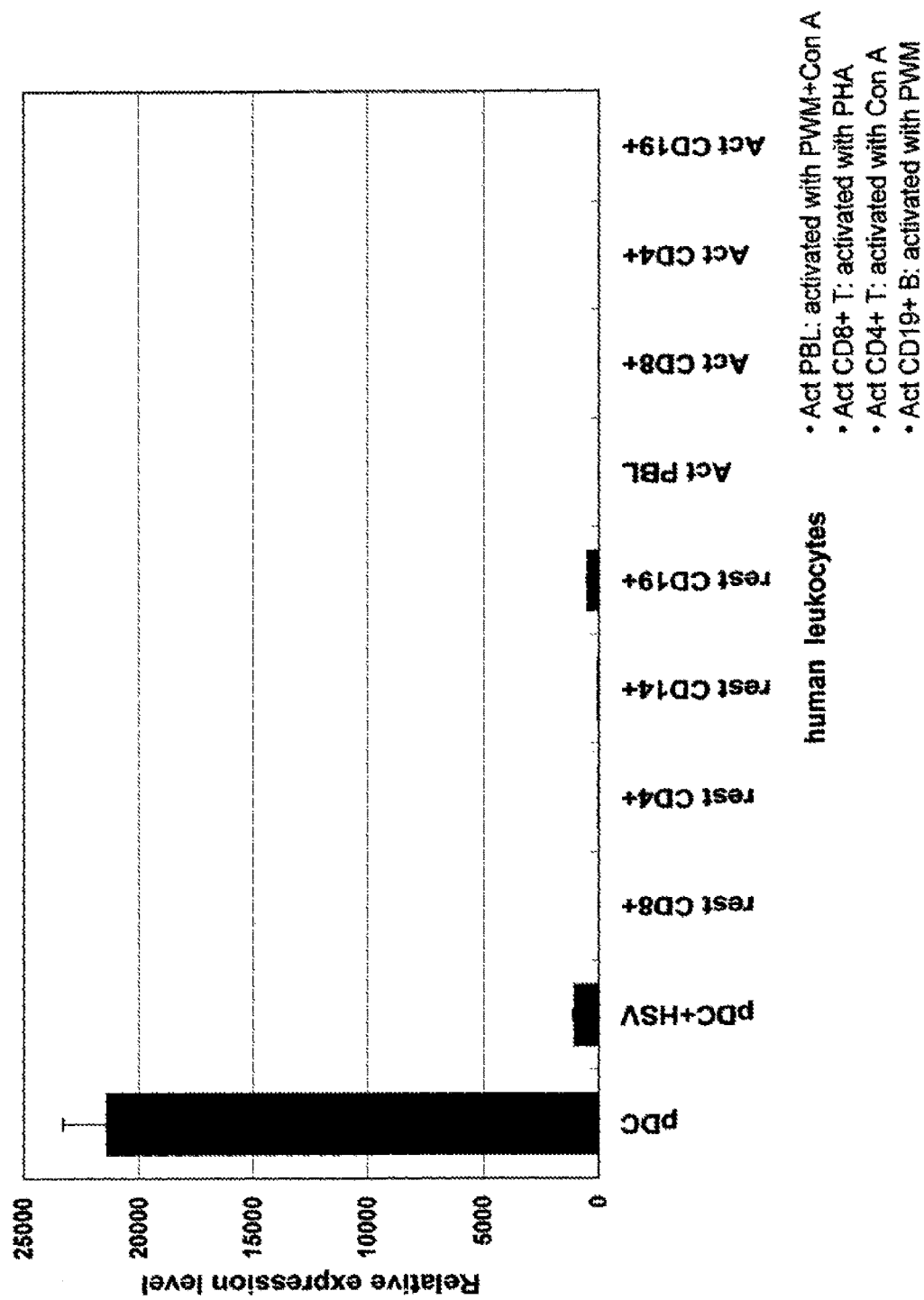
FIG. 5 is a graph that illustrates human pDC-specific expression of PLD4 gene in a cell responsible for human immunity. Expression of PLD4 gene is high in pDC at the resting stage, and the expression is low in $CD19^+$ B cell.

1 cycle at 58° C. for 2 minutes,
1 cycle at 95° C. for 10 minutes,
50 cycles of [95° C. for 15 second, and 60° C. for 60 seconds], pDC, pDC (pDC+HSV) stimulated with HSV, B cell (CD19+ cell), activated B cell (CD19+ cell), T cell (CD3+ cell), and activated T cell stimulated with Inomycin and PMA (Phorbol 12-myristate 13-acetate) were reviewed. As a result, it was illustrated that PLD4 expression was specifically high in the pDC at the resting stage, and low in the CDI9+ B cell. The other human blood fraction cDNA used BD™ MTC Multiple Tissue cDNA Panels (Cat. No. 636750, Takara Bio company) (FIG. 5).

A-3) Expression Analysis of PLD4 mRNA in Human Tissue by Quantitative Real Time PCR Furthermore, expressions in other organs or tissues were reviewed by quantitative PCR using ABI PRISM 7000 (Applied Biosystem company). As the cDNA panel, BD™ MTC multiple tissue cDNA panel (Human I; Cat. No. 636742, Human immune; Cat. No. 636748; all Takara Bio company) was used. The base sequences of the used primers are represented as follows.

```
Forward primer for PLD4:
                                      (SEQ ID NO: 49)
5' ATG GAC TGG CGG TCT CTG 3'

Reverse primer for PLD4:
                                      (SEQ ID NO: 50)
5' TGG AAG GTC TTC TCC AGG TC 3'

Forward primer for GAPDH:
                                      (SEQ ID NO: 51)
5' AGC CAC ATC GCT CAG ACA C 3'

Reverse primer for GAPDH:
                                      (SEQ ID NO: 52)
5' GCC AAA TAC GAC CAA ATC C 3'
```

The quantitative PCR was performed with ABI PRISM 7000 using Platinum SYBR Green qPCR Super Mix-UDG kit (Invitrogen company). Sequence Detection System Software (Applied Biosystem company) was used in the analysis. The reaction conditions are as described below.

Figure 6:
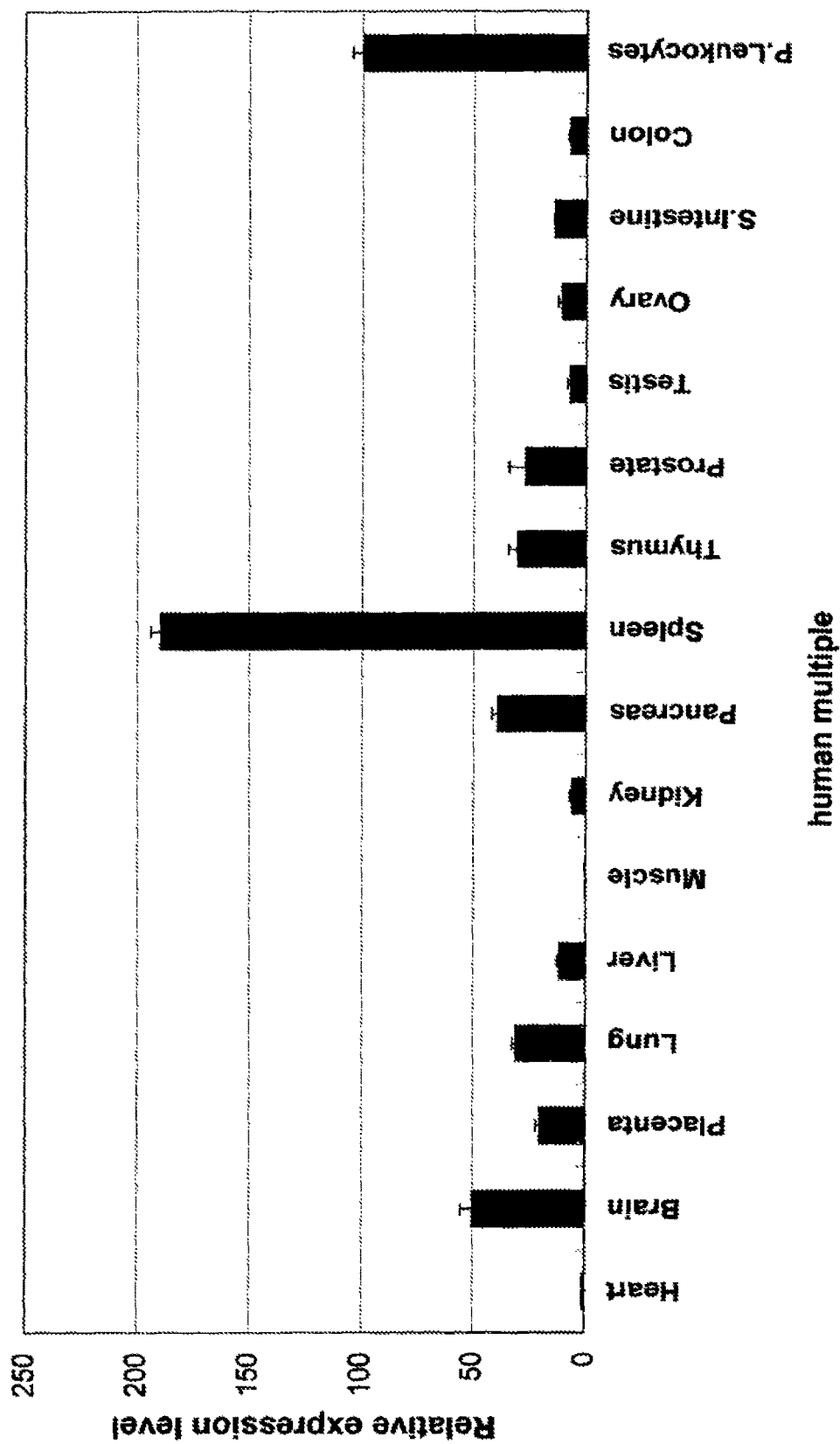
FIG. 6 is a graph that illustrates the tissue expression pattern of human PLD4 mRNA. The expression is high in the spleen and the peripheral blood leucocyte.

Step 1: 1 cycle at 5° C. for 2 minutes
Step 2: 1 cycle at 95° C. for 10 minutes
Step 3: 50 cycles at 95° C. for 15 seconds and 60° C. for 1 minute Expressions of PLD4 genes were compared between each of the tissues by standardization with gene expression level of GAPDH (glyceraldehyde-3-phosphate dehydrogenase), which is known to be expressed homeostatically. As a result thereof, PLD4 mRNA exhibited relatively high expression in the spleen and the peripheral blood leucocyte. In addition, it was revealed that PLD4 mRNA was expressed widely in other tissues. However, the expression level of the PLD4 mRNA was less than 100 folds of the expression level of the resting pDC cell (FIG. 6).

Preparation of Human PLD4 Expression Vector

Preparation of PLD4 gene expression vector was performed in order to express a human PLD4 protein. From PLD4 cDNA clone incorporated into a pCR4-TOPO cloning vector (Open Biosystem, Cat, No. MHS4771-99610856), only PLD4 gene was taken out with EcoRI enzyme, and incorporated into a pcDNA3.1 expression vector (human PLD4-pcDNA3.1 vector). Using the obtained human PLD4-pcDNA3.1 plasmid as a template, the PLD4 gene was amplified with a primer containing EcoRI, Not I, and Kozak sequences (GCC GCC ACC) (The information of the primers is as described below). The PCR product was cloned at EcoRI and Not I sites with pMX-IP retrovirus vector (human PLD4-pMX-IP retrovirus vector). In the PCR reaction, 1 unit of KOD Plus DNA polymerase (TOYOBO company) was used, and the reaction conditions were 1 cycle at 94° C. for 2 minutes, and then 25 cycle of [94° C. for 15 seconds and 68° C. for 1 minutes 30 seconds].

```
Forward primer
                                    (SEQ ID NO: 53):
5' ttt GAA TTC gcc gcc acc ATG CTG AAG CCT 3'

(30-mer)

Reverse primer
                                    (SEQ ID NO: 54):
5' aaa gcg gcc gcT CAG CCC TGC CAA ACG CAG TCC T 3' (34-mer)
```

Along with the sequence analysis, HEK (Human Embryonic Kidney)-293T cell (Hereinafter, 293T cell) was transiently transfected with human PLD4-pMX-IP retrovirus vector, and whether the human PLD4 was expressed on the surface of the 293T cell was confirmed with cell staining, and then FACS method.

Example 2

Review of Specificity of Anti-Human PLD4 Antibody

The fact that the anti-PLD4 monoclonal antibody does not cross with other molecules of PLD family, can be confirmed employing a cell in which each of the PLD family is mandatorily expressed. Human PLD4 belongs to PLD family, and there are multiple molecules having high homology. Human PLD4 illustrates about 41% homology to human PLD3 and about 29.3% homology to human PLD5 (FIG. 4).

1) Preparation of Expression Vectors of Human PLD3 and Human PLD5

For human PLD3 (cDNA SEQ ID NO: 55, amino acid SEQ ID NO: 127) and human PLD5 (cDNA SEQ ID NO: 56, amino acid SEQ ID NO: 123), from human PLD3 clone (K.K.DNAFORM company, Cat. No 5189261) incorporated into pCMV-SPORT6 vector, and human PLD5 clone (K.K.DNAFORM company, Cat. No 40025860) incorporated into pCR-Blunt II-TOPO vector, only PLD3 and PLD5 genes were amplified with PCR, and each of the genes was cloned at Hind III and EcoRI sites of Flag-tagged pcDNA3.1 (Invitrogen company), whereby to prepare an expression vector (The information of the primers is as described below).

```
(For human PLD3)
Forward primer: huPLD3-IF (Hind III)
Sequence:
                                      SEQ ID NO: 57)
5' ttt AAG CTT gcc gcc acc ATG AAG CCT AAA CTG ATG TAC 3' (39-mer)

Reverse primer: huPLD4-1518R (EcoRI)
Sequence:
                                      (SEQ ID NO: 58)
5' ttt gaa ttc TCA ctt atc gtc gtc atc ctt gta atc GAG CAG GCG GCA GGC GTT GCC 3' (57-mer)

(For human PLD5)
Forward primer: huPLD5-IF (Hind III).
Sequence:
                                      (SEQ ID NO: 59)
5' ttt AAG CTT gcc gcc acc ATG GGA GAG GAT GAG GAT GGA 3' (39-mer)

Reverse primer: huPLD5-1383R (EcoRI)
Sequence:
                                      (SEQ ID NO: 60)
5' ttt gaa ttc TCA ctt atc gtc gtc atc ctt gta atc TAC GTT CCG GGG ATC CTT TCC 3' (57-mer)
```

Among the aforementioned primer sequences, the underlined parts represent base sequences that encode the added FLAG tags, and the italic type represents Hind III cutting site or EcoRI site of the restriction enzymes.

Along with the sequence analysis, 293T cell was transiently transfected with human PLD3-pcDNA3.1 vector or human PLD5-pcDNA3.1 vector, and whether the human PLD4 was expressed on the surface of the 293T cell was confirmed with cell staining, and then FACS method.

Figure 8:
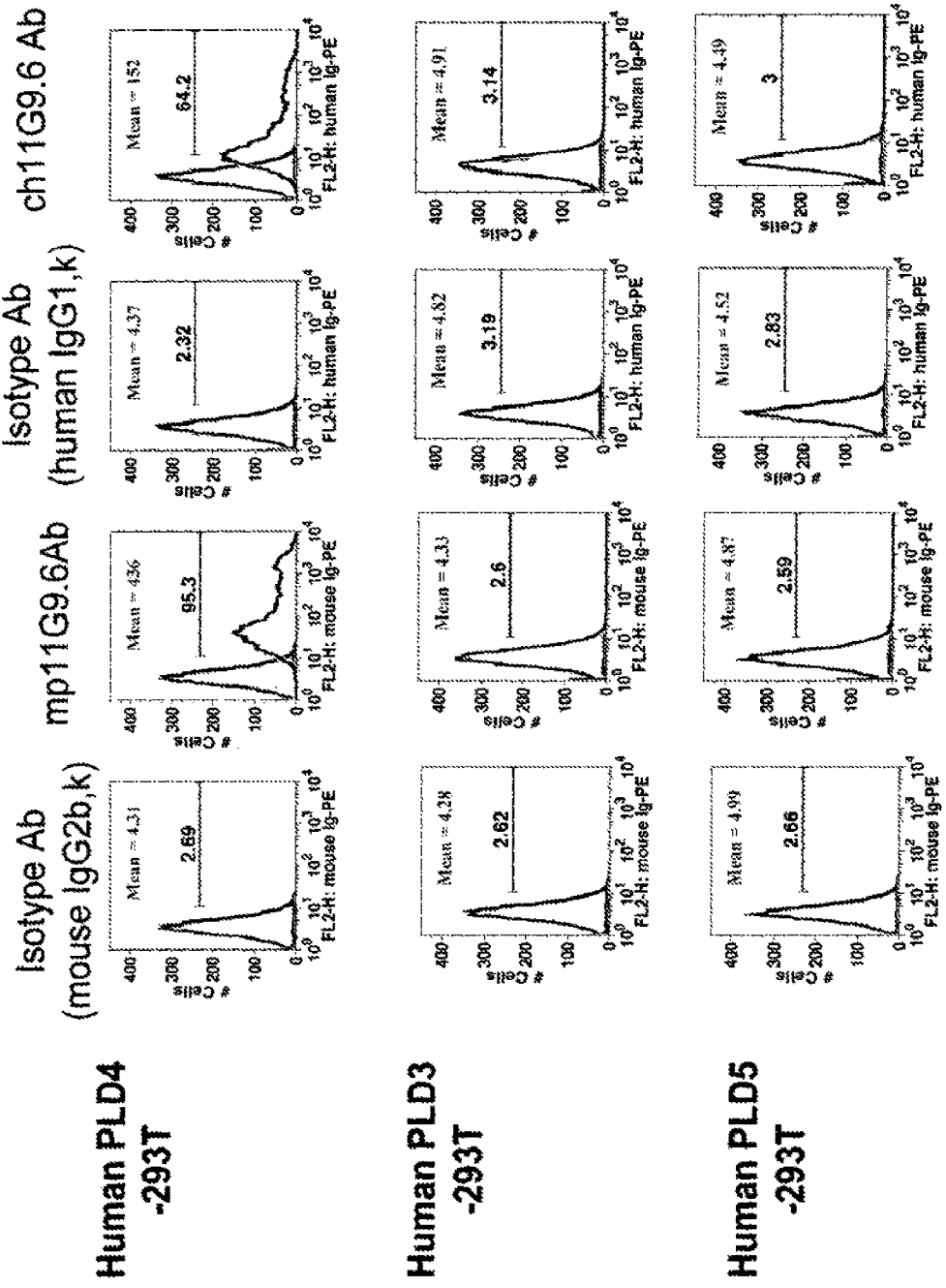
FIG. 8 is a FACS analysis diagram that illustrates binding specificity to human PLD4. The mp11G9.6 and ch11G9.6 antibodies specifically recognized human PLD4, but did not recognize human PLD3-293T or PLD5-293T transfectants.
Figure 9:
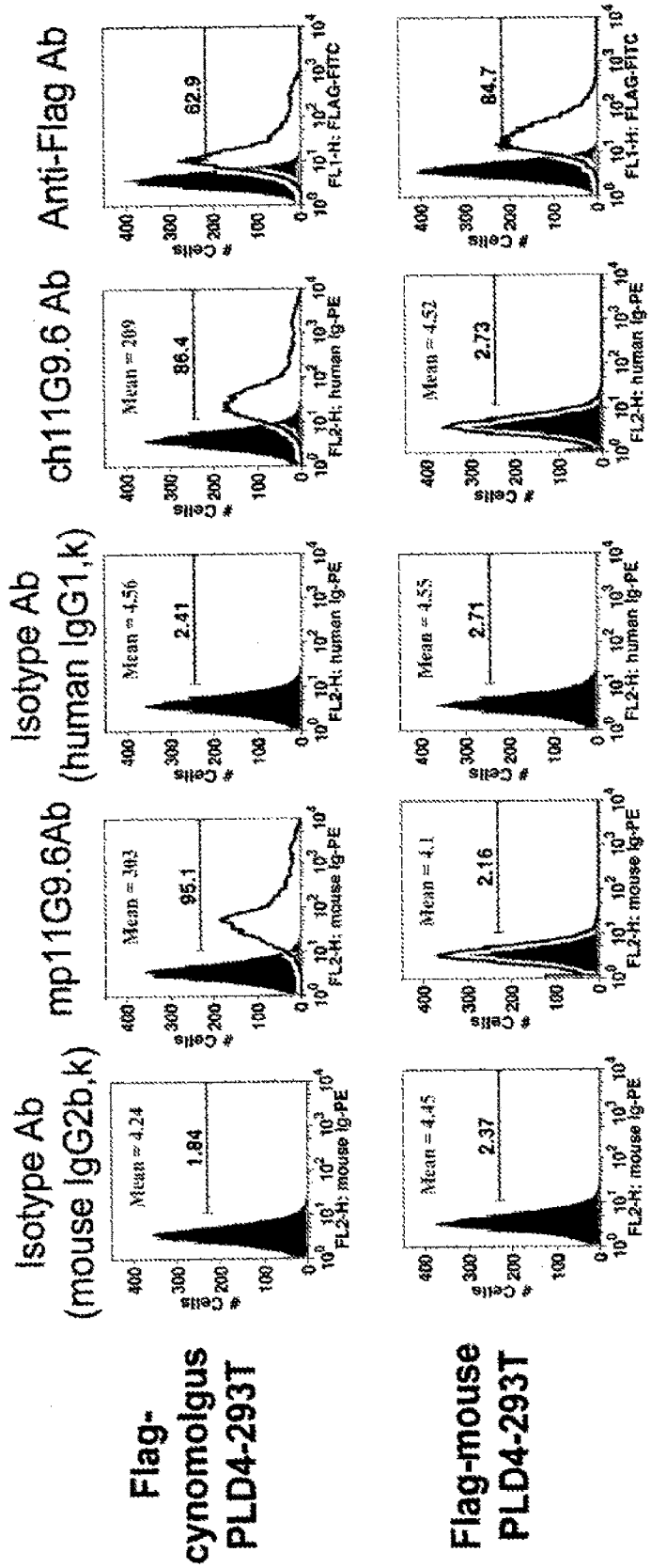
FIG. 9 is a FACS analysis diagram that illustrates cross-reactivity with cynomolgus monkey PLD4. The mp11G9.6 and ch11G9.6 antibodies were capable of recognizing cynomolgus monkey PLD4 on the 293T transfectant.

As a result thereof, the antibodies did not react with a cell in which human PLB3 or human PLD5 appeared to be expressed, which suggested that these anti-PLD4 antibodies recognized human PLD4 molecules specifically (FIG. 8).

Preparation of Human PLD4 Expression Cell Stable Strain

The prepared human PLD4-pMX-IP vector was cotransfected to 293T cell along with pCL-Eco vector (IMGENEX, Cat. No. 10045P), which is a retrovirus packaging vector, whereby to perform gene introduction. The gene introduction experiment used FuGENE (registered trademark) HD Transfection Reagent (Roche) as the transfection reagent. After 2 days, the cell culture supernatant, in which human PLD4 gene-containing retrovirus was secreted, was collected, and was infected to CT125 cell strain (2B4 mouse T cell lymphocyte tumor cell series). From the fact that pMX-IP retrovirus vector contains puromycin-resistant gene, culture of infected CT125 cell in the presence of puromycin allows survival of only cells that express human PLD4, leading to selection thereof. The selected human PLD4 expression CT125 cells (hereinafter, human PLD4-CT125) were further selected to only the CT125 cells allowing higher expression of human PLD4 by FACS sorting, and cultured. For confirmation of the human PLD4 expression, the CT125 cells were stained with commercially available mouse anti-human PLD4 polyclonal antibody (Abnova, Cat #:H00122618-B01P) adjusted to 5 µg/mL, and FACS analysis was performed. As a result thereof, human PLD4-CT125 cell stable strain was established, and used in FACS screening of the hybridoma.

Construction of PLD4 expression vectors of cynomolgus monkey and rhesus monkey, and preparation of human PLD4 expression cell stable strain For expressions of the PLD4 proteins of cynomolgus monkey and rhesus monkey, cloning of monkey PLD4 gene and construction of expression vectors were performed. 1) Cloning of cynomolgus monkey PLD4 and rhesus monkey PLD4 gene The cDNA sequence of PLD4 of rhesus monkey is reported at Genbank database (XM_002805227.1) and the like, but a partial, total length cDNA thereof is not reported. Furthermore, since the PLD4 gene sequence of cynomolgus monkey is not yet reported, from PBMC (10 mL respectively; SHIN NIPPON BIOMEDICAL LABORATORIES, LTD.) of cynomolgus monkey and rhesus monkey, gene cloning was performed.

Total RNA was extracted from the peripheral blood of the monkey, and from 5 µg thereof, cDNA was synthesized using oligo-dT primer and SuperScript Choice System for cDNA Synthesis kit.

Using the prepared cDNA as a template, the cynomolgus monkey PLD4 and the rhesus monkey PLD4 gene were amplified with PCR method using the primers of the following base sequences.

```
Forward primer (cynoPLD4-32F):
                              (SEQ ID NO: 61)
5' AGA TGC TGA AGC CTC TTC GGA GAG Cg 3'

Reverse primer (cynoPLD4-1554R):
                              (SEQ ID NO: 62)
5' TCA GCC CTG CCA AAC GCA GTC CTG G3'
```

Amplified about 1521 base pairs of cynomolgus monkey PLD4 and 1521 base pairs of rhesus monkey PLD4 cDNA fragment were isolated by electrophoresis using 1% agarose gel, and collected, and cloned to pCR4Blunt-TOPO plasmid vector (Invitrogen company) using Zero Blunt TOPO PCR Cloning kit (Invitrogen company). The base sequences of the obtained gene were analyzed, which are represented by SEQ ID NO: 63 and SEQ ID NO: 124. It was confirmed that intended cynomolgus monkey PLD4 and rhesus monkey PLD4 gene were able to be cloned.

Figure 14:
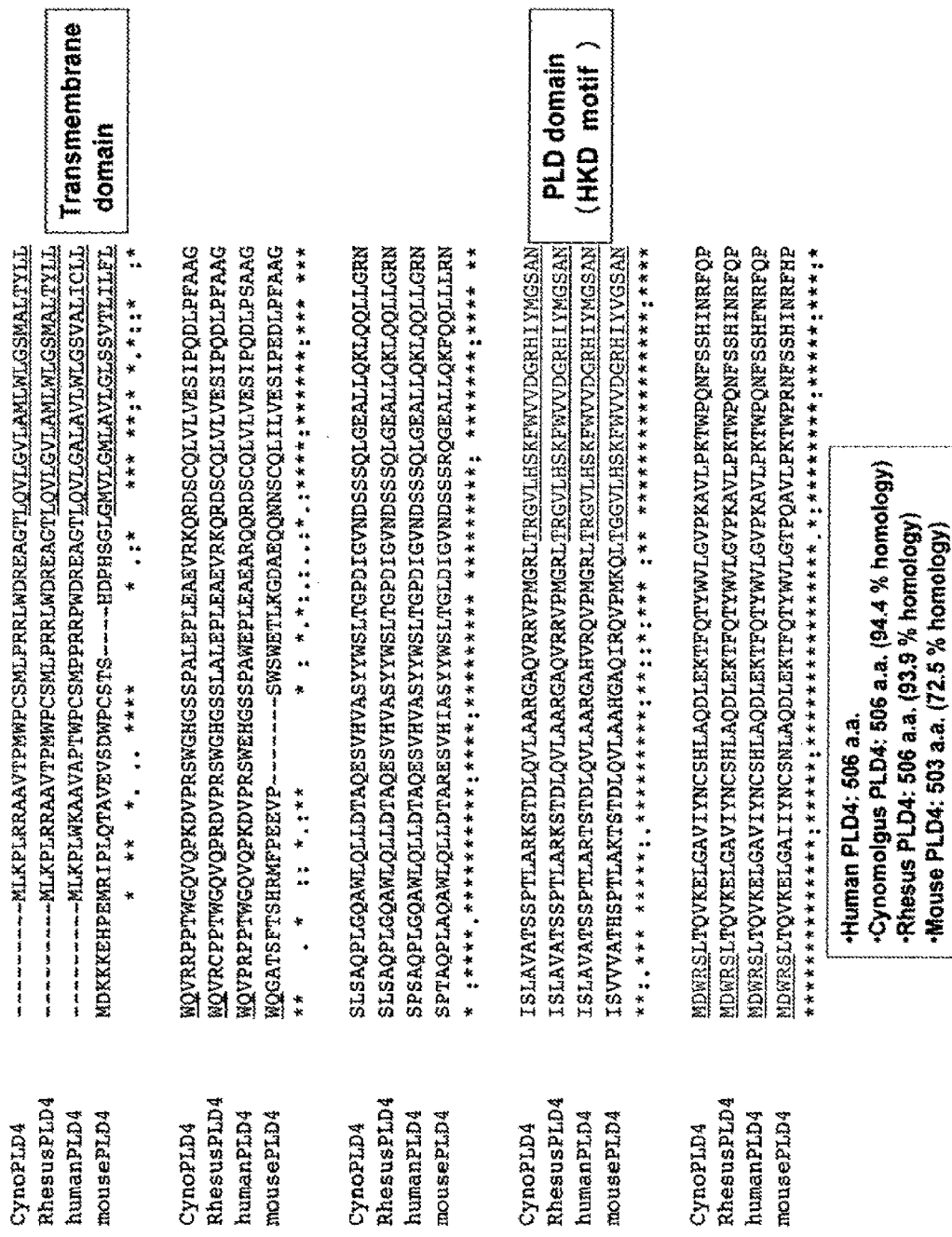
FIG. 14 is a diagram that represents the multiple alignment, and the homology of the proteins of human PLD, cynomolgus monkey PLD4, rhesus monkey PLD4, and mouse PLD4.

The human PLD4 protein represents about 94.4% identity to the protein sequence with cynomolgus monkey PLD4 (SEQ ID NO: 129), and about 94% identity to the protein sequence with rhesus monkey PLD4 (SEQ ID NO: 130). FIG. 14 illustrates the homology of the protein sequences of human PLD4 to cynomolgus monkey PLD4, rhesus monkey PLD4, and mouse PLD4 (cDNA SEQ ID NO: 131, amino acid SEQ ID NO: 132).

2) Preparation of Cynomolgus Monkey PLD4 Expression Cell Stable Strain

Cynomolgus monkey PLD4 expression cell stable strain was established by culturing CT125 cell infected with a retrovirus vector in the presence of puromycin, in the same method as the method of preparing human PLD4 expression cell stable strain using the prepared cynomolgus monkey PLD4-pMX-IP vector.

For confirmation of PLD4 expression of cynomolgus monkey, the cells were stained with commercially available mouse anti-human PLD4 polyclonal antibody (Abnova, Cat #: H00122618-B01P) that represent cross-reactivity also with monkey PLD4, and FACS analysis was performed. As a result thereof, cynomolgus monkey PLD4-CT125 cell stable strain was established, and used in FACS screening of the hybridoma (FIG. 16).

Preparation of Human PLD4-Ig Fusion Protein

For use as an immunogen in preparation of anti-human PLD4 monoclonal antibody, 2142 bps of a DNA fragment, in which the extracellular region of human PLD4 protein (56-506 a.a) and mouse IgG2a Fc fragment (234 a.a containing a portion of the heavy chain hinge, CH2, and CH3) were fused, were amplified with 2 step PCR method, and expression vector plasmids of human PLD4-Ig pcDNA3.1 and human PLD4-Ig pEE14.4 were constructed (The sequences of the cDNA and the protein are specified in the sequence list).

In order to obtain a protein from the culture supernatant, Maxi-prep DNA was transiently transfected to Freestyle 293F cell (hereinafter, 293F cell, catalog No. R790-07; Invitrogen). At day 7 after the transfection, the culture liquid of the cotransfected 293F cell was collected in 50 mL tube, and centrifuge was performed under conditions of 2,070 g at 4° C. for 5 minutes. The supernatant was filtered with a syringe filter having 0.45 µm pore size (catalog No. 431220; CORNING), and the culture supernatants were collected together.

Figure 7:
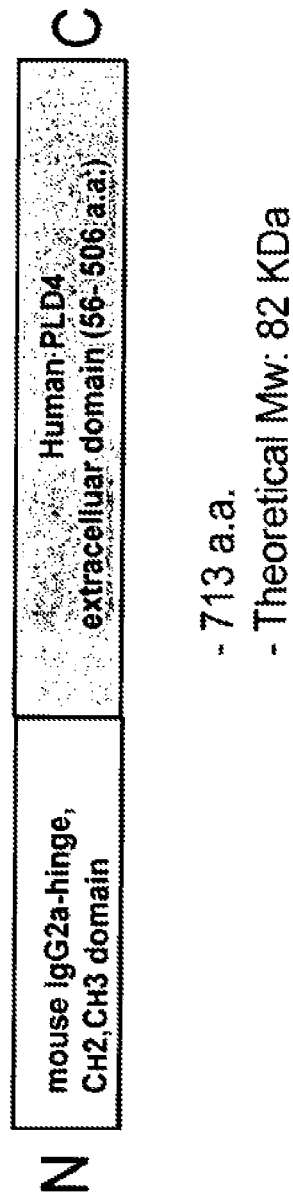
FIG. 7 is a schematic diagram that illustrates the structure of recombinant human PLD4-Ig fusion protein. A cDNA fragment that corresponds to human PLD4 extracellular domain (56-506 amino acids) was amplified by PCR. This fragment was inserted into the BamHI-EcoRI cloning site of N-Flag pcDNA3.1 expression vector containing mouse IgK leader segment and mouse IgG2a heavy chain constant Fc region (hinge+CH2+CH3) at the N terminal. 293F cell was transfected temporarily with a plasmid, and the culture supernatant was collected.

The collected cell culture supernatant was purified with protein A affinity column of AKTA-FPLC system, and the protein of recombinant human PLD4-Ig fusion protein was purified (FIG. 7).

Example 3

A. Preparation of Anti-Human PLD4 Monoclonal Antibody

A-1) Immunization

As an immunogen, the aforementioned recombinant PLD4-Ig fusion protein was used. PLD4-Ig fusion protein was administered subcutaneously to the back part of 3 mice of BALB/c mouse. Freund's Adjuvant, Complete and Incomplete (SIGMA) were used as an adjuvant, and 200 µg/mouse at the first time and 50 µg/mouse at the second to fourth time, were administered.

A-2) Confirmation of Anti-Serum Titer

The blood was collected after the third immunization and the fourth immunization, and the anti-PLD4-Ig titer in the serum was evaluated with ELISA.

PLD4-Ig fusion protein was solid-phased to a 96 well microtiter plate. The anti-serum was diluted stepwise from 1,000 folds by 3 folds, and dilution series were prepared to 729,000 folds. Each of the samples was added to the antigen solid-phased plate by 50 µL, and primary reaction was performed. After washing, secondary reaction was performed with HRP label anti-mouse IgG (κ, λ) antibody, and color-detected (490 nm) with OPD (ortho-phenylenediamine).

A-3) Cell Fusion

Splenic cells were isolated from a mouse for which increase of the anti-serum titer was recognized. The isolated splenic cell and the mouse myeloma cell (P3U1) were fused with PEG method, and selection and culture of the fusion splenic cell was performed from HAT medium.

FACS Screening of Hybridoma Using CAL-1 Cell

Figure 11:
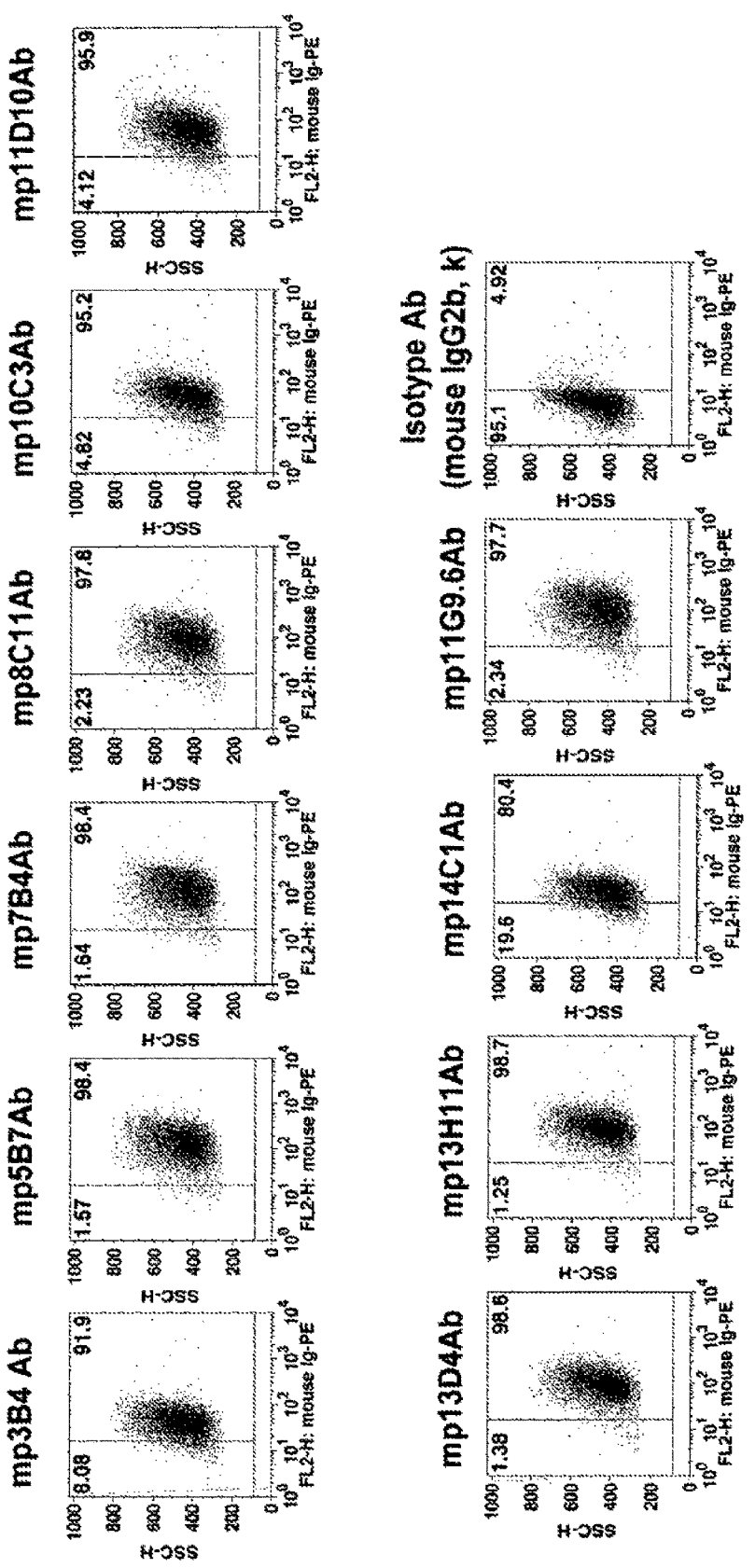
FIG. 11 is a FACS analysis diagram that illustrates staining in the purified anti-PLD4 antibody of CAL-1 cell.

Antibodies producing each clone of the fusion splenic cell obtained from HAT selection culture were evaluated with FACS. Human pDC-like cell strain CAL-1 cells in $2\times10^5$ were reacted with 50 µL culture supernatant of each of the hybridomas described below for 15 minutes at 4° C. The cells were washed with FACS buffer (1% FBS+PBS) twice, centrifuged, and the supernatant was removed. Reaction was performed for 20 minutes at 4° C. using PE labeled anti-mouse IgG antibody (BD Bioscience: 550589) as a secondary antibody. The culture liquid after 10 days from the start of HAT selection culture was used as original fold for the culture supernatant of each clone. As a result thereof, 3B4, 5B7, 7B4, 8C11, 10C3, 11D10, 13D4, 13H11, 14C1, and 11G9.6 of the hybridoma culture supernatants were well reacted to CAL-1 cell (FIG. 11).

FACS Screening of Hybridoma Using Human PLD4-CT125 Stable Cell Strain

Figure 12:
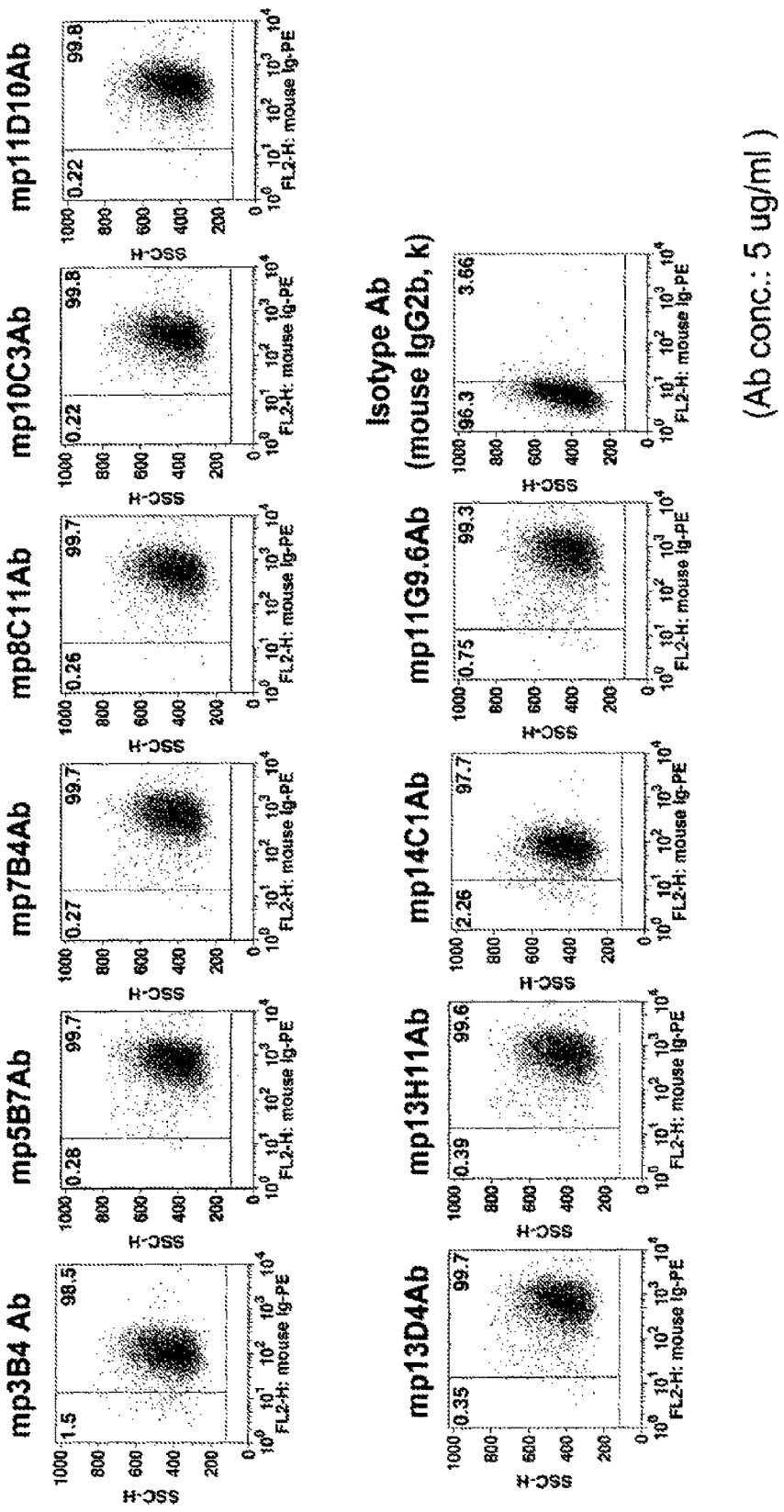
FIG. 12 is a FACS analysis diagram that illustrates staining in anti-PLD4 antibody of human PLD4-CT125 stable cell strain.

Antibodies producing each clone of the fusion splenic cell obtained from HAT selection culture were evaluated with FACS. Human PLD4-CT125 in $2\times10^5$ was reacted for 15 minutes at 4° C. with 50 µL of culture supernatant of each of the hybridomas described below. The cells were washed with FACS buffer (1% FBS+PBS) twice, centrifuged, and the supernatant was removed. Reaction was performed for 20 minutes at 4° C. using PE labeled anti-mouse IgG antibody (BD Bioscience: 550589) as a secondary antibody. As a result thereof, 3B4, 5B7, 7B4, 8C11, 10C3, 11D10, 13D4, 13H11, 14C1, and 11G9.6 of the hybridoma culture supernatants were well reacted to human PLD4-CT125 cell (FIG. 12).

A-5) FACS Screening Using Human Peripheral Blood pDC

[Isolation of Human PBMC]

Figure 10:
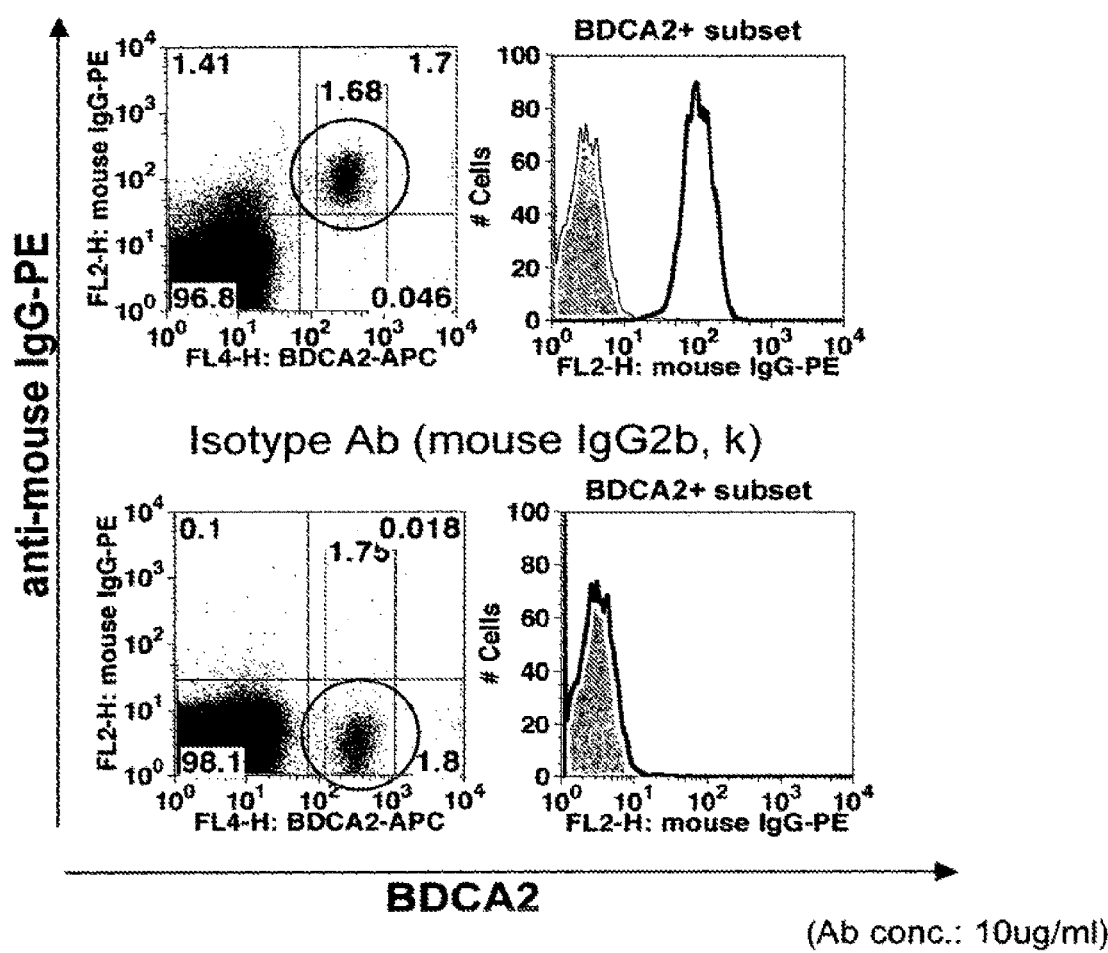
FIG. 10 is a FACS measurement diagram that illustrates staining in the mp11G9.6 antibody of human PBMC. The mp11G9.6 antibody strongly recognized $BDCA2^+$ pDC in human PBMC.

20 mL of peripheral blood of a healthy individual was collected, and the peripheral blood mononuclear cell (PBMC) was isolated with specific gravity centrifuge using HISTOPAQUE-1077 (SIGMA company). $1\times10^6$ PBMCs were stained for every sample. The cells were washed with FACS buffer, and then added with 25 µL of 5 fold dilution of Fc block reagent (Militenyi company), and reacted at 4° C. for 15 minutes. The cells were washed with FACS buffer, and then was added with 50 µL of the cell culture supernatant of each hybridoma and mouse IgG2b, K, and reacted at 4° C. for 20 minutes. The cells were washed with FACS buffer, and then added with PE-labeled anti-mouse IgG antibody, and reacted at 4° C. for 20 minutes. The cells were washed with FACS buffer, and then added with 50 µL of 10 fold dilution of APC-labeled anti-BDCA2 antibody, and reacted with at 4° C. for 20 minutes. The cells were washed with FACS buffer, and then resuspended in 300 µL of FACS buffer, and analyzed with FACS Calibur (BD). The mp11G9.6 antibody exhibited the binding to pDC (FIG. 10).

Figure 13:
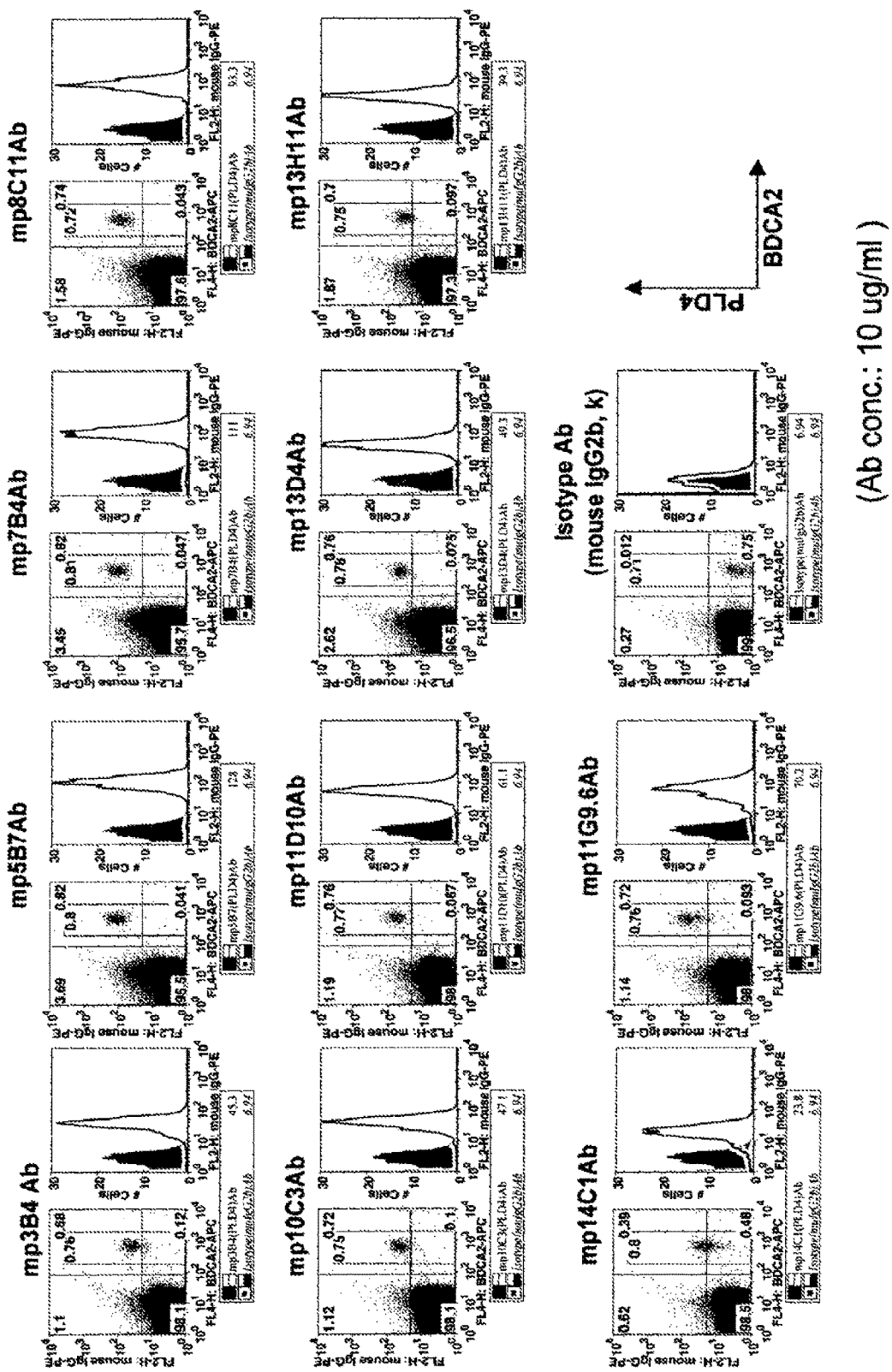
FIG. 13 is a FACS analysis diagram that illustrates staining in anti-PLD4 antibody of human PBMC. All of the anti-PLD4 antibodies were capable of recognizing $BDCA2^+$ pDC in human PBMC.

Furthermore, 9 kinds of PLD4 antibodies of 3B4, 5B7, 7B4, 8C11, 10C3, 11D10, 13D4, 13H11, and 14C1 exhibited specific binding reaction for pDC cell population, which was a BDCA2 positive cell (FIG. 13).

A-6) Cross-Reactivity of Anti-PLD4 Antibody to Monkey

Figure 15:
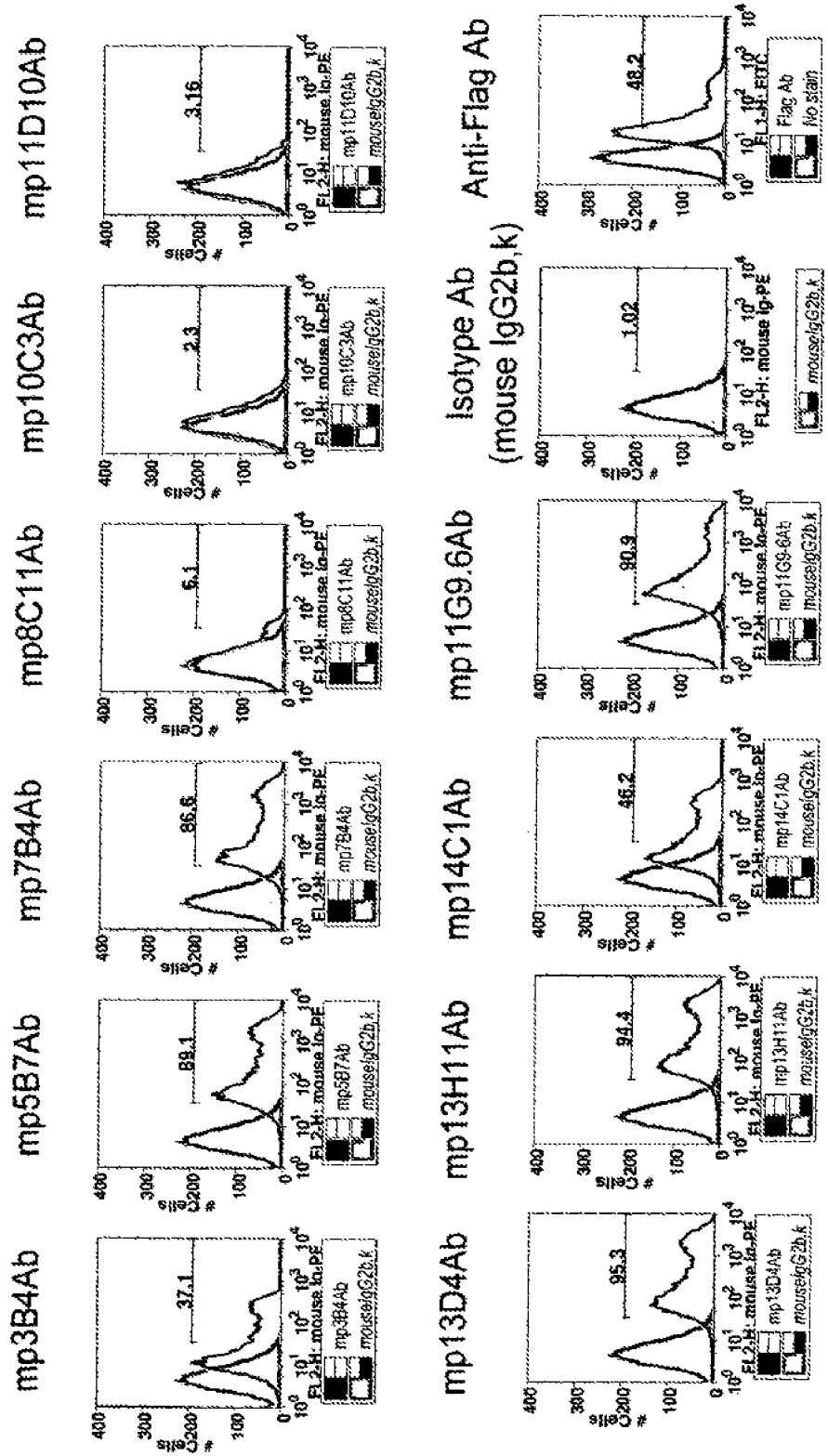
FIG. 15 is a FACS analysis diagram that illustrates staining in anti-PLD4 antibody with transient gene introduction of Flag tagged cynomolgus monkey PLD4 expression vector into human PLD4-293T cell. Cell surface expression of the cynomolgus monkey PLD4 protein was confirmed in the anti-Flag antibody.

FACS screening of hybridoma using cynomolgus monkey PLD4-CT125 stable cell strain and rhesus monkey PLD4-293T transient transfectant cell Antibodies producing each clone of the fusion splenic cell obtained from HAT selection culture were evaluated with FACS. Human PLD4-CT125 in $2\times10^5$ was reacted with 50 µL culture supernatant of each of the hybridomas described below for 15 minutes at 4° C. The cells were washed with FACS buffer (1% FBS+PBS) twice, centrifuged, and the supernatant was removed. Reaction was performed for 20 minutes at 4° C. using PE labeled anti-mouse IgG antibody (BD Bioscience: 550589) as a secondary antibody. As a result thereof, 7 kinds antibodies of 3B4, 5B7, 7B4, 13D4, 13H11, 14C1, and 11G9.6 antibodies among 10 kinds of the PLD4 antibodies were well reacted to cynomolgus monkey PLD4-CT125 cell and rhesus monkey PLD4-293T cell (FIG. 15, FIG. 16, and FIG. 17).

A-7) Cross-Reactivity of Anti-PLD4 Antibody to Monkey PBMC

Figure 18A:
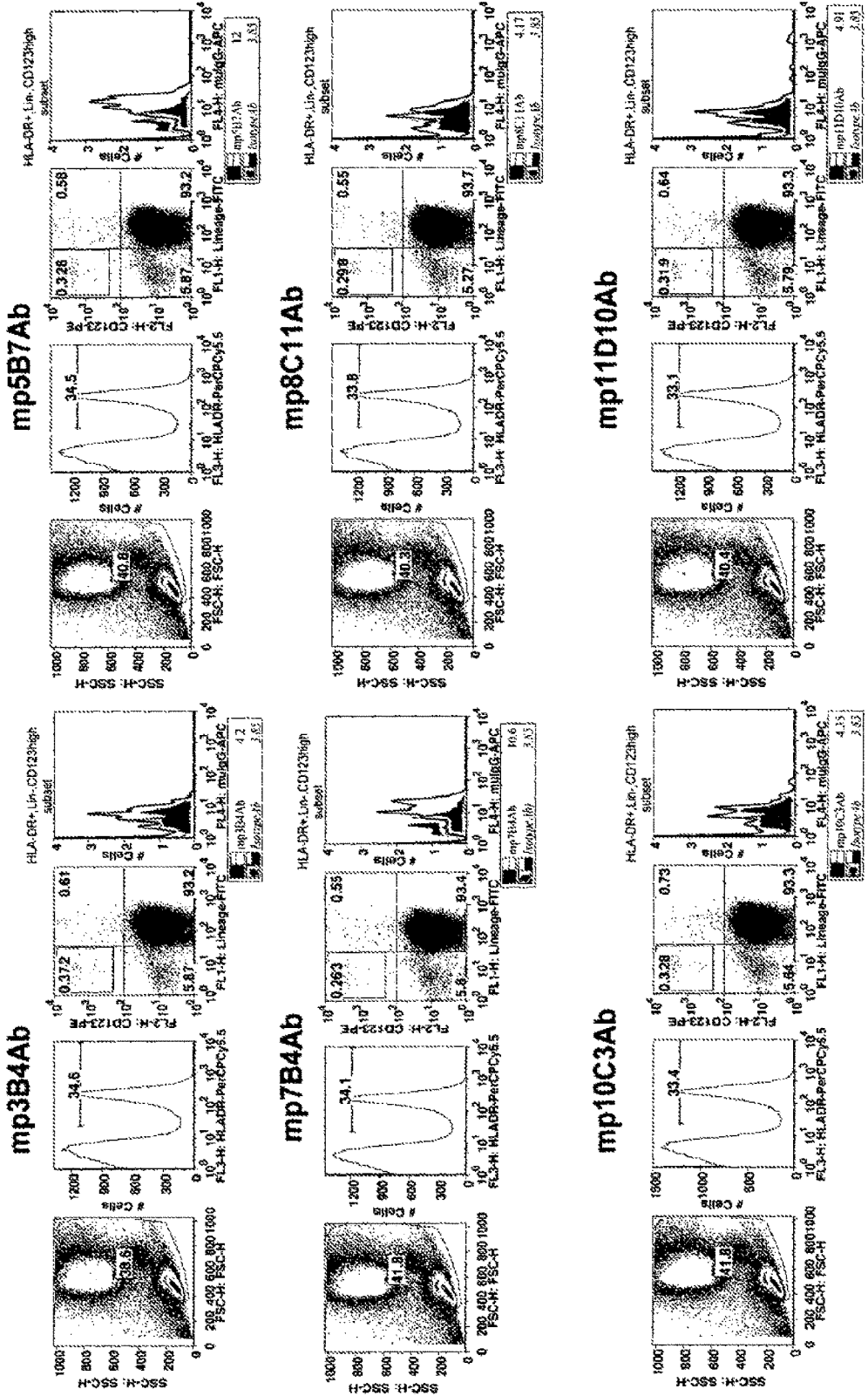
FIGS. 18A-B are FACS analyses diagrams that illustrate staining in anti-PLD4 antibody of rhesus monkey PBMC. Among the anti-PLD4 antibodies, five (5B7, 7B4, 13D4, 13H11, and 14C1) antibodies bound specifically to pDC cell population (Lineage-CD123+HLA-DR+) of cynomolgus monkey in rhesus monkey PBMC.
Figure 18B:
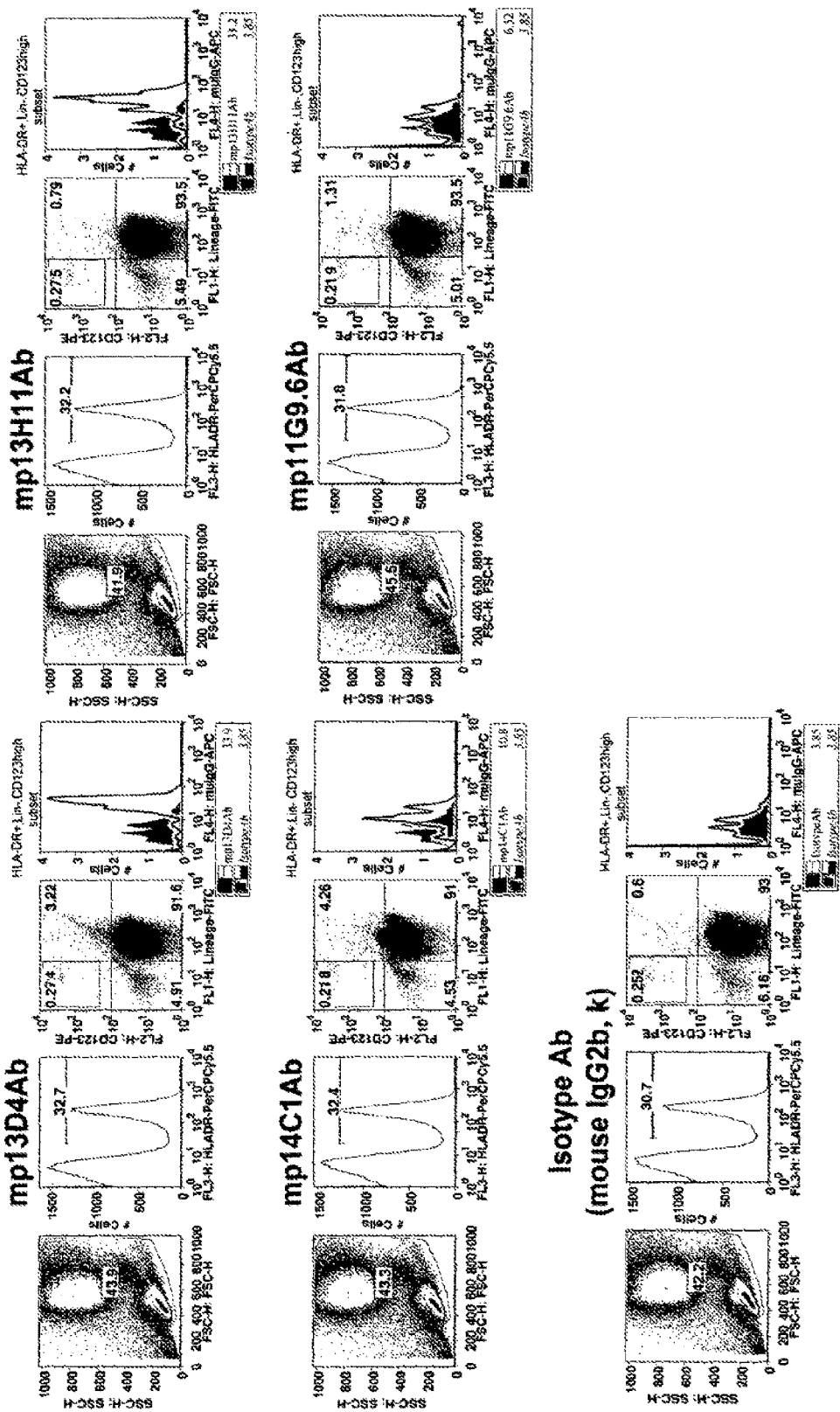

PBMC of rhesus monkey from the peripheral blood (10 mL; SHIN NIPPON BIOMEDICAL LABORATORIES, LTD.), was centrifuged with specific gravity using 96% Ficoll-Paque™ PLUS (GE Healthcare company, Cat No. 17-1440-02). For FACS, $5\times10^5$ of cells were used per sample. The cells were washed with FACS buffer cell, and then added with 10 µL of 10% cynomolgus monkey serum diluted with FACS buffer, and reacted at 4° C. for 20 minutes. The cells were washed with FACS buffer, and then added with 100 µL of the cell culture supernatant of each hybridoma and 10 µg/mL of mouse IgG2a, κ or mouse IgG1, κ, and reacted at 4° C. for 15 minutes. The cells were washed with FACS buffer, and then added with 1 µg/mL of APC-labeled anti-mouse IgG antibody, and reacted at 4° C. for 20 minutes. The cells were washed with FACS buffer, and then reacted with 25 µL of 10 fold dilution of FITC-labeled anti-Lineage 1 antibody, PE-labeled anti-CD123 antibody, and PcrCP-Cy5.5-labeled anti-HLA-DR antibody at 4° C. for 15 minutes. The cells were washed with FACS buffer, and then resuspended in 300 µL of FACS buffer, and analyzed with FACS calibur. The used hybridoma culture supernatant was specific to PLD4, and 10 kinds of 3B4, 5B7, 7B4, 8C11, 10C3, 11D10, 13D4, 13H11, 14C1, and 11G9.6, which bound well to CAL-1 cell or human pDC, were selected. As a result thereof, 5 kinds of the hybridoma cell culture supernatants, i.e., 5B7, 7B4, 13D4, 13H11, and 14C1 specifically bound to pDC cell population of cynomolgus monkey (Lineage-CD123+HLA-DR+) (FIGS. 18A-B).

A-8) Cloning of Hybridoma by Limiting Dilution Method

1) Cloning and 2nd Screening by Limiting Dilution Method

For cloning of selected 9 kinds (3B4, 5B7, 7B4, 8C11, 10C3, 11D10, 13D4, 13H11, and 14C1) of hybridomas except 11G9.6 hybridoma, limiting dilution was performed. The limiting dilution was seeded on 2 pieces of 96 well plate. After 6 days from the seeding, the cells were observed under a microscope, and culture supernatants that were monoclone-derived and exhibited good growth in all wells were collected. FACS analysis was performed for the collected culture supernatant as a sample.

In FACS analysis, the surface antigen of cell strain CAL-1 was stained using the culture supernatant of each clone followed by PE-labeled anti-mouse IgG antibody (BD Bioscience: 550589) as a secondary antibody. As the culture supernatant of each clone, the culture liquid after 7 days from the seeding of the limiting dilution was used as original fold.

2) Cloning and 3rd Screening

Based on FACS analysis results of the 2nd screening and the cell state in each well, 1 well was selected from each clone, and limiting dilution was performed again. The limiting dilution was similarly performed as in 2), and FACS analysis (3rd) was performed for the collected culture supernatant as a sample. Based on the FACS analysis data and the like, following 9 kinds (3B4, 5B7, 7B4, 8C11, 10C3, 11D10, 13D4, 13H11, and 14C1) of the clones were cloned by limiting dilution method, and anti-human PLD4 antibody-producing hybridoma was established as a stable cell strain.

3) Conversion to Single 11G9.6 Hybridoma

The 11G9.6 hybridoma other than the aforementioned 9 kinds was collected, and suspended with a sorting buffer (1% FBS/PBS) to be 1×10$^5$ cells/mL. Single cell sorting was performed using FACS Aria (BD). The data were incorporated, and the incorporated data was developed to two dimensional dot plot of X axis: FSC and Y axis: SSC. On the dot plot, live cells were surrounded with a gate. The gate was draped to exclude doublet from the cells in the live cell gate, the cell population was isolated and taken into 96 well flat plate to be 1 cell/well. The cells after Single cell sorting were cultured in HAT medium (RPMI 1640+2 mM L-Glutamine, 10 Unit/mL Penicillin-Streptomycin, 10 mM HEPES, 1 mM Sodium Pyruvate, 50 μM 2-ME)+hybridoma growth supplement HFCS (Roche company). Then, CAL-1 cell, human PLD4-CT125 expression stable cell strain, human PBMC, and the monkey PLD4-CT125 expression stable cell strain were stained using the cell culture supernatant of the hybridoma, and 11G9.6 of single hybridoma was selected.

4) Preparation of Frozen Cell Vial and Collection of Culture Supernatant

Based on the FACS analysis results described above and the cell state of each well, 1 well was selected from each clone. For the selected well, expansion culture was performed at 50 mL scale. The medium was RPMI 1640 containing 10% FCS and penicillin streptomycin. The cells were cultured to subconfluent, and freezed and conserved in cell number 1×10$^6$ cells/tube. As the liquid for freezing and conserving, BAMBANKER (NIPPON Genetics, Co. Ltd.) was used. In addition, the culture supernatant at this time was collected and conserved.

Example 4

Purification of Antibody

10 Kinds (3B4, 5B7, 7B4, 8C11, 10C3, 11D10, 13D4, 13H11, 14C1, and 11G9.6) of purified antibodies were obtained from the culture supernatants of the hybridomas by purification using protein A affinity column (rProtein A Sepharose Fast Flow (catalog No. 17-1279-01, GE Healthcare company). Isotypes were confirmed using Pierce Rapid ELISA Mouse mAb Isotyping Kit (Thermo Fisher Scientific company). As a result thereof, 3B4 and 14C1 were mouse IgG1, κ, 10C3 was mouse IgG2a, κ, and the others were mouse IgG2b, κ. Measurement of endotoxin concentration was performed since if endotoxin was contained in the purified antibody, it could have influence on the results of a property determination test. The Kits used were Endospecy ES-50M set, Toxicolor DIA-MP set, and endotoxin standard CSE-L set (SEIKAGAKU BIOBUSINESS CORPORATION company). As a result thereof, endotoxin concentration of any purified antibody was 0.3 EU/mg or less Ab that was the reference value.

Review of Reactivity of Purified Antibody Binding ability of the purified antibody was confirmed with CAL-1 cell that is human pDC-like cell strain. As a result, it could be confirmed that any antibody maintained the binding ability to human PLD4 on the cell surface (FIG. 11). In addition, the antibody also specifically bound to pDC cell population (BDCA2+) of the human peripheral blood (FIG. 13).

Calculation of Kd Value of Purified PLD4 Antibody

For binding ability of the purified antibody, human PLD4-CT125 expression stable cell strain was reacted to nearly 100% of the positive staining rate at low concentration to high concentration (0.001 μg/mL to 30 μg/mL) of purified PLD4 antibody concentration. The frequency of staining positive cell and the antibody were data-analyzed using Graph Pad Prism version 5 software, and the dissociation constant molar concentration (Kd value) was computed in nM unit. From the fact that Kd values (nM) of the anti-PLD4 antibodies were all 1 nM or less or 1 nM nearly except the 2 clones of 3B4 and 14C1, the anti-PLD4 antibodies bound very strongly to the human PLD4-CT125 cell (FIG. 19).

Example 5

Figure 20:
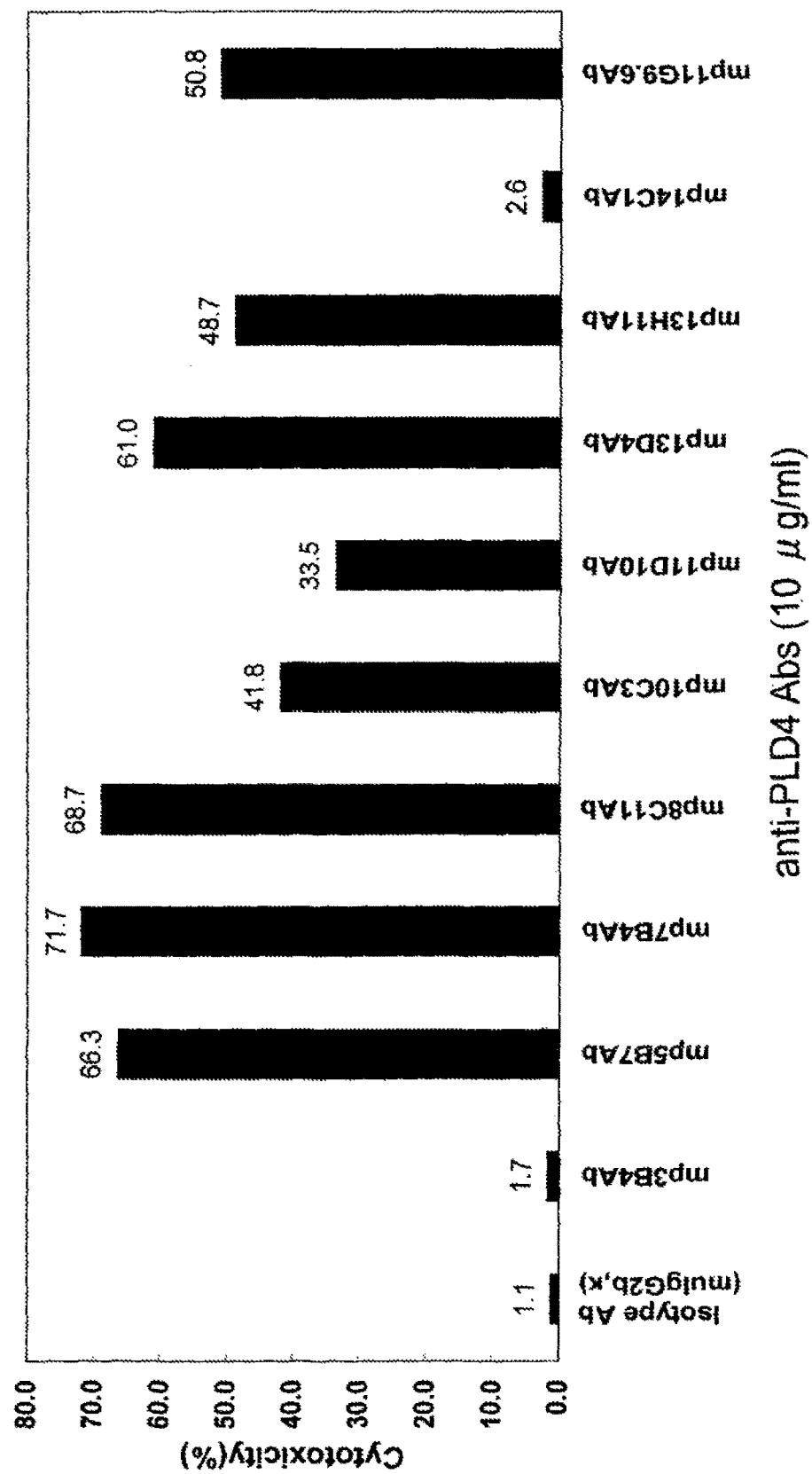
FIG. 20 is a graph that illustrates CDC activity of ten kinds of the anti-PLD4 antibodies. Target cell: human PLD4-CT125 (mouse 2B4 T cell lymphocyte) stable transfectant antibody concentration: 10 µg/mL effector: 1% immature rabbit complement.

Complement Dependent Cytotoxicity Activity of Anti-PLD4 Antibody for Human PLD4-CT125 Expression Cell The complement dependent cytotoxicity activity (hereinafter, referred to as CDC activity) of the anti-PLD4 antibody was measured for CT125 cell stable strain that expresses human PLD4 (hereinafter, referred to as HuPLD4-CT-125) using immature rabbit serum as a complement source. The index of the activity was cell toxicity calculated from measured value of Lactase dehydrogenase (LDH) released from the cell. Each cell was dispensed to 96 well U bottom plate by 2×10$^4$ cells/50 μL/well. 1% Baby rabbit complement (CEDARLANE company) was prepared at CDC medium (RPMI 1640+0.1% BSA+10 mM HEPES+2 mM L-Glutamine+1% Pen-Strep). The cells were added with 10 μg/mL of mouse isotype control antibody (mouse IgG2b, κ) and 10 kinds of the anti-PLD4 mouse purified antibodies (3B4, 5B7, 7B4, 8C11, 10C3, 11D10, 13D4, 13H11, 14C1, and 11G9.6), and reacted for 1 hour. For the assay system, CytoTox 96 Non-Radioactive Cytotoxicity Assay (Promega company) Kit was used. As a result thereof, for the target cell of HuPLD4-CT-125, 8 kinds of the PLD4 antibodies (5B7, 7B4, 8C11, 10C3, 11D10, 13D4, 13H11, and 11G9.6) exhibited CDC activity of from about 33.5% to 71.1% at 10 μg/mL of antibody concentration except 2 kinds of the PLD4 antibodies, 3B4 and 14C of which the heavy chain isotype was mouse IgG1 (FIG. 20).

Example 6

Figure 21:
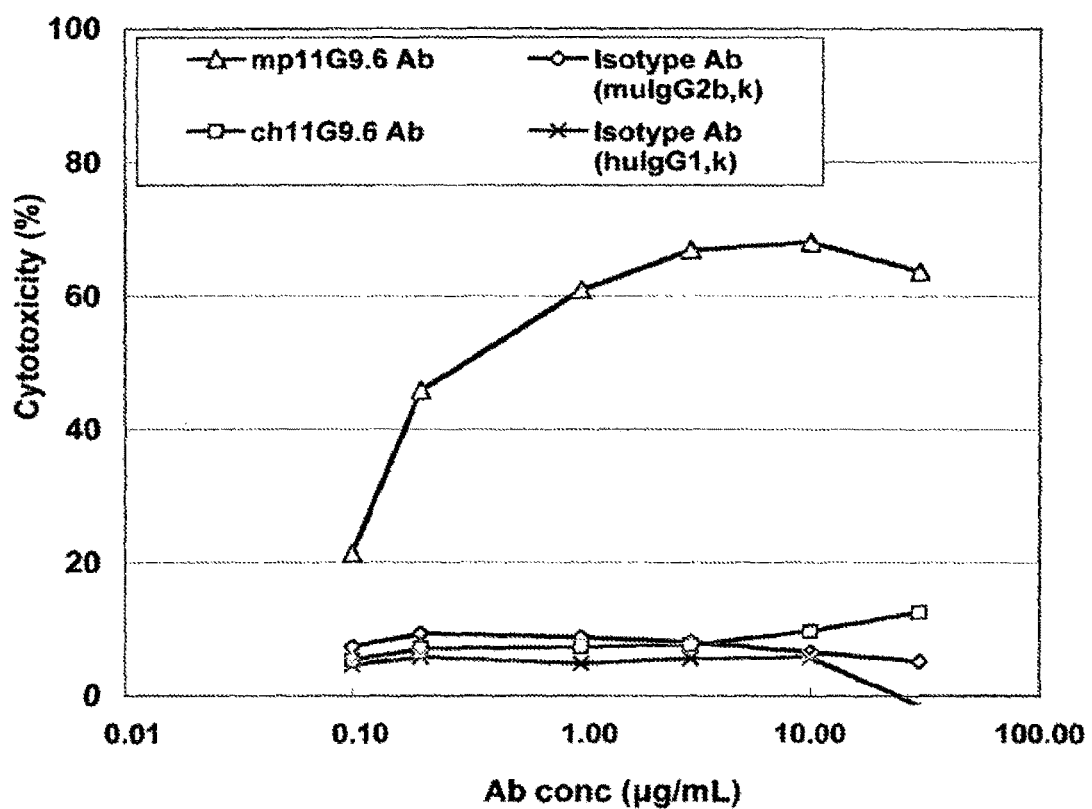
FIG. 21 is a graph that illustrates CDC activity of the anti-PLD4 antibodies (mp11G9.6 antibody and ch11G9.6 antibody). Target cell: human PLD4-CT125 (mouse 2B4 T cell lymphocyte) stable transfectant antibody concentration: 0.1 µg/mL to 30 µg/mL effector: 1% immature rabbit complement.

Concentration-dependent, complement-dependent cytotoxicity activity mouse isotype control antibody (mouse IgG2b, κ) of anti-PLD4 antibody (11G9.6), anti-PLD4 mouse antibody (mp11G9.6 Ab), human isotype control antibody (human IgG1, κ), and anti-PLD4 chimeric antibody (ch11G9 Ab) were adjusted to total 6 points of the antibody concentration of 0.1 μg/mL to 30 μg/mL. As the assay system, CytoTox 96 Non-Radioactive Cytotoxicity Assay (Promega company) kit was used. As a result thereof, for the target cell of HuPLD4-CT-125, mp11G9.6Ab exhibited about 70% CDC activity concentration-dependently at 3 μg/mL of the antibody concentration. On the other hand, ch11G9Ab, which was a chimeric antibody, exhibited 10% or less of the CDC activity even at 30 μg/mL of high concentration (FIG. 21).

Example 7

Preparation of Chimeric Antibody

10 Kinds were prepared as a hybridoma that produces mouse anti-PLD4 antibody, and used.

1. Confirmation of Isotype of Constant Region

The isotype of the constant region of the mouse anti-PLD4 antibody produced from the hybridoma that produces the anti-PLD4 antibody was confirmed. From the culture supernatants of the hybridomas of 10 kinds (3B4, 5B7, 7B4, 8C11, 10C3, 11D10, 13D4, 13H11, 14C1, and 11G9.6), the isotype was confirmed using Pierce Rapid ELISA Mouse mAb Isotyping Kit (Thermo Fisher Scientific company). As a result thereof, 3B4 and 14C1 were mouse IgG1 and mouse Ig kappa, 10C3 was mouse IgG2a and mouse Ig kappa, and the others are mouse IgG2b and mouse Ig kappa.

2. Cloning of cDNA that Encodes Variable Region of Mouse Anti-PLD4 Antibody 2-1) Isolation of Total RNA From the 11 G9.6 hybridoma, total RNA was isolated using a commercially available kit, "RNeasy Mini Kit" (Qiagen company, catalog No.: 74106) according to the instruction attached to the kit. It was prepared from 5×10⁶ cell number of the hybridoma cell strain, and about 79 μg of total RNA was obtained.

2-2) Amplification and Fragmentation of cDNA that Encodes Mouse Heavy Chain Variable Region 5 μg of the total RNA isolated in 2-1) was used, and cDNA that encodes the mouse heavy chain variable region was amplified by 5' RACE PCR method. In the amplification, a commercially available kit, "5' RACE System for Rapid Amplification of cDNA ENDs, Version 2.0 Kit" (Invitrogen company, catalog No.: 18374-058) was used. The details are as follows. First, single-stranded cDNA was synthesized by the reverse transcription enzyme from total RNA obtained in 2-1). At this time, the antisense primer (GSP1) used was as follows. The GSP1 primers used in amplification of cDNA were used differently depending on the isotype of each mouse heavy chain.

For example, in cloning of the heavy chain variable regions of 3B4 and 14C1 hybridomas having mouse IgG1 heavy chains, the following antisense primers are used.

GSP1 primer: mu IgG1VH-GSP1
Sequence:
(SEQ ID NO: 64)
5'-CCA GGA GAG TGG GAG AGG CTC TTC TCA GTA TGG TGG-3' (36-mer)

GSP2 primer: mu IgG1VH-GSP2
Sequence:
(SEQ ID NO: 65)
5'-GGC TCA GGG AAA TAG CCC TTG ACC AGG CAT CC-3' (32-mer)

In cloning of the heavy chain variable regions of 10C3 hybridoma having mouse IgG2a heavy chain, the following antisense primers are used.

GSP1 primer: mu IgGHγ1-GSP1
Sequence:
(SEQ ID NO: 66)
5' TCC AGA GTT CCA GGT CAC TGT CAC 3' (24-mer)

GSP2 primer: mu IgGHγ1-GSP2
Sequence:
(SEQ ID NO: 67)
5' AGG GGC CAG TGG ATA GAC AGA TGG 3' (24-mer)

In cloning of the heavy chain variable regions of 5B7, 7B4, 8C11, 11D10, 13D4, 13H11, and 11G9.6 hybridomas having mouse IgG2b heavy chain, the following antisense primers are used.

GSP 1 primer: mu IgGHγ2B-GSP1
Sequence:
(SEQ ID NO: 68)
5' TCC AGA GTT CCA AGT CAC AGT CAC 3' (24-mer)

GSP2 primer: mu IgGHγ2B-GSP2
Sequence:
(SEQ ID NO: 69)
5' AGG GGC CAG TGG ATA GAC TGA TGG 3' (24-mer)

Furthermore, to the 3'-terminal of the single-stranded cDNA, dC, which is a nucleotide homopolymer, was added using terminal deoxynucleotidyl transferase (TdT). Then, cDNA was amplified by PCR method using an anchor primer having a nucleotide polymer complementary to dC (anchor sequence) (SEQ ID NO: 70) at the 3'-terminal, and an antisense primer (GSP2). Furthermore, cDNA was amplified by Nested PCR method using the obtained PCR product as a template and using AUAP primer (SEQ ID NO: 71) and the antisense primer shown in Table 1 (GSP2). Furthermore, this PCR product was purified by 1.5% low melting point agarose method.

Anchor primer for 5' RACE
(SEQ ID NO: 70)
5'-GGC CAC GCG TCG ACT AGT ACG GGI IGG GII GGG IIG-3' 36-mer)

AUAP primer for 5' RACE
(SEQ ID NO: 71)
5'-GGC CAC GCG TCG ACT AGT AC-3' 20-mer)

2-3) Amplification and Fragmentation of cDNA that Encodes Mouse Light Chain Variable Region cDNA that encodes the mouse light chain variable region was amplified from the total RNA in isolated 2-1), similarly to 2-2). At this time, the GSP1 primers used in amplification of cDNA were used differently depending on the isotype of each mouse light chain.

The following antisense primers are used for light chain cloning since the 10 kinds of the PLD4 antibodies have mouse Ig kappa light chain.

GSP1 primer: mu IgG VL kappa-GSP1
Sequence:
(SEQ ID NO: 72)
5'-CAC TAC TTC CTG TTG AAG CTC TTG ACG ATG G-3' (31-mer)

GSP2 primer: mu IgG VL kappa-GSP2
Sequence:
(SEQ ID NO: 73)
5'-GTG AGT GGC CTC ACA GGT ATA GC-3' (23-mer)

The obtained PCR product was purified by 1.5% low melting point agarose method.

2-4) Confirmation of the cDNA Base Sequence and Determination of CDR Region

The cDNA fragments of the heavy chain variable region obtained in 2-2), and the light chain variable region obtained in 2-3) were cloned, respectively with pCR4Blunt-TOPO vector using a commercially available kit "Zero Blunt TOPO PCR Cloning Kit" (Invitrogen company, catalog No.: 1325137), according to the instruction attached to the kit, and transformed to *Escherichia coli* competent cell to obtain an *Escherichia coli* transformant. A plasmid was obtained from this transformant, and the plasmid DNA sample was sent for sequence analysis to Operon Biotechnology Co. Ltd company (Tokyo), and the cDNA base sequence in the plasmid was confirmed. In analysis of the sequence, softwares of "Sequencher DNA sequence assembly and analysis software version 4.2.2 (Gene Codes Corporation)" and "GENETYX-MAC Version. 11.1.1" software (GENETYX CORPORATION)" were used.

A transcript of a right sequence was extracted excluding a transcript of inactive RNA, as frame shift, nonsense mutation, and the like occur at the periphery of a complementarity-determining region (hereinafter referred to as "CDR region"). Furthermore, for the cDNA base sequence contained in the plasmid, the homology with Immunoglobulins database (IgBLAST, URL: www.ncbi.nlm.nih.gov/Ig-blast/) was confirmed, and the sequences of the CDR region in each variable region (CDRs; CDR1, CDR2, and CDR3), the FW region (Frame work regions), and the variable regions were determined according to the analysis method of Kabat numbering system (Kabat et al, 1991, Sequences of Proteins of Immunological Interest, National Institutes of Health Publication No. 91-3242, 5th ed., united States Department of Health and Human Services, Bethesda, Md.).

The nucleic acid sequence of the heavy chain variable region of the obtained mouse 11G9.6 antibody is SEQ ID NO: 74, and the amino acid sequence is SEQ ID NO: 75. The amino acid sequences of CDR1, CDR2, and CDR3 in the heavy chain variable region of the mouse 11G9.6 antibody are SEQ ID NO: 2, SEQ ID NO: 3, and SEQ ID NO: 4, respectively.

The nucleic acid sequence of the heavy chain variable region of the obtained mouse 3B4 antibody is SEQ ID NO: 76, and the amino acid sequence is SEQ ID NO: 77. The amino acid sequences of CDR1, CDR2, and CDR3 in the heavy chain variable region of the mouse 3B4 antibody are SEQ ID NO: 8, SEQ ID NO: 9, and SEQ ID NO: 10, respectively.

The nucleic acid sequence of the heavy chain variable region of the obtained mouse 5B7 antibody is SEQ ID NO: 78, and the amino acid sequence is SEQ ID NO: 79. The amino acid sequences of CDR1, CDR2, and CDR3 in the heavy chain variable region of the mouse 5B7 antibody are SEQ ID NO: 14, SEQ ID NO: 15, and SEQ ID NO: 16, respectively.

The nucleic acid sequence of the heavy chain variable region of the obtained mouse 7B4 antibody is SEQ ID NO: 80, and the amino acid sequence is SEQ ID NO: 81. The amino acid sequences of CDR1, CDR2, and CDR3 in the heavy chain variable region of the mouse 7B4 antibody are SEQ ID NO: 14, SEQ ID NO: 15, and SEQ ID NO: 16, respectively. The 7B4 antibody is an antibody having the same heavy chain and the light chain variable region CDR sequences as those of the 5B7 antibody.

The nucleic acid sequence of the heavy chain variable region of the obtained mouse 8C11 antibody is SEQ ID NO: 82, and the amino acid sequence is SEQ ID NO: 83. The amino acid sequences of CDR1, CDR2 and CDR3 in the heavy chain variable region of the mouse 8C11 antibody are SEQ ID NO: 20, SEQ ID NO: 21 and SEQ ID NO: 22, respectively.

The nucleic acid sequence of the heavy chain variable region of the obtained mouse 10C3 antibody is SEQ ID NO: 84, and the amino acid sequence is SEQ ID NO: 85. The amino acid sequences of CDR1, CDR2 and CDR3 in the heavy chain variable region of the mouse 10C3 antibody are SEQ ID NO: 26, SEQ ID NO: 27, and SEQ ID NO: 28, respectively.

The nucleic acid sequence of the heavy chain variable region of the obtained mouse 11D10 antibody is SEQ ID NO: 86, and the amino acid sequence is SEQ ID NO: 87. The amino acid sequences of CDR1, CDR2, and CDR3 in the heavy chain variable region of the mouse 11D10 antibody are SEQ ID NO: 26, SEQ ID NO: 27, and SEQ ID NO: 28, respectively. The 11D10 antibody is an antibody having the same light chain variable region CDR sequence to the heavy chain of the 10C3 antibody. However, the heavy chain isotype (10C3 is the constant region of the mouse IgG2a, and 11D10 is the constant region of the mouse IgG2b) is different.

The nucleic acid sequence of the heavy chain variable region of the obtained mouse 13D4 antibody is SEQ ID NO: 88, and the amino acid sequence is SEQ ID NO: 89. The amino acid sequences of CDR1, CDR2, and CDR3 in the heavy chain variable region of the mouse 13D4 antibody are SEQ ID NO: 32, SEQ ID NO: 33 and SEQ ID NO: 34, respectively.

The nucleic acid sequence of the heavy chain variable region of the obtained mouse 13H11 antibody is SEQ ID NO: 90, and the amino acid sequence is SEQ ID NO: 91. The amino acid sequences of CDR1, CDR2, and CDR3 in the heavy chain variable region of the mouse 13H11 antibody are SEQ ID NO: 38, SEQ ID NO: 39, and SEQ ID NO: 40, respectively.

The nucleic acid sequence of the heavy chain variable region of the obtained mouse 14C1 antibody is SEQ ID NO: 92, and the amino acid sequence is SEQ ID NO: 93. The amino acid sequences of CDR1, CDR2, and CDR3 in the heavy chain variable region of the mouse 14C1 antibody are SEQ ID NO: 38, SEQ ID NO: 39, and SEQ ID NO: 40, respectively. The 14C1 antibody is an antibody having the same CDR sequences of the heavy chain and light chain variable regions as those of the 13H11 antibody. However, the heavy chain isotype (13H11 is the constant region of Mouse IgG2b, and 14C1 is the constant region of mouse IgG1) is different.

The nucleic acid sequence of the light chain variable region of the mouse 11G9.6 antibody is SEQ ID NO: 94, and the amino acid sequence is SEQ ID NO: 95. The amino acid sequences of CDR1, CDR2, and CDR3 in the light chain variable region of the mouse 11G9.6 antibody are SEQ ID NO: 5, SEQ ID NO: 6, and SEQ ID NO: 7, respectively.

The nucleic acid sequence of the light chain variable region of the mouse 3B4 antibody is SEQ ID NO: 96, and the amino acid sequence is SEQ ID NO: 97. The amino acid sequences of CDR1, CDR2, and CDR3 in the light chain variable region of the mouse 3B4 antibody are SEQ ID NO: 11, SEQ ID NO: 12, and SEQ ID NO: 13, respectively.

The nucleic acid sequence of the light chain variable region of the mouse 5B7 antibody is SEQ ID NO: 98, and the amino acid sequence is SEQ ID NO: 99. The amino acid sequences of CDR1, CDR2, and CDR3 in the light chain variable region of the mouse 5B7 antibody are SEQ ID NO: 17, SEQ ID NO: 18, and SEQ ID NO: 19, respectively.

The nucleic acid sequence of the light chain variable region of the mouse 7B4 antibody is SEQ ID NO: 100, and the amino acid sequence is SEQ ID NO: 101. The amino acid sequences of CDR1, CDR2, and CDR3 in the light chain variable region of the mouse 7B4 antibody are SEQ ID NO: 17, SEQ ID NO: 18, and SEQ ID NO: 19, respectively.

The nucleic acid sequence of the light chain variable region of the mouse 8C11 antibody is SEQ ID NO: 102, and the amino acid sequence is SEQ ID NO: 103. The amino acid sequences of CDR1, CDR2, and CDR3 in the light chain variable region of the mouse 8C11 antibody are SEQ ID NO: 23, SEQ ID NO: 24, and SEQ ID NO: 25, respectively.

The nucleic acid sequence of the light chain variable region of the mouse 10C3 antibody is SEQ ID NO: 104, and the amino acid sequence is SEQ ID NO: 105. The amino acid sequences of CDR1, CDR2, and CDR3 in the light chain variable region of the mouse 10C3 antibody are SEQ ID NO: 29, SEQ ID NO: 30, and SEQ ID NO: 31, respectively.

The nucleic acid sequence of the light chain variable region of the mouse 11D10 antibody is SEQ ID NO: 106, and the amino acid sequence is SEQ ID NO: 107. The amino acid sequences of CDR1, CDR2, and CDR3 in the light chain variable region of the mouse 11D10 antibody are SEQ ID NO: 29, SEQ ID NO: 30, and SEQ ID NO: 31, respectively.

The nucleic acid sequence of the light chain variable region of the mouse 13D4 antibody is SEQ ID NO: 108, and the amino acid sequence is SEQ ID NO: 109. The amino acid sequences of CDR1, CDR2, and CDR3 in the light chain variable region of the mouse 13D4 antibody are SEQ ID NO: 35, SEQ ID NO: 36, and SEQ ID NO: 37, respectively.

The nucleic acid sequence of the light chain variable region of the mouse 13H11 antibody is SEQ ID NO: 100, and the amino acid sequence is SEQ ID NO: 111. The amino acid sequences of CDR1, CDR2, and CDR3 in the light chain variable region of the mouse 13H11 antibody are SEQ ID NO: 41, SEQ ID NO: 42, and SEQ ID NO: 43, respectively.

The nucleic acid sequence of the light chain variable region of the mouse 14C1 antibody is SEQ ID NO: 112, and the amino acid sequence is SEQ ID NO: 113. The amino acid sequences of CDR1, CDR2, and CDR3 in the light chain variable region of the mouse 14C1 antibody are SEQ ID NO: 41, SEQ ID NO: 42, and SEQ ID NO: 43, respectively.

3. Preparation of Expression Vector of Chimeric Antibody 11G9.6

3-1. Cloning of cDNA that Encodes Human Ig Constant Region

From total RNA of human PBMC, cDNAs of the human IgG1 heavy chain constant region and the human Ig kappa light chain constant region were cloned, and cloned with pCR4Blunt-TOPO vector, respectively using a commercially available kit "Zero Blunt TOPO PCR Cloning Kit" (manufactured by Invitrogen company, catalog No.: 1325137) according to the instruction attached to the kit, and transformed to *Escherichia coli* competent cell to obtain an *Escherichia coli* transformant. A plasmid was obtained from this transformant, and the plasmid DNA sample was sent for sequence analysis to Operon Biotechnology Co. Ltd (Tokyo), and the cDNA base sequence in the plasmid was confirmed.

3-2. Preparation of cDNA that Encodes Heavy Chain of Chimeric PLD4 Antibody cDNA that encodes the heavy chain of a chimeric PLD4 antibody was prepared by ligation with pEE6.4 vector expression vector that has the heavy chain variable region of the mouse 11G9.6 antibody obtained in 2-2, and the heavy chain constant region of the human IgG1. The heavy chain variable region of the mouse 11G9.6 antibody was amplified with PCR method, and a PCR product of about 450 base lengths was obtained. At this time, the primer is as shown in Table 1. The obtained PCR product was purified by 1.5% low melting point agarose method.

TABLE 1

| Primer name | Sequence |
|---|---|
| Chimera 11G9.6 antibody heavy chain expression primer | |
| 1) chi11G9VH-IF(Hind3) | 5 ace AAG CTT gcc gcc acc ATG AAA GTG TTG AGT CTG TTG TAC CTG TTG ACA GCC ATT CCT GGT ATC CTG TCT cag GTC CAA CTG CAG CAG CCT 3' (93-mer) (SEQ ID NO: 114) |
| 2) chi11G9VH-444R(ApaI) | 5' cga tgg gcc ctt ggt gct agc TGA GGA GAC GGT GAC TGA GGT 3' (42-mer) (SEQ ID NO: 115) |
| Chimera 11G9 antibody light chain expression primer | |
| 5) chi11G9VL-IF(Hind) | 5' acc AAG CTT gcc gcc acc ATG ATG TCC TCT GCT CAG TTC 3' (39-mer) (SEQ ID NO: 116) |
| 6 chi11G9VL-408R | 5' agc cac agt tcg TTT GAT TTC CAG CTT GGT GCC 3' (33-mer) (SEQ ID NO: 117) |
| 7 chi11G9VL-385F | 5' CTG GAA ATC AAA cga act gtg gct gca cca tct 3' (33-mer) (SEQ ID NO: 118) |
| 8) chi11G9VL-726R(RI) | 5' aaa GAA TTC cta gca ctc tcc cct gtt gaa 3' (30-mer) (SEQ ID NO: 119) |

The heavy chain variable region of the mouse 11G9.6 antibody obtained in 2-2 was subjected to PCR method to obtain "PCR Product that encodes 11G9.6 heavy chain variable region". The PCR Product that encodes the heavy chain variable region of the 11G9.6 was digested with Hind III and Apa I restriction enzymes, and purified with 1.5% agarose gel method. This was dissolved in ddH$_2$O, which was taken as a solution of a cDNA fragment that encodes the heavy chain variable region.

The obtained cDNA was amplified with PCR from pCR4Blunt-TOPO plasmid clone containing 11G9.6 V$_H$ region, using primers chi11G9VH-IF (Hind III) and chi11G9VL-408R, in which the restriction sites (Hind III and Apa I) preferred for cloning of the V$_H$ code region of chimeric 11G9.6 to pEE6.4 vector (manufactured by Lonza Biologics, Slough, UK), and ideal Kozak sequence (GCCGCCACC) were introduced as the cloning sites of Hind III and Apa I. Chi11G9VH-pEE6.4 vector contains the heavy chain constant region of human IgG1. The V$_H$ PCR fragment was inserted into pEE6.4 vector with an in-frame using Hind III and Apa I. The construct was investigated by cDNA base sequence analysis. For the sequence analysis, the plasmid DNA sample was sent to Operon Biotechnology Co. Ltd (Tokyo), and the cDNA base sequence in the plasmid was confirmed.

3.3 Preparation of cDNA that Encodes the Light Chain of Chimeric PLD4 Antibody

In order to prepare cDNA that encodes the light chain of the chimeric PLD4 antibody, the light chain variable region of the mouse 11G9.6 antibody obtained in 2-3, and the light chain constant region of the human Ig kappa obtained in 3-2 were fused to give a PCR fragment, and the PCR fragment was amplified to a PCR product of about 730 base lengths by an approach based on an overlap extension PCR method.

The PCR product that encodes the light chain variable region of the 11G9.6 was digested with Hind III and EcoR I restriction enzymes, and purified with 1.5% agarose gel method. This was dissolved in ddH$_2$O, which was taken as a solution of a cDNA fragment that encodes the light chain variable region.

The obtained cDNA that encodes VL of the chimeric 11 G9 was amplified with PCR from pCR4Blunt-TOPO plasmid clone containing 11G9.6 VL region, using primers chi11G9VL-IF (Hind) and chi11G9VL-726R (R I), in which the restriction sites (Hind III and EcoR I) preferred for cloning of pEE14.4 vector (manufactured by Lonza Biologics), and ideal Kozak sequence were introduced. The Chi11G9VL-pEE14.4 vector contains the light chain constant region of kappa. The VL PCR fragment was inserted into pEE14.4 vector with an in-frame using Hind III and EcoR I. The construct was investigated by cDNA base sequence analysis.

3.4 Construction of Double Gene Lonza Expression Vector of Chimeric PLD4 Antibody (ch11G9VH/VL)

The chimeric PLD4 antibody (chi11G9DG vector) Lonza expression vector combined in one 2-gene vector was constructed from chimeric PLD4 antibody heavy chain expression vector (chi11G9VH-pEE6.4), and chimeric PLD4 antibody light chain vector (chi11G9VL-pEE14.4) by standard cloning technology.

4. Transient Expression in 293F Cell

80 μg of chi11G9DG Lonza vector DNA, a transient expression vector plasmid, was used.

293F cells were combined to 80 mL in 8×10$^5$ cells/mL in 250 mL Erlenmyer flask (catalog No. 431144; manufactured by CORNING) on the previous day of transfection, and cultured at the conditions of 37° C. and 8% CO$_2$ concentration for 7 days with shaking.

After the culture for 7 days, the culture liquid of the transfected 293F cell was collected to 50 mL tube, and centrifuge was performed at the conditions of 2,070 g at 4° C. for 5 minutes. The supernatant was filtered with a syringe filter having 0.45 μm pore size (catalog No. 431220; manufactured by CORNING), and the culture supernatant was collected for antibody purification.

5. Purification of Anti-PLD4 Chimeric Antibody

Using the collected culture supernatant, antibody purification was performed using AKTA-FPLC (manufactured by GE Healthcare Japan) and software Unicorn 5.0.

As the column for chimeric 11G9.6 antibody purification, HiTrap MabSelect SuRe 1 mL (catalog No. 11-0034-93, Lot No. 10032458; manufactured by GE Healthcare Japan) was used. The column conditions are as follows. Affinity purification was performed using a binding buffer (20 mM Sodium phosphate, 0.15 M NaCl, pH 7.4) and an elution buffer (20 mM Sodium citrate, pH 3.4). In order to replace the buffer of the antibody after purification with PBS, buffer exchange was performed using Slide-A-Lyzer MINI Dialysis Unit 10kMWCO.

The concentration of the purified antibody was calculated by measuring the absorbance at 280 nm, wherein 1 mg/mL was calculated as 1.38 OD.

For the ch11G9.6Ab of the purified anti-PLD4 chimeric antibody, the protein quality was analyzed with Flow cytometry method and SDS-PAGE.

Example 8

Figure 22:
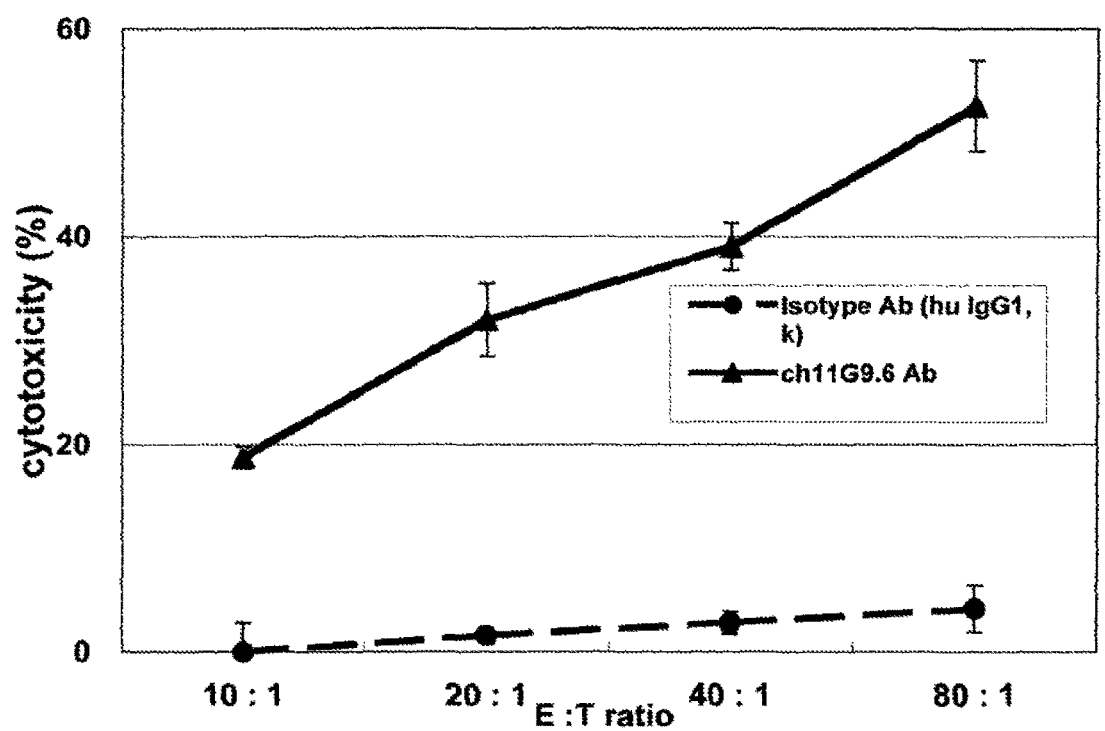
FIG. 22 is a graph that illustrates ADCC activity of anti-PLD4 chimeric antibody. Target cell: human PLD4-CHO stable transfectant antibody concentration: 10 µg/mL.

Antibody-dependent cellular cytotoxicity (ADCC activity) of the prepared anti-human PLD4 chimeric antibody (ch11G9.6 Ab) was measured. For the activity, cell toxicity calculated from measurement value of lactase dehydrogenase (LDH) released from the cell was used an index. The human peripheral blood mononuclear cell that became an effector cell was purified with specific gravity centrifuge using HISTOPAQUE-1077. As the cell to be a target, mandatory transformed cell of human PLD4 gene employing a CHO-K1 cell strain (Chinese hamster ovary cell strain) (Hereinafter, HuPLD4-CHO) was used (2×10$^4$/well). The effector and the target cell were mixed in a ratio of 10:1, 20:1, 40:1, and 80:1, and added with 10 mg/mL of ch11G9Ab or isotype control antibody (human IgG1, κ), cultured at 37° C. for 4 hours, and the effect of cytotoxicity activity of the antibody was evaluated. As a result thereof, ch11 G9Ab of the anti-hPLD4 chimeric antibody exhibited maximum about 50% or so of ADCC activity to the HuPLD4-CHO cells that was the target, dependently on the effector cell (FIG. 22). Such results proved that the prepared anti-PLD4 chimeric antibody damaged the cells that expressed PLD4 selectively.

Figure 24:
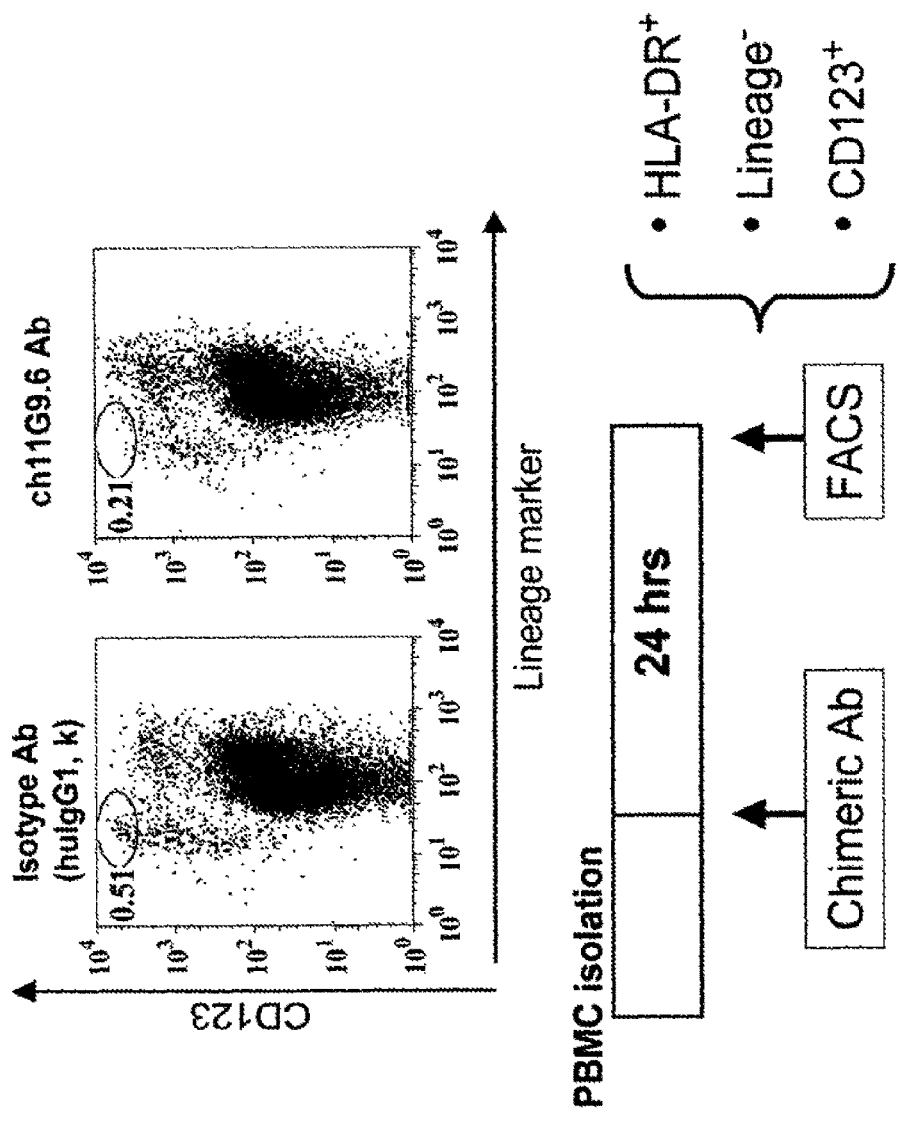
FIG. 24 is a diagram that illustrates human pDC loss after treatment with anti-PLD4 chimeric antibody.

The effects of the anti-PLD4 antibody on pDC were reviewed. PBMC from the human peripheral blood was purified, mixed with 10 μg/mL of anti-human PLD4 chimeric antibody and cultured for 24 hours. Then, the cells were stimulated for 24 hours with CpG2216, which was a ligand of Toll-like receptor 9 expressed in pDC, to induce IFNα production. After the CpG stimulation, the amount of produced IFNα was tested, and it was confirmed that IFNα production was completely inhibited by treatment of ch11G9Ab of the anti-PLD4 chimeric antibody (FIG. 23). As for this mechanism, it was found out that when the cells were collected 24 hours after the ch11G9Ab treatment, and pDC cells were confirmed with triple staining of the anti- CD123 antibody, anti-HLA-DR antibody and anti-Lineage 1 antibody, pDC cell population decreased more than treatment of isotype control antibody (human IgG1, κ) (FIG. 24). These results indicated that the anti-PLD4 chimeric antibody damaged pDC that specifically expressed PLD4, and as a result thereof, IFNα production by CpG2216 stimulation was inhibited.

Figure 25:
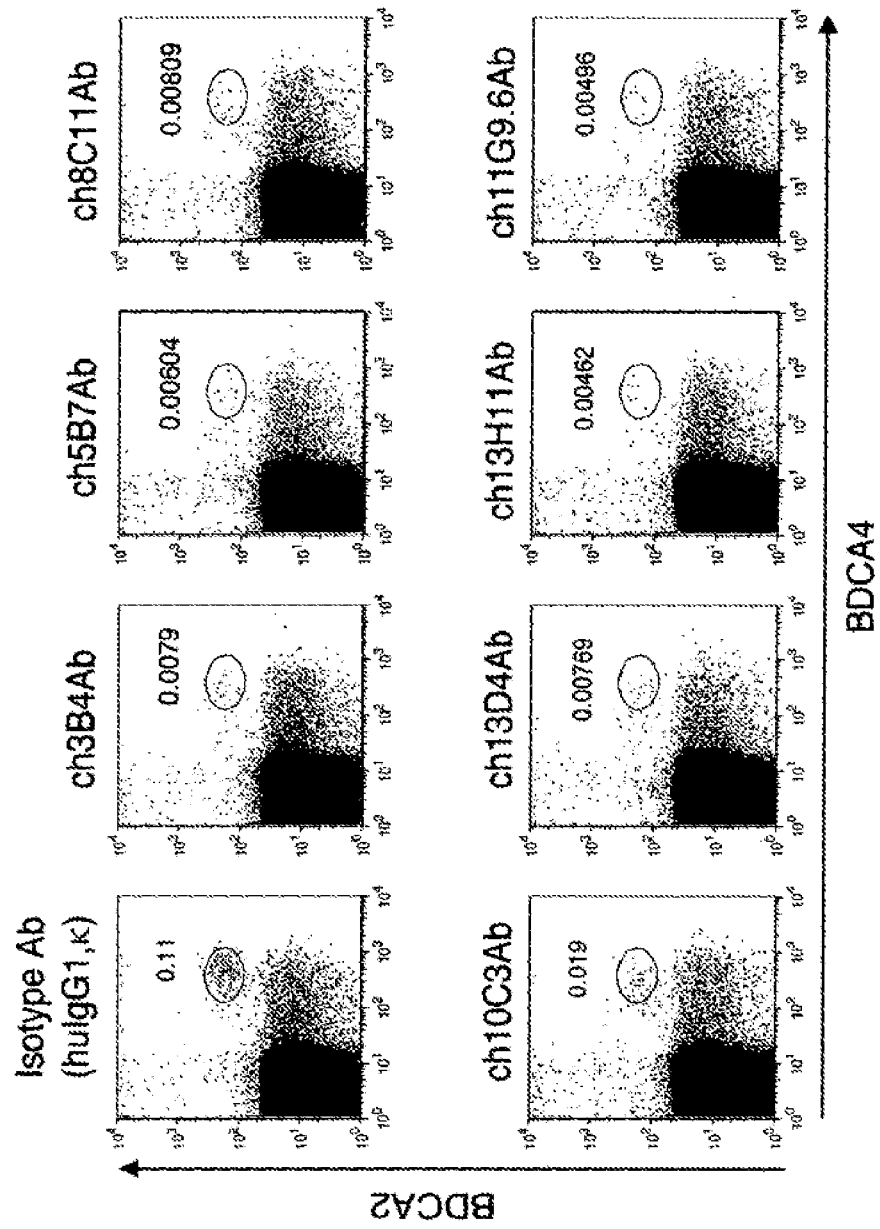
FIG. 25 is a result of ADCC assay with chimeric anti-PLD4 Abs against human primary pDCs.

In addition to ch11G9.6Ab, biological function of the chimeric anti-PLD4 Abs such as ch3B4Ab, ch5B7Ab, ch8C11Ab, ch10C3Ab, ch13D4Ab, ch13H11Ab were examined in human primary pDCs. In order to examine ADCC assay for pDCs, whole human PBMCs were cultured with ch3B4Ab, ch5B7Ab, ch8C11Ab, ch10C3Ab, ch13D4Ab, ch13H11Ab, ch11G9.6Ab, or isotyope Ab for 14 h. The cells were harvested and stained BDCA2 and BDCA4 to identify pDCs by flow cytometry. The treatment with the chimeric PLD4 Abs completely depleted pDCs compared to isotype Ab-treated PBMCs (FIG. 25). IFNα production was also measured in the culture of PBMCs with the chimeric anti-PLD4 Abs. Whole human PBMCs were treated with the ch3B4Ab, ch5B7Ab, ch8C11Ab, ch10C3Ab, ch13D4Ab, ch13H11Ab, ch11G9.6Ab, or isotype Ab. 24 h later, IFNα inducible CpG2216 was added to the culture and the cells were further cultured for 24 h. The culture supernatants were harvested and measured IFNα production by ELISA. All of the chimeric PLD4 Ab-treated PBMCs completely abolished IFNα production compared to isotype Ab-treated PBMCs (FIG. 26). These results indicated that the chimeric anti-PLD4 Ab abolished pDC function such as a large amount of IFNα production by depleting pDCs via ADCC activity.

1. The nucleic acid sequence of the heavy chain variable region of the obtained anti-PLD4 mouse 11G9.6 antibody is SEQ ID NO: 74, and the amino acid sequence is SEQ ID NO: 75. The amino acid sequences of CDR1, CDR2, and CDR3 in the heavy chain variable region of the mouse 11G9.6 antibody are SEQ ID NO: 2, SEQ ID NO: 3, and SEQ ID NO: 4, respectively.

The nucleic acid sequence of the heavy chain variable region of anti-PLD4 mouse 11G9.6 antibody (504 bp) [Upper case: mouse 11G9.6VH variable region, lower case: mouse IgG2b heavy chain constant region] (SEQ ID NO: 74)

ATGAGATCACAGTTCTCTATACAGTTACTGAGCACACAGAACCTCACCTT

GGGATGGAGCTGTATCATCCTCTTCTTGGTAGCAACAGCTACAGGTGTCC

ACTCCCAGGTCCAACTGCAGCAGCCTGGGGCTGAACTGGTGAAGCCTGGG

ACTTCAGTGAAAATGTCCTGCAAGGCTTCTGGCTACACCTTCACCAGCTA

CTGGATGCACTGGGTGAAGCAGAGGCCGGGACAAGGCCTTGAGTGGATTG

GAGATATTTATCCTGGTAGTGATAGTACTAACTACAATGAGAAGTTCAAG

AGCAAGGCCACACTGACTGTAGACACATCCTCCAGCACAGCCTACATGCA

ACTCAGCAGCCTGACATCTGAGGACTCTGCGGTCTATTACTGTGCAAGAG

GAGGGTGGTTGGATGCTATGGACTACTGGGGTCAAGGAACCTCAGTCACC

GTCTCCTCAgccaaaacaacaccccatcagtctatccactggcccctaa gggc

The amino acid sequence of the heavy chain variable region of mouse 11G9.6 antibody (168 a.a.) [Upper case: mouse 11G9.6VH variable region, lower case: mouse IgG2b heavy chain constant region]. The underlined sequence represents a signal sequence, and the double underline represents CDR regions (CDR1, CDR2, and CDR3) (SEQ ID NO: 75).

MRSQFSIQLLSTQNLTLGWSCIILFLVATATGVHSQVQLQQPGAELVKPG

TSVKMSCKASGYTFT<u>SYWMH</u>WVKQRPGQGLEWIG<u>DIYPGSDSTNYNEKFK</u>

<u>S</u>KATLTVDTSSSTAYMQLSSLTSEDSAVYYCAR<u>GGWLDAMDY</u>WGQGTSVT

VSSakttppsvyplapkg

CDR1 of the heavy chain variable region of 11G9.6 antibody (SEQ ID NO: 2)
SYWMH

CDR2 of the heavy chain variable region of 11G9.6 antibody (SEQ ID NO: 3)
DIYPGSDSTNYNEKFKS CDR3 of the heavy chain variable region of 11G9.6 antibody (SEQ ID NO: 4)
GGWLDAMDY The nucleic acid sequence of the light chain variable region of the obtained anti-PLD4 mouse 11G9.6 antibody is SEQ ID NO: 38, and the amino acid sequence is SEQ ID NO: 39. The amino acid sequences of CDR1, CDR2, and CDR3 in the light chain variable region of the mouse 11G9.6 antibody are SEQ ID NO: 40, SEQ ID NO: 41, and SEQ ID NO: 42, respectively.

The nucleic acid sequence of the light chain variable region of anti-PLD4 mouse 11G9.6 antibody (421 bp) [Upper case: mouse 11G9.6VL variable region, lower case: mouse Igκ light chain constant region] (SEQ ID NO: 94)

ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGAGACAGAGTCACCATCAGTTGCAGGGCAAGTCAGGACATTAGC

AATTATTTAAACTGGTATCAGCAGAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAGCAA

GAAGATATTGCCACTTACTTTTGCCAACAGGGTAATACGCTTCCGTGGAC

GTTCGGTGGAGGCACCAAGCTGGAAATCAAAcgggctgatgctgcaccaa ctgtatccatcaagggcgaat

The amino acid sequence of the light chain variable region of the mouse 11G9.6 antibody (140 a.a.) [Upper case: mouse 11G9.6VL variable region, lower case: light chain constant region of mouse IgK]. The underlined sequence represents a signal sequence, and the double underline represents CDR regions (CDR1, CDR2, and CDR3) (SEQ ID NO: 95).

MMSSAQFLGLLLLCFQGTRCDIQMTQTTSSLSASLGDRVTISC<u>RASQDIS</u>

<u>NYLN</u>WYQQKPDGTVKLLIY<u>YTSRLHS</u>GVPSRFSGSGSGTDYSLTISNLEQ

EDIATYFC<u>QQGNTLPW</u>TFGGGTKLEIKradaaptvsikge

CDR1 of the light chain variable region of 11G9.6
antibody
(SEQ ID NO: 5)
RASQDISNYLN CDR2 of the light chain variable region of 11G9.6
antibody
(SEQ ID NO: 6)
YTSRLHS CDR3 of the light chain variable region of 11G9.6
antibody
(SEQ ID NO: 7)
QQGNTLPW 2. The nucleic acid sequence of the heavy chain variable region of the obtained anti-PLD4 mouse 3B4 antibody is SEQ ID NO: 76, and the amino acid sequence is SEQ ID NO: 77. The amino acid sequences of CDR1, CDR2, and CDR3 in the heavy chain variable region of the mouse 3B4 antibody are SEQ ID NO: 8, SEQ ID NO: 9, and SEQ ID NO: 10, respectively.

The nucleic acid sequence of the heavy chain variable region of anti-PLD4 mouse 3B4 antibody (437 bp) [Upper case: mouse 3B4VH variable region, lower case: mouse IgG1 heavy chain constant region] (SEQ ID NO:76)

ATGGAATGTAACTGGATACTTCCTTTTATTCTGTCGGTAATTTCAGGGGT

CTCCTCAGAGGTTCAGCTCCAGCAGTCTGGGACTGTGCTGTCAAGGCCTG

GGGCTTCCGTGACGATGTCCTGCAAGGCTTCTGGCGACAGCTTTACCACC

TACTGGATGCACTGGGTAAAACAGAGGCCTGGACAGGGTCTAGAATGGAT

TGGTGCTATCTATCCTGGAAATAGTGAAACTAGCTACAACCAGAAGTTCA

AGGGCAAGGCCAAACTGACTGCAGTCACATCCGCCAGCACTGCCTATATG

GAGTTCACTAGCCTGACAAATGAGGACTCTGCGGTCTATTACTGTACGGG

GGGTTATTCCGACTTTGACTACTGGGGCCAAGGCACCACTCTCACAGTCT

CCTCAgccaaaacgacacccccatctgtctatccact

The amino acid sequence of the heavy chain variable region of the mouse 3B4 antibody (145 a.a.) [Upper case: mouse 3B4VH variable region, lower case: mouse IgG1 heavy chain constant region]. The underlined sequence represents a signal sequence, and the double underline represents CDR regions (CDR1, CDR2, and CDR3). (SEQ ID NO:77)

<u>MECNWILPFILSVISGVSS</u>EVQLQQSGTVLSRPGASVTMSCKASGDSFT<u>T</u>

<u>YWMH</u>WVKQRPGQGLEWIG<u>AIYPGNSETSYNQKFKG</u>KAKLTAVTSASTAYM

EFTSLTNEDSAVYYCTGGYSDFDYWGQGTTLTVSSakttppsvyp

CDR1 of the heavy chain variable region of 3B4
antibody
(SEQ ID NO: 8)
TYWMH

CDR2 of the heavy chain variable region of 3B4
antibody
(SEQ ID NO: 9)
AIYPGNSETSYNQKFKG CDR3 of the heavy chain variable region of 3B4
antibody
(SEQ ID NO: 10)
GYSDFDY The nucleic acid sequence of the light chain variable region of the obtained anti-PLD4 mouse 3B4 antibody is SEQ ID NO: 96, and the amino acid sequence is SEQ ID NO: 97. The amino acid sequences of CDR1, CDR2, and CDR3 in the light chain variable region of the mouse 3B4 antibody are SEQ ID NO: 11, SEQ ID NO: 12, and SEQ ID NO: 13, respectively.

The nucleic acid sequence of the light chain variable region of anti-PLD4 mouse 3B4 antibody (459 bp) [Upper case: mouse 3B4VL variable region, lower case: mouse IgK light chain constant region] (SEQ ID NO:96)

ATGATGGTCCTTGCTCAGTTTCTTGCATTCTTGTTGCTTTGGTTTCCAGG

TGCAGGATGTGACATCCTGATGACCCAATCTCCATCCTCCATGTCTGTAT

CTCTGGGAGACACAGTCAGCATCACTTGCCATGCAAGTCAGGGCATTAGA

AGTAATATAGGGTGGTTGCAGCAGAAACCAGGGAAATCATTTAAGGGCCT

GATCTTTCATGGAACCAACTTGGAAGATGGAGTTCCATCAAGGTTCAGTG

GCAGAGGATCTGGAGCAGATTATTCTCTCACCATCAACAGCCTGGAATCT

GAAGATTTTGCAGACTATTACTGTGTACAGTATGTTCAGTTTCCTCCAAC

GTTCGGCTCGGGGACAAAGTTGGAAATAAGAcgggctgatgctgcaccaa ctgtatccatcttcccaccatccagtgagcagttaacatctggaggtgcc tcagtcgtg The amino acid sequence of the light chain variable region of the mouse 3B4 antibody (153 a.a.) [Upper case: mouse 3B4VL variable region, lower case: mouse IgK light chain constant region]. The underlined sequence represents a signal sequence, and the double underline represents CDR regions (CDR1, CDR2, and CDR3). (SEQ ID NO:97)

<u>MMVLAQFLAFLLLWFPGAGC</u>DILMTQSPSSMSVSLGDTVSITC<u>HASQGIR</u>

<u>SNIG</u>WLQQKPGKSFKGLIF<u>HGTNLED</u>GVPSRFSGRGSGADYSLTINSLES

EDFADYYC<u>VQYVQFP</u>PTFGSGTKLEIRradaaptvsifppsseqltsgga svv

CDR1 of the light chain variable region of 3B4
antibody
(SEQ ID NO: 11)
HASQGIRSNIG CDR2 of the light chain variable region of 3B4
antibody
(SEQ ID NO: 12)
HGTNLED CDR3 of the light chain variable region of 3B4
antibody
(SEQ ID NO: 13)
VQYVQFP 3. The nucleic acid sequence of the heavy chain variable region of the obtained anti-PLD4 mouse 5B7 antibody is SEQ ID NO: 78, and the amino acid sequence is SEQ ID NO: 79. The amino acid sequences of CDR1, CDR2, and CDR3 in the heavy chain variable region of the mouse 5B7 antibody are SEQ ID NO: 14, SEQ ID NO: 15, and SEQ ID NO: 16, respectively.

The nucleic acid sequence of the heavy chain variable region of anti-PLD4 mouse 5B7 antibody (475 bp) [Upper case: mouse 5B7VH variable region, lower case: mouse IgG2b heavy chain constant region] (SEQ ID NO:78)

ATGGGATGGAGCTGGATCTTTCTCTTCCTCCTGTCAGGAACTGCAGGCGT

CCACTCTGAGGTCCAGCTTCAGCAGTCAGGACCTGAACTGGTGAAACCTG

GGGCCTCAGTGAAGATATCCTGCAAGGCTTCTGGATACACATTCACTGAC

TACAACTTGCACTGGGTGAAGCAGAGCCATGGAAAGAGCCTTGAGTGGAT

TGGATATATTTATCCTTACAATGGTAATACTGGCTACAACCAGAAGTTCA

AGAGGAAGGCCACATTGACTGTAGACAATTCCTCCGGCACAGTCTACATG

GAGCTCCGCAGCCTGACATCTGAGGACTCTGCAGTCTATTACTGTGCAAG

AGGAGGGATCTATGATGATTACTACGACTATGCTATCGACTATTGGGGTC

AAGGAACCTCAGTCACCGTCTCCTCAgccaaaacaacacccccatcagtc tatccactggcccctaagggcgaat

The amino acid sequence of the heavy chain variable region of the mouse 5B7 antibody (158 a.a.) [Upper case: mouse 5B7VH variable region, lower case: mouse IgG2b heavy chain constant region]. The underlined sequence represents a signal sequence, and the double underline represents CDR regions (CDR1, CDR2, and CDR3). (SEQ ID NO:79)

<u>MGWSWIFLFLLSGTAGVHS</u>EVQLQQSGPELVKPGASVKISCKASGYTFT<u>D</u>

<u>YNLH</u>WVKQSHGKSLEWIG<u>YIYPYNGNTGYNQKFKR</u>KATLTVDNSSGTVYM

ELRSLTSEDSAVYYCAR<u>GGIYDDYYDYAIDY</u>WGQGTSVTVSSakttppsv yplapkge

CDR1 of the heavy chain variable region of 5B7 antibody
(SEQ ID NO: 14)
DYNLH

CDR2 of the heavy chain variable region of 5B7 antibody
(SEQ ID NO: 15)
YIYPYNGNTGYNQKFKR CDR3 of the heavy chain variable region of 5B7 antibody
(SEQ ID NO: 16)
GGIYDDYYDYAIDY The nucleic acid sequence of the light chain variable region of the obtained anti-PLD4 mouse 5B7 antibody is SEQ ID NO: 98, and the amino acid sequence is SEQ ID NO: 99. The amino acid sequences of CDR1, CDR2, and CDR3 in the light chain variable region of the mouse 5B7 antibody are SEQ ID NO: 17, SEQ ID NO: 18, and SEQ ID NO: 19, respectively.

The nucleic acid sequence of the light chain variable region of anti-PLD4 mouse 5B7 antibody (467 bp) [Upper case: mouse 5B7VL variable region, lower case: mouse IgK light chain constant region] (SEQ ID NO:98)

ATGAGTGTGCCCACTCAGGTCCTGGGGTTGCTGCTGCTGTGGCTTACAGA

TGCCAGATGTGACATCCAGATGACTCAGTCTCCAGCCTCCCTATCTGTAT

CTGTGGGAGAAACTGTCGCCATCACATGTCGAGCAAGTGAGAATATTTAC

AGTCATATAGCATGGTATCAGCAGAAAGAGGGAAAATCTCCTCAGCGCCT

GGTCTATGGTGCAACAAACTTAGCACATGGTGTGCCATCAAGGTTCAGTG

GCAGTGGATCAGGCACACAGTATTCCCTCAAGATCAACAGCCTTCAGTCT

GAAGATTTTGGGAGTTATTACTGTCAACATTTTTGGGGTACTCCGTGGAC

GTTCGGTGGAGGCACCAAGCTGGAAATCAAAcgggctgatgctgcaccaa ctgtatccatcttcccaccatccagtgagcagttaacatctggaggtgcc tcagtcgtgtgcttctt The amino acid sequence of the light chain variable region of the mouse 5B7 antibody (155 a.a.) [Upper case: mouse 5B7VL variable region, lower case: mouse IgK light chain constant region]. The underlined sequence represents a signal sequence, and the double underline represents CDR regions (CDR1, CDR2, and CDR3). (SEQ ID NO:99)

<u>MSVPTQVLGLLLLWLTDARC</u>DIQMTQSPASLSVSVGETVAITC<u>RASENIY</u>

<u>SHIA</u>WYQQKEGKSPQRLVY<u>GATNLAH</u>GVPSRFSGSGSGTQYSLKINSLQS

EDFGSYYC<u>QHFWGTP</u>WTFGGGTKLEIKradaaptvsifppsseqltsgga svvcf

CDR1 of the light chain variable region of 5B7 antibody
(SEQ ID NO: 17)
RASENIYSHIA CDR2 of the light chain variable region of 5B7 antibody
(SEQ ID NO: 18)
GATNLAH CDR3 of the light chain variable region of 5B7 antibody
(SEQ ID NO: 19)
QHFWGTP 4. The nucleic acid sequence of the heavy chain variable region of the obtained anti-PLD4 mouse 7B4 antibody is SEQ ID NO: 80, and the amino acid sequence is SEQ ID NO: 81. The amino acid sequences of CDR1, CDR2, and CDR3 in the heavy chain variable region of the mouse 7B4 antibody are SEQ ID NO: 14, SEQ ID NO: 15, and SEQ ID NO: 16, respectively.

The nucleic acid sequence of the heavy chain variable region of anti-PLD4 mouse 7B4 antibody (470 bp) [Upper case: mouse 7B4VH variable region, lower case: mouse IgG2b heavy chain constant region] (SEQ ID NO:80)

ATGGGATGGAGCTGGATCTTTCTCTTCCTCCTGTCAGGAACTGCAGGCGT

CCACTCTGAGGTCCAGCTTCAGCAGTCAGGACCTGAACTGGTGAAACCTG

GGGCCTCAGTGAAGATATCCTGCAAGGCTTCTGGATACACATTCACTGAC

TACAACTTGCACTGGGTGAAGCAGAGCCATGGAAAGAGCCTTGAGTGGAT

TGGATATATTTATCCTTACAATGGTAATACTGGCTACAACCAGAAGTTCA

AGAGGAAGGCCACATTGACTGTAGACAATTCCTCCGGCACAGTCTACATG

GAGCTCCGCAGCCTGACATCTGAGGACTCTGCAGTCTATTACTGTGCAAG

-continued
AGGAGGGATCTATGATGATTACTACGACTATGCTATCGACTATTGGGGTC

AAGGAACCTCAGTCACCGTCTCCTCAgccaaaacaacaccccatcagtc tatccactggcccctaaggg

The amino acid sequence of the heavy chain variable region of the mouse 7B4 antibody (156 a.a.) [Upper case: mouse 7B4VH variable region, lower case: mouse IgG2b heavy chain constant region]. The underlined sequence represents a signal sequence, and the double underline represents CDR regions (CDR1, CDR2, and CDR3). (SEQ ID NO:81)

MGWSWIFLFLLSGTAGVHSEVQLQQSGPELVKPGASVKISCKASGYTFTD

YNLHWVKQSHGKSLEWIGYIYPYNGNTGYNQKFKRKATLTVDNSSGTVYM

ELRSLTSEDSAVYYCARGGIYDDYYDYAIDYWGQGTSVTVSSakttppsv yplapk

CDR1 of the heavy chain variable region of 7B4 antibody
(SEQ ID NO: 14)
DYNLH

CDR2 of the heavy chain variable region of 7B4 antibody
(SEQ ID NO: 15)
YIYPYNGNTGYNQKFKR CDR3 of the heavy chain variable region of 7B4 antibody
(SEQ ID NO: 16)
GGIYDDYYDYAIDY The nucleic acid sequence of the light chain variable region of the obtained anti-PLD4 mouse 7B4 antibody is SEQ ID NO: 100, and the amino acid sequence is SEQ ID NO: 101. The amino acid sequences of CDR1, CDR2, and CDR3 in the light chain variable region of the mouse 7B4 antibody are SEQ ID NO: 17, SEQ ID NO: 18, and SEQ ID NO: 19, respectively.

The nucleic acid sequence of the light chain variable region of anti-PLD4 mouse 7B4 antibody (454 bp) [Upper case: mouse 7B4VL variable region, lower case: mouse IgK light chain constant region] (SEQ ID NO: 100)

ATGAGTGTGCCCACTCAGGTCCTGGGGTTGCTGCTGCTGTGGCTTACAGA

TGCCAGATGTGACATCCAGATGACTCAGTCTCCAGCCTCCCTATCTGTAT

CTGTGGGAGAAACTGTCGCCATCACATGTCGAGCAAGTGAGAATATTTAC

AGTCATATAGCATGGTATCAGCAGAAAGAGGGAAAATCTCCTCAGCGCCT

GGTCTATGGTGCAACAAACTTAGCACATGGTGTGCCATCAAGGTTCAGTG

GCAGTGGATCAGGCACACAGTATTCCCTCAAGATCAACAGCCTTCAGTCT

GAAGATTTTGGGAGTTATTACTGTCAACATTTTTGGGGTACTCCGTGGAC

GTTCGGTGGAGGCACCAAGCTGGAAATCAAAcgggctgatgctgcaccaa ctgtatccatcttccaccatccagtgagcagttaacatctggaggtgcc tcag The amino acid sequence of the light chain variable region of the mouse 7B4 antibody (151 a.a.) [Upper case: mouse 7B4VL variable region, lower case: mouse IgK light chain constant region]. The underlined sequence represents a signal sequence, and the double underline represents CDR regions (CDR1, CDR2, and CDR3). (SEQ ID NO:101)

MSVPTQVLGLLLLWLTDARCDIQMTQSPASLSVSVGETVAITCRASENIY

SHIAWYQQKEGKSPQRLVYGATNLAHGVPSRFSGSGSGTQYSLKINSLQS

EDFGSYYCQHFWGTPWTFGGGTKLEIKradaaptvsifppsseqltsgga s

CDR1 of the light chain variable region of 7B4 antibody
(SEQ ID NO: 17)
RASENIYSHIA CDR2 of the light chain variable region of 7B4 antibody
(SEQ ID NO: 18)
GATNLAH CDR3 of the light chain variable region of 7B4 antibody
(SEQ ID NO: 19)
QHFWGTP 5. The nucleic acid sequence of the heavy chain variable region of the obtained anti-PLD4 mouse 8C11 antibody is SEQ ID NO: 82, and the amino acid sequence is SEQ ID NO: 83. The amino acid sequences of CDR1, CDR2, and CDR3 in the heavy chain variable region of the mouse 8C11 antibody are SEQ ID NO: 20, SEQ ID NO: 21, and SEQ ID NO: 22, respectively.

The nucleic acid sequence of the heavy chain variable region of anti-PLD4 mouse 8C11 antibody (462 bp) [Upper case: mouse 8C11VH variable region, lower case: mouse IgG2b heavy chain constant region] (SEQ ID NO:82)

ATGGGATGGAGCTATATCATCCTCTTTTTGGTAGCAACAGCAACAGGGGT

CCACTCCCAGGTCCAACTGCAGCAGTCGGGGGCTGAACTGGTGAAGCCTG

GGGCTTCAGTGAAGTTGTCCTGCAAGGCTTCTGGCTACACCTTCACCAGC

TACTATTTGTACTGGGTGAGGCAGAGGCCTGGACAAGGCCTTGAGTGGAT

TGGACTGATTAATCCTACCAATAGTGATACTATCTTCAATGAGAAGTTCA

AGAGCAAGGCCACACTGACTGTAGACAAATCCTCCAGCACAGCATACATG

CAACTCAGCAGCCTGACATCTGAGGACTCTGCGGTCTATTACTGTACACG

AGAGGGGGATATGGTTACGGCCCGTTTGCTTACTGGGGCCAAGGGACTC

TGGTCACTGTCTCTGCAgccaaaacaacaccccatcagtctatccactg gcccctaagggc

The amino acid sequence of the heavy chain variable region of the mouse 7B4 antibody (154 a.a.) [Upper case: mouse 8C11VH variable region, lower case: mouse IgG2b heavy chain constant region]. The underlined sequence represents a signal sequence, and the double underline represents CDR regions (CDR1, CDR2, and CDR3). (SEQ ID NO:83)

MGWSYIILFLVATATGVHSQVQLQQSGAELVKPGASVKLSCKASGYTFTS

YYLYWVRQRPGQGLEWIGLINPTNSDTIFNEKFKSKATLTVDKSSSTAYM

-continued
QLSSLTSEDSAVYYCTR<u>EGGYGYGPFAY</u>WGQGTLVTVSAakttppsvypl apkg

CDR1 of the heavy chain variable region of 8C11
antibody
(SEQ ID NO: 20)
SYYLY

CDR2 of the heavy chain variable region of 8C11
antibody
(SEQ ID NO: 21)
LINPTNSDTIFNEKFKS CDR3 of the heavy chain variable region of 8C11
antibody
(SEQ ID NO: 22)
EGGYGYGPFAY The nucleic acid sequence of the light chain variable region of the obtained anti-PLD4 mouse 8C11 antibody is SEQ ID NO: 102, and the amino acid sequence is SEQ ID NO: 103. The amino acid sequences of CDR1, CDR2, and CDR3 in the light chain variable region of the mouse 8C11 antibody are SEQ ID NO: 23, SEQ ID NO: 24, SEQ ID NO: 25, respectively.

The nucleic acid sequence of the light chain variable region of anti-PLD4 mouse 8C11 antibody (457 bp) [Upper case: mouse 8C11VL variable region, lower case: mouse Igκ light chain constant region] (SEQ ID NO: 102)

ATGAAGTTGCCTGTTAGGCTGTTGGTGCTGATGTTCTGGATTCCTGCTTC

CAGCAGTGATGTTGTGATGACCCAAACTCCACTCTCCCTGCCTGTCAGTC

TTGGAGATCAAGCCTCCATCTCTTGCACATCTAGTCAGACCCTTGTACAC

AGTAATGGAAACACCTATTTACATTGGTACCTGCAGAAGCCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAGTTTATTTCTGCTCTCACAGTACACA

TGTTCCATTCACGTTCGGCTCGGGGACAAAGTTGGAAATAAAAcgggctg atgctgcaccaactgtatccatcttcccaccatccagtgagcagttaaca tctggag The amino acid sequence of the light chain variable region of the mouse 8C11 antibody (152 a.a.) [Upper case: mouse 8C11VL variable region, lower case: mouse IgK light chain constant region]. The underlined sequence represents a signal sequence, and the double underline represents CDR regions (CDR1, CDR2, and CDR3). (SEQ ID NO: 103)

<u>MKLPVRLLVLMFWIPASSS</u>DVVMTQTPLSLPVSLGDQASISC<u>TSSQTLVH</u>

<u>SNGNTYLH</u>WYLQKPGQSPKLLIY<u>KVSNRFS</u>GVPDRFSGSGSGTDFTLKIS

RVEAEDLGVYFC<u>SHSTHVP</u>FTFGSGTKLEIKradaaptvsifppsseqlt sg

CDR1 of the light chain variable region of 8C11
antibody
(SEQ ID NO: 23)
TSSQTLVHSNGNTYLH CDR2 of the light chain variable region of 8C11
antibody
(SEQ ID NO: 24)
KVSNRFS CDR3 of the light chain variable region of 8C11
antibody
(SEQ ID NO: 25)
HSTHVP 6. The nucleic acid sequence of the heavy chain variable region of the obtained anti-PLD4 mouse 10C3 antibody is SEQ ID NO: 84, and the amino acid sequence is SEQ ID NO: 85. The amino acid sequences of CDR1, CDR2, and CDR3 in the heavy chain variable region of the mouse 10C3 antibody are SEQ ID NO: 26, SEQ ID NO: 27, and SEQ ID NO: 28, respectively.

The nucleic acid sequence of the heavy chain variable region of anti-PLD4 mouse 10C3 antibody (450 bp) [Upper case: mouse 10C3VH variable region, lower case: mouse IgG2a heavy chain constant region] (SEQ ID NO:84)

ATGAACTTCGGGCTCAGCTTGATTTTCCTTGCCCTCATTTTAAAAGGTGT

CCAGTGTGAGGTGCAGCTGGTGGAGTCTGGGGGAGACTTAGTGAGGCCTG

GAGGGTCCCTGAAACTCTCCTGTGCAGCCTCTGGATTCAGTTTCAGTAGC

TATGGCATGTCTTGGTTTCGCCAGACTCCAGACAAGAGGCTGGAGTGGGT

CGCAACCATTAGTAGTGGTGGTAGTTACATCTACTATCCAGAAAGTGTGA

AGGGGCGATTCACCATCTCCAGAGACAATGCCAGGAACATCCTGTACCTG

CAAATGAGCAGTCTGAAGTCTGAGGACACAGCCATGTATTATTGTGTAAG

ACTCTACGGTGGTAGGAGAGGCTATGGTTTGGACTACTGGGGTCAAGGAA

CCTCAGTCACCGTCTCCTCAgccaaaacaacagccccatcggtctatcca

The amino acid sequence of the heavy chain variable region of the mouse 10C3 antibody (150 a.a.) [Upper case: mouse 10C3VH variable region, lower case: mouse IgG2a heavy chain constant region]. The underlined sequence represents a signal sequence, and the double underline represents CDR regions (CDR1, CDR2, and CDR3). (SEQ ID NO:85)

<u>MNFGLSLIFLALILKGVQC</u>EVQLVESGGDLVRPGGSLKLSCAASGFSFS<u>S</u>

<u>YGMS</u>WFRQTPDKRLEWVA<u>TISSGGSYIYYPESVKG</u>RFTISRDNARNILYL

QMSSLKSEDTAMYYCVR<u>LYGGRRGYGLDY</u>WGQGTSVTVSSakttapsvyp

CDR1 of the heavy chain variable region of 10C3
antibody
(SEQ ID NO: 26)
SYGMS

CDR2 of the heavy chain variable region of 10C3
antibody
(SEQ ID NO: 27)
TISSGGSYIYYPESVKG CDR3 of the heavy chain variable region of 10C3
antibody
(SEQ ID NO: 28)
LYGGRRGYGLDY The nucleic acid sequence of the light chain variable region of the obtained anti-PLD4 mouse 10C3 antibody is SEQ ID NO: 104, and the amino acid sequence is SEQ ID NO: 105. The amino acid sequences of CDR1, CDR2, and CDR3 in the light chain variable region of the mouse 10C3 antibody are SEQ ID NO: 29, SEQ ID NO: 30, and SEQ ID NO: 31, respectively.

The nucleic acid sequence of the light chain variable region of anti-PLD4 mouse 10C3 antibody (423 bp) [Upper case: mouse 10C3VL variable region, lower case: mouse Igκ light chain constant region] (SEQ ID NO: 104)

ATGAGGTTCTCTGCTCAGCTTCTGGGGCTGCTTGTGCTCTGGATCCCTGG

ATCCACTGCGGAAATTGTGATGACGCAGGCTGCATTCTCCAATCCAGTCA

CTCTTGGAACATCAGCTTCCATCTCCTGCAGGTCTAGTAAGAGTCTCCTA

CATAGTGATGGCATCACTTATTTGTATTGGTATCTGCAGAAGCCAGGCCA

GTCTCCTCAGCTCCTGATTTATCAGATGTCCAACCTTGCCTCAGGAGTCC

CAGACAGGTTCAGTAGCAGTGGGTCAGGAACTGATTTCACACTGAGAATC

AGCAGAGTGGAGGCTGAGGATGTGGGTGTTTATTACTGTGCTCAAAATCT

AGAACTTTACACGTTCGGAGGGGGGACCAAGCTGGAAATAAAAcgggctg atgctgcaccaactgtatccatc

The amino acid sequence of the light chain variable region of the mouse 10C3 antibody (141 a.a.) [Upper case: mouse 10C3VL variable region, lower case: mouse IgK light chain constant region]. The underlined sequence represents a signal sequence, and the double underline represents CDR regions (CDR1, CDR2, and CDR3). (SEQ ID NO: 105)

<u>MRFSAQLLGLLVLWIPGSTA</u>EIVMTQAAFSNPVTLGTSASISC<u>RSSKSLL</u>

<u>HSDGITYLY</u>WYLQKPGQSPQLLIY<u>QMSNLAS</u>GVPDRFSSSGSGTDFTLRI

SRVEAEDVGVYYC<u>AQNLEL</u>YTFGGGTKLEIKradaaptvsi

CDR1 of the light chain variable region of 10C3 antibody
(SEQ ID NO: 29)
RSSKSLLHSDGITYLY CDR2 of the light chain variable region of 10C3 antibody
(SEQ ID NO: 30)
QMSNLAS CDR3 of the light chain variable region of 10C3 antibody
(SEQ ID NO: 31)
AQNLEL 7. The nucleic acid sequence of the heavy chain variable region of the obtained anti-PLD4 mouse 11D10 antibody is SEQ ID NO: 86, and the amino acid sequence is SEQ ID NO: 87. The amino acid sequences of CDR1, CDR2, and CDR3 in the heavy chain variable region of the mouse 11D10 antibody are SEQ ID NO: 26, SEQ ID NO: 27, and SEQ ID NO: 28, respectively.

The nucleic acid sequence of the heavy chain variable region of anti-PLD4 mouse 11D10 antibody (450 bp) [Upper case: mouse 11D10VH variable region, lower case: mouse IgG2b heavy chain constant region] (SEQ ID NO:86)

ATGAACTTCGGGCTCAGCTTGATTTTCCTTGCCCTCATTTTAAAAGGTGT

CCAGTGTGAGGTGCAGCTGGTGGAGTCTGGGGGAGACTTAGTGAGGCCTG

GAGGGTCCCTGAAACTCTCCTGTGCAGCCTCTGGATTCAGTTTCAGTAGC

TATGGCATGTCTTGGTTTCGCCAGACTCCAGACAAGAGGCTGGAGTGGGT

CGCAACCATTAGTAGTGGTGGTAGTTACATCTACTATCCAGAAAGTGTGA

AGGGGCGATTCACCATCTCCAGAGACAATGCCAGGAACATCCTGTACCTG

CAAATGAGCAGTCTGAAGTCTGAGGACACAGCCATGTATTATTGTGTAAG

ACTCTACGGTGGTAGGAGAGGCTATGGTTTGGACTACTGGGGTCAAGGAA

CCTCAGTCACCGTCTCCTCAgccaaaacaacaccccccatcagtctatcca

The amino acid sequence of the heavy chain variable region of the mouse 11D10 antibody (150 a.a.) [Upper case: mouse 11D10VH variable region, lower case: mouse IgG2b heavy chain constant region]. The underlined sequence represents a signal sequence, and the double underline represents CDR regions (CDR1, CDR2, and CDR3). (SEQ ID NO:87)

<u>MNFGLSLIFLALILKGVQC</u>EVQLVESGGDLVRPGGSLKLSCAASGFSFS<u>S</u>

<u>YGMS</u>WFRQTPDKRLEWVA<u>TISSGGSYIYYPESVKG</u>RFTISRDNARNILYL

QMSSLKSEDTAMYYCVR<u>LYGGRRGYGLDY</u>WGQGTSVTVSS aktppsvy p

CDR1 of the heavy chain variable region of 11D10 antibody
(SEQ ID NO: 26)
SYGMS

CDR2 of the heavy chain variable region of 11D10 antibody
(SEQ ID NO: 27)
TISSGGSYIYYPESVKG CDR3 of the heavy chain variable region of 11D10 antibody
(SEQ ID NO: 28)
LYGGRRGYGLDY The nucleic acid sequence of the light chain variable region of the obtained anti-PLD4 mouse 11D10 antibody is SEQ ID NO: 106, and the amino acid sequence is SEQ ID NO: 107. The amino acid sequences of CDR1, CDR2, and CDR3 in the light chain variable region of the mouse 11D10 antibody are SEQ ID NO: 29, SEQ ID NO: 30, and SEQ ID NO: 31, respectively.

The nucleic acid sequence of the light chain variable region of anti-PLD4 mouse 11D10 antibody (423 bp) [Upper case: mouse 11D10VL variable region, lower case: mouse Igκ light chain constant region] (SEQ ID NO: 106)

ATGAGGTTCTCTGCTCAGCTTCTGGGGCTGCTTGTGCTCTGGATCCCTGG

ATCCACTGCGGAAATTGTGATGACGCAGGCTGCATTCTCCAATCCAGTCA

CTCTTGGAACATCAGCTTCCATCTCCTGCAGGTCTAGTAAGAGTCTCCTA

CATAGTGATGGCATCACTTATTTGTATTGGTATCTGCAGAAGCCAGGCCA

GTCTCCTCAGCTCCTGATTTATCAGATGTCCAACCTTGCCTCAGGAGTCC

CAGACAGGTTCAGTAGCAGTGGGTCAGGAACTGATTTCACACTGAGAATC

AGCAGAGTGGAGGCTGAGGATGTGGGTGTTTATTACTGTGCTCAAAATCT

AGAACTTTACACGTTCGGAGGGGGGACCAAGCTGGAAATAAAAcgggctg atgctgcaccaactgtatccatc

The amino acid sequence of the light chain variable region (141 a.a.) of the mouse 11D10 antibody [Upper case:

mouse 11D10VL variable region, lower case: mouse IgK light chain constant region]. The underlined sequence represents a signal sequence, and the double underline represents CDR regions (CDR1, CDR2, and CDR3). (SEQ ID NO: 107)

<u>MRFSAQLLGLLVLWIPGSTAE</u>IVMTQAAFSNPVTLGTSASISC<u>RSSKSLL</u>

<u>HSDGITYLY</u>WYLQKPGQSPQLLIY<u>QMSNLAS</u>GVPDRFSSSGSGTDFTLRI

SRVEAEDVGVYYC<u>AQNLEL</u>YTFGGGTKLEIKradaaptvsi

CDR1 of the light chain variable region of 11D10 antibody
(SEQ ID NO: 29)
RSSKSLLHSDGITYLY CDR2 of the light chain variable region of 11D10 antibody
(SEQ ID NO: 30)
QMSNLAS CDR3 of the light chain variable region of 11D10 antibody
(SEQ ID NO: 31)
AQNLEL 8. The nucleic acid sequence of the heavy chain variable region of the obtained anti-PLD4 mouse 13D4 antibody is SEQ ID NO: 88, and the amino acid sequence is SEQ ID NO: 89. The amino acid sequences of CDR1, CDR2, and CDR3 in the heavy chain variable region of the mouse 13D4 antibody are SEQ ID NO: 32, SEQ ID NO: 33, and SEQ ID NO: 34, respectively.

The nucleic acid sequence of the heavy chain variable region of anti-PLD4 mouse 13D4 antibody (472 bp) [Upper case: mouse 13D4VH variable region, lower case: mouse IgG2b heavy chain constant region] (SEQ ID NO:88)

ATGAAAGTGTTGAGTCTGTTGTACCTGTTGACAGCCATTCCTGGTATCCT

GTCTGATGTACAGCTTCAGGAGTCAGGACCTGGCCTCGTGAAACCTTCTC

AATCTCTGTCTCTCACCTGCTCTGTCACTGGCTACTCCATCACCAGTCAT

TATTACTGGACCTGGATCCGGCAGTTTCCAGGAAACAAACTGGAATGGAT

GGGCTACATAAGCTACGACGGTAGCAATAACTACAACCCATCTCTCAAAA

ATCGAATCTCCATCACTCGTGACACATCTAAGAACCAGTTTTTCCTGAAG

TTGAATTCTGTGACTACTGAGGACACAGCTACATATAACTGTGCAAGAGA

GGGCCCGCTCTACTATGGTAACCCCTACTGGTATTTCGATGTCTGGGGCG

CAGGGACCACGGTCACCGTCTCCTCAgccaaaacaacaccccatcagtc tatccactggcccctaagggcg

The amino acid sequence of the heavy chain variable region of the mouse 13D4 antibody (157 a.a.) [Upper case: mouse 13D4VH variable region, lower case: mouse IgG2b heavy chain constant region]. The underlined sequence represents a signal sequence, and the double underline represents CDR regions (CDR1, CDR2, and CDR3). (SEQ ID NO:89)

<u>MKVLSLLYLLTAIPGILS</u>DVQLQESGPGLVKPSQSLSLTCSVTGYSIT<u>SH

YYWT</u>WIRQFPGNKLEWMG<u>YISYDGSNNYNPSLKN</u>RISITRDTSICNQFFL

KLNSVTTEDTATYNCAR<u>EGPLYYGNPYWYFDV</u>WGAGTTVTVSSaktipps vyplapkg

CDR1 of the heavy chain variable region of 13D4 antibody
(SEQ ID NO: 32)
SHYYWT

CDR2 of the heavy chain variable region of 13D4 antibody
(SEQ ID NO: 33)
YISYDGSNNYNPSLKN CDR3 of the heavy chain variable region of 13D4 antibody
(SEQ ID NO: 34)
EGPLYYGNPYWYFDV The nucleic acid sequence of the light chain variable region of the obtained anti-PLD4 mouse 13D4 antibody is SEQ ID NO: 108, and the amino acid sequence is SEQ ID NO: 109. The amino acid sequences of CDR1, CDR2, and CDR3 in the light chain variable region of the mouse 13D4 antibody are SEQ ID NO: 35, SEQ ID NO: 36, and SEQ ID NO: 37, respectively.

The nucleic acid sequence of the light chain variable region of anti-PLD4 mouse 13D4 antibody (404 bp) [Upper case: mouse 13D4VL variable region, lower case: mouse Igκ light chain constant region] (SEQ ID NO: 108)

ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGGGACAGAGTCACCATCAGTTGCAGGGCAAGTCAGGACATTGAC

AATTATTTAAACTGGTATCAGCAGAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAGCAA

GAAGATGTTGCCACTTACTTTTGCCAGCAGTTTAATACGCTTCCTCGGAC

GTTCGGTGGAGGCACCAAACTGGAAATCAAAcgggctgatgctgcaccaa ctgt

The amino acid sequence of the light chain variable region of the mouse 13D4 antibody (134 a.a.) [Upper case: mouse 13D4VL variable region, lower case: mouse IgK light chain constant region]. The underlined sequence represents a signal sequence, and the double underline represents CDR regions (CDR1, CDR2, and CDR3). (SEQ ID NO:109)

<u>MMSSAQFLGLLLLCFQGTRC</u>DIQMTQTTSSLSASLGDRVTISC<u>RASQDID

NYLN</u>WYQQKPDGTVKLLIY<u>YTSRLHS</u>GVPSRFSGSGSGTDYSLTISNLEQ

EDVATYFC<u>QQFNTLPRT</u>FGGGTKLEIKradaapt

CDR1 of the light chain variable region of 13D4 antibody
(SEQ ID NO: 35)
RASQDIDNYLN CDR2 of the light chain variable region of 13D4 antibody
(SEQ ID NO: 36)
YTSRLHS -continued CDR3 of the light chain variable region of 13D4 antibody
(SEQ ID NO: 37)
QQFNTLP 9. The nucleic acid sequence of the heavy chain variable region of the obtained anti-PLD4 mouse 13H11 antibody is SEQ ID NO: 90, and the amino acid sequence is SEQ ID NO: 91. The amino acid sequences of CDR1, CDR2, and CDR3 in the heavy chain variable region of the mouse 13H11 antibody are SEQ ID NO: 38, SEQ ID NO: 39, and SEQ ID NO: 40, respectively.

The nucleic acid sequence of the heavy chain variable region of anti-PLD4 mouse 13H11 antibody (471 bp) [Upper case: mouse 13H11VH variable region, lower case: mouse IgG2b heavy chain constant region] (SEQ ID NO:90)

ATGAAAGTGTTGAGTCTGTTGTACCTGTTGACAGCCATTCCTGGTATCCT

GTCTGATGTACAGCTTCAGGAGTCAGGACCTGGCCTCGTGAAACCTTCTC

AGTCTCTGTCTCTCACCTGCTCTGTCACTGGCTACTCCATCTCCAGTCAT

TATTACTGGAGTTGGATCCGGCAGTTTCCAGGAAACAGACTGGAATGGAT

GGGCTACATAAGCTACGACGGTAGCAATAACTACAACCCATCTCTCAAAA

ATCGAATCTCCATCACTCGTGACACATCTAAGAACCAGTTTTTCCTGAAG

TTGAATTCTGTGACTACTGAGGACACAGCTACATATAACTGTGCAAGAGA

GGGCCCGCTCTACTATGGTAACCCCTACTGGTATTTCGATGTCTGGGGCG

CAGGGACCACGGTCACCGTCTCCTCAgccaaaacaacaccccatcagtc tatccactggcccctaagggc

The amino acid sequence of the heavy chain variable region of the mouse 13H11 antibody (157 a.a.) [Upper case: mouse 13H11VH variable region, lower case: mouse IgG2b heavy chain constant region]. The underlined sequence represents a signal sequence, and the double underline represents CDR regions (CDR1, CDR2, and CDR3). (SEQ ID NO:91)

MKVLSLLYLLTAIPGILSDVQLQESGPGLVKPSQSLSLTCSVTGYSISSH

YYWSWIRQFPGNRLEWMGYISYDGSNNYNPSLKNRISITRDTSKNQFFLK

LNSVTTEDTATYNCAREGPLYYGNPYWYFDVWGAGTTVTVSSakttppsv yplapkg

CDR1 of the heavy chain variable region of the 13H11 antibody
(SEQ ID NO: 38)
SHYYWS CDR2 of the heavy chain variable region of the 13H11 antibody
(SEQ ID NO: 39)
YISYDGSNNYNPSLKN CDR3 of the heavy chain variable region of the 13H11 antibody
(SEQ ID NO: 40)
EGPLYYGNPYWYFDV The nucleic acid sequence of the light chain variable region of the obtained anti-PLD4 mouse 13H11 antibody is SEQ ID NO: 110, and the amino acid sequence is SEQ ID NO: 111. The amino acid sequences of CDR1, CDR2, and CDR3 in the light chain variable region of the mouse 13H11 antibody are SEQ ID NO: 41, SEQ ID NO: 42, and SEQ ID NO: 43, respectively.

The nucleic acid sequence of the light chain variable region of anti-PLD4 mouse 13H11 antibody (414 bp) [Upper case: mouse 13H11VL variable region, lower case: mouse Igκ light chain constant region] (SEQ ID NO: 110)

ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGGGGCAGCGTCACCATCAGTTGCAGGGCAAGTCAGGACATTGAC

AATTATTTAAACTGGTATCAGCAAAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAACAA

GAAGATATTGCCACTTACTTTTGCCAACAGTTTAATACGCTTCCTCGGAC

GTTCGGTGGAGGCACCAAGCTGGAAATCAAAcgggctgatgctgcaccaa ctgtatccatcttc

The amino acid sequence of the light chain variable region of the mouse 13H11 antibody (138 a.a.) [Upper case: mouse 13H11VL variable region, lower case: mouse IgK light chain constant region]. The underlined sequence represents a signal sequence, and the double underline represents CDR regions (CDR1, CDR2, and CDR3). (SEQ ID NO:111)

MMSSAQFLGLLLLCFQGTRCDIQMTQTTSSLSASLGGSVTISCRASQDID

NYLNWYQQKPDGTVKLLIYYTSRLHSGVPSRFSGSGSGTDYSLTISNLEQ

EDIATYFCQQFNTLPRTFGGGTKLEIKradaaptvsif

CDR1 of the light chain variable region of the 13H11 antibody
(SEQ ID NO: 41)
RASQDIDNYLN CDR2 of the light chain variable region of the 13H11 antibody
(SEQ ID NO: 42)
YTSRLHS CDR3 of the light chain variable region of the 13H11 antibody
(SEQ ID NO: 43)
QQFNTLP 10. The nucleic acid sequence of the heavy chain variable region of the obtained anti-PLD4 mouse 14C1 antibody is SEQ ID NO: 92, and the amino acid sequence is SEQ ID NO: 93. The amino acid sequences of CDR1, CDR2, and CDR3 in the heavy chain variable region of the mouse 14C1 antibody are SEQ ID NO: 38, SEQ ID NO: 39, and SEQ ID NO: 40, respectively.

The nucleic acid sequence of the heavy chain variable region of anti-PLD4 mouse 14C1 antibody (470 bp) [Upper case: mouse 14C1VH variable region, lower case: mouse IgG1 heavy chain constant region] (SEQ ID NO:92)

ATGAAAGTGTTGAGTCTGTTGTACCTGTTGACAGCCATTCCTGGTATCCT

GTCTGATGTACAGCTTCAGGAGTCAGGACCTGGCCTCGTGAAACCTTCTC

AGTCTCTGTCTCTCACCTGCTCTGTCACTGGCTACTCCATCTCCAGTCAT

TATTACTGGAGTTGGATCCGGCAGTTTCCAGGAAACAGACTGGAATGGAT

GGGCTACATAAGCTACGACGGTAGCAATAACTACAACCCATCTCTCAAAA

-continued

```
ATCGAATCTCCATCACTCGTGACACATCTAAGAACCAGTTTTTCCTGAAG

TTGAATTCTGTGACTACTGAGGACACAGCTACATATAACTGTGCAAGAGA

GGGCCCGCTCTACTATGGTAACCCCTACTGGTATTTCGATGTCTGGGGCG

CAGGGACCACGGTCACCGTCTCCTCAgccaaaacgacacccccatctgtc tatccactggcccctaaggg
```

The amino acid sequence of the heavy chain variable region of the mouse 14C1 antibody (156 a.a.) [Upper case: mouse 14C1VH variable region, lower case: mouse IgG1 heavy chain constant region]. The underlined sequence represents a signal sequence, and the double underline represents CDR regions (CDR1, CDR2, and CDR3). (SEQ ID NO:93)

```
MKVLSLLYLLTAIPGILSDVQLQESGPGLVKPSQSLSLTCSVTGYSISSH

YYWSWIRQFPGNRLEWMGYISYDGSNNYNPSLKNRISITRDTSKNQFFLK

LNSVTTEDTATYNCAREGPLYYGNPYWYFDVWGAGTTVTSS aktt pps vyplapk

CDR1 of the heavy chain variable region of 14C1
antibody
                                        (SEQ ID NO: 38)
SHYYWS CDR2 of the heavy chain variable region of 14C1
antibody
                                        (SEQ ID NO: 39)
YISYDGSNNYNPSLKN CDR3 of the heavy chain variable region of 14C1
antibody
                                        (SEQ ID NO: 40)
EGPLYYGNPYWYFDV
```

The nucleic acid sequence of the light chain variable region of the obtained anti-PLD4 mouse 14C1 antibody is SEQ ID NO: 112, and the amino acid sequence is SEQ ID NO: 113. The amino acid sequences of CDR1, CDR2, and CDR3 in the light chain variable region of the mouse 14C1 antibody are SEQ ID NO: 41, SEQ ID NO: 42, and SEQ ID NO: 43, respectively.

The nucleic acid sequence of the light chain variable region of anti-PLD4 mouse 14C1 antibody (465 bp) [Upper case: mouse 14C1VL variable region, lower case: mouse Igκ light chain constant region] (SEQ ID NO: 112)

```
ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGGGGCAGCGTCACCATCAGTTGCAGGGCAAGTCAGGACATTGAC

AATTATTTAAACTGGTATCAGCAAAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAACAA

GAAGATATTGCCACTTACTTTTGCCAACAGTTTAATACGCTTCCTCGGAC

GTTCGGTGGAGGCACCAAGCTGGAAATCAAAcgggctgatgctgccaa ctgtatccatcttccaccatccagtgagcagttaacatctggaggtgcc tcagtcgtgtgcttc
```

The amino acid sequence of the light chain variable region of the mouse 14C1 antibody (155 a.a.) [Upper case: mouse 14C1VL variable region, lower case: mouse Igκ light chain constant region]. The underlined sequence represents a signal sequence, and the double underline represents CDR regions (CDR1, CDR2, and CDR3). (SEQ ID NO:113)

```
MMSSAQFLGLLLLCFQGTRCDIQMTQTTSSLSASLGGSVTISCRASQDID

NYLNWYQQKPDGTVKLLIYYTSRLHSGVPSRFSGSGSGTDYSLTISNLEQ

EDIATYFCQQFNTLPRTFGGGTKLEIKradaaptvsifppsseqltsgga svvcf

CDR1 of the light chain variable region of 14C1
antibody
                                        (SEQ ID NO: 41)
RASQDIDNYLN CDR2 of the light chain variable region of 14C1
antibody
                                        (SEQ ID NO: 42)
YTSRLHS CDR3 of the light chain variable region of 14C1
antibody
                                        (SEQ ID NO: 43)
QQFNTLP
```

The base sequences and the amino acid sequences of the heavy chain and the light chain of the prepared chimeric 11G9 antibody are following Sequence Nos., respectively.
Heavy Chain
SEQ ID NO: 120 (base sequence)
SEQ ID NO: 121 (amino acid sequence)
Light Chain
SEQ ID NO: 122 (base sequence)
SEQ ID NO: 123 (amino acid sequence)
11. The nucleic acid sequence of the heavy chain of anti-PLD4 chimeric 11G9 antibody (1401 bp) [Upper case: chimeric 11G9VH variable region, lower case: human IgG1 heavy chain constant region] (SEQ ID NO: 120)

```
ATGAAAGTGTTGAGTCTGTTGTACCTGTTGACAGCCATTCCTGGTATCCT

GTCTCagGTCCAACTGCAGCAGCCTGGGGCTGAACTGGTGAAGCCTGGGA

CTTCAGTGAAAATGTCCTGCAAGGCTTCTGGCTACACCTTCACCAGCTAC

TGGATGCACTGGGTGAAGCAGAGGCCGGGACAAGGCCTTGAGTGGATTGG

AGATATTTATCCTGGTAGTGATAGTACTAACTACAATGAGAAGTTCAAGA

GCAAGGCCACACTGACTGTAGACACATCCTCCAGCACAGCCTACATGCAA

CTCAGCAGCCTGACATCTGAGGACTCTGCGGTCTATTACTGTGCAAGAGG

AGGGTGGTTGGATGCTATGGACTACTGGGGTCAAGGAACCTCAGTCACCG

TCTCCTCAgctagcaccaaggcccatcggtcttcccctggcaccctcc tccaagagcacctctgggggcacagcggccctgggctgcctggtcaagga ctacttccccgaaccggtgacggtgtcgtggaactcaggcgccctgacca gcggcgtgcacaccttcccggctgtcctacagtcctcaggactctactcc ctcagcagcgtggtgaccgtgccctccagcagcttgggcacccagaccta catctgcaacgtgaatcacaagcccagcaacaccaaggtggacaagaaag ttgagcccaaatcttgtgacaaaactcacacatgcccaccgtgcccagca cctgaactcctgggggaccgtcagtcttcctcttccccccaaaacccaa
```

-continued

```
ggacaccctcatgatctcccggacccctgaggtcacatgcgtggtggtgg acgtgagccacgaagaccctgaggtcaagttcaactggtacgtggacggc gtggaggtgcataatgccaagacaaagccgcgggaggagcagtacaacag cacgtaccgtgtggtcagcgtcctcaccgtcctgcaccaggactggctga atggcaaggagtacaagtgcaaggtctccaacaaagccctcccagccccc atcgagaaaaccatctccaaagccaaagggcagccccgagaaccacaggt gtacaccctgcccccatcccgggatgagctgaccaagaaccaggtcagcc tgacctgcctggtcaaaggcttctatcccagcgacatcgccgtggagtgg gagagcaatgggcagccggagaacaactacaagaccacgcctcccgtgct ggactccgacggctccttcttcctctacagcaagctcaccgtggacaaga gcaggtggcagcaggggaacgtcttctcatgctccgtgatgcatgaggct ctgcacaaccactacacgcagaagagcctctccctgtctccgggtaaatg a
```

12. The amino acid sequence of the heavy chain of anti-PLD4 chimeric 11G9 antibody (466 a.a.) [Upper case: chimeric 11G9VH variable region, lower case: human IgG1 heavy chain constant region] (SEQ ID NO: 121)

```
MKVLSLLYLLTAIPGILSQVQLQQPGAELVKPGTSVKMSCKASGYTFTSY

WMHWVKQRPGQGLEWIGDIYPGSDSTNYNEKFKSKATLTVDTSSSTAYMQ

LSSLTSEDSAVYYCARGGWLDAMDYWGQGTSVTVSSastkgpsvfplaps skstsggtaalgclvkdyfpepvtvswnsgaltsgvhtfpavlqssglys lssvvtvpssslgtqtyicnvnhkpsntkvdkkvepkscdkthtcppcpa pellggpsvflfppkpkdtlmisrtpevtcvvvdvshedpevkfnwyvdg vevhnaktkpreeqynstyrvvsvltvlhqdwlngkeykckvsnkalpap iektiskakgprepqvytlppsrdeltknqvsltclvkgfypsdiavewe sngqpennykttppyldsdgsfflyskltvdksrwqqgnvfscsvmheal hnhytqkslslspgk
```

13. The nucleic acid sequence of the light chain of anti-PLD4 chimeric 11 G9 antibody (705 bp) [Upper case: chimeric 11G9VL variable region, lower case: human Igκ× light chain constant region] (SEQ ID NO: 122)

```
ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGAGACAGAGTCACCATCAGTTGCAGGGCAAGTCAGGACATTAGC

AATTATTTAAACTGGTATCAGCAGAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAGCAA

GAAGATATTGCCACTTACTTTTGCCAACAGGGTAATACGCTTCCGTGGAC

GTTCGGTGGAGGCACCAAGCTGGAAATCAAAcgaactgtggctgcaccat ctgtcttcatcttcccgccatctgatgagcagttgaaatctggaactgcc tctgttgtgtgcctgctgaataacttctatcccagagaggccaaagtaca gtggaaggtggataacgccctccaatcgggtaactcccaggagagtgtca cagagcaggacagcaaggacagcacctacagcctcagcagcaccctgacg ctgagcaaagcagactacgagaaacacaaagtctacgcctgcgaagtcac ccatcagggcctgagctcgcccgtcacaaagagcttcaacaggggagagt gctag
```

14. The amino acid sequence of the light chain of anti-PLD4 chimeric 11G9 antibody (234 a.a.) [Upper case: chimeric 11G9VL variable region, lower case: human IgK light chain constant region] (SEQ ID NO: 123)

```
MMSSAQFLGLLLLCFQGTRCDIQMTQTTSSLSASLGDRVTISCRASQDIS

NYLNWYQGKPDGTVKLLIYYTSRLHSGVPSRFSGSGSGTDYSLTISNLEQ

EDIATYFCQQGNTLPWTFGGGTKLEIKrtvaapsvfifppsdeqlksgta svvcllnnfypreakvqwkvdnalqsgnsqesvteqdskdstyslsstlt lskadyekhkvyacevthqglsspvtksfnrgec
```

Sequence of cDNA and protein in PLD4-related molecular

> Human PLD4 cDNA (1521 bp)
(SEQ ID NO: 44)
```
ATGCTGAAGCCTCTTTGGAAAGCAGCAGTGGCCCCCACATGGCCATGCTCCATGCCGCCCCGCCGCCCGTGGGACAGAGA

GGCTGGCACGTTGCAGGTCCTGGGAGCGCTGGCTGTGCTGTGGCTGGCTCCGTGGCTCTTATCTGCCTCCTGTGGCAAG

TGCCCCGTCCTCCCACCTGGGGCCAGGTGCAGCCCAAGGACGTGCCCAGGTCCTGGGAGCATGGCTCCAGCCCAGCTTGG

GAGCCCTGGAAGCAGAGGCCAGGCAGCAGAGGGACTCCTGCCAGCTTGTCCTTGTGGAAAGCATCCCCCAGGACCTGCC

ATCTGCAGCCGGCAGCCCCTCTGCCCAGCCTCTGGGCCAGGCCTGGCTGCAGCTGCTGGACACTGCCCAGGAGAGCGTCC

ACGTGGCTTCATACTACTGGTCCCTCACAGGGCCTGACATCGGGGTCAACGACTCGTCTTCCCAGCTGGGAGAGGCTCTT

CTGCAGAAGCTGCAGCAGCTGCTGGGCAGGAACATTTCCCTGGCTGTGGCCACCAGCAGCCCGACACTGGCCAGGACATC

CACCGACCTGCAGGTTCTGGCTGCCCGAGGTGCCCATGTACGACAGGTGCCCATGGGCGGCTCACCAGGGGTGTTTTGC

ACTCCAAATTCTGGGTTGTGGATGGACGGCACATATACATGGGCAGTGCCAACATGGACTGGCGGTCTCTGACGCAGGTG

AAGGAGCTTGGCGCTGTCATCTATAACTGCAGCCACCTGGCCCAAGACCTGGAGAAGACCTTCCAGACCTACTGGGTACT

GGGGGTGCCCAAGGCTGTCCTCCCCAAAACCTGGCCTCAGAACTTCTCATCTCACTTCAACCGTTTCCAGCCCTTCCACG
```

-continued

```
GCCTCTTTGATGGGGTGCCCACCACTGCCTACTTCTCAGCGTCGCCACCAGCACTCTGTCCCCAGGGCCGCACCCGGGAC
CTGGAGGCGCTGCTGGCGGTGATGGGGAGCGCCCAGGAGTTCATCTATGCCTCCGTGATGGAGTATTTCCCCACCACGCG
CTTCAGCCACCCCCCGAGGTACTGGCCGGTGCTGGACAACGCGCTGCGGGCGGCAGCCTTCGGCAAGGGCGTGCGCGTGC
GCCTGCTGGTCGGCTGCGGACTCAACACGGACCCCACCATGTTCCCCTACCTGCGGTCCCTGCAGGCGCTCAGCAACCCC
GCGGCCAACGTCTCTGTGGACGTGAAAGTCTTCATCGTGCCGGTGGGGAACCATTCCAACATCCCATTCAGCAGGGTGAA
CCACAGCAAGTTCATGGTCACGGAGAAGGCAGCCTACATAGGCACCTCCAACTGGTCGGAGGATTACTTCAGCAGCACGG
CGGGGGTGGGCTTGGTGGTCACCCAGAGCCCTGGCGCGCAGCCCGCGGGGGCCACGGTGCAGGAGCAGCTGCGGCAGCTC
TTTGAGCGGGACTGGAGTTCGCGCTACGCCGTCGGCCTGGACGGACAGGCTCCGGGCCAGGACTGCGTTTGGCAGGGCTG
A
```

> Human PLD4 protein (506 amino acids)
(SEQ ID NO: 1)

```
MLKPLWKAAVAPTWPCSMPPRRPWDREAGTLQVLGALAVLWLGSVALICLLWQVPRPPTWGQVQPKDVPR
SWEHGSSPAWEPLEAEARQQRDSCQLVLVESIPQDLPSAAGSPSAQPLGQAWLQLLDTAQESVHVASYYW
SLTGPDIGVNDSSSQLGEALLQKLQQLLGRNISLAVATSSPTLARTSTDLQVLAARGAHVRQVPMGRLTR
GVLHSKFWVVDGRHIYMGSANMDWRSLTQVKELGAVIYNCSHLAQDLEKTFQTYWVLGVPKAVLPKTWPQ
NFSSHFNRFQPFHGLFDGVPTTAYFSASPPALCPQGRTRDLEALLAVMGSAQEFIYASVMEYFPTTRFSH
PPRYWPVLDKALRAAAFGKGVRVRLLVGCGLNTDPTMFPYLRSLQALSNPAANVSVDVKVFIVPVGNHSN
IPFSRVNHSKFMVTEKAAYIGTSNWSEDYFSSTAGVGLVVTQSPGAQPAGATVQEQLRQLFERDWSSRYA
VGLDGQAPGQDCVWQG
```

> cynomolgus monkey PLD4 cDNA (1521 bp)
(SEQ ID NO: 63)

```
ATGCTGAAGCCTCTTCGGAGAGCgGCAGTGACCCCCATGTGGCCGTGCTCCATGCTGCCCCGCCGCCTGTGGGACAGAGA
GGCTGGCACGTTGCAGGTCCTGGGAGTGCTGGCTATGCTGTGGCTGGGCTCCATGGCTCTTACCTACCTCCTGTGGCAAG
TGCGCCGTCCTCCCACCTGGGGCCAGGTGCAGCCCAAGGACGTGCCCAGGTCCTGGGGGCATGGTTCCAGCCCAGCTCTG
GAGCCCCTGGAAGCGGAGGTCAGGAAGCAGAGGGACTCCTGCCAGCTTGTCCTTGTGGAAAGCATCCCCCAGGACCTGCC
ATTTGCAGCCGGCAGCCTCTCCGCCCAGCCTCTGGGCCAGGCCTGGCTGCAGCTGCTGGACACTGCCCAGGAGAGCGTCC
ACGTGGCTTCATACTACTGGTCCCTCACAGGGCCCGACATTGGGGTCAACGACTCATCTTCCCAGCTGGGAGAGGCCCTT
CTGCAGAAGCTGCAGCAGCTGCTGGGCAGGAACATTTCCTTGGCTGTGGCCACCAGCAGTCCAACACTGGCCAGGAAGTC
CACCGACCTGCAGGTCCTGGCCTGCCCGAGGTGCCCAGGTACGACGGGTGCCCATGGGGCGGCTCACCAGGGGCGTTTTGC
ACTCCAAATTCTGGGTTGTGGATGGACgGCACATATACATGGGCAGTGCcAACATGGACTGGCGGTCCCTGACGCAGGTG
AAGGAGCTTGGCGCTGTCATCTATAACTGCAGCCACCTGGCCCAAGACCTGGAGAAGACCTTCCAGACCTACTGGGTGCT
GGGGGTGCCCAAGGCTGTCCTCCCCAAAAACCTGGCCTCAGAACTTCTCATCTCACATCAACCGTTTCCAGCCCTTCCAGG
GCCTCTTTGATGGGGTGCCCACCACTGCCTACTTCTCAGCATCGCCACCcGCACTCTGTCCCCAGGGCCGCACCCCTGAC
CTGGAGGCGCTGTTGGCGGTGATGGGGAGCGCCCAGGAGTTCATCTATGCCTCCGTGATGGAGTATTTCCCTACCACgCG
CTTCAGCCACCCCCGCAGGTACTGGCCGGTGCTGGACAACGCGCTGCGGGCGGCAGCCTTCAGCAAGGGTGTGCGCGTGC
GCCTGCTGGTCAGCTGCGGACTCAACACGGACCCCACCATGTTCCCCTATCTGCGGTCCCTGCAGGCGCTCAGCAACCCC
GCGGCCAACGTCTCTGTGGACGTGAAAGTCTTCATCGTGCCGGTGGGGAATCATTCCAACATCCCGTTCAGCAGGGTGAA
CCACAGCAAGTTCATGGTCACGGAGAAGGCAGCCTACATAGGCACCTCCAACTGGTCGGAGGATTACTTCAGCAGCACGA
CGGGGGTGGGCCTGGTGGTCACCCAGAGCCCCGGCGCGCAGCCCGCGGGGGCCACGGTACAGGAGCAGCTGCGGCAGCTC
TTTGAGCGGGACTGGAGTTCGCGCTACGCCGTCGGCCTGGACGGACAGGCTCCGGGCCAGGACTGCGTTTGGCAGGGCTG
A
```

> cynomolgus monkey PLD4 protein (506 amino acids)

(SEQ ID NO: 129)
MLKPLRRAAVTPMWPCSMLPRRLWDREAGTLQVLGVLAMLWLGSMALTYLLWQVRRPPTWGQVQPKDVPRSWGHGSSPAL
EPLEAEYRKQRDSCQLVLYESIPQDLPFAAGSLSAQPLGQAWLQLLDTAQESYHVASYYWSLTGPDIGVKDSSSQLGEAL
LQKLQQLLGRNISLAVATSSPTLARKSTDLQVLAARGAQVRRVPMGRLTRGVLHSKFWVVDGRHIYMGSANMDWRSLTQV
KELGAVIYNCSHLAQDLEKTFQTYWYLGVPKAVLPKTWPQNFSSHINRFQPFQGLFDGVPTTAYFSASPPALCPQGRTPD
LEALLAVMGSAQEFIYASVMEYFPTTRFSHPRRYWPVLDNALRAAAFSKGYRVRLLVSCGLNTDPTMFPYLRSLQALSNP
AANVSVDYKVFIVPVGNHSNIPFSRVNHSKFMVTEKAAYIGTSNWSEDYFSSTTGYGLVVTQSPGAQPAGATVQEQLRQL
FERDWSSRYAVGLDGQAPGQDCVWQG

> rhesus monkey PLD4 cDNA (1521 bp)

(SEQ ID NO: 124)
ATGCTGAAGCCTCTTCGGAGAGCGGCAGTGACCCCCATGTGGCCGTGCTCCATGCTGCCCCGCCGCCTGTGGGACAGAGA
GGCTGGCACGTTGCAGGTCCTGGGAGTGCTGGCTATGCTGTGGCTGGGCTCCATGGCTCTTACCTACCTCCTGTGGCAAG
TGCGCTGTCCTCCCACCTGGGGCCAGGTGCAGCCCAGGGACGTGCCCAGGTCCTGGGGGCATGGTTCCAGCCTAGCTCTG
GAGGCCCTGGAAGCGGAGGTCAGGAAGCAGAGGGACTCCTGCCAGCTTGTCCTTGTGGAAAGCATCCCCCAGGACCTGCC
ATTTGCAGCCGGCAGCCTCTCCGCCCAGCCTCTGGGCCAGGCCTGGCTGCAGCTGCTGGACACTGCCCAGGAGAGCGTCC
ACGTGGCTTCATACTACTGGTCCCTCACAGGGCCCGACATTGGGGTCAACGACTCATCTTCCCAGCTGGGAGAGGCCCTT
CTGCAGAAGCTGCAGCAGCTGCTGGGCAGGAACATTTCCTTGGCTGTGGCCACCAGCAGTCCAACACTGGCCAGGAAGTC
CACCGACCTGCAGGTCCTGGCTGCCCGAGGTGCCCAGGTACGACGGGTGCCCATGGGCGGCTCACCAGGGGCGTTTTGC
ACTCCAAATTCTGGGTTGTGGATGGACGGCACATATACATGGGCAGTGCCAACATGGACTGGCGGTCCTGACGCAGGTG
AAGGAGCTTGGCGCTGTCATCTATAACTGCAGCCACCTGGCCCAAGACCTGGAGAAGACCTTCCAGACCTACTGGGTGCT
GGGGGTGCCCAAGGCTGTCCTCCCCAAAACCTGGCCTCAGAACTTCTCATCTCACATCAACCGTTTCCAGCCCTTCCAGG
GCCTCTTTGATGGGGTGCCCACCACTGCCTACTTCTCAGCATCGCCACCCGCACTCTGTCCCCAGGGCCGCACCCCTGAC
CTGGAGGCGCTGTTGGCGGTGATGGGGAGCGCCCAGGAGTTCATCTATGCCTCCGTGATGGAGTATTTCCCTACCACGCG
CTTCAGCCACCCCCGCAGGTACTGGCCGGTGCTGGACAACGCGCTGCGGGCGGCAGCCTTCAGCAAGGGTGTGCGCGTGC
GCCTGCTGGTCAGCTGCGGACTCAACACGGACCCCACCATGTTCCCCTATCTGCGGTCCCTGCAGGCGCTCAGCAACCCC
GCGGCCAACGTCTCTGTGGACGTGAAAGTCTTCATCGTGCCGGTGGGGAATCATTCCAACATCCCGTTCAGCAGGGTGAA
CCACAGCAAGTTCATGGTCACGGAGAAGGCAGCCTACATAGGCACCTCCAACTGGTCGGAGGATTACTTCAGCAGCACGA
CGGGGGTGGGCCTGGTGGTCACCCAGAGCCCCGGCGCGCAGCCCGCGGGGGCCACGGTACAGGAGCAGCTGCGGCAGCTC
TTTGAGCGGGACTGGAGTTCGCGCTACGCCGTCGGCCTGGACGGACAGGCTCCGGGCCAGGACTGCGTTTGGCAGGGCTG
A

> rhesus monkey PLD4 protein (506 amino acids)

(SEQ ID NO: 130)
MLKPLRRAAVTPMWPCSMLPRRLWDREAGTLQVLGYLAMLWLGSMALTYLLWQVRCPPTWGQVQPRDVPRSWGHGSSLAL
EPLEAEVRKQRDSCQLVLVESIPQDLPFAAGSLSAQPLGQAWLQLLDTAQESVHVASYYWSLTGPDIGVNDSSSQLGEAL
LQKLQQLLGRNISLAVATSSPTLARKSTDLQVLAARGAQVRRVPMGRLTRGVLHSKFWVVDGRHIYMGSANMDWRSLTQV
KELGAVIYNCSHLAQDLEKTFQTYWVLGVPKAVLPKTWPQNFSSHINRFQPFQGLFDGVPTTAYFSASPPALCPQGRTPD
LEALLAVMGSAQEFIYASVMEYFPTTRFSHPRRWPVLDNALRAAAFSKGVRVRLLVSCGLNTDPTMFPYLRSLQALSNP
AANVSVDVKVFIVPVGNHSNIPFSRVNHSKFMVTEKAAYIGTSNWSEDYFSSTTGVGLVVTQSPGAQPAGATVQEQLRQL
FERDWSSRYAVGLDGQAPGQDCVWQG

> Mouse PLD4 cDNA (1512 base pairs)

(SEQ ID NO: 131)
ATGGACAAGAAGAAAGAGCACCCAGAGATGCGGATACCACTCCAGACAGCAGTGGAGGTCTCTGATTGGCCCTGCTCCAC
ATCTCATGATCCACATAGCGGACTTGGCATGGTACTGGGGATGCTAGCTGTACTGGGACTCAGCTCTGTGACTCTCATCT
TGTTCCTGTGGCAAGGGGCCACTTCTTTCACCAGTCATCGGATGTTCCCTGAGGAAGTGCCCTCCTGGTCCTGGGAGACC

-continued

```
CTGAAAGGAGACGCTGAGCAGCAGAATAACTCCTGTCAGCTCATCCTTGTGGAAAGCATCCCCGAGGACTTGCCATTTGC

AGCTGGCAGCCCCACTGCCCAGCCCCTGGCCCAGGCTTGGCTGCAGCTTCTTGACACTGCTCGGGAGAGCGTCCACATTG

CCTCGTACTACTGGTCCCTCACTGGACTGGACATTGGAGTCAATGACTCGTCTTCTCGGCAGGGAGAGGCCCTTCTACAG

AAGTTCCAACAGCTTCTTCTCAGGAACATCTCTGTGGTGGTGGCCACCCACAGCCCAACATTGGCCAAGACATCCACTGA

CCTCCAGGTCTTGGCTGCCCATGGTGCCCAGATACGACAAGTGCCCATGAAACAGCTTACTGGGGTGTTCTACACTCCA

AATTCTGGGTTGTGGATGGGCGACACGTCTACGTGGGCAGCGCCAACATGGACTGGCGGTCCCTGACTCAGGTGAAGGAA

CTTGGTGCAATCATCTACAACTGCAGCAACCTGGCTCAAGACCTTGAGAAAACATTCCAGACCTACTGGGTGCTAGGGAC

TCCCCAAGCTGTTCTCCCTAAAACCTGGCCTCGGAACTTCTCATCCCACATCAACCGCTTCCATCCCTTGCGGGGTCCCT

TTGATGGGGTTCCCACCACGGCCTATTTCTCGGCCTCCCCTCCCTCCCTCTGCCCGCATGGCCGGACCCGGGATCTGGAC

GCAGTGTTGGGAGTGATGGAGGGTGCTCGCCAGTTCATCTATGTCTCGGTGATGGAGTATTTCCCTACCACGCGCTTCAC

CCACCATGCCAGGTACTGGCCCGTGCTGGACAATGCGCTACGGGCAGCGGCCCTCAATAAGGGTGTGCATGTGCGCTTAC

TGGTCAGCTGCTGGTTCAACACAGACCCCACCATGTTCGCTTATCTGAGGTCCCTGCAGGCTTTCAGTAACCCCTCGGCT

GGCATCTCAGTGGATGTGAAAGTCTTCATCGTGCCTGTGGGAAATCATTCCAACATCCCGTTCAGCCGCGTGAACCACAG

CAAGTTCATGGTCACAGACAAGACAGCCTATGTAGGCACCTCTAACTGGTCAGAAGACTACTTCAGCCACACCGCTGGTG

TGGGCCTGATTGTCAGCCAGAAGACCCCCAGAGCCCAGCCAGGCGCAACCACCGTGCAGGAGCAGCTGAGGCAACTCTTT

GAACGAGACTGGAGTTCCCACTATGCTATGGACCTAGACAGACAAGTCCCGAGCCAGGACTGTGTCTGGTAG
```

> Mouse PLD4 protein (503 amino acids)

(SEQ ID NO: 132)

```
MDKKKEHPEMRIPLQTAVEVSDWPCSTSHDPHSGLGMVLGMLAVLGLSSVTLILFLWQGATSFTSHRMFPEEVPSWSWET
LKGDAEQQNNSCQLILVESIPEDLPFAAGSPTAQPLAQAWLQLLDTARESVHIASYYWSLTGLDIGVNDSSSRQGEALLQ
KFQQLLLRNISVVVATHSPTLAKTSTDLQVLAAHGAQIRQVPMKQLTGGVLHSKFWVVDGRHYYVGSANMDWRSLTQVKE
LGAIIYNCSNLAQDLEKTFQTYWYLGTPQAVLPKTWPRNFSSHINRFHPLRGPFDGVPTTAYFSASPPSLCPHGRTRDLD
AVLGVMEGARQFIYVSVMEYFPTTRFTHHARYWPVLDNALRAAALNKGVHVRLLVSCWFNTDPTMFAYLRSLQAFSNPSA
GISVDVKVFIVPVGNHSNIPFSRVNHSKFMVTDKTAYVGTSNWSEDYFSHTAGVGLIVSQKTPRAQPGATTVQEQLRQLF
ERDWSSHYAMDLDRQVPSQDCVW
```

> Human PLD3 cDNA sequence (SEQ ID NO: 55)

```
ATGAAGCCTAAACTGATGTACCAGGAGCTGAAGGTGCCTGCAGAGGAGCCCGCCAATGAGCTGCCCATGAATGAGATTGA

GGCGTGGAAGGCTGCGGAAAAGAAAGCCCGCTGGGTCCTGCTGGTCCTCATTCTGGCGGTTGTGGGCTTCGGAGCCCTGA

TGACTCAGCTGTTTCTATGGGAATACGGCGACTTGCATCTCTTTGGGCCCAACCAGCGCCCAGCCCCTGCTATGACCCT

TGCGAAGCAGTGCTGGTGGAAAGCATTCCTGAGGCCTGGACTTCCCCAATGCCTCCACGGGGAACCCTTCCACCAGCCA

GGCCTGGCTGGGCCTGCTCGCCGGTGCGCACAGCAGCCTGGACATCGCCTCCTTCTACTGGACCCTCACCAACAATGACA

CCCACACGCAGGAGCCCTCTGCCCAGCAGGGTGAGGAGGTCCTCCGGCAGCTGCAGACCCTGGCACCAAAGGGCGTGAAC

GTCCGCATCGCTGTGAGCAAGCCCAGCGGGCCCCAGCCACAGGCGGACCTGCAGGCTCTGCTGCAGAGCGGTGCCCAGGT

CCGCATGGTGGACATGCAGAAGCTGACCCATGGCGTCCTGCATACCAAGTTCTGGGTGGTGGACCAGACCCACTTCTACC

TGGGCAGTGCCAACATGGACTGGCGTTCACTGACCCAGGTCAAGGAGCTGGGCGTGGTCATGTACAACTGCAGCTGCCTG

GCTCGAGACCTGACCAAGATCTTTGAGGCCTACTGGTTCCTGGGCCAGGCAGCAGCTCCATCCCATCAACTTGGCCCCG

GTTCTATGACACCCGCTACAACCAAGAGACACCAATGGAGATCTGCCTCAATGGAACCCCTGCTCTGGCCTACCTGGCGA

GTGCGCCCCACCCCTGTGTCCAAGTGGCCGCACTCCAGACCTGAAGGCTCTACTCAACGTGGTGGACAATGCCCGGAGT

TCATCTACGTCGCTGTCATGAACTACCTGCCCACTCTGGAGTTCTCCCACCCTCACAGGTTCTGGCCTGCCATTGACGA

TGGGCTGCGGCGGGCCACCTACGAGCGTGGCGTCAAGGTGCGCCTGCTCATCAGCTGCTGGGACACTCGGAGCCATCCA

TGCGGGCCTTCCTGCTCTCTCTGGCTGCCCTGCGTGACAACCATACCCACTCTGACATCCAGGTGAAACTCTTTGTGGTC
```

CCCGCGGATGAGGCCCAGGCTCGAATCCCATATGCCCGTGTCAACCACAACAAGTACATGGTGACTGAACGCGCCACCTA

CATCGGAACCTCCAACTGGTCTGGCAACTACTTCACGGAGACGGCGGGCACCTCGCTGCTGGTGACGCAGAATGGGAGGG

GCGGCCTGCGGAGCCAGCTGGAGGCCATTTTCCTGAGGGACTGGGACTCCCCTTACAGCCATGACCTTGACACCTCAGCT

GACAGCGTGGGCAACGCCTGCCGCCTGCTCTGA

> Human PLD3 protein (490 amino acids)

(SEQ ID NO: 127)

MKPKLMYQELKVPAEEPANELPMNEIEAWKAAEKKARWVLLVLILAVVGFGALMTQLFLWEYGDLHLFGPNQRPAPCYDP

CEAVLVESIPEGLDFPNASTGNPSTSQAWLGLLAGAHSSLDIASFYWTLTNNDTHTQEPSAQQGEEVLRQLQTLAPKGVN

VRIAVSKPSGPQPQADLQALLQSGAQVRMVDMQKLTHGVLHTKFWVVDQTHFYLGSANMDWRSLTQVKELGVVMYNCSCL

ARDLTKIFEAYWFLGQAGSSIPSTWPRFYDTRYNQETPMEICLNGTPALAYLASAPPPLCPSGRTPDLKALLNVYDNARS

FIYVAVMNYLPTLEFSHPHRFWPAIDDGLRRATYERGVKVRLLISCWGHSEPSMRAFLLSLAALRDNHTHSDIQVKLFVV

PADEAQARIPYARVNHNKYMVTERATYIGTSNWSGNYFTETAGTSLLVTQNGRGGLRSQLEAIFLRDWDSPYSHDLDTSA

DSVGNACRLL

> Human PLD5 cDNA (1338 base pairs)

(SEQ ID NO: 56)

ATGGGAGAGGATGAGGATGGACTCTCAGAAAAAAATTGCCAAAATAAATGTCGAATTGCCCTGGTGGAAAATATTCCTGA

AGGCCTTAACTATTCAGAAAATGCACCATTTCACTTATCACTTTTCCAAGGCTGGATGAATTTACTCAACATGGCCAAAA

AGTCTGTTGACATAGTGTCTTCCCATTGGGATCTCAACCACACTCATCCATCAGCATGTCAGGGTCAACGTCTTTTTGAA

AAGTTGCTCCAGCTGACTTCGCAAAATATTGAAATCAAGCTAGTGAGTGATGTAACAGCTGATTCAAAGGTATTAGAAGC

CTTGAAATTAAAGGGAGCCGAGGTGACGTACATGAACATGACCGCTTACAACAAGGGCCGGCTGCAGTCCTCCTTCTGGA

TCGTGGACAAACAGCACGTGTATATCGGCAGTGCCGGTTTGGACTGGCAATCCCTGGGACAGATGAAAGAACTCGGTGTC

ATCTTCTACAACTGCAGCTGCCTGGTCCTAGATTTACAAAGGATATTTGCTCTATATAGTTCATTAAAATTCAAAAGCAG

AGTGCCTCAAACCTGGTCCAAAAGACTCTATGGAGTCTATGACAATGAAAAGAAATTGCAACTTCAGTTGAATGAAACCA

AATCTCAAGCATTTGTATCGAATTCTCCAAAACTCTTTTGCCCTAAAAACAGAAGTTTTGACATAGATGCCATCTACAGT

GTGATAGATGATGCCAAGCAGTATGTGTACATCGCTGTCATGGACTACCTGCCTATCTCCAGCACAAGCACCAAAAGGAC

TTACTGGCCAGACTTGGATGCAAAAATAAGAGAAGCATTAGTTTTACGAAGCGTTAGAGTTCGACTCCTTTTAAGCTTCT

GGAAGGAAACTGATCCCCTTACGTTTAACTTTATTTCATCTCTTAAAGCGATTTGCACTGAAATAGCCAACTGCAGTTTG

AAAGTTAAATTTTTTGATCTGGAAAGAGAGAATGCTTGTGCTACAAAAGAACAAAAGAATCACACCTTTCCTAGGTTAAA

TCGCAACAAGTACATGGTGACAGATGGAGCAGCTTATATTGGAAATTTTGATTGGGTAGGGAATGATTTCACTCAGAATG

CTGGCACGGGCCTTGTTATCAACCAGGCAGATGTGAGGAACAACAGAAGCATCATTAAGCAACTTAAAGATGTGTTTGAA

AGGGACTGGTATTCACCGTATGCCAAAACCTTACAGCCAACCAAACAGCCGAACTGCTCAAGCCTGTTCAAACTCAAACC

CCTCTCCAACAAAACTGCCACAGACGACACAGGCGGAAAGGATCCCCGGAACGTATGA

> Human PLD5 protein (445 amino acids)

(SEQ ID NO: 128)

MGEDEDGLSEKNCQNKCRIALVENIPEGLNYSENAPFHLSLFQGWMNLLNMAKKSVDIVSSHWDLNHTHPSACQGQRLFE

KLLQLTSQNIEIKLVSDVTADSKVLEALKLKGAEVTVMNMTAYNKGRLQSSFWIVDKQHVYIGSAGLDWQSLGQMKELGV

IFYNCSCLVLDLQKIFALYSSLKFKSRVPQTWSKRLYGVYDNEKKLQLQLNETKSQAFVSNSPKLFCPKNRSFDIDAIYS

VIDDAKQYVYIAVMDYLPISSTSTKRTYWPDLDAKIREALVLRSVRVRLLLSFWKETDPLTFNFISSLKAICTEIANCSL

KVKFFDLERENACATKEQKNHTFPRLNRNKYMVTDGAAYIGNFDWVGNDFTQNAGTGLVINQADVRNNRSIIKQLKDVFE

RDWYSPYAKTLQPTKQPNCSSLFKLKPLSNKTATDDTGGKDPRNV

> Human PLD4-Ig fusion protein cDNA (2142 bp)

(SEQ ID NO: 125)

ATGGAGTTTCAGACCCAGGTCTTTGTATTCGTGTTGCTCTGGTTGTCTGGTGTTGATGGAgattacaaggatgacgacga taaaGGATCCcccagagggcccacaatcaagccctgtcctccatgcaaatgcccagcacctaacctcttgggtggaccat ccgtcttcatcttccctccaaagatcaaggatgtactcatgatctccctgagccccatagtcacatgtgtggtggtggat -continued

```
gtgagcgaggatgacccagatgtccagatcagctggtttgtgaacaacgtggaagtacacacagctcagacacaaaccca
tagagaggattacaacagtactctccgggtggtcagtgccctccccatccagcaccaggactggatgagtggcaaggagt
tcaaatgcaaggtcaacaacaaagacctcccagcgcccatcgagagaaccatctcaaaacccaaagggtcagtaagagct
ccacaggtatatgtcttgcctccaccagaagaagagatgactaagaaacaggtcactctgacctgcatggtcacagactt
catgcctgaagacatttacgtggagtggaccaacaacgggaaaacagagctaaactacaagaacactgaaccagtcctgg
actctgatggttcttacttcatgtacagcaagctgagagtggaaaagaagaactgggtggaaagaaatagctactcctgt
tcagtggtccacgagggtctgcacaatcaccacacgactaagagcttctcccggactccgggtaaaCGTCCTCCCACCTG
GGGCCAGGTGCAGCCCAAGGACGTGCCCAGGTCCTGGGAGCATGGCTCCAGCCCAGCTTGGGAGCCCCTGGAAGCAGAGG
CCAGGCAGCAGAGGGACTCCTGCCAGCTTGTCCTTGTGGAAAGCATCCCCCAGGACCTGCCATCTGCAGCCGGCAGCCCC
TCTGCCCAGCCTCTGGGCCAGGCCTGGCTGCAGCTGCTGGACACTGCCCAGGAGAGCGTCCACGTGGCTTCATACTACTG
GTCCCTCACAGGGCCTGACATCGGGGTCAACGACTCGTCTTCCCAGCTGGGAGAGGCTCTTCTGCAGAAGCTGCAGCAGC
TGCTGGGCAGGAACATTTCCCTGGCTGTGGCCACCAGCAGCCCGACACTGGCCAGGACATCCACCGACCTGCAGGTTCTG
GCTGCCCGAGGTGCCCATGTACGACAGGTGCCCATGGGGCGGCTCACCAGGGGTGTTTTGCACTCCAAATTCTGGGTTGT
GGATGGACGGCACATATACATGGGCAGTGCCAACATGGACTGGCGGTCTCTGACGCAGGTGAAGGAGCTTGGCGCTGTCA
TCTATAACTGCAGCCACCTGGCCCAAGACCTGGAGAAGACCTTCCAGACCTACTGGGTACTGGGGGTGCCCAAGGCTGTC
CTCCCCAAAACCTGGCCTCAGAACTTCTCATCTCACTTCAACCGTTTCCAGCCCTTCCACGGCCTCTTTGATGGGGTGCC
CACCACTGCCTACTTCTCAGCGTCGCCACCAGCACTCTGTCCCCAGGGCCGCACCCGGGACCTGGAGGCGCTGCTGGCGG
TGATGGGGAGCGCCCAGGAGTTCATCTATGCCTCCGTGATGGAGTATTTCCCCACCACGCGCTTCAGCCACCCCCCGAGG
TACTGGCCGGTGCTGGACAACGCGCTGCGGGCGGCAGCCTTCGGCAAGGGCGTGCGCGTGCGCCTGCTGGTCGGCTGCGG
ACTCAACACGGACCCCACCATGTTCCCCTACCTGCGGTCCCTGCAGGCGCTCAGCAACCCCGCGGCCAACGTCTCTGTGG
ACGTGAAAGTCTTCATCGTGCCGGTGGGGAACCATTCCAACATCCCATTCAGCAGGGTGAACCACAGCAAGTTCATGGTC
ACGGAGAAGGCAGCCTACATAGGCACCTCCAACTGGTCGGAGGATTACTTCAGCAGCACGGCGGGGGTGGGCTTGGTGGT
CACCCAGAGCCCTGGCGCGCAGCCCGCGGGGGCCACGGTGCAGGAGCAGCTGCGGCAGCTCTTTGAGCGGGACTGGAGTT
CGCGCTACGCCGTCGGCCTGGACGGACAGGCTCCGGGCCAGGACTGCGTTTGGCAGGGCTGA
```

> Human PLD4-Ig fusion protein (713 amino acids)
(SEQ ID NO: 126)

MEFQTQVFVFVLLWLSGVDGDYKDDDDKGSPRGPTIKPCPPCKCPAPNLLGGPSVFIFPPKIKDVLMISLSPIVTCVVVD

VSEDDPDVQISWFVNNVEVHTAQTQTHREDYNSTLRVVSALPIQHQDWMSGKEFKCKVNNKDLPAPIERTISKPKGSVRA

PQVYVLPPPEEEMTKKQVTLTCMVTDFMPEDIYVEWTNNGKTELNYKNTEPVLDSDGSYFMYSKLRVEKKNWVERNSYSC

SVVHEGLHNHHTTKSFSRTPGKRPPTWGQVQPKDVPRSWEHGSSPAWEPLEAEARQQRDSCQLVLVESIPQDLPSAAGSP

SAQPLGQAWLQLLDTAQESVHYASYYWSLTGPDIGVNDSSSQLGEALLQKLQQLLGRNISLAVATSSPTLARTSTDLQVL

AARGAHYRQYPMGRLTRGVLHSKFWVVDGRHIYMGSAMDWRSLTQVKELGAVIYNCSHLAQDLEKIFQTYWVLGVPKAV

LPKTWPQNFSSHFNRFQPFHGLFDGVPTTAYFSASPPALCPQGRTRDLEALLAVMGSAQEFIYASVMEYFPTTRFSHPPR

YWPVLDNALRAAAFGKGYRYRLLVGCGLNTDPTMFPYLRSLQALSNPAANVSVDVKYFIVPVGNHSNIPFSRVNHSKFMV

TEKAAYIGTSNWSEDYFSSTAGVGLWTQSPGAQPAGATVQEQLRQLFERDWSSRYAVGLDGQAPGQDCVWQG

[Accession Number]
NITE BP-1211
NITE BP-1212
NITE BP-1213
NITE BP-1214
[Sequence List Free Text]
SEQ ID NO 45: Forward primer
SEQ ID NO 46: Reverse primer
SEQ ID NO 47: Forward primer
SEQ ID NO 48: Reverse primer
SEQ ID NO 49: Forward primer
SEQ ID NO 50: Reverse primer
SEQ ID NO 51: Forward primer
SEQ ID NO 52: Reverse primer
SEQ ID NO 53: Forward primer
SEQ ID NO 54: Reverse primer
SEQ ID NO 70: Anchor primer
SEQ ID NO 70: n is deoxyinosine
SEQ ID NO 71: AUAP primer
SEQ ID NO 72: Primer
SEQ ID NO 73: Primer
SEQ ID NO 114: Primer
SEQ ID NO 115: Primer
SEQ ID NO 116: Primer
SEQ ID NO 117: Primer
SEQ ID NO 118: Primer
SEQ ID NO 119: Primer

The invention claimed is:

1. A method for suppressing an activity of a plasmacytoid dendritic cell in a living organism, comprising administering to the living organism an antibody, or antigen-binding fragment thereof, that binds to human phospholipase D4 (PLD4) protein on the plasmacytoid dendritic cell and suppresses the activity of the plasmacytoid dendritic cell, wherein the activity of the plasmacytoid dendritic cell is production of interferon, survival, or production of interferon and survival, and wherein the antibody or antigen-binding fragment thereof comprises:

a heavy chain variable region comprising a heavy chain CDR1 set forth in SEQ ID NO:2, a heavy chain CDR2 set forth in SEQ ID NO:3, and a heavy chain CDR3 set forth in SEQ ID NO:4, and a light chain variable region comprising a light chain CDR1 set forth in SEQ ID NO:5, a light chain CDR2 set forth in SEQ ID NO:6, and a light chain CDR3 set forth in SEQ ID NO:7;

a heavy chain variable region comprising a heavy chain CDR1 set forth in SEQ ID NO:8, a heavy chain CDR2 set forth in SEQ ID NO:9, and a heavy chain CDR3 set forth in SEQ ID NO:10, and a light chain variable region comprising a light chain CDR1 set forth in SEQ ID NO:11, a light chain CDR2 set forth in SEQ ID NO:12, and a light chain CDR3 set forth in SEQ ID NO:13;

a heavy chain variable region comprising a heavy chain CDR1 set forth in SEQ ID NO:14, a heavy chain CDR2 set forth in SEQ ID NO:15, and a heavy chain CDR3 set forth in SEQ ID NO:16, and a light chain variable region comprising a light chain CDR1 set forth in SEQ ID NO:17, a light chain CDR2 set forth in SEQ ID NO:18, and a light chain CDR3 set forth in SEQ ID NO:19;

a heavy chain variable region comprising a heavy chain CDR1 set forth in SEQ ID NO:20, a heavy chain CDR2 set forth in SEQ ID NO:21, and a heavy chain CDR3 set forth in SEQ ID NO:22, and a light chain variable region comprising a light chain CDR1 set forth in SEQ ID NO:23, a light chain CDR2 set forth in SEQ ID NO:24, and a light chain CDR3 set forth in SEQ ID NO:25;

a heavy chain variable region comprising a heavy chain CDR1 set forth in SEQ ID NO:26, a heavy chain CDR2 set forth in SEQ ID NO:27, and a heavy chain CDR3 set forth in SEQ ID NO:28, and a light chain variable region comprising a light chain CDR1 set forth in SEQ ID NO:29, a light chain CDR2 set forth in SEQ ID NO:30, and a light chain CDR3 set forth in SEQ ID NO:31;

a heavy chain variable region comprising a heavy chain CDR1 set forth in SEQ ID NO:32, a heavy chain CDR2 set forth in SEQ ID NO:33, and a heavy chain CDR3 set forth in SEQ ID NO:34, and a light chain variable region comprising a light chain CDR1 set forth in SEQ ID NO:35, a light chain CDR2 set forth in SEQ ID NO:36, and a light chain CDR3 set forth in SEQ ID NO:37; or a heavy chain variable region comprising a heavy chain CDR1 set forth in SEQ ID NO:38, a heavy chain CDR2 set forth in SEQ ID NO:39, and a heavy chain CDR3 set forth in SEQ ID NO:40, and a light chain variable region comprising a light chain CDR1 set forth in SEQ ID NO:41, a light chain CDR2 set forth in SEQ ID NO:42, and a light chain CDR3 set forth in SEQ ID NO:43.

2. The method of claim 1, wherein the antibody or antigen-binding fragment thereof is chimerized.

3. The method of claim 1, wherein the antibody or antigen-binding fragment thereof is humanized.

4. A method for suppressing an activity of a plasmacytoid dendritic cell in a living organism, comprising administering to the living organism an antibody, or antigen-binding fragment thereof, that binds to human phospholipase D4 (PLD4) protein on the plasmacytoid dendritic cell and suppresses the activity of the plasmacytoid dendritic cell, wherein the activity of the plasmacytoid dendritic cell is production of interferon, survival, or production of interferon and survival, and wherein the antibody or antigen-binding fragment thereof comprises the heavy and light chain complementarity determining regions of the antibody produced by hybridoma mp5B7 deposited as Accession No. NITE BP-1211, hybridoma mp7B4 deposited as Accession No. NITE BP-1212, hybridoma mp13D4 deposited as Accession No. NITE BP-1213, or hybridoma mp13H11 deposited as Accession No. NITE BP-1214.

5. A method for suppressing an activity of a plasmacytoid dendritic cell in a living organism, comprising administering to the living organism an antibody, or antigen-binding fragment thereof, that binds to human phospholipase D4 (PLD4) protein on the plasmacytoid dendritic cell and suppresses the activity of the plasmacytoid dendritic cell, wherein the activity of the plasmacytoid dendritic cell is production of interferon, survival, or production of interferon and survival, and wherein the antibody or antigen-binding fragment thereof comprises an antibody produced by hybridoma mp5B7 deposited as Accession No. NITE BP-1211, hybridoma mp7B4 deposited as Accession No. NITE BP-1212, hybridoma mp13D4 deposited as Accession No. NITE BP-1213, or hybridoma mp13H11 deposited as Accession No. NITE BP-1214, or an antigen-binding fragment thereof.

6. The method of claim 4, wherein the antibody or antigen-binding fragment thereof is chimerized.

7. The method of claim 4, wherein the antibody or antigen-binding fragment thereof is humanized.

* * * * *

```
                          SEQUENCE LISTING

<160> NUMBER OF SEQ ID NOS: 132

<210> SEQ ID NO 1
<211> LENGTH: 506
<212> TYPE: PRT
<213> ORGANISM: Homo sapiens
<220> FEATURE:
<221> NAME/KEY: PEPTIDE
<222> LOCATION: (1)..(506)

<400> SEQUENCE: 1

Met Leu Lys Pro Leu Trp Lys Ala Ala Val Ala Pro Thr Trp Pro Cys
1               5                   10                  15

Ser Met Pro Pro Arg Arg Pro Trp Asp Arg Glu Ala Gly Thr Leu Gln
            20                  25                  30

Val Leu Gly Ala Leu Ala Val Leu Trp Leu Gly Ser Val Ala Leu Ile
        35                  40                  45

Cys Leu Leu Trp Gln Val Pro Arg Pro Thr Trp Gly Gln Val Gln
    50                  55                  60

Pro Lys Asp Val Pro Arg Ser Trp Glu His Gly Ser Ser Pro Ala Trp
65                  70                  75                  80

Glu Pro Leu Glu Ala Glu Ala Arg Gln Gln Arg Asp Ser Cys Gln Leu
                85                  90                  95

Val Leu Val Glu Ser Ile Pro Gln Asp Leu Pro Ser Ala Ala Gly Ser
            100                 105                 110

Pro Ser Ala Gln Pro Leu Gly Gln Ala Trp Leu Gln Leu Leu Asp Thr
        115                 120                 125

Ala Gln Glu Ser Val His Val Ala Ser Tyr Tyr Trp Ser Leu Thr Gly
    130                 135                 140

Pro Asp Ile Gly Val Asn Asp Ser Ser Ser Gln Leu Gly Glu Ala Leu
145                 150                 155                 160

Leu Gln Lys Leu Gln Gln Leu Leu Gly Arg Asn Ile Ser Leu Ala Val
                165                 170                 175

Ala Thr Ser Ser Pro Thr Leu Ala Arg Thr Ser Thr Asp Leu Gln Val
            180                 185                 190

Leu Ala Ala Arg Gly Ala His Val Arg Gln Val Pro Met Gly Arg Leu
        195                 200                 205

Thr Arg Gly Val Leu His Ser Lys Phe Trp Val Val Asp Gly Arg His
    210                 215                 220

Ile Tyr Met Gly Ser Ala Asn Met Asp Trp Arg Ser Leu Thr Gln Val
225                 230                 235                 240

Lys Glu Leu Gly Ala Val Ile Tyr Asn Cys Ser His Leu Ala Gln Asp
                245                 250                 255
```

-continued

```
Leu Glu Lys Thr Phe Gln Thr Tyr Trp Val Leu Gly Val Pro Lys Ala
            260                 265                 270

Val Leu Pro Lys Thr Trp Pro Gln Asn Phe Ser Ser His Phe Asn Arg
        275                 280                 285

Phe Gln Pro Phe His Gly Leu Phe Asp Gly Val Pro Thr Thr Ala Tyr
    290                 295                 300

Phe Ser Ala Ser Pro Pro Ala Leu Cys Pro Gln Gly Arg Thr Arg Asp
305                 310                 315                 320

Leu Glu Ala Leu Leu Ala Val Met Gly Ser Ala Gln Glu Phe Ile Tyr
                325                 330                 335

Ala Ser Val Met Glu Tyr Phe Pro Thr Thr Arg Phe Ser His Pro Pro
            340                 345                 350

Arg Tyr Trp Pro Val Leu Asp Asn Ala Leu Arg Ala Ala Ala Phe Gly
        355                 360                 365

Lys Gly Val Arg Val Arg Leu Leu Val Gly Cys Gly Leu Asn Thr Asp
    370                 375                 380

Pro Thr Met Phe Pro Tyr Leu Arg Ser Leu Gln Ala Leu Ser Asn Pro
385                 390                 395                 400

Ala Ala Asn Val Ser Val Asp Val Lys Val Phe Ile Val Pro Val Gly
                405                 410                 415

Asn His Ser Asn Ile Pro Phe Ser Arg Val Asn His Ser Lys Phe Met
            420                 425                 430

Val Thr Glu Lys Ala Ala Tyr Ile Gly Thr Ser Asn Trp Ser Glu Asp
        435                 440                 445

Tyr Phe Ser Ser Thr Ala Gly Val Gly Leu Val Val Thr Gln Ser Pro
    450                 455                 460

Gly Ala Gln Pro Ala Gly Ala Thr Val Gln Glu Gln Leu Arg Gln Leu
465                 470                 475                 480

Phe Glu Arg Asp Trp Ser Ser Arg Tyr Ala Val Gly Leu Asp Gly Gln
                485                 490                 495

Ala Pro Gly Gln Asp Cys Val Trp Gln Gly
            500                 505

<210> SEQ ID NO 2
<211> LENGTH: 5
<212> TYPE: PRT
<213> ORGANISM: Homo sapiens

<400> SEQUENCE: 2

Ser Tyr Trp Met His
1               5

<210> SEQ ID NO 3
<211> LENGTH: 17
<212> TYPE: PRT
<213> ORGANISM: Homo sapiens

<400> SEQUENCE: 3

Asp Ile Tyr Pro Gly Ser Asp Ser Thr Asn Tyr Asn Glu Lys Phe Lys
1               5                   10                  15

Ser

<210> SEQ ID NO 4
<211> LENGTH: 9
<212> TYPE: PRT
<213> ORGANISM: Homo sapiens

<400> SEQUENCE: 4
```

Gly Gly Trp Leu Asp Ala Met Asp Tyr
1               5

<210> SEQ ID NO 5
<211> LENGTH: 11
<212> TYPE: PRT
<213> ORGANISM: Homo sapiens

<400> SEQUENCE: 5

Arg Ala Ser Gln Asp Ile Ser Asn Tyr Leu Asn
1               5                   10

<210> SEQ ID NO 6
<211> LENGTH: 7
<212> TYPE: PRT
<213> ORGANISM: Homo sapiens

<400> SEQUENCE: 6

Tyr Thr Ser Arg Leu His Ser
1               5

<210> SEQ ID NO 7
<211> LENGTH: 8
<212> TYPE: PRT
<213> ORGANISM: Homo sapiens

<400> SEQUENCE: 7

Gln Gln Gly Asn Thr Leu Pro Trp
1               5

<210> SEQ ID NO 8
<211> LENGTH: 5
<212> TYPE: PRT
<213> ORGANISM: Homo sapiens

<400> SEQUENCE: 8

Thr Tyr Trp Met His
1               5

<210> SEQ ID NO 9
<211> LENGTH: 17
<212> TYPE: PRT
<213> ORGANISM: Homo sapiens

<400> SEQUENCE: 9

Ala Ile Tyr Pro Gly Asn Ser Glu Thr Ser Tyr Asn Gln Lys Phe Lys
1               5                   10                  15

Gly

<210> SEQ ID NO 10
<211> LENGTH: 7
<212> TYPE: PRT
<213> ORGANISM: Homo sapiens

<400> SEQUENCE: 10

Gly Tyr Ser Asp Phe Asp Tyr
1               5

<210> SEQ ID NO 11
<211> LENGTH: 11
<212> TYPE: PRT
<213> ORGANISM: Homo sapiens

<400> SEQUENCE: 11

His Ala Ser Gln Gly Ile Arg Ser Asn Ile Gly
1               5                   10

<210> SEQ ID NO 12
<211> LENGTH: 7
<212> TYPE: PRT
<213> ORGANISM: Homo sapiens

<400> SEQUENCE: 12

His Gly Thr Asn Leu Glu Asp
1               5

<210> SEQ ID NO 13
<211> LENGTH: 7
<212> TYPE: PRT
<213> ORGANISM: Homo sapiens

<400> SEQUENCE: 13

Val Gln Tyr Val Gln Phe Pro
1               5

<210> SEQ ID NO 14
<211> LENGTH: 5
<212> TYPE: PRT
<213> ORGANISM: Homo sapiens

<400> SEQUENCE: 14

Asp Tyr Asn Leu His
1               5

<210> SEQ ID NO 15
<211> LENGTH: 17
<212> TYPE: PRT
<213> ORGANISM: Homo sapiens

<400> SEQUENCE: 15

Tyr Ile Tyr Pro Tyr Asn Gly Asn Thr Gly Tyr Asn Gln Lys Phe Lys
1               5                   10                  15

Arg

<210> SEQ ID NO 16
<211> LENGTH: 14
<212> TYPE: PRT
<213> ORGANISM: Homo sapiens

<400> SEQUENCE: 16

Gly Gly Ile Tyr Asp Asp Tyr Asp Tyr Ala Ile Asp Tyr
1               5                   10

<210> SEQ ID NO 17
<211> LENGTH: 11
<212> TYPE: PRT
<213> ORGANISM: Homo sapiens

<400> SEQUENCE: 17

Arg Ala Ser Glu Asn Ile Tyr Ser His Ile Ala
1               5                   10

<210> SEQ ID NO 18
<211> LENGTH: 7
<212> TYPE: PRT
<213> ORGANISM: Homo sapiens

<400> SEQUENCE: 18

```
Gly Ala Thr Asn Leu Ala His
1               5

<210> SEQ ID NO 19
<211> LENGTH: 7
<212> TYPE: PRT
<213> ORGANISM: Homo sapiens

<400> SEQUENCE: 19

Gln His Phe Trp Gly Thr Pro
1               5

<210> SEQ ID NO 20
<211> LENGTH: 5
<212> TYPE: PRT
<213> ORGANISM: Homo sapiens

<400> SEQUENCE: 20

Ser Tyr Tyr Leu Tyr
1               5

<210> SEQ ID NO 21
<211> LENGTH: 17
<212> TYPE: PRT
<213> ORGANISM: Homo sapiens

<400> SEQUENCE: 21

Leu Ile Asn Pro Thr Asn Ser Asp Thr Ile Phe Asn Glu Lys Phe Lys
1               5                   10                  15

Ser

<210> SEQ ID NO 22
<211> LENGTH: 11
<212> TYPE: PRT
<213> ORGANISM: Homo sapiens

<400> SEQUENCE: 22

Glu Gly Gly Tyr Gly Tyr Gly Pro Phe Ala Tyr
1               5                   10

<210> SEQ ID NO 23
<211> LENGTH: 16
<212> TYPE: PRT
<213> ORGANISM: Homo sapiens

<400> SEQUENCE: 23

Thr Ser Ser Gln Thr Leu Val His Ser Asn Gly Asn Thr Tyr Leu His
1               5                   10                  15

<210> SEQ ID NO 24
<211> LENGTH: 7
<212> TYPE: PRT
<213> ORGANISM: Homo sapiens

<400> SEQUENCE: 24

Lys Val Ser Asn Arg Phe Ser
1               5

<210> SEQ ID NO 25
<211> LENGTH: 6
<212> TYPE: PRT
<213> ORGANISM: Homo sapiens

<400> SEQUENCE: 25
```

```
His Ser Thr His Val Pro
1               5

<210> SEQ ID NO 26
<211> LENGTH: 5
<212> TYPE: PRT
<213> ORGANISM: Homo sapiens

<400> SEQUENCE: 26

Ser Tyr Gly Met Ser
1               5

<210> SEQ ID NO 27
<211> LENGTH: 17
<212> TYPE: PRT
<213> ORGANISM: Homo sapiens

<400> SEQUENCE: 27

Thr Ile Ser Ser Gly Gly Ser Tyr Ile Tyr Tyr Pro Glu Ser Val Lys
1               5                   10                  15

Gly

<210> SEQ ID NO 28
<211> LENGTH: 12
<212> TYPE: PRT
<213> ORGANISM: Homo sapiens

<400> SEQUENCE: 28

Leu Tyr Gly Gly Arg Arg Gly Tyr Gly Leu Asp Tyr
1               5                   10

<210> SEQ ID NO 29
<211> LENGTH: 16
<212> TYPE: PRT
<213> ORGANISM: Homo sapiens

<400> SEQUENCE: 29

Arg Ser Ser Lys Ser Leu Leu His Ser Asp Gly Ile Thr Tyr Leu Tyr
1               5                   10                  15

<210> SEQ ID NO 30
<211> LENGTH: 7
<212> TYPE: PRT
<213> ORGANISM: Homo sapiens

<400> SEQUENCE: 30

Gln Met Ser Asn Leu Ala Ser
1               5

<210> SEQ ID NO 31
<211> LENGTH: 6
<212> TYPE: PRT
<213> ORGANISM: Homo sapiens

<400> SEQUENCE: 31

Ala Gln Asn Leu Glu Leu
1               5

<210> SEQ ID NO 32
<211> LENGTH: 6
<212> TYPE: PRT
<213> ORGANISM: Homo sapiens

<400> SEQUENCE: 32
```

Ser His Tyr Tyr Trp Thr
1               5

<210> SEQ ID NO 33
<211> LENGTH: 16
<212> TYPE: PRT
<213> ORGANISM: Homo sapiens

<400> SEQUENCE: 33

Tyr Ile Ser Tyr Asp Gly Ser Asn Asn Tyr Asn Pro Ser Leu Lys Asn
1               5                   10                  15

<210> SEQ ID NO 34
<211> LENGTH: 15
<212> TYPE: PRT
<213> ORGANISM: Homo sapiens

<400> SEQUENCE: 34

Glu Gly Pro Leu Tyr Tyr Gly Asn Pro Tyr Trp Tyr Phe Asp Val
1               5                   10                  15

<210> SEQ ID NO 35
<211> LENGTH: 11
<212> TYPE: PRT
<213> ORGANISM: Homo sapiens

<400> SEQUENCE: 35

Arg Ala Ser Gln Asp Ile Asp Asn Tyr Leu Asn
1               5                   10

<210> SEQ ID NO 36
<211> LENGTH: 7
<212> TYPE: PRT
<213> ORGANISM: Homo sapiens

<400> SEQUENCE: 36

Tyr Thr Ser Arg Leu His Ser
1               5

<210> SEQ ID NO 37
<211> LENGTH: 7
<212> TYPE: PRT
<213> ORGANISM: Homo sapiens

<400> SEQUENCE: 37

Gln Gln Phe Asn Thr Leu Pro
1               5

<210> SEQ ID NO 38
<211> LENGTH: 6
<212> TYPE: PRT
<213> ORGANISM: Homo sapiens

<400> SEQUENCE: 38

Ser His Tyr Tyr Trp Ser
1               5

<210> SEQ ID NO 39
<211> LENGTH: 16
<212> TYPE: PRT
<213> ORGANISM: Homo sapiens

<400> SEQUENCE: 39

Tyr Ile Ser Tyr Asp Gly Ser Asn Asn Tyr Asn Pro Ser Leu Lys Asn

<210> SEQ ID NO 40
<211> LENGTH: 15
<212> TYPE: PRT
<213> ORGANISM: Homo sapiens

<400> SEQUENCE: 40

Glu Gly Pro Leu Tyr Tyr Gly Asn Pro Tyr Trp Tyr Phe Asp Val
1               5                   10                  15

<210> SEQ ID NO 41
<211> LENGTH: 11
<212> TYPE: PRT
<213> ORGANISM: Homo sapiens

<400> SEQUENCE: 41

Arg Ala Ser Gln Asp Ile Asp Asn Tyr Leu Asn
1               5                   10

<210> SEQ ID NO 42
<211> LENGTH: 7
<212> TYPE: PRT
<213> ORGANISM: Homo sapiens

<400> SEQUENCE: 42

Tyr Thr Ser Arg Leu His Ser
1               5

<210> SEQ ID NO 43
<211> LENGTH: 7
<212> TYPE: PRT
<213> ORGANISM: Homo sapiens

<400> SEQUENCE: 43

Gln Gln Phe Asn Thr Leu Pro
1               5

<210> SEQ ID NO 44
<211> LENGTH: 1521
<212> TYPE: DNA
<213> ORGANISM: Homo sapiens

<400> SEQUENCE: 44

```
atgctgaagc ctctttggaa agcagcagtg gcccccacat ggccatgctc catgccgccc      60
cgccgcccgt gggacagaga ggctggcacg ttgcaggtcc tgggagcgct ggctgtgctg     120
tggctgggct ccgtggctct tatctgcctc ctgtggcaag tgccccgtcc tcccacctgg     180
ggccaggtgc agcccaagga cgtgcccagg tcctgggagc atggctccag cccagcttgg     240
gagcccctgg aagcagaggc caggcagcag agggactcct gccagcttgt ccttgtggaa     300
agcatccccc aggacctgcc atctgcagcc ggcagcccct ctgccagcc tctgggccag      360
gcctggctgc agctgctgga cactgcccag gagagcgtcc acgtggcttc atactactgg     420
tccctcacag ggcctgacat cggggtcaac gactcgtctt cccagctggg agaggctctt     480
ctgcagaagc tgcagcagct gctgggcagg aacatttccc tggctgtggc caccagcagc     540
ccgacactgg ccaggacatc caccgacctg caggttctgg ctgcccgagg tgcccatgta     600
cgacaggtgc ccatggggcg gctcaccagg ggtgttttgc actccaaatt ctgggttgtg     660
gatgacggc acatatacat gggcagtgcc aacatggact gcggtctct gacgcaggtg       720
aaggagcttg gcgctgtcat ctataactgc agccacctgg cccaagacct ggagaagacc     780
```

```
ttccagacct actgggtact gggggtgccc aaggctgtcc tccccaaaac ctggcctcag    840
aacttctcat ctcacttcaa ccgtttccag cccttccacg gcctctttga tggggtgccc    900
accactgcct acttctcagc gtcgccacca gcactctgtc cccagggccg cacccgggac    960
ctggaggcgc tgctggcggt gatggggagc gcccaggagt tcatctatgc ctccgtgatg   1020
gagtatttcc ccaccacgcg cttcagccac ccccgaggt actggccggt gctggacaac   1080
gcgctgcggg cggcagcctt cggcaagggc gtgcgcgtgc gcctgctggt cggctgcgga   1140
ctcaacacgg accccaccat gttcccctac ctgcggtccc tgcaggcgct cagcaacccc   1200
gcggccaacg tctctgtgga cgtgaaagtc ttcatcgtgc cggtggggaa ccattccaac   1260
atcccattca gcagggtgaa ccacagcaag ttcatggtca cggagaaggc agcctacata   1320
ggcacctcca actggtcgga ggattacttc agcagcacgg cggggtggg cttggtggtc   1380 acccagagcc ctggcgcgca gcccgcgggg gccacggtgc aggagcagct gcggcagctc   1440
tttgagcggg actggagttc gcgctacgcc gtcggcctgg acggacaggc tccgggccag   1500
gactgcgttt ggcagggctg a                                              1521
```

```
<210> SEQ ID NO 45
<211> LENGTH: 18
<212> TYPE: DNA
<213> ORGANISM: Artificial
<220> FEATURE:
<223> OTHER INFORMATION: forward primer

<400> SEQUENCE: 45
atggactggc ggtctctg                                                    18

<210> SEQ ID NO 46
<211> LENGTH: 20
<212> TYPE: DNA
<213> ORGANISM: Artificial
<220> FEATURE:
<223> OTHER INFORMATION: reverse primer

<400> SEQUENCE: 46
tggaaggtct tctccaggtc                                                  20

<210> SEQ ID NO 47
<211> LENGTH: 19
<212> TYPE: DNA
<213> ORGANISM: Artificial
<220> FEATURE:
<223> OTHER INFORMATION: forward primer

<400> SEQUENCE: 47
agccacatcg ctcagacac                                                   19

<210> SEQ ID NO 48
<211> LENGTH: 19
<212> TYPE: DNA
<213> ORGANISM: Artificial
<220> FEATURE:
<223> OTHER INFORMATION: reverse primer

<400> SEQUENCE: 48
gcccaatacg accaaatcc                                                   19

<210> SEQ ID NO 49
<211> LENGTH: 18
<212> TYPE: DNA
```

```
<213> ORGANISM: Artificial
<220> FEATURE:
<223> OTHER INFORMATION: forward primer

<400> SEQUENCE: 49
atggactggc ggtctctg                                                   18

<210> SEQ ID NO 50
<211> LENGTH: 20
<212> TYPE: DNA
<213> ORGANISM: Artificial
<220> FEATURE:
<223> OTHER INFORMATION: reverse primer

<400> SEQUENCE: 50
tggaaggtct tctccaggtc                                                 20

<210> SEQ ID NO 51
<211> LENGTH: 19
<212> TYPE: DNA
<213> ORGANISM: Artificial
<220> FEATURE:
<223> OTHER INFORMATION: forward primer

<400> SEQUENCE: 51
agccacatcg ctcagacac                                                  19

<210> SEQ ID NO 52
<211> LENGTH: 19
<212> TYPE: DNA
<213> ORGANISM: Artificial
<220> FEATURE:
<223> OTHER INFORMATION: reverse primer

<400> SEQUENCE: 52
gcccaatacg accaaatcc                                                  19

<210> SEQ ID NO 53
<211> LENGTH: 30
<212> TYPE: DNA
<213> ORGANISM: Artificial
<220> FEATURE:
<223> OTHER INFORMATION: forward primer

<400> SEQUENCE: 53
tttgaattcg ccgccaccat gctgaagcct                                      30

<210> SEQ ID NO 54
<211> LENGTH: 34
<212> TYPE: DNA
<213> ORGANISM: Artificial
<220> FEATURE:
<223> OTHER INFORMATION: reverse primer

<400> SEQUENCE: 54
aaagcggccg ctcagccctg ccaaacgcag tcct                                 34

<210> SEQ ID NO 55
<211> LENGTH: 1473
<212> TYPE: DNA
<213> ORGANISM: Homo sapiens
<220> FEATURE:
<221> NAME/KEY: gene
<222> LOCATION: (1)..(1473)

<400> SEQUENCE: 55
```

| | |
|---|---|
| atgaagccta aactgatgta ccaggagctg aaggtgcctg cagaggagcc cgccaatgag | 60 |
| ctgcccatga atgagattga ggcgtggaag gctgcggaaa agaaagcccg ctgggtcctg | 120 |
| ctggtcctca ttctggcggt tgtgggcttc ggagccctga tgactcagct gtttctatgg | 180 |
| gaatacggcg acttgcatct ctttgggccc aaccagcgcc cagcccctg ctatgaccct | 240 |
| tgcgaagcag tgctggtgga aagcattcct gagggcctgg acttccccaa tgcctccacg | 300 |
| gggaacccttt ccaccagcca ggcctggctg gcctgctcg ccggtgcgca cagcagcctg | 360 |
| gacatcgcct ccttctactg gaccctcacc aacaatgaca cccacacgca ggagccctct | 420 |
| gcccagcagg gtgaggaggt cctccggcag ctgcagaccc tgcaccaaa gggcgtgaac | 480 |
| gtccgcatcg ctgtgagcaa gcccagcggg ccccagccac aggcggacct gcaggctctg | 540 |
| ctgcagagcg gtgcccaggt ccgcatggtg gacatgcaga agctgaccca tggcgtcctg | 600 |
| cataccaagt tctgggtggt ggaccagacc cacttctacc tgggcagtgc caacatggac | 660 |
| tggcgttcac tgacccaggt caaggagctg ggcgtggtca tgtacaactg cagctgcctg | 720 |
| gctcgagacc tgaccaagat cttttgaggcc tactggttcc tgggccaggc aggcagctcc | 780 |
| atcccatcaa cttggccccg gttctatgac acccgctaca accaagagac accaatggag | 840 |
| atctgcctca atggaacccc tgctctggcc tacctggcga gtgcgccccc accctgtgt | 900 |
| ccaagtggcc gcactccaga cctgaaggct ctactcaacg tggtggacaa tgcccggagt | 960 |
| ttcatctacg tcgctgtcat gaactacctg cccactctgg agttctccca ccctcacagg | 1020 |
| ttctggcctg ccattgacga tgggctgcgg cgggccacct acgagcgtgg cgtcaaggtg | 1080 |
| cgcctgctca tcagctgctg gggacactcg gagccatcca tgcgggcctt cctgctctct | 1140 |
| ctggctgccc tgcgtgacaa ccatacccac tctgacatcc aggtgaaact ctttgtggtc | 1200 |
| cccgcggatg aggcccaggc tcgaatccca tatgcccgtg tcaaccacaa caagtacatg | 1260 |
| gtgactgaac gcgccaccta catcggaacc tccaactggt ctggcaacta cttcacggag | 1320 |
| acggcgggca cctcgctgct ggtgacgcag aatgggaggg cggcctgcg gagccagctg | 1380 |
| gaggccattt tcctgaggga ctgggactcc ccttacagcc atgaccttga cacctcagct | 1440 |
| gacagcgtgg gcaacgcctg ccgcctgctc tga | 1473 |

<210> SEQ ID NO 56
<211> LENGTH: 1338
<212> TYPE: DNA
<213> ORGANISM: Homo sapiens
<220> FEATURE:
<221> NAME/KEY: gene
<222> LOCATION: (1)..(1338)

<400> SEQUENCE: 56

| | |
|---|---|
| atgggagagg atgaggatgg actctcagaa aaaaattgcc aaaataaatg tcgaattgcc | 60 |
| ctggtggaaa atattcctga aggccttaac tattcagaaa atgcaccatt tcacttatca | 120 |
| cttttccaag gctggatgaa tttactcaac atggccaaaa agtctgttga catagtgtct | 180 |
| tcccatttggg atctcaacca cactcatcca tcagcatgtc agggtcaacg tcttttttgaa | 240 |
| aagttgctcc agctgacttc gcaaaatatt gaaatcaagc tagtgagtga tgtaacagct | 300 |
| gattcaaagg tattagaagc cttgaaatta aagggagccg aggtgacgta catgaacatg | 360 |
| accgcttaca acaagggccg gctgcagtcc tccttctgga tcgtggacaa acagcacgtg | 420 |
| tatatcggca gtgccggttt ggactggcaa tccctgggac agatgaaaga actcggtgtc | 480 |
| atcttctaca actgcagctg cctggtccta gatttacaaa ggatatttgc tctatatagt | 540 |

```
tcattaaaat tcaaaagcag agtgcctcaa acctggtcca aaagactcta tggagtctat    600
gacaatgaaa agaaattgca acttcagttg aatgaaacca aatctcaagc atttgtatcg    660
aattctccaa aactcttttg ccctaaaaac agaagttttg acatagatgc catctacagt    720
gtgatagatg atgccaagca gtatgtgtac atcgctgtca tggactacct gcctatctcc    780
agcacaagca ccaaaaggac ttactggcca gacttggatg caaaaataag agaagcatta    840
gttttacgaa gcgttagagt tcgactcctt ttaagcttct ggaaggaaac tgatcccctt    900
acgtttaact ttatttcatc tcttaaagcg atttgcactg aaatagccaa ctgcagtttg    960
aaagttaaat tttttgatct ggaaagagag aatgcttgtg ctacaaaaga acaaaagaat   1020
cacacctttc ctaggttaaa tcgcaacaag tacatggtga cagatggagc agcttatatt   1080
ggaaattttg attgggtagg gaatgatttc actcagaatg ctggcacggg ccttgttatc   1140
aaccaggcag atgtgaggaa caacagaagc atcattaagc aacttaaaga tgtgtttgaa   1200
agggactggt attcaccgta tgccaaaacc ttacagccaa ccaaacagcc gaactgctca   1260
agcctgttca aactcaaacc cctctccaac aaaactgcca cagacgacac aggcggaaag   1320
gatccccgga acgtatga                                                 1338

<210> SEQ ID NO 57
<211> LENGTH: 39
<212> TYPE: DNA
<213> ORGANISM: Artificial
<220> FEATURE:
<223> OTHER INFORMATION: forward primer

<400> SEQUENCE: 57
tttaagcttg ccgccaccat gaagcctaaa ctgatgtac                            39

<210> SEQ ID NO 58
<211> LENGTH: 57
<212> TYPE: DNA
<213> ORGANISM: Artificial
<220> FEATURE:
<223> OTHER INFORMATION: reverse primer

<400> SEQUENCE: 58
tttgaattct cacttatcgt cgtcatcctt gtaatcgagc aggcggcagg cgttgcc        57

<210> SEQ ID NO 59
<211> LENGTH: 39
<212> TYPE: DNA
<213> ORGANISM: Artificial
<220> FEATURE:
<223> OTHER INFORMATION: forward primer

<400> SEQUENCE: 59
tttaagcttg ccgccaccat gggagaggat gaggatgga                            39

<210> SEQ ID NO 60
<211> LENGTH: 57
<212> TYPE: DNA
<213> ORGANISM: Artificial
<220> FEATURE:
<223> OTHER INFORMATION: reverse primer

<400> SEQUENCE: 60
tttgaattct cacttatcgt cgtcatcctt gtaatctacg ttccggggat cctttcc        57

<210> SEQ ID NO 61
<211> LENGTH: 26
```

```
<212> TYPE: DNA
<213> ORGANISM: Artificial
<220> FEATURE:
<223> OTHER INFORMATION: forward primer

<400> SEQUENCE: 61
agatgctgaa gcctcttcgg agagcg                                          26

<210> SEQ ID NO 62
<211> LENGTH: 25
<212> TYPE: DNA
<213> ORGANISM: Artificial
<220> FEATURE:
<223> OTHER INFORMATION: reverse primer

<400> SEQUENCE: 62
tcagccctgc caaacgcagt cctgg                                           25

<210> SEQ ID NO 63
<211> LENGTH: 1521
<212> TYPE: DNA
<213> ORGANISM: Macaca fascicularis
<220> FEATURE:
<221> NAME/KEY: gene
<222> LOCATION: (1)..(1521)

<400> SEQUENCE: 63
atgctgaagc ctcttcggag agcggcagtg accccatgt ggccgtgctc catgctgccc       60
cgccgcctgt gggacagaga ggctggcacg ttgcaggtcc tgggagtgct ggctatgctg      120
tggctgggct ccatggctct tacctacctc ctgtggcaag tgcgccgtcc tcccacctgg      180
ggccaggtgc agcccaagga cgtgcccagg tcctggggc atggttccag cccagctctg      240
gagcccctgg aagcggaggt caggaagcag agggactcct gccagcttgt ccttgtggaa     300
agcatccccc aggacctgcc atttgcagcc ggcagcctct ccgcccagcc tctgggccag     360
gcctggctgc agctgctgga cactgcccag gagagcgtcc acgtggcttc atactactgg     420
tccctcacag ggcccgacat tggggtcaac gactcatctt cccagctggg agaggccctt     480
ctgcagaagc tgcagcagct gctgggcagg aacatttcct tggctgtggc caccagcagt     540
ccaacactgg ccaggaagtc caccgacctg caggtcctgg ctgcccgagg tgcccaggta     600
cgacgggtgc ccatggggcg gctcaccagg ggcgttttgc actccaaatt ctgggttgtg     660
gatggacggc acatatacat gggcagtgcc aacatggact ggcggtccct gacgcaggtg     720
aaggagcttg gcgctgtcat ctataactgc agccacctgg cccaagacct ggagaagacc     780
ttccagacct actgggtgct gggggtgccc aaggctgtcc tccccaaaac ctggcctcag     840
aacttctcat ctcacatcaa ccgtttccag cccttccagg gcctctttga tggggtgccc     900
accactgcct acttctcagc atcgccaccc gcactctgtc cccagggccg caccccctgac    960 ctggaggcgc tgttggcggt gatggggagc gcccaggagt tcatctatgc ctccgtgatg    1020
gagtatttcc ctaccacgcg cttcagccac ccccgcaggt actggccggt gctggacaac    1080
gcgctgcggg cggcagcctt cagcaagggt gtgcgcgtgc gcctgctggt cagctgcgga    1140
ctcaacacgg accccaccat gttccccatt ctgcggtccc tgcaggcgct cagcaacccc    1200
gcggccaacg tctctgtgga cgtgaaagtc ttcatcgtgc cggtggggaa tcattccaac    1260
atcccgttca gcagggtgaa ccacagcaag ttcatggtca cggagaaggc agcctacata    1320
ggcacctcca actggtcgga ggattacttc agcagcacga cggggtggg cctggtggtc    1380 acccagagcc ccggcgcgca gcccgcgggg gccacggtac aggagcagct gcggcagctc    1440
```
tttgagcggg actggagttc gcgctacgcc gtcggcctgg acggacaggc tccgggccag    1500
gactgcgttt ggcagggctg a    1521

<210> SEQ ID NO 64
<211> LENGTH: 36
<212> TYPE: DNA
<213> ORGANISM: Artificial
<220> FEATURE:
<223> OTHER INFORMATION: primer

<400> SEQUENCE: 64
ccaggagagt gggagaggct cttctcagta tggtgg    36

<210> SEQ ID NO 65
<211> LENGTH: 32
<212> TYPE: DNA
<213> ORGANISM: Artificial
<220> FEATURE:
<223> OTHER INFORMATION: primer

<400> SEQUENCE: 65
ggctcaggga aatagccctt gaccaggcat cc    32

<210> SEQ ID NO 66
<211> LENGTH: 24
<212> TYPE: DNA
<213> ORGANISM: Artificial
<220> FEATURE:
<223> OTHER INFORMATION: primer

<400> SEQUENCE: 66
tccagagttc caggtcactg tcac    24

<210> SEQ ID NO 67
<211> LENGTH: 24
<212> TYPE: DNA
<213> ORGANISM: Artificial
<220> FEATURE:
<223> OTHER INFORMATION: primer

<400> SEQUENCE: 67
aggggccagt ggatagacag atgg    24

<210> SEQ ID NO 68
<211> LENGTH: 24
<212> TYPE: DNA
<213> ORGANISM: Artificial
<220> FEATURE:
<223> OTHER INFORMATION: primer

<400> SEQUENCE: 68
tccagagttc caagtcacag tcac    24

<210> SEQ ID NO 69
<211> LENGTH: 24
<212> TYPE: DNA
<213> ORGANISM: Artificial
<220> FEATURE:
<223> OTHER INFORMATION: primer

<400> SEQUENCE: 69
aggggccagt ggatagactg atgg    24

<210> SEQ ID NO 70

```
<211> LENGTH: 36
<212> TYPE: DNA
<213> ORGANISM: Artificial
<220> FEATURE:
<223> OTHER INFORMATION: anchor primer
<220> FEATURE:
<221> NAME/KEY: misc_feature
<222> LOCATION: (24)..(25)
<223> OTHER INFORMATION: n is deoxyisosine.
<220> FEATURE:
<221> NAME/KEY: misc_feature
<222> LOCATION: (29)..(30)
<223> OTHER INFORMATION: n is deoxyisosine.
<220> FEATURE:
<221> NAME/KEY: misc_feature
<222> LOCATION: (34)..(35)
<223> OTHER INFORMATION: n is deoxyisosine.

<400> SEQUENCE: 70
ggccacgcgt cgactagtac gggnngggnn gggnng                            36

<210> SEQ ID NO 71
<211> LENGTH: 20
<212> TYPE: DNA
<213> ORGANISM: Artificial
<220> FEATURE:
<223> OTHER INFORMATION: AUAP primer

<400> SEQUENCE: 71
ggccacgcgt cgactagtac                                              20

<210> SEQ ID NO 72
<211> LENGTH: 31
<212> TYPE: DNA
<213> ORGANISM: Artificial
<220> FEATURE:
<223> OTHER INFORMATION: primer

<400> SEQUENCE: 72
cactacttcc tgttgaagct cttgacgatg g                                 31

<210> SEQ ID NO 73
<211> LENGTH: 23
<212> TYPE: DNA
<213> ORGANISM: Artificial
<220> FEATURE:
<223> OTHER INFORMATION: primer

<400> SEQUENCE: 73
gtgagtggcc tcacaggtat agc                                          23

<210> SEQ ID NO 74
<211> LENGTH: 504
<212> TYPE: DNA
<213> ORGANISM: Mus musculus

<400> SEQUENCE: 74
atgagatcac agttctctat acagttactg agcacacaga acctcacctt gggatggagc    60
tgtatcatcc tcttcttggt agcaacagct acaggtgtcc actcccaggt ccaactgcag   120
cagcctgggg ctgaactggt gaagcctggg acttcagtga aaatgtcctg caaggcttct   180
ggctacacct tcaccagcta ctggatgcac tgggtgaagc agaggccggg acaaggcctt   240
gagtggattg agatattta tcctggtagt gatagtacta actacaatga gaagttcaag   300
agcaaggcca cactgactgt agacacatcc tccagcacag cctacatgca actcagcagc   360
ctgacatctg aggactctgc ggtctattac tgtgcaagag gagggtggtt ggatgctatg   420
```

```
gactactggg gtcaaggaac ctcagtcacc gtctcctcag ccaaaacaac accccatca    480 gtctatccac tggcccctaa gggc                                          504
```

<210> SEQ ID NO 75
<211> LENGTH: 168
<212> TYPE: PRT
<213> ORGANISM: Mus musculus

<400> SEQUENCE: 75

```
Met Arg Ser Gln Phe Ser Ile Gln Leu Leu Ser Thr Gln Asn Leu Thr
1               5                   10                  15

Leu Gly Trp Ser Cys Ile Ile Leu Phe Leu Val Ala Thr Ala Thr Gly
            20                  25                  30

Val His Ser Gln Val Gln Leu Gln Gln Pro Gly Ala Glu Leu Val Lys
        35                  40                  45

Pro Gly Thr Ser Val Lys Met Ser Cys Lys Ala Ser Gly Tyr Thr Phe
    50                  55                  60

Thr Ser Tyr Trp Met His Trp Val Lys Gln Arg Pro Gly Gln Gly Leu
65                  70                  75                  80

Glu Trp Ile Gly Asp Ile Tyr Pro Gly Ser Asp Ser Thr Asn Tyr Asn
                85                  90                  95

Glu Lys Phe Lys Ser Lys Ala Thr Leu Thr Val Asp Thr Ser Ser Ser
            100                 105                 110

Thr Ala Tyr Met Gln Leu Ser Ser Leu Thr Ser Glu Asp Ser Ala Val
        115                 120                 125

Tyr Tyr Cys Ala Arg Gly Gly Trp Leu Asp Ala Met Asp Tyr Trp Gly
    130                 135                 140

Gln Gly Thr Ser Val Thr Val Ser Ser Ala Lys Thr Thr Pro Pro Ser
145                 150                 155                 160

Val Tyr Pro Leu Ala Pro Lys Gly
                165
```

<210> SEQ ID NO 76
<211> LENGTH: 437
<212> TYPE: DNA
<213> ORGANISM: Mus musculus

<400> SEQUENCE: 76

```
atggaatgta actggatact tccttttatt ctgtcggtaa tttcaggggt ctcctcagag    60
gttcagctcc agcagtctgg gactgtgctg tcaaggcctg ggcttccgt gacgatgtcc    120 tgcaaggctt ctggcgacag ctttaccacc tactggatgc actgggtaaa acagaggcct    180
ggacagggtc tagaatggat tggtgctatc tatcctggaa atagtgaaac tagctacaac    240
cagaagttca gggcaaggc caaactgact gcagtcacat ccgccagcac tgcctatatg    300
gagttcacta gcctgacaaa tgaggactct gcggtctatt actgtacggg gggttattcc    360
gactttgact actggggcca aggcaccact ctcacagtct cctcagccaa aacgacaccc    420
ccatctgtct atccact                                                  437
```

<210> SEQ ID NO 77
<211> LENGTH: 145
<212> TYPE: PRT
<213> ORGANISM: Mus musculus

<400> SEQUENCE: 77

```
Met Glu Cys Asn Trp Ile Leu Pro Phe Ile Leu Ser Val Ile Ser Gly
```

```
  1               5                   10                  15
Val Ser Ser Glu Val Gln Leu Gln Gln Ser Gly Thr Val Leu Ser Arg
         20                  25                  30
Pro Gly Ala Ser Val Thr Met Ser Cys Lys Ala Ser Gly Asp Ser Phe
         35                  40                  45
Thr Thr Tyr Trp Met His Trp Val Lys Gln Arg Pro Gly Gln Gly Leu
     50                  55                  60
Glu Trp Ile Gly Ala Ile Tyr Pro Gly Asn Ser Glu Thr Ser Tyr Asn
65                  70                  75                  80
Gln Lys Phe Lys Gly Lys Ala Lys Leu Thr Ala Val Thr Ser Ala Ser
             85                  90                  95
Thr Ala Tyr Met Glu Phe Thr Ser Leu Thr Asn Glu Asp Ser Ala Val
             100                 105                 110
Tyr Tyr Cys Thr Gly Gly Tyr Ser Asp Phe Asp Tyr Trp Gly Gln Gly
             115                 120                 125
Thr Thr Leu Thr Val Ser Ser Ala Lys Thr Thr Pro Pro Ser Val Tyr
         130                 135                 140
Pro
145

<210> SEQ ID NO 78
<211> LENGTH: 475
<212> TYPE: DNA
<213> ORGANISM: Mus musculus

<400> SEQUENCE: 78
atgggatgga gctggatctt tctcttcctc ctgtcaggaa ctgcaggcgt ccactctgag    60
gtccagcttc agcagtcagg acctgaactg gtgaaacctg gggcctcagt gaagatatcc   120
tgcaaggctt ctggatacac attcactgac tacaacttgc actgggtgaa gcagagccat   180
ggaaagagcc ttgagtggat tggatatatt tatccttaca atggtaatac tggctacaac   240
cagaagttca gaggaaggc cacattgact gtagacaatt cctccggcac agtctacatg   300
gagctccgca gcctgacatc tgaggactct gcagtctatt actgtgcaag aggagggatc   360
tatgatgatt actacgacta tgctatcgac tattggggtc aaggaacctc agtcaccgtc   420
tcctcagcca aaacaacacc cccatcagtc tatccactgg cccctaaggg cgaat        475

<210> SEQ ID NO 79
<211> LENGTH: 158
<212> TYPE: PRT
<213> ORGANISM: Mus musculus

<400> SEQUENCE: 79

Met Gly Trp Ser Trp Ile Phe Leu Phe Leu Leu Ser Gly Thr Ala Gly
1               5                   10                  15
Val His Ser Glu Val Gln Leu Gln Gln Ser Gly Pro Glu Leu Val Lys
             20                  25                  30
Pro Gly Ala Ser Val Lys Ile Ser Cys Lys Ala Ser Gly Tyr Thr Phe
             35                  40                  45
Thr Asp Tyr Asn Leu His Trp Val Lys Gln Ser His Gly Lys Ser Leu
         50                  55                  60
Glu Trp Ile Gly Tyr Ile Tyr Pro Tyr Asn Gly Asn Thr Gly Tyr Asn
65                  70                  75                  80
Gln Lys Phe Lys Arg Lys Ala Thr Leu Thr Val Asp Asn Ser Ser Gly
             85                  90                  95
```

```
Thr Val Tyr Met Glu Leu Arg Ser Leu Thr Ser Glu Asp Ser Ala Val
            100                 105                 110

Tyr Tyr Cys Ala Arg Gly Gly Ile Tyr Asp Asp Tyr Tyr Asp Tyr Ala
        115                 120                 125

Ile Asp Tyr Trp Gly Gln Gly Thr Ser Val Thr Val Ser Ser Ala Lys
    130                 135                 140

Thr Thr Pro Pro Ser Val Tyr Pro Leu Ala Pro Lys Gly Glu
145                 150                 155

<210> SEQ ID NO 80
<211> LENGTH: 470
<212> TYPE: DNA
<213> ORGANISM: Mus musculus

<400> SEQUENCE: 80
atgggatgga gctggatctt tctcttcctc ctgtcaggaa ctgcaggcgt ccactctgag      60
gtccagcttc agcagtcagg acctgaactg gtgaaacctg gggcctcagt gaagatatcc     120
tgcaaggctt ctggatacac attcactgac tacaacttgc actgggtgaa gcagagccat     180
ggaaagagcc ttgagtggat tggatatatt tatccttaca atggtaatac tggctacaac     240
cagaagttca gaggaaggc cacattgact gtagacaatt cctccggcac agtctacatg      300
gagctccgca gcctgacatc tgaggactct gcagtctatt actgtgcaag aggagggatc     360
tatgatgatt actacgacta tgctatcgac tattggggtc aaggaacctc agtcaccgtc     420
tcctcagcca aaacaacacc cccatcagtc tatccactgg cccctaaggg                470

<210> SEQ ID NO 81
<211> LENGTH: 156
<212> TYPE: PRT
<213> ORGANISM: Mus musculus

<400> SEQUENCE: 81

Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Leu His Trp Val Lys Gln Ser His Gly Lys Ser Leu
    50                  55                  60

Glu Trp Ile Gly Tyr Ile Tyr Pro Tyr Asn Gly Asn Thr Gly Tyr Asn
65                  70                  75                  80

Gln Lys Phe Lys Arg Lys Ala Thr Leu Thr Val Asp Asn Ser Ser Gly
                85                  90                  95

Thr Val Tyr Met Glu Leu Arg Ser Leu Thr Ser Glu Asp Ser Ala Val
            100                 105                 110

Tyr Tyr Cys Ala Arg Gly Gly Ile Tyr Asp Asp Tyr Tyr Asp Tyr Ala
        115                 120                 125

Ile Asp Tyr Trp Gly Gln Gly Thr Ser Val Thr Val Ser Ser Ala Lys
    130                 135                 140

Thr Thr Pro Pro Ser Val Tyr Pro Leu Ala Pro Lys
145                 150                 155

<210> SEQ ID NO 82
<211> LENGTH: 462
<212> TYPE: DNA
<213> ORGANISM: Mus musculus
```

<400> SEQUENCE: 82

```
atgggatgga gctatatcat cctcttttg gtagcaacag caacaggggt ccactcccag      60
gtccaactgc agcagtcggg ggctgaactg gtgaagcctg gggcttcagt gaagttgtcc     120
tgcaaggctt ctggctacac cttcaccagc tactatttgt actgggtgag gcagaggcct    180
ggacaaggcc ttgagtggat tggactgatt aatcctacca atagtgatac tatcttcaat    240
gagaagttca gagcaaggc cacactgact gtagacaaat cctccagcac agcatacatg     300
caactcagca gcctgacatc tgaggactct gcggtctatt actgtacacg agagggggga    360
tatggttacg gcccgtttgc ttactggggc caagggactc tggtcactgt ctctgcagcc    420
aaaacaacac ccccatcagt ctatccactg gcccctaagg gc                        462
```

<210> SEQ ID NO 83
<211> LENGTH: 154
<212> TYPE: PRT
<213> ORGANISM: Mus musculus

<400> SEQUENCE: 83

```
Met Gly Trp Ser Tyr Ile Ile Leu Phe Leu Val Ala Thr Ala Thr Gly
1               5                   10                  15
Val His Ser Gln Val Gln Leu Gln Gln Ser Gly Ala Glu Leu Val Lys
            20                  25                  30
Pro Gly Ala Ser Val Lys Leu Ser Cys Lys Ala Ser Gly Tyr Thr Phe
        35                  40                  45
Thr Ser Tyr Tyr Leu Tyr Trp Val Arg Gln Arg Pro Gly Gln Gly Leu
    50                  55                  60
Glu Trp Ile Gly Leu Ile Asn Pro Thr Asn Ser Asp Thr Ile Phe Asn
65                  70                  75                  80
Glu Lys Phe Lys Ser Lys Ala Thr Leu Thr Val Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Thr Arg Glu Gly Gly Tyr Gly Tyr Gly Pro Phe Ala Tyr
        115                 120                 125
Trp Gly Gln Gly Thr Leu Val Thr Val Ser Ala Ala Lys Thr Thr Pro
    130                 135                 140
Pro Ser Val Tyr Pro Leu Ala Pro Lys Gly
145                 150
```

<210> SEQ ID NO 84
<211> LENGTH: 450
<212> TYPE: DNA
<213> ORGANISM: Mus musculus

<400> SEQUENCE: 84

```
atgaacttcg ggctcagctt gattttcctt gccctcattt taaaaggtgt ccagtgtgag      60
gtgcagctgg tggagtctgg gggagactta gtgaggcctg agggtccct gaaactctcc     120
tgtgcagcct ctggattcag tttcagtagc tatggcatgt cttggtttcg ccagactcca    180
gacaagaggc tggagtgggt cgcaaccatt agtagtggtg gtagttacat ctactatcca    240
gaaagtgtga aggggcgatt caccatctcc agagacaatg ccaggaacat cctgtacctg    300
caaatgagca gtctgaagtc tgaggacaca gccatgtatt attgtgtaag actctacggt    360
ggtaggagag gctatggttt ggactactgg ggtcaaggaa cctcagtcac cgtctcctca    420
```

-continued

```
gccaaaacaa cagccccatc ggtctatcca                                        450
```

<210> SEQ ID NO 85
<211> LENGTH: 150
<212> TYPE: PRT
<213> ORGANISM: Mus musculus

<400> SEQUENCE: 85

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Arg
            20                  25                  30

Pro Gly Gly Ser Leu Lys Leu Ser Cys Ala Ala Ser Gly Phe Ser Phe
        35                  40                  45

Ser Ser Tyr Gly Met Ser Trp Phe Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Glu Ser Val Lys Gly Arg Phe Thr Ile Ser Arg Asp Asn Ala Arg Asn
                85                  90                  95

Ile Leu Tyr Leu Gln Met Ser Ser Leu Lys Ser Glu Thr Ala Met
            100                 105                 110

Tyr Tyr Cys Val Arg Leu Tyr Gly Gly Arg Arg Gly Tyr Gly Leu Asp
        115                 120                 125

Tyr Trp Gly Gln Gly Thr Ser Val Thr Val Ser Ala Lys Thr Thr
    130                 135                 140

Ala Pro Ser Val Tyr Pro
145                 150

<210> SEQ ID NO 86
<211> LENGTH: 450
<212> TYPE: DNA
<213> ORGANISM: Mus musculus

<400> SEQUENCE: 86

```
atgaacttcg ggctcagctt gattttcctt gccctcattt taaaaggtgt ccagtgtgag    60
gtgcagctgg tggagtctgg gggagactta gtgaggcctg agggtccct gaaactctcc    120
tgtgcagcct ctggattcag tttcagtagc tatggcatgt cttggtttcg ccagactcca    180
gacaagaggc tggagtgggt cgcaaccatt agtagtggtg gtagttacat ctactatcca    240
gaaagtgtga aggggcgatt caccatctcc agagacaatg ccaggaacat cctgtacctg    300
caaatgagca gtctgaagtc tgaggacaca gccatgtatt attgtgtaag actctacggt    360
ggtaggagag ctatggtttt ggactactgg ggtcaaggaa cctcagtcac cgtctcctca    420
gccaaaacaa cacccccatc agtctatcca                                      450
```

<210> SEQ ID NO 87
<211> LENGTH: 150
<212> TYPE: PRT
<213> ORGANISM: Mus musculus

<400> SEQUENCE: 87

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Arg
            20                  25                  30

Pro Gly Gly Ser Leu Lys Leu Ser Cys Ala Ala Ser Gly Phe Ser Phe

```
                35                  40                  45
Ser Ser Tyr Gly Met Ser Trp Phe Arg Gln Thr Pro Asp Lys Arg Leu
    50                  55                  60

Glu Trp Val Ala Thr Ile Ser Gly Gly Ser Tyr Ile Tyr Tyr Pro
65                  70                  75                  80

Glu Ser Val Lys Gly Arg Phe Thr Ile Ser Arg Asp Asn Ala Arg Asn
                85                  90                  95

Ile Leu Tyr Leu Gln Met Ser Ser Leu Lys Ser Glu Asp Thr Ala Met
                100                 105                 110

Tyr Tyr Cys Val Arg Leu Tyr Gly Gly Arg Arg Gly Tyr Gly Leu Asp
            115                 120                 125

Tyr Trp Gly Gln Gly Thr Ser Val Thr Val Ser Ser Ala Lys Thr Thr
        130                 135                 140

Pro Pro Ser Val Tyr Pro
145                 150

<210> SEQ ID NO 88
<211> LENGTH: 472
<212> TYPE: DNA
<213> ORGANISM: Mus musculus

<400> SEQUENCE: 88
atgaaagtgt tgagtctgtt gtacctgttg acagccattc ctggtatcct gtctgatgta      60
cagcttcagg agtcaggacc tggcctcgtg aaaccttctc aatctctgtc tctcacctgc     120
tctgtcactg gctactccat caccagtcat tattactgga cctggatccg gcagtttcca     180
ggaaacaaac tggaatggat gggctacata agctacgacg gtagcaataa ctacaaccca     240
tctctcaaaa atcgaatctc catcactcgt gacacatcta agaaccagtt tttcctgaag     300
ttgaattctg tgactactga ggacacagct acatataact gtgcaagaga gggcccgctc     360
tactatggta accctactg gtatttcgat gtctggggcg cagggaccac ggtcaccgtc     420
tcctcagcca aaacaacacc cccatcagtc tatccactgg cccctaaggg cg             472

<210> SEQ ID NO 89
<211> LENGTH: 157
<212> TYPE: PRT
<213> ORGANISM: Mus musculus

<400> SEQUENCE: 89

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Ser Val Thr Gly Tyr Ser Ile Thr
            35                  40                  45

Ser His Tyr Tyr Trp Thr Trp Ile Arg Gln Phe Pro Gly Asn Lys Leu
    50                  55                  60

Glu Trp Met Gly Tyr Ile Ser Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
                100                 105                 110

Asn Cys Ala Arg Glu Gly Pro Leu Tyr Tyr Gly Asn Pro Tyr Trp Tyr
            115                 120                 125
```

Phe Asp Val Trp Gly Ala Gly Thr Thr Val Thr Val Ser Ser Ala Lys
130                 135                 140

Thr Thr Pro Pro Ser Val Tyr Pro Leu Ala Pro Lys Gly
145                 150                 155

<210> SEQ ID NO 90
<211> LENGTH: 471
<212> TYPE: DNA
<213> ORGANISM: Mus musculus

<400> SEQUENCE: 90

```
atgaaagtgt tgagtctgtt gtacctgttg acagccattc ctggtatcct gtctgatgta      60
cagcttcagg agtcaggacc tggcctcgtg aaaccttctc agtctctgtc tctcacctgc     120
tctgtcactg gctactccat ctccagtcat tattactgga gttggatccg gcagtttcca     180
ggaaacagac tggaatggat gggctacata agctacgacg gtagcaataa ctacaaccca     240
tctctcaaaa atcgaatctc catcactcgt gacacatcta agaaccagtt tttcctgaag     300
ttgaattctg tgactactga ggacacagct acatataact gtgcaagaga gggcccgctc     360
tactatggta accccactg gtatttcgat gtctggggcg cagggaccac ggtcaccgtc     420
tcctcagcca aaacaacacc cccatcagtc tatccactgg cccctaaggg c             471
```

<210> SEQ ID NO 91
<211> LENGTH: 157
<212> TYPE: PRT
<213> ORGANISM: Mus musculus

<400> SEQUENCE: 91

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Ser
        35                  40                  45

Ser His Tyr Tyr Trp Ser Trp Ile Arg Gln Phe Pro Gly Asn Arg Leu
    50                  55                  60

Glu Trp Met Gly Tyr Ile Ser Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
            100                 105                 110

Asn Cys Ala Arg Glu Gly Pro Leu Tyr Tyr Gly Asn Pro Tyr Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Lys Gly
145                 150                 155

<210> SEQ ID NO 92
<211> LENGTH: 470
<212> TYPE: DNA
<213> ORGANISM: Mus musculus

<400> SEQUENCE: 92

```
atgaaagtgt tgagtctgtt gtacctgttg acagccattc ctggtatcct gtctgatgta      60
cagcttcagg agtcaggacc tggcctcgtg aaaccttctc agtctctgtc tctcacctgc     120
```

```
tctgtcactg gctactccat ctccagtcat tattactgga gttggatccg gcagtttcca    180
ggaaacagac tggaatggat gggctacata agctacgacg tagcaataa ctacaaccca     240 tctctcaaaa atcgaatctc catcactcgt gacacatcta agaaccagtt tttcctgaag    300
ttgaattctg tgactactga ggacacagct acatataact gtgcaagaga gggcccgctc    360
tactatggta acccctactg gtatttcgat gtctggggcg cagggaccac ggtcaccgtc    420
tcctcagcca aaacgacacc cccatctgtc tatccactgg cccctaaggg               470
```

<210> SEQ ID NO 93
<211> LENGTH: 156
<212> TYPE: PRT
<213> ORGANISM: Mus musculus

<400> SEQUENCE: 93

```
Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Ser
        35                  40                  45

Ser His Tyr Tyr Trp Ser Trp Ile Arg Gln Phe Pro Gly Asn Arg Leu
    50                  55                  60

Glu Trp Met Gly Tyr Ile Ser Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
            100                 105                 110

Asn Cys Ala Arg Glu Gly Pro Leu Tyr Tyr Gly Asn Pro Tyr Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Lys
145                 150                 155
```

<210> SEQ ID NO 94
<211> LENGTH: 421
<212> TYPE: DNA
<213> ORGANISM: Mus musculus

<400> SEQUENCE: 94

```
atgatgtcct ctgctcagtt ccttggtctc ctgttgctct gttttcaagg taccagatgt    60
gatatccaga tgacacagac tacatcctcc ctgtctgcct ctctgggaga cagagtcacc    120
atcagttgca gggcaagtca ggacattagc aattatttaa actggtatca gcagaaacca    180
gatggaactg ttaaactcct gatctactac acatcaagat acactcagg agtcccatca     240 aggttcagtg gcagtgggtc tggaacagat tattctctca ccattagcaa cctggagcaa    300
gaagatattg ccacttactt ttgccaacag gtaatacgc ttccgtggac gttcggtgga     360
ggcaccaagc tggaaatcaa acgggctgat gctgcaccaa ctgtatccat caagggcgaa    420
t                                                                    421
```

<210> SEQ ID NO 95
<211> LENGTH: 140
<212> TYPE: PRT

<213> ORGANISM: Mus musculus

<400> SEQUENCE: 95

Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Trp Thr Phe Gly Gly Gly Thr Lys Leu Glu Ile Lys Arg
        115                 120                 125

Ala Asp Ala Ala Pro Thr Val Ser Ile Lys Gly Glu
    130                 135                 140

<210> SEQ ID NO 96
<211> LENGTH: 459
<212> TYPE: DNA
<213> ORGANISM: Mus musculus

<400> SEQUENCE: 96
atgatggtcc ttgctcagtt tcttgcattc ttgttgcttt ggtttccagg tgcaggatgt        60
gacatcctga tgacccaatc tccatcctcc atgtctgtat ctctgggaga cacagtcagc       120
atcacttgcc atgcaagtca gggcattaga agtaatatag gtggttgca gcagaaacca        180
gggaaatcat ttaagggcct gatctttcat ggaaccaact tggaagatgg agttccatca       240
aggttcagtg gcagaggatc tggagcagat tattctctca ccatcaacag cctggaatct       300
gaagattttg cagactatta ctgtgtacag tatgttcagt ttcctccaac gttcggctcg       360
gggacaaagt tggaaataag acgggctgat gctgcaccaa ctgtatccat cttcccacca       420
tccagtgagc agttaacatc tggaggtgcc tcagtcgtg                              459

<210> SEQ ID NO 97
<211> LENGTH: 153
<212> TYPE: PRT
<213> ORGANISM: Mus musculus

<400> SEQUENCE: 97

Met Met Val Leu Ala Gln Phe Leu Ala Phe Leu Leu Leu Trp Phe Pro
1               5                   10                  15

Gly Ala Gly Cys Asp Ile Leu Met Thr Gln Ser Pro Ser Ser Met Ser
            20                  25                  30

Val Ser Leu Gly Asp Thr Val Ser Ile Thr Cys His Ala Ser Gln Gly
        35                  40                  45

Ile Arg Ser Asn Ile Gly Trp Leu Gln Gln Lys Pro Gly Lys Ser Phe
    50                  55                  60

Lys Gly Leu Ile Phe His Gly Thr Asn Leu Glu Asp Gly Val Pro Ser
65                  70                  75                  80

Arg Phe Ser Gly Arg Gly Ser Gly Ala Asp Tyr Ser Leu Thr Ile Asn

```
                85                  90                  95
Ser Leu Glu Ser Glu Asp Phe Ala Asp Tyr Tyr Cys Val Gln Tyr Val
            100                 105                 110

Gln Phe Pro Pro Thr Phe Gly Ser Gly Thr Lys Leu Glu Ile Arg Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val
145                 150

<210> SEQ ID NO 98
<211> LENGTH: 467
<212> TYPE: DNA
<213> ORGANISM: Mus musculus

<400> SEQUENCE: 98
atgagtgtgc ccactcaggt cctggggttg ctgctgctgt ggcttacaga tgccagatgt      60
gacatccaga tgactcagtc tccagcctcc ctatctgtat ctgtgggaga aactgtcgcc     120
atcacatgtc gagcaagtga gaatatttac agtcatatag catggtatca gcagaaagag     180
ggaaaatctc ctcagcgcct ggtctatggt gcaacaaact tagcacatgg tgtgccatca     240
aggttcagtg gcagtggatc aggcacacag tattccctca agatcaacag ccttcagtct     300
gaagattttg ggagttatta ctgtcaacat ttttggggta ctccgtggac gttcggtgga     360
ggcaccaagc tggaaatcaa acgggctgat gctgcaccaa ctgtatccat cttcccacca     420
tccagtgagc agttaacatc tggaggtgcc tcagtcgtgt gcttctt                   467

<210> SEQ ID NO 99
<211> LENGTH: 155
<212> TYPE: PRT
<213> ORGANISM: Mus musculus

<400> SEQUENCE: 99

Met Ser Val Pro Thr Gln Val Leu Gly Leu Leu Leu Leu Trp Leu Thr
1               5                  10                  15

Asp Ala Arg Cys Asp Ile Gln Met Thr Gln Ser Pro Ala Ser Leu Ser
            20                  25                  30

Val Ser Val Gly Glu Thr Val Ala Ile Thr Cys Arg Ala Ser Glu Asn
        35                  40                  45

Ile Tyr Ser His Ile Ala Trp Tyr Gln Gln Lys Glu Gly Lys Ser Pro
    50                  55                  60

Gln Arg Leu Val Tyr Gly Ala Thr Asn Leu Ala His Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe
145                 150                 155

<210> SEQ ID NO 100
<211> LENGTH: 454
```

```
<212> TYPE: DNA
<213> ORGANISM: Mus musculus

<400> SEQUENCE: 100
atgagtgtgc ccactcaggt cctggggttg ctgctgctgt ggcttacaga tgccagatgt      60
gacatccaga tgactcagtc tccagcctcc ctatctgtat ctgtgggaga aactgtcgcc     120
atcacatgtc gagcaagtga gaatatttac agtcatatag catggtatca gcagaaagag     180
ggaaaatctc ctcagcgcct ggtctatggt gcaacaaact agcacatggg tgtgccatca     240
aggttcagtg gcagtggatc aggcacacag tattccctca agatcaacag ccttcagtct     300
gaagattttg ggagttatta ctgtcaacat ttttgggggta ctccgtggac gttcggtgga     360
ggcaccaagc tggaaatcaa acgggctgat gctgcaccaa ctgtatccat cttcccacca     420
tccagtgagc agttaacatc tggaggtgcc tcag                                 454

<210> SEQ ID NO 101
<211> LENGTH: 151
<212> TYPE: PRT
<213> ORGANISM: Mus musculus

<400> SEQUENCE: 101

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Ala Ile Thr Cys Arg Ala Ser Glu Asn
        35                  40                  45

Ile Tyr Ser His Ile Ala Trp Tyr Gln Gln Lys Glu Gly Lys Ser Pro
    50                  55                  60

Gln Arg Leu Val Tyr Gly Ala Thr Asn Leu Ala His Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser
145                 150

<210> SEQ ID NO 102
<211> LENGTH: 457
<212> TYPE: DNA
<213> ORGANISM: Mus musculus

<400> SEQUENCE: 102
atgaagttgc ctgttaggct gttggtgctg atgttctgga ttcctgcttc cagcagtgat      60
gttgtgatga cccaaactcc actctccctg cctgtcagtc ttggagatca agcctccatc     120
tcttgcacat ctagtcagac ccttgtacac agtaatggaa acacctattt acattggtac     180
ctgcagaagc caggccagtc tccaaagctc ctgatctaca agtttccaa ccgattttct      240
ggggtcccag acaggttcag tggcagtgga tcagggacag atttcacact caagatcagc     300
agagtggagg ctgaggatct gggagtttat ttctgctctc acagtacaca tgttccattc     360
```

```
acgttcggct cggggacaaa gttggaaata aaacgggctg atgctgcacc aactgtatcc    420
atcttcccac catccagtga gcagttaaca tctggag                            457
```

<210> SEQ ID NO 103
<211> LENGTH: 152
<212> TYPE: PRT
<213> ORGANISM: Mus musculus

<400> SEQUENCE: 103

```
Met Lys Leu Pro Val Arg Leu Leu Val Leu Met Phe Trp Ile Pro Ala
1               5                  10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Thr Ser Ser Gln Thr Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser His Ser Thr His Val Pro Phe Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly
145                 150
```

<210> SEQ ID NO 104
<211> LENGTH: 423
<212> TYPE: DNA
<213> ORGANISM: Mus musculus

<400> SEQUENCE: 104

```
atgaggttct ctgctcagct tctggggctg cttgtgctct ggatccctgg atccactgcg    60
gaaattgtga tgacgcaggc tgcattctcc aatccagtca ctcttggaac atcagcttcc   120
atctcctgca ggtctagtaa gagtctccta catagtgatg gcatcactta tttgtattgg   180
tatctgcaga agccaggcca gtctcctcag ctcctgattt atcagatgtc caaccttgcc   240
tcaggagtcc cagacaggtt cagtagcagt gggtcaggaa ctgatttcac actgagaatc   300
agcagagtgg aggctgagga tgtgggtgtt tattactgtg ctcaaaatct agaactttac   360
acgttcggag gggggaccaa gctggaaata aaacgggctg atgctgcacc aactgtatcc   420
atc                                                                 423
```

<210> SEQ ID NO 105
<211> LENGTH: 141
<212> TYPE: PRT
<213> ORGANISM: Mus musculus

<400> SEQUENCE: 105

```
Met Arg Phe Ser Ala Gln Leu Leu Gly Leu Leu Val Leu Trp Ile Pro
1               5                  10                  15

Gly Ser Thr Ala Glu Ile Val Met Thr Gln Ala Ala Phe Ser Asn Pro
            20                  25                  30
```

Val Thr Leu Gly Thr Ser Ala Ser Ile Ser Cys Arg Ser Ser Lys Ser
            35                  40                  45

Leu Leu His Ser Asp Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Tyr Thr Phe Gly Gly Gly Thr Lys Leu
            115                 120                 125

Glu Ile Lys Arg Ala Asp Ala Ala Pro Thr Val Ser Ile
            130                 135                 140

<210> SEQ ID NO 106
<211> LENGTH: 423
<212> TYPE: DNA
<213> ORGANISM: Mus musculus

<400> SEQUENCE: 106
atgaggttct ctgctcagct tctggggctg cttgtgctct ggatccctgg atccactgcg    60
gaaattgtga tgacgcaggc tgcattctcc aatccagtca ctcttggaac atcagcttcc   120
atctcctgca ggtctagtaa gagtctccta catagtgatg gcatcactta tttgtattgg   180
tatctgcaga agccaggcca gtctcctcag ctcctgattt atcagatgtc caaccttgcc   240
tcaggagtcc cagacaggtt cagtagcagt gggtcaggaa ctgatttcac actgagaatc   300
agcagagtgg aggctgagga tgtgggtgtt tattactgtg ctcaaaatct agaactttac   360
acgttcggag gggggaccaa gctggaaata aaacgggctg atgctgcacc aactgtatcc   420
atc                                                                 423

<210> SEQ ID NO 107
<211> LENGTH: 141
<212> TYPE: PRT
<213> ORGANISM: Mus musculus

<400> SEQUENCE: 107

Met Arg Phe Ser Ala Gln Leu Leu Gly Leu Leu Val Leu Trp Ile Pro
1               5                   10                  15

Gly Ser Thr Ala Glu Ile Val Met Thr Gln Ala Ala Phe Ser Asn Pro
            20                  25                  30

Val Thr Leu Gly Thr Ser Ala Ser Ile Ser Cys Arg Ser Ser Lys Ser
            35                  40                  45

Leu Leu His Ser Asp Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Tyr Thr Phe Gly Gly Gly Thr Lys Leu
            115                 120                 125

Glu Ile Lys Arg Ala Asp Ala Ala Pro Thr Val Ser Ile

<210> SEQ ID NO 108
<211> LENGTH: 404
<212> TYPE: DNA
<213> ORGANISM: Mus musculus

<400> SEQUENCE: 108

```
atgatgtcct ctgctcagtt ccttggtctc ctgttgctct gttttcaagg taccagatgt    60
gatatccaga tgacacagac tacatcctcc ctgtctgcct ctctggggga cagagtcacc   120
atcagttgca gggcaagtca ggacattgac aattatttaa actggtatca gcagaaacca   180
gatggaactg ttaaactcct gatctactac acatcaagat acactcagg agtcccatca    240
aggttcagtg gcagtgggtc tggaacagat tattctctca ccattagcaa cctggagcaa   300
gaagatgttg ccacttactt tgccagcag tttaatacgc ttcctcggac gttcggtgga    360
ggcaccaaac tggaaatcaa acgggctgat gctgcaccaa ctgt                    404
```

<210> SEQ ID NO 109
<211> LENGTH: 134
<212> TYPE: PRT
<213> ORGANISM: Mus musculus

<400> SEQUENCE: 109

```
Met Met Ser Ser Ala Gln Phe Leu Gly Leu Leu Leu Leu Cys Phe Gln
1               5                   10                  15
Gly Thr Arg Cys Asp Ile Gln Met Thr Gln Thr Thr Ser Ser Leu Ser
            20                  25                  30
Ala Ser Leu Gly Asp Arg Val Thr Ile Ser Cys Arg Ala Ser Gln Asp
        35                  40                  45
Ile Asp Asn Tyr Leu Asn Trp Tyr Gln Gln Lys Pro Asp Gly Thr Val
    50                  55                  60
Lys Leu Leu Ile Tyr Tyr Thr Ser Arg Leu His Ser Gly Val Pro Ser
65                  70                  75                  80
Arg Phe Ser Gly Ser Gly Ser Gly Thr Asp Tyr Ser Leu Thr Ile Ser
                85                  90                  95
Asn Leu Glu Gln Glu Asp Val Ala Thr Tyr Phe Cys Gln Gln Phe Asn
            100                 105                 110
Thr Leu Pro Arg Thr Phe Gly Gly Gly Thr Lys Leu Glu Ile Lys Arg
        115                 120                 125
Ala Asp Ala Ala Pro Thr
    130
```

<210> SEQ ID NO 110
<211> LENGTH: 414
<212> TYPE: DNA
<213> ORGANISM: Mus musculus

<400> SEQUENCE: 110

```
atgatgtcct ctgctcagtt ccttggtctc ctgttgctct gttttcaagg taccagatgt    60
gatatccaga tgacacagac tacatcctcc ctgtctgcct ctctgggggg cagcgtcacc   120
atcagttgca gggcaagtca ggacattgac aattatttaa actggtatca gcaaaaacca   180
gatggaactg ttaaactcct gatctactac acatcaagat acactcagg agtcccatca    240
aggttcagtg gcagtgggtc tggaacagat tattctctca ccattagcaa cctgaacaa    300
gaagatattg ccacttactt tgccaacag tttaatacgc ttcctcggac gttcggtgga    360
```
ggcaccaagc tggaaatcaa acgggctgat gctgcaccaa ctgtatccat cttc     414

<210> SEQ ID NO 111
<211> LENGTH: 138
<212> TYPE: PRT
<213> ORGANISM: Mus musculus

<400> SEQUENCE: 111

Met Met Ser Ser Ala Gln Phe Leu Gly Leu Leu Leu Cys Phe Gln
1               5                   10                  15

Gly Thr Arg Cys Asp Ile Gln Met Thr Gln Thr Ser Ser Leu Ser
                20                  25                  30

Ala Ser Leu Gly Gly Ser Val Thr Ile Ser Cys Arg Ala Ser Gln Asp
                35                  40                  45

Ile Asp Asn Tyr Leu Asn Trp Tyr Gln Gln Lys Pro Asp Gly Thr Val
            50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Phe Asn
                100                 105                 110

Thr Leu Pro Arg Thr Phe Gly Gly Gly Thr Lys Leu Glu Ile Lys Arg
                115                 120                 125

Ala Asp Ala Ala Pro Thr Val Ser Ile Phe
            130                 135

<210> SEQ ID NO 112
<211> LENGTH: 465
<212> TYPE: DNA
<213> ORGANISM: Mus musculus

<400> SEQUENCE: 112
atgatgtcct ctgctcagtt ccttggtctc ctgttgctct gttttcaagg taccagatgt     60
gatatccaga tgacacagac tacatcctcc ctgtctgcct ctctggggggg cagcgtcacc    120 atcagttgca gggcaagtca ggacattgac aattatttaa actggtatca gcaaaaacca    180
gatggaactg ttaaactcct gatctactac acatcaagat tacactcagg agtcccatca    240
aggttcagtg gcagtgggtc tggaacagat tattctctca ccattagcaa cctggaacaa    300
gaagatattg ccacttactt ttgccaacag tttaatacgc ttcctcggac gttcggtgga    360
ggcaccaagc tggaaatcaa acgggctgat gctgcaccaa ctgtatccat cttcccacca    420
tccagtgagc agttaacatc tggaggtgcc tcagtcgtgt gcttc                    465

<210> SEQ ID NO 113
<211> LENGTH: 155
<212> TYPE: PRT
<213> ORGANISM: Mus musculus

<400> SEQUENCE: 113

Met Met Ser Ser Ala Gln Phe Leu Gly Leu Leu Leu Cys Phe Gln
1               5                   10                  15

Gly Thr Arg Cys Asp Ile Gln Met Thr Gln Thr Ser Ser Leu Ser
                20                  25                  30

Ala Ser Leu Gly Gly Ser Val Thr Ile Ser Cys Arg Ala Ser Gln Asp
                35                  40                  45

Ile Asp Asn Tyr Leu Asn Trp Tyr Gln Gln Lys Pro Asp Gly Thr Val

```
            50                  55                  60
Lys Leu Leu Ile Tyr Tyr Thr Ser Arg Leu His Ser Gly Val Pro Ser
 65                  70                  75                  80

Arg Phe Ser Gly Ser Gly Ser Gly Thr Asp Tyr Ser Leu Thr Ile Ser
                 85                  90                  95

Asn Leu Glu Gln Glu Asp Ile Ala Thr Tyr Phe Cys Gln Gln Phe Asn
            100                 105                 110

Thr Leu Pro Arg Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe
145                 150                 155
```

<210> SEQ ID NO 114
<211> LENGTH: 93
<212> TYPE: DNA
<213> ORGANISM: Artificial
<220> FEATURE:
<223> OTHER INFORMATION: primer

<400> SEQUENCE: 114
accaagcttg ccgccaccat gaaagtgttg agtctgttgt acctgttgac agccattcct    60
ggtatcctgt ctcaggtcca actgcagcag cct                                 93

<210> SEQ ID NO 115
<211> LENGTH: 42
<212> TYPE: DNA
<213> ORGANISM: Artificial
<220> FEATURE:
<223> OTHER INFORMATION: primer

<400> SEQUENCE: 115
cgatgggccc ttggtgctag ctgaggagac ggtgactgag gt                       42

<210> SEQ ID NO 116
<211> LENGTH: 39
<212> TYPE: DNA
<213> ORGANISM: Artificial
<220> FEATURE:
<223> OTHER INFORMATION: primer

<400> SEQUENCE: 116
accaagcttg ccgccaccat gatgtcctct gctcagttc                           39

<210> SEQ ID NO 117
<211> LENGTH: 33
<212> TYPE: DNA
<213> ORGANISM: Artificial
<220> FEATURE:
<223> OTHER INFORMATION: primer

<400> SEQUENCE: 117
agccacagtt cgtttgattt ccagcttggt gcc                                 33

<210> SEQ ID NO 118
<211> LENGTH: 33
<212> TYPE: DNA
<213> ORGANISM: Artificial
<220> FEATURE:
<223> OTHER INFORMATION: primer

<400> SEQUENCE: 118

```
ctggaaatca aacgaactgt ggctgcacca tct                                    33
```

<210> SEQ ID NO 119
<211> LENGTH: 30
<212> TYPE: DNA
<213> ORGANISM: Artificial
<220> FEATURE:
<223> OTHER INFORMATION: primer

<400> SEQUENCE: 119

```
aaagaattcc tagcactctc ccctgttgaa                                        30
```

<210> SEQ ID NO 120
<211> LENGTH: 1401
<212> TYPE: DNA
<213> ORGANISM: Chimaera sp.

<400> SEQUENCE: 120

```
atgaaagtgt tgagtctgtt gtacctgttg acagccattc ctggtatcct gtctcaggtc       60
caactgcagc agcctggggc tgaactggtg aagcctggga cttcagtgaa aatgtcctgc      120
aaggcttctg gctacacctt caccagctac tggatgcact gggtgaagca gaggccggga      180
caaggccttg agtggattgg agatatttat cctggtagtg atagtactaa ctacaatgag      240
aagttcaaga gcaaggccac actgactgta gacacatcct ccagcacagc ctacatgcaa      300
ctcagcagcc tgacatctga ggactctgcg gtctattact gtgcaagagg agggtggttg      360
gatgctatgg actactgggg tcaaggaacc tcagtcaccg tctcctcagc tagcaccaag      420
ggcccatcgg tcttccccct ggcaccctcc tccaagagca cctctggggg cacagcggcc      480
ctgggctgcc tggtcaagga ctacttcccc gaaccggtga cggtgtcgtg gaactcaggc      540
gccctgacca gcggcgtgca caccttcccg gctgtcctac agtcctcagg actctactcc      600
ctcagcagcg tggtgaccgt gccctccagc agcttgggca cccagaccta catctgcaac      660
gtgaatcaca agcccagcaa caccaaggtg gacaagaaag ttgagcccaa atcttgtgac      720
aaaactcaca catgcccacc gtgcccagca cctgaactcc tggggggacc gtcagtcttc      780
ctcttccccc caaaacccaa ggacaccctc atgatctccc ggacccctga ggtcacatgc      840
gtggtggtgg acgtgagcca cgaagaccct gaggtcaagt tcaactggta cgtggacggc      900
gtggaggtgc ataatgccaa gacaaagccg cgggaggagc agtacaacag cacgtaccgt      960
gtggtcagcg tcctcaccgt cctgcaccag gactggctga atggcaagga gtacaagtgc     1020
aaggtctcca acaaagccct cccagccccc atcgagaaaa ccatctccaa agccaaaggg     1080
cagccccgag aaccacaggt gtacaccctg cccccatccc gggatgagct gaccaagaac     1140
caggtcagcc tgacctgcct ggtcaaaggc ttctatccca gcgacatcgc cgtggagtgg     1200
gagagcaatg ggcagccgga gaacaactac aagaccacgc ctcccgtgct ggactccgac     1260
ggctccttct tcctctacag caagctcacc gtggacaaga gcaggtggca gcaggggaac     1320
gtcttctcat gctccgtgat gcatgaggct ctgcacaacc actacacgca gaagagcctc     1380
tccctgtctc cgggtaaatg a                                               1401
```

<210> SEQ ID NO 121
<211> LENGTH: 466
<212> TYPE: PRT
<213> ORGANISM: Chimaera sp.

<400> SEQUENCE: 121

```
Met Lys Val Leu Ser Leu Leu Tyr Leu Leu Thr Ala Ile Pro Gly Ile
1               5                   10                  15
Leu Ser Gln Val Gln Leu Gln Gln Pro Gly Ala Glu Leu Val Lys Pro
                20                  25                  30
Gly Thr Ser Val Lys Met Ser Cys Lys Ala Ser Gly Tyr Thr Phe Thr
            35                  40                  45
Ser Tyr Trp Met His Trp Val Lys Gln Arg Pro Gly Gln Gly Leu Glu
    50                  55                  60
Trp Ile Gly Asp Ile Tyr Pro Gly Ser Asp Thr Asn Tyr Asn Glu
65                  70                  75                  80
Lys Phe Lys Ser Lys Ala Thr Leu Thr Val Asp Thr Ser Ser Ser Thr
                85                  90                  95
Ala Tyr Met Gln Leu Ser Ser Leu Thr Ser Glu Asp Ser Ala Val Tyr
                100                 105                 110
Tyr Cys Ala Arg Gly Gly Trp Leu Asp Ala Met Asp Tyr Trp Gly Gln
            115                 120                 125
Gly Thr Ser Val Thr Val Ser Ser Ala Ser Thr Lys Gly Pro Ser Val
    130                 135                 140
Phe Pro Leu Ala Pro Ser Ser Lys Ser Thr Ser Gly Gly Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
                180                 185                 190
Leu Gln Ser Ser Gly Leu Tyr Ser Leu Ser Ser Val Val Thr Val Pro
            195                 200                 205
Ser Ser Ser Leu Gly Thr Gln Thr Tyr Ile Cys Asn Val Asn His Lys
    210                 215                 220
Pro Ser Asn Thr Lys Val Asp Lys Lys Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
                260                 265                 270
Ser Arg Thr Pro Glu Val Thr Cys Val Val Val Asp Val Ser His Glu
            275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
                340                 345                 350
Lys Thr Ile Ser Lys Ala Lys Gly Gln Pro Arg Glu Pro Gln Val Tyr
            355                 360                 365
Thr Leu Pro Pro Ser Arg Asp Glu Leu Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
```

```
            420             425             430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 122
<211> LENGTH: 705
<212> TYPE: DNA
<213> ORGANISM: Chimaera sp.

<400> SEQUENCE: 122
atgatgtcct ctgctcagtt ccttggtctc ctgttgctct gttttcaagg taccagatgt      60
gatatccaga tgacacagac tacatcctcc ctgtctgcct ctctgggaga cagagtcacc     120
atcagttgca gggcaagtca ggacattagc aattatttaa actggtatca gcagaaacca     180
gatggaactg ttaaactcct gatctactac acatcaagat tacactcagg agtcccatca     240
aggttcagtg gcagtgggtc tggaacagat tattctctca ccattagcaa cctggagcaa     300
gaagatattg ccacttactt ttgccaacag gtaatacgc ttccgtggac gttcggtgga      360
ggcaccaagc tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacctgacg     600 ctgagcaaag cagactacga gaaacacaaa gtctacgcct gcgaagtcac ccatcagggc     660
ctgagctcgc ccgtcacaaa gagcttcaac aggggagagt gctag                    705

<210> SEQ ID NO 123
<211> LENGTH: 234
<212> TYPE: PRT
<213> ORGANISM: Chimaera sp.

<400> SEQUENCE: 123

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
```

```
                145                 150                 155                 160
Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 124
<211> LENGTH: 1521
<212> TYPE: DNA
<213> ORGANISM: Macaca mulatta
<220> FEATURE:
<221> NAME/KEY: gene
<222> LOCATION: (1)..(1521)

<400> SEQUENCE: 124
atgctgaagc tcttcggag agcggcagtg acccccatgt ggccgtgctc catgctgccc     60
cgccgcctgt gggacagaga ggctggcacg ttgcaggtcc tgggagtgct ggctatgctg    120
tggctgggct ccatgctct tacctacctc ctgtggcaag tgcgctgtcc tcccacctgg     180
ggccaggtgc agcccaggga cgtgcccagg tcctgggggc atggttccag cctagctctg    240
gagcccctgg aagcggaggt caggaagcag agggactcct gccagcttgt ccttgtggaa    300
agcatccccc aggacctgcc atttgcagcc ggcagcctct ccgcccagcc tctgggccag    360
gcctggctgc agctgctgga cactgcccag gagagcgtcc acgtggcttc atactactgg    420
tccctcacag ggcccgacat tggggtcaac gactcatctt cccagctggg agaggccctt    480
ctgcagaagc tgcagcagct gctgggcagg aacatttcct ggctgtggc caccagcagt    540 ccaacactgg ccaggaagtc caccgacctg caggtcctgg ctgcccgagg tgcccaggta    600
cgacgggtgc ccatggggcg gctcaccagg ggcgttttgc actccaaatt ctgggttgtg    660
gatggacggc acatatacat gggcagtgcc aacatggact ggcggtccct gacgcaggtg    720
aaggagcttg cgctgtcat ctataactgc agccacctgg cccaagacct ggagaagacc    780
ttccagacct actgggtgct gggggtgccc aaggctgtcc tccccaaaac ctggcctcag    840
aacttctcat ctcacatcaa ccgtttccag cccttccagg gcctctttga tggggtgccc    900
accactgcct acttctcagc atcgccaccc gcactctgtc cccagggccg cacccctgac    960
ctggaggcgc tgttggcggt gatggggagc gcccaggagt tcatctatgc ctccgtgatg   1020
gagtatttcc ctaccacgcg cttcagccac ccccgcaggt actggccggt gctggacaac   1080
gcgctgcggg cggcagcctt cagcaagggt gtgcgcgtgc gcctgctggt cagctgcgga   1140
ctcaacacgg accccaccat gttcccctat ctgcggtccc tgcaggcgct cagcaacccc   1200
gcggccaacg tctctgtgga cgtgaaagtc ttcatcgtgc cggtggggaa tcattccaac   1260
atcccgttca gcagggtgaa ccacagcaag ttcatggtca cggagaaggc agcctacata   1320
ggcacctcca actggtcgga ggattacttc agcagcacga cggggtggg cctggtggtc   1380 acccagagcc ccggcgcgca gcccgcgggg ccacggtac aggagcagct gcggcagctc   1440
tttgagcggg actggagttc gcgctacgcc gtcggcctgg acggacaggc tccgggccag   1500
gactgcgttt ggcagggctg a                                             1521
```

<210> SEQ ID NO 125
<211> LENGTH: 2142
<212> TYPE: DNA
<213> ORGANISM: Homo sapiens

<400> SEQUENCE: 125

| | | | | | |
|---|---|---|---|---|---|
| atggagtttc | agacccaggt | ctttgtattc | gtgttgctct | ggttgtctgg | tgttgatgga | 60 |
| gattacaagg | atgacgacga | taaaggatcc | cccagagggc | ccacaatcaa | gccctgtcct | 120 |
| ccatgcaaat | gcccagcacc | taacctcttg | ggtggaccat | ccgtcttcat | cttccctcca | 180 |
| aagatcaagg | atgtactcat | gatctccctg | agccccatag | tcacatgtgt | ggtggtggat | 240 |
| gtgagcgagg | atgacccaga | tgtccagatc | agctggtttg | tgaacaacgt | ggaagtacac | 300 |
| acagctcaga | cacaaaccca | tagagaggat | tacaacagta | ctctccgggt | ggtcagtgcc | 360 |
| ctccccatcc | agcaccagga | ctggatgagt | ggcaaggagt | tcaaatgcaa | ggtcaacaac | 420 |
| aaagacctcc | cagcgcccat | cgagagaacc | atctcaaaac | ccaagggtc | agtaagagct | 480 |
| ccacaggtat | atgtcttgcc | tccaccagaa | gaagagatga | ctaagaaaca | ggtcactctg | 540 |
| acctgcatgg | tcacagactt | catgcctgaa | gacatttacg | tggagtggac | caacaacggg | 600 |
| aaaacagagc | taaactacaa | gaacactgaa | ccagtcctgg | actctgatgg | ttcttacttc | 660 |
| atgtacagca | agctgagagt | ggaaaagaag | aactgggtgg | aaagaaatag | ctactcctgt | 720 |
| tcagtggtcc | acgagggtct | gcacaatcac | cacacgacta | agagcttctc | ccggactccg | 780 |
| ggtaaacgtc | ctcccacctg | gggccaggtg | cagcccaagg | acgtgcccag | gtcctgggag | 840 |
| catggctcca | gcccagcttg | ggagcccctg | gaagcagagg | ccaggcagca | gagggactcc | 900 |
| tgccagcttg | tccttgtgga | aagcatcccc | caggacctgc | catctgcagc | cggcagcccc | 960 |
| tctgcccagc | ctctgggcca | ggcctggctg | cagctgctgg | acactgccca | ggagagcgtc | 1020 |
| cacgtggctt | catactactg | gtccctcaca | gggcctgaca | tcggggtcaa | cgactcgtct | 1080 |
| tcccagctgg | agaggctct | tctgcagaag | ctgcagcagc | tgctgggcag | gaacatttcc | 1140 |
| ctggctgtgg | ccaccagcag | cccgacactg | gccaggacat | ccaccgacct | gcaggttctg | 1200 |
| gctgcccgag | gtgcccatgt | acgacaggtg | cccatggggc | ggctcaccag | gggtgttttg | 1260 |
| cactccaaat | tctgggttgt | ggatggacgg | cacatataca | tgggcagtgc | caacatggac | 1320 |
| tggcggtctc | tgacgcaggt | gaaggagctt | ggcgctgtca | tctataactg | cagccacctg | 1380 |
| gcccaagacc | tggagaagac | cttcagacc | tactgggtac | tgggggtgcc | caaggctgtc | 1440 |
| ctccccaaaa | cctggcctca | gaacttctca | tctcacttca | accgtttcca | gcccttccac | 1500 |
| ggcctctttg | atggggtgcc | caccactgcc | tacttctcag | cgtcgccacc | agcactctgt | 1560 |
| ccccagggcc | gcacccggga | cctggaggcg | ctgctggcgg | tgatggggag | cgcccaggag | 1620 |
| ttcatctatg | cctccgtgat | ggagtatttc | cccaccacgc | gcttcagcca | cccccgagg | 1680 |
| tactggccgt | gctggacaa | cgcgctgcgg | cggcagcct | tcggcaaggg | cgtgcgcgtg | 1740 |
| cgcctgctgg | tcggctgcgg | actcaacacg | gaccccacca | tgttcccta | cctgcggtcc | 1800 |
| ctgcaggcgc | tcagcaaccc | cgcggccaac | gtctctgtgg | acgtgaaagt | cttcatcgtg | 1860 |
| ccggtgggga | accattccaa | catcccattc | agcagggtga | ccacagcaa | gttcatggtc | 1920 |
| acggagaagg | cagcctacat | aggcacctcc | aactggtcgg | aggattactt | cagcagcacg | 1980 |
| gcggggggtgg | gcttggtggt | cacccagagc | cctggcgcgc | agcccgcggg | ggccacggtg | 2040 |
| caggagcagc | tgcggcagct | cttttgagcgg | gactggagtt | cgcgctacgc | cgtcggcctg | 2100 | gacggacagg ctccgggcca ggactgcgtt tggcagggct ga        2142

<210> SEQ ID NO 126
<211> LENGTH: 713
<212> TYPE: PRT
<213> ORGANISM: Homo sapiens

<400> SEQUENCE: 126

Met Glu Phe Gln Thr Gln Val Phe Val Phe Val Leu Leu Trp Leu Ser
1               5                   10                  15

Gly Val Asp Gly Asp Tyr Lys Asp Asp Asp Lys Gly Ser Pro Arg
                20                  25                  30

Gly Pro Thr Ile Lys Pro Cys Pro Pro Cys Lys Cys Pro Ala Pro Asn
            35                  40                  45

Leu Leu Gly Gly Pro Ser Val Phe Ile Phe Pro Pro Lys Ile Lys Asp
        50                  55                  60

Val Leu Met Ile Ser Leu Ser Pro Ile Val Thr Cys Val Val Val Asp
65                  70                  75                  80

Val Ser Glu Asp Asp Pro Asp Val Gln Ile Ser Trp Phe Val Asn Asn
                85                  90                  95

Val Glu Val His Thr Ala Gln Thr Gln Thr His Arg Glu Asp Tyr Asn
            100                 105                 110

Ser Thr Leu Arg Val Val Ser Ala Leu Pro Ile Gln His Gln Asp Trp
        115                 120                 125

Met Ser Gly Lys Glu Phe Lys Cys Lys Val Asn Asn Lys Asp Leu Pro
130                 135                 140

Ala Pro Ile Glu Arg Thr Ile Ser Lys Pro Lys Gly Ser Val Arg Ala
145                 150                 155                 160

Pro Gln Val Tyr Val Leu Pro Pro Pro Glu Glu Glu Met Thr Lys Lys
                165                 170                 175

Gln Val Thr Leu Thr Cys Met Val Thr Asp Phe Met Pro Glu Asp Ile
            180                 185                 190

Tyr Val Glu Trp Thr Asn Asn Gly Lys Thr Glu Leu Asn Tyr Lys Asn
        195                 200                 205

Thr Glu Pro Val Leu Asp Ser Asp Gly Ser Tyr Phe Met Tyr Ser Lys
    210                 215                 220

Leu Arg Val Glu Lys Lys Asn Trp Val Glu Arg Asn Ser Tyr Ser Cys
225                 230                 235                 240

Ser Val Val His Glu Gly Leu His Asn His His Thr Thr Lys Ser Phe
                245                 250                 255

Ser Arg Thr Pro Gly Lys Arg Pro Pro Thr Trp Gly Gln Val Gln Pro
            260                 265                 270

Lys Asp Val Pro Arg Ser Trp Glu His Gly Ser Ser Pro Ala Trp Glu
        275                 280                 285

Pro Leu Glu Ala Glu Ala Arg Gln Gln Arg Asp Ser Cys Gln Leu Val
    290                 295                 300

Leu Val Glu Ser Ile Pro Gln Asp Leu Pro Ser Ala Ala Gly Ser Pro
305                 310                 315                 320

Ser Ala Gln Pro Leu Gly Gln Ala Trp Leu Gln Leu Leu Asp Thr Ala
                325                 330                 335

Gln Glu Ser Val His Val Ala Ser Tyr Tyr Trp Ser Leu Thr Gly Pro
            340                 345                 350

Asp Ile Gly Val Asn Asp Ser Ser Gln Leu Gly Glu Ala Leu Leu
        355                 360                 365

```
Gln Lys Leu Gln Gln Leu Leu Gly Arg Asn Ile Ser Leu Ala Val Ala
    370                 375                 380

Thr Ser Ser Pro Thr Leu Ala Arg Thr Ser Asp Leu Gln Val Leu
385                 390                 395                 400

Ala Ala Arg Gly Ala His Val Arg Gln Val Pro Met Gly Arg Leu Thr
                405                 410                 415

Arg Gly Val Leu His Ser Lys Phe Trp Val Asp Gly Arg His Ile
            420                 425                 430

Tyr Met Gly Ser Ala Asn Met Asp Trp Arg Ser Leu Thr Gln Val Lys
                435                 440                 445

Glu Leu Gly Ala Val Ile Tyr Asn Cys Ser His Leu Ala Gln Asp Leu
    450                 455                 460

Glu Lys Thr Phe Gln Thr Tyr Trp Val Leu Gly Val Pro Lys Ala Val
465                 470                 475                 480

Leu Pro Lys Thr Trp Pro Gln Asn Phe Ser Ser His Phe Asn Arg Phe
                485                 490                 495

Gln Pro Phe His Gly Leu Phe Asp Gly Val Pro Thr Thr Ala Tyr Phe
                500                 505                 510

Ser Ala Ser Pro Pro Ala Leu Cys Pro Gln Gly Arg Thr Arg Asp Leu
            515                 520                 525

Glu Ala Leu Leu Ala Val Met Gly Ser Ala Gln Glu Phe Ile Tyr Ala
    530                 535                 540

Ser Val Met Glu Tyr Phe Pro Thr Thr Arg Phe Ser His Pro Pro Arg
545                 550                 555                 560

Tyr Trp Pro Val Leu Asp Asn Ala Leu Arg Ala Ala Phe Gly Lys
                565                 570                 575

Gly Val Arg Val Arg Leu Leu Val Gly Cys Gly Leu Asn Thr Asp Pro
            580                 585                 590

Thr Met Phe Pro Tyr Leu Arg Ser Leu Gln Ala Leu Ser Asn Pro Ala
    595                 600                 605

Ala Asn Val Ser Val Asp Val Lys Val Phe Ile Val Pro Val Gly Asn
    610                 615                 620

His Ser Asn Ile Pro Phe Ser Arg Val Asn His Ser Lys Phe Met Val
625                 630                 635                 640

Thr Glu Lys Ala Ala Tyr Ile Gly Thr Ser Asn Trp Ser Glu Asp Tyr
                645                 650                 655

Phe Ser Ser Thr Ala Gly Val Gly Leu Val Val Thr Gln Ser Pro Gly
                660                 665                 670

Ala Gln Pro Ala Gly Ala Thr Val Gln Glu Gln Leu Arg Gln Leu Phe
            675                 680                 685

Glu Arg Asp Trp Ser Ser Arg Tyr Ala Val Gly Leu Asp Gly Gln Ala
    690                 695                 700

Pro Gly Gln Asp Cys Val Trp Gln Gly
705                 710

<210> SEQ ID NO 127
<211> LENGTH: 490
<212> TYPE: PRT
<213> ORGANISM: Homo sapiens

<400> SEQUENCE: 127

Met Lys Pro Lys Leu Met Tyr Gln Glu Leu Lys Val Pro Ala Glu Glu
1               5                   10                  15

Pro Ala Asn Glu Leu Pro Met Asn Glu Ile Glu Ala Trp Lys Ala Ala
                20                  25                  30
```

```
Glu Lys Lys Ala Arg Trp Val Leu Leu Val Leu Ile Leu Ala Val Val
         35                  40                  45

Gly Phe Gly Ala Leu Met Thr Gln Leu Phe Leu Trp Glu Tyr Gly Asp
 50                  55                  60

Leu His Leu Phe Gly Pro Asn Gln Arg Pro Ala Pro Cys Tyr Asp Pro
 65                  70                  75                  80

Cys Glu Ala Val Leu Val Glu Ser Ile Pro Glu Gly Leu Asp Phe Pro
                 85                  90                  95

Asn Ala Ser Thr Gly Asn Pro Ser Thr Ser Gln Ala Trp Leu Gly Leu
                100                 105                 110

Leu Ala Gly Ala His Ser Ser Leu Asp Ile Ala Ser Phe Tyr Trp Thr
                115                 120                 125

Leu Thr Asn Asn Asp Thr His Thr Gln Glu Pro Ser Ala Gln Gln Gly
130                 135                 140

Glu Glu Val Leu Arg Gln Leu Gln Thr Leu Ala Pro Lys Gly Val Asn
145                 150                 155                 160

Val Arg Ile Ala Val Ser Lys Pro Ser Gly Pro Gln Pro Gln Ala Asp
                165                 170                 175

Leu Gln Ala Leu Leu Gln Ser Gly Ala Gln Val Arg Met Val Asp Met
                180                 185                 190

Gln Lys Leu Thr His Gly Val Leu His Thr Lys Phe Trp Val Val Asp
                195                 200                 205

Gln Thr His Phe Tyr Leu Gly Ser Ala Asn Met Asp Trp Arg Ser Leu
                210                 215                 220

Thr Gln Val Lys Glu Leu Gly Val Val Met Tyr Asn Cys Ser Cys Leu
225                 230                 235                 240

Ala Arg Asp Leu Thr Lys Ile Phe Glu Ala Tyr Trp Phe Leu Gly Gln
                245                 250                 255

Ala Gly Ser Ser Ile Pro Ser Thr Trp Pro Arg Phe Tyr Asp Thr Arg
                260                 265                 270

Tyr Asn Gln Glu Thr Pro Met Glu Ile Cys Leu Asn Gly Thr Pro Ala
                275                 280                 285

Leu Ala Tyr Leu Ala Ser Ala Pro Pro Leu Cys Pro Ser Gly Arg
                290                 295                 300

Thr Pro Asp Leu Lys Ala Leu Leu Asn Val Val Asp Asn Ala Arg Ser
305                 310                 315                 320

Phe Ile Tyr Val Ala Val Met Asn Tyr Leu Pro Thr Leu Glu Phe Ser
                325                 330                 335

His Pro His Arg Phe Trp Pro Ala Ile Asp Asp Gly Leu Arg Arg Ala
                340                 345                 350

Thr Tyr Glu Arg Gly Val Lys Val Arg Leu Leu Ile Ser Cys Trp Gly
                355                 360                 365

His Ser Glu Pro Ser Met Arg Ala Phe Leu Leu Ser Leu Ala Ala Leu
                370                 375                 380

Arg Asp Asn His Thr His Ser Asp Ile Gln Val Lys Leu Phe Val Val
385                 390                 395                 400

Pro Ala Asp Glu Ala Gln Ala Arg Ile Pro Tyr Ala Arg Val Asn His
                405                 410                 415

Asn Lys Tyr Met Val Thr Glu Arg Ala Thr Tyr Ile Gly Thr Ser Asn
                420                 425                 430

Trp Ser Gly Asn Tyr Phe Thr Glu Thr Ala Gly Thr Ser Leu Leu Val
                435                 440                 445
```

Thr Gln Asn Gly Arg Gly Gly Leu Arg Ser Gln Leu Glu Ala Ile Phe
450                 455                 460

Leu Arg Asp Trp Asp Ser Pro Tyr Ser His Asp Leu Asp Thr Ser Ala
465                 470                 475                 480

Asp Ser Val Gly Asn Ala Cys Arg Leu Leu
                485                 490

<210> SEQ ID NO 128
<211> LENGTH: 445
<212> TYPE: PRT
<213> ORGANISM: Homo sapiens

<400> SEQUENCE: 128

Met Gly Glu Asp Glu Asp Gly Leu Ser Glu Lys Asn Cys Gln Asn Lys
1               5                   10                  15

Cys Arg Ile Ala Leu Val Glu Asn Ile Pro Glu Gly Leu Asn Tyr Ser
                20                  25                  30

Glu Asn Ala Pro Phe His Leu Ser Leu Phe Gln Gly Trp Met Asn Leu
            35                  40                  45

Leu Asn Met Ala Lys Lys Ser Val Asp Ile Val Ser Ser His Trp Asp
50                  55                  60

Leu Asn His Thr His Pro Ser Ala Cys Gln Gly Gln Arg Leu Phe Glu
65                  70                  75                  80

Lys Leu Leu Gln Leu Thr Ser Gln Asn Ile Glu Ile Lys Leu Val Ser
                85                  90                  95

Asp Val Thr Ala Asp Ser Lys Val Leu Glu Ala Leu Lys Leu Lys Gly
            100                 105                 110

Ala Glu Val Thr Tyr Met Asn Met Thr Ala Tyr Asn Lys Gly Arg Leu
        115                 120                 125

Gln Ser Ser Phe Trp Ile Val Asp Lys Gln His Val Tyr Ile Gly Ser
    130                 135                 140

Ala Gly Leu Asp Trp Gln Ser Leu Gly Gln Met Lys Glu Leu Gly Val
145                 150                 155                 160

Ile Phe Tyr Asn Cys Ser Cys Leu Val Leu Asp Leu Gln Arg Ile Phe
                165                 170                 175

Ala Leu Tyr Ser Ser Leu Lys Phe Lys Ser Arg Val Pro Gln Thr Trp
            180                 185                 190

Ser Lys Arg Leu Tyr Gly Val Tyr Asp Asn Glu Lys Lys Leu Gln Leu
        195                 200                 205

Gln Leu Asn Glu Thr Lys Ser Gln Ala Phe Val Ser Asn Ser Pro Lys
    210                 215                 220

Leu Phe Cys Pro Lys Asn Arg Ser Phe Asp Ile Asp Ala Ile Tyr Ser
225                 230                 235                 240

Val Ile Asp Asp Ala Lys Gln Tyr Val Tyr Ile Ala Val Met Asp Tyr
                245                 250                 255

Leu Pro Ile Ser Ser Thr Ser Thr Lys Arg Thr Tyr Trp Pro Asp Leu
            260                 265                 270

Asp Ala Lys Ile Arg Glu Ala Leu Val Leu Arg Ser Val Arg Val Arg
        275                 280                 285

Leu Leu Leu Ser Phe Trp Lys Glu Thr Asp Pro Leu Thr Phe Asn Phe
    290                 295                 300

Ile Ser Ser Leu Lys Ala Ile Cys Thr Glu Ile Ala Asn Cys Ser Leu
305                 310                 315                 320

Lys Val Lys Phe Phe Asp Leu Glu Arg Glu Asn Ala Cys Ala Thr Lys
                325                 330                 335

```
Glu Gln Lys Asn His Thr Phe Pro Arg Leu Asn Arg Asn Lys Tyr Met
                340                 345                 350

Val Thr Asp Gly Ala Ala Tyr Ile Gly Asn Phe Asp Trp Val Gly Asn
            355                 360                 365

Asp Phe Thr Gln Asn Ala Gly Thr Gly Leu Val Ile Asn Gln Ala Asp
        370                 375                 380

Val Arg Asn Asn Arg Ser Ile Ile Lys Gln Leu Lys Asp Val Phe Glu
385                 390                 395                 400

Arg Asp Trp Tyr Ser Pro Tyr Ala Lys Thr Leu Gln Pro Thr Lys Gln
                405                 410                 415

Pro Asn Cys Ser Ser Leu Phe Lys Leu Lys Pro Leu Ser Asn Lys Thr
            420                 425                 430

Ala Thr Asp Asp Thr Gly Gly Lys Asp Pro Arg Asn Val
            435                 440                 445

<210> SEQ ID NO 129
<211> LENGTH: 506
<212> TYPE: PRT
<213> ORGANISM: Macaca fascicularis

<400> SEQUENCE: 129

Met Leu Lys Pro Leu Arg Arg Ala Ala Val Thr Pro Met Trp Pro Cys
1               5                   10                  15

Ser Met Leu Pro Arg Arg Leu Trp Asp Arg Glu Ala Gly Thr Leu Gln
                20                  25                  30

Val Leu Gly Val Leu Ala Met Leu Trp Leu Gly Ser Met Ala Leu Thr
            35                  40                  45

Tyr Leu Leu Trp Gln Val Arg Arg Pro Pro Thr Trp Gly Gln Val Gln
        50                  55                  60

Pro Lys Asp Val Pro Arg Ser Trp Gly His Gly Ser Ser Pro Ala Leu
65                  70                  75                  80

Glu Pro Leu Glu Ala Glu Val Arg Lys Gln Arg Asp Ser Cys Gln Leu
                85                  90                  95

Val Leu Val Glu Ser Ile Pro Gln Asp Leu Pro Phe Ala Ala Gly Ser
                100                 105                 110

Leu Ser Ala Gln Pro Leu Gly Gln Ala Trp Leu Gln Leu Leu Asp Thr
            115                 120                 125

Ala Gln Glu Ser Val His Val Ala Ser Tyr Tyr Trp Ser Leu Thr Gly
        130                 135                 140

Pro Asp Ile Gly Val Asn Asp Ser Ser Ser Gln Leu Gly Glu Ala Leu
145                 150                 155                 160

Leu Gln Lys Leu Gln Gln Leu Leu Gly Arg Asn Ile Ser Leu Ala Val
                165                 170                 175

Ala Thr Ser Ser Pro Thr Leu Ala Arg Lys Ser Thr Asp Leu Gln Val
                180                 185                 190

Leu Ala Ala Arg Gly Ala Gln Val Arg Arg Val Pro Met Gly Arg Leu
            195                 200                 205

Thr Arg Gly Val Leu His Ser Lys Phe Trp Val Val Asp Gly Arg His
        210                 215                 220

Ile Tyr Met Gly Ser Ala Asn Met Asp Trp Arg Ser Leu Thr Gln Val
225                 230                 235                 240

Lys Glu Leu Gly Ala Val Ile Tyr Asn Cys Ser His Leu Ala Gln Asp
                245                 250                 255

Leu Glu Lys Thr Phe Gln Thr Tyr Trp Val Leu Gly Val Pro Lys Ala
```

260                 265                 270
Val Leu Pro Lys Thr Trp Pro Gln Asn Phe Ser Ser His Ile Asn Arg
            275                 280                 285

Phe Gln Pro Phe Gln Gly Leu Phe Asp Gly Val Pro Thr Thr Ala Tyr
        290                 295                 300

Phe Ser Ala Ser Pro Ala Leu Cys Pro Gln Gly Arg Thr Pro Asp
305                 310                 315                 320

Leu Glu Ala Leu Leu Ala Val Met Gly Ser Ala Gln Glu Phe Ile Tyr
                325                 330                 335

Ala Ser Val Met Glu Tyr Phe Pro Thr Thr Arg Phe Ser His Pro Arg
            340                 345                 350

Arg Tyr Trp Pro Val Leu Asp Asn Ala Leu Arg Ala Ala Phe Ser
        355                 360                 365

Lys Gly Val Arg Val Arg Leu Leu Val Ser Cys Gly Leu Asn Thr Asp
                370                 375                 380

Pro Thr Met Phe Pro Tyr Leu Arg Ser Leu Gln Ala Leu Ser Asn Pro
385                 390                 395                 400

Ala Ala Asn Val Ser Val Asp Val Lys Val Phe Ile Val Pro Val Gly
            405                 410                 415

Asn His Ser Asn Ile Pro Phe Ser Arg Val Asn His Ser Lys Phe Met
        420                 425                 430

Val Thr Glu Lys Ala Ala Tyr Ile Gly Thr Ser Asn Trp Ser Glu Asp
            435                 440                 445

Tyr Phe Ser Ser Thr Thr Gly Val Gly Leu Val Val Thr Gln Ser Pro
        450                 455                 460

Gly Ala Gln Pro Ala Gly Ala Thr Val Gln Glu Gln Leu Arg Gln Leu
465                 470                 475                 480

Phe Glu Arg Asp Trp Ser Ser Arg Tyr Ala Val Gly Leu Asp Gly Gln
            485                 490                 495

Ala Pro Gly Gln Asp Cys Val Trp Gln Gly
        500                 505

<210> SEQ ID NO 130
<211> LENGTH: 506
<212> TYPE: PRT
<213> ORGANISM: Macaca mulatta

<400> SEQUENCE: 130

Met Leu Lys Pro Leu Arg Arg Ala Ala Val Thr Pro Met Trp Pro Cys
1               5                   10                  15

Ser Met Leu Pro Arg Arg Leu Trp Asp Arg Glu Ala Gly Thr Leu Gln
            20                  25                  30

Val Leu Gly Val Leu Ala Met Leu Trp Leu Gly Ser Met Ala Leu Thr
        35                  40                  45

Tyr Leu Leu Trp Gln Val Arg Cys Pro Pro Thr Trp Gly Gln Val Gln
    50                  55                  60

Pro Arg Asp Val Pro Arg Ser Trp Gly His Gly Ser Ser Leu Ala Leu
65                  70                  75                  80

Glu Pro Leu Glu Ala Glu Val Arg Lys Gln Arg Asp Ser Cys Gln Leu
                85                  90                  95

Val Leu Val Glu Ser Ile Pro Gln Asp Leu Pro Phe Ala Ala Gly Ser
            100                 105                 110

Leu Ser Ala Gln Pro Leu Gly Gln Ala Trp Leu Gln Leu Leu Asp Thr
        115                 120                 125

```
Ala Gln Glu Ser Val His Val Ala Ser Tyr Tyr Trp Ser Leu Thr Gly
    130                 135                 140
Pro Asp Ile Gly Val Asn Asp Ser Ser Gln Leu Gly Glu Ala Leu
145                 150                 155                 160
Leu Gln Lys Leu Gln Gln Leu Leu Gly Arg Asn Ile Ser Leu Ala Val
                165                 170                 175
Ala Thr Ser Ser Pro Thr Leu Ala Arg Lys Ser Thr Asp Leu Gln Val
            180                 185                 190
Leu Ala Ala Arg Gly Ala Gln Val Arg Arg Val Pro Met Gly Arg Leu
        195                 200                 205
Thr Arg Gly Val Leu His Ser Lys Phe Trp Val Asp Gly Arg His
210                 215                 220
Ile Tyr Met Gly Ser Ala Asn Met Asp Trp Arg Ser Leu Thr Gln Val
225                 230                 235                 240
Lys Glu Leu Gly Ala Val Ile Tyr Asn Cys Ser His Leu Ala Gln Asp
                245                 250                 255
Leu Glu Lys Thr Phe Gln Thr Tyr Trp Val Leu Gly Val Pro Lys Ala
            260                 265                 270
Val Leu Pro Lys Thr Trp Pro Gln Asn Phe Ser Ser His Ile Asn Arg
        275                 280                 285
Phe Gln Pro Phe Gln Gly Leu Phe Asp Gly Val Pro Thr Thr Ala Tyr
    290                 295                 300
Phe Ser Ala Ser Pro Pro Ala Leu Cys Pro Gln Gly Arg Thr Pro Asp
305                 310                 315                 320
Leu Glu Ala Leu Leu Ala Val Met Gly Ser Ala Gln Glu Phe Ile Tyr
                325                 330                 335
Ala Ser Val Met Glu Tyr Phe Pro Thr Thr Arg Phe Ser His Pro Arg
            340                 345                 350
Arg Tyr Trp Pro Val Leu Asp Asn Ala Leu Arg Ala Ala Ala Phe Ser
        355                 360                 365
Lys Gly Val Arg Val Arg Leu Leu Val Ser Cys Gly Leu Asn Thr Asp
    370                 375                 380
Pro Thr Met Phe Pro Tyr Leu Arg Ser Leu Gln Ala Leu Ser Asn Pro
385                 390                 395                 400
Ala Ala Asn Val Ser Val Asp Val Lys Val Phe Ile Val Pro Val Gly
                405                 410                 415
Asn His Ser Asn Ile Pro Phe Ser Arg Val Asn His Ser Lys Phe Met
            420                 425                 430
Val Thr Glu Lys Ala Ala Tyr Ile Gly Thr Ser Asn Trp Ser Glu Asp
        435                 440                 445
Tyr Phe Ser Ser Thr Gly Val Gly Leu Val Val Thr Gln Ser Pro
    450                 455                 460
Gly Ala Gln Pro Ala Gly Ala Thr Val Gln Glu Gln Leu Arg Gln Leu
465                 470                 475                 480
Phe Glu Arg Asp Trp Ser Ser Arg Tyr Ala Val Gly Leu Asp Gly Gln
                485                 490                 495
Ala Pro Gly Gln Asp Cys Val Trp Gln Gly
            500                 505

<210> SEQ ID NO 131
<211> LENGTH: 1512
<212> TYPE: DNA
<213> ORGANISM: Mus musculus

<400> SEQUENCE: 131
```

```
atggacaaga agaaagagca cccagagatg cggataccac tccagacagc agtggaggtc      60
tctgattggc cctgctccac atctcatgat ccacatagcg gacttggcat ggtactgggg     120
atgctagctg tactgggact cagctctgtg actctcatct tgttcctgtg gcaaggggcc     180
acttctttca ccagtcatcg gatgttccct gaggaagtgc cctcctggtc ctgggagacc     240
ctgaaaggag acgctgagca gcagaataac tcctgtcagc tcatccttgt ggaaagcatc     300
cccgaggact tgccattgc agctggcagc cccactgccc agcccctggc caggcttgg      360
ctgcagcttc ttgacactgc tcgggagagc gtccacattg cctcgtacta ctggtccctc     420
actggactgg acattggagt caatgactcg tcttctcggc agggagaggc ccttctacag     480
aagttccaac agcttcttct caggaacatc tctgtggtgg tggccaccca gcccaaca      540
ttggccaaga catccactga cctccaggtc ttggctgccc atggtgccca gatacgacaa     600
gtgcccatga acagcttac tgggggtgtt ctacactcca aattctgggt tgtggatggg     660
cgacacgtct acgtgggcag cgccaacatg gactggcggt ccctgactca ggtgaaggaa     720
cttggtgcaa tcatctacaa ctgcagcaac ctggctcaag accttgagaa acattccag     780
acctactggg tgctagggac tccccaagct gttctcccta aaacctggcc tcggaacttc     840
tcatcccaca tcaaccgctt ccatcccttg cggggtccct ttgatggggt tcccaccacg     900
gcctatttct cggcctcccc tccctccctc tgcccgcatg gccggacccg ggatctggac     960
gcagtgttgg gagtgatgga gggtgctcgc cagttcatct atgtctcggt gatggagtat    1020
ttccctacca cgcgcttcac ccaccatgcc aggtactggc ccgtgctgga caatgcgcta    1080
cgggcagcgg ccctcaataa gggtgtgcat gtgcgcttac tggtcagctg ctggttcaac    1140
acagacccca ccatgttcgc ttatctgagg tccctgcagg ctttcagtaa ccctcggct    1200
ggcatctcag tggatgtgaa agtcttcatc gtgcctgtgg aaatcattc caacatcccg    1260
ttcagccgcg tgaaccacag caagttcatg gtcacagaca agacagccta tgtaggcacc    1320
tctaactggt cagaagacta cttcagccac accgctggtg tgggcctgat tgtcagccag    1380
aagaccccca gagcccagcc aggcgcaacc accgtgcagg agcagctgag gcaactcttt    1440
gaacgagact ggagttccca ctatgctatg gacctagaca gcaagtccc gagccaggac    1500
tgtgtctggt ag                                                        1512
```

<210> SEQ ID NO 132
<211> LENGTH: 503
<212> TYPE: PRT
<213> ORGANISM: Mus musculus

<400> SEQUENCE: 132

Met Asp Lys Lys Glu His Pro Glu Met Arg Ile Pro Leu Gln Thr
1               5                   10                  15

Ala Val Glu Val Ser Asp Trp Pro Cys Ser Thr Ser His Asp Pro His
            20                  25                  30

Ser Gly Leu Gly Met Val Leu Gly Met Leu Ala Val Leu Gly Leu Ser
        35                  40                  45

Ser Val Thr Leu Ile Leu Phe Leu Trp Gln Gly Ala Thr Ser Phe Thr
    50                  55                  60

Ser His Arg Met Phe Pro Glu Glu Val Pro Ser Trp Ser Trp Glu Thr
65                  70                  75                  80

Leu Lys Gly Asp Ala Glu Gln Gln Asn Asn Ser Cys Gln Leu Ile Leu
                85                  90                  95

```
Val Glu Ser Ile Pro Glu Asp Leu Pro Phe Ala Ala Gly Ser Pro Thr
                100                 105                 110

Ala Gln Pro Leu Ala Gln Ala Trp Leu Gln Leu Leu Asp Thr Ala Arg
            115                 120                 125

Glu Ser Val His Ile Ala Ser Tyr Tyr Trp Ser Leu Thr Gly Leu Asp
        130                 135                 140

Ile Gly Val Asn Asp Ser Ser Arg Gln Gly Glu Ala Leu Leu Gln
145                 150                 155                 160

Lys Phe Gln Gln Leu Leu Arg Asn Ile Ser Val Val Ala Thr
                165                 170                 175

His Ser Pro Thr Leu Ala Lys Thr Ser Thr Asp Leu Gln Val Leu Ala
            180                 185                 190

Ala His Gly Ala Gln Ile Arg Gln Val Pro Met Lys Gln Leu Thr Gly
        195                 200                 205

Gly Val Leu His Ser Lys Phe Trp Val Val Asp Gly Arg His Val Tyr
    210                 215                 220

Val Gly Ser Ala Asn Met Asp Trp Arg Ser Leu Thr Gln Val Lys Glu
225                 230                 235                 240

Leu Gly Ala Ile Ile Tyr Asn Cys Ser Asn Leu Ala Gln Asp Leu Glu
                245                 250                 255

Lys Thr Phe Gln Thr Tyr Trp Val Leu Gly Thr Pro Gln Ala Val Leu
            260                 265                 270

Pro Lys Thr Trp Pro Arg Asn Phe Ser Ser His Ile Asn Arg Phe His
        275                 280                 285

Pro Leu Arg Gly Pro Phe Asp Gly Val Pro Thr Thr Ala Tyr Phe Ser
    290                 295                 300

Ala Ser Pro Pro Ser Leu Cys Pro His Gly Arg Thr Arg Asp Leu Asp
305                 310                 315                 320

Ala Val Leu Gly Val Met Glu Gly Ala Arg Gln Phe Ile Tyr Val Ser
                325                 330                 335

Val Met Glu Tyr Phe Pro Thr Thr Arg Phe Thr His His Ala Arg Tyr
            340                 345                 350

Trp Pro Val Leu Asp Asn Ala Leu Arg Ala Ala Ala Leu Asn Lys Gly
        355                 360                 365

Val His Val Arg Leu Leu Val Ser Cys Trp Phe Asn Thr Asp Pro Thr
    370                 375                 380

Met Phe Ala Tyr Leu Arg Ser Leu Gln Ala Phe Ser Asn Pro Ser Ala
385                 390                 395                 400

Gly Ile Ser Val Asp Val Lys Val Phe Ile Val Pro Val Gly Asn His
                405                 410                 415

Ser Asn Ile Pro Phe Ser Arg Val Asn His Ser Lys Phe Met Val Thr
            420                 425                 430

Asp Lys Thr Ala Tyr Val Gly Thr Ser Asn Trp Ser Glu Asp Tyr Phe
        435                 440                 445

Ser His Thr Ala Gly Val Gly Leu Ile Val Ser Gln Lys Thr Pro Arg
    450                 455                 460

Ala Gln Pro Gly Ala Thr Thr Val Gln Glu Gln Leu Arg Gln Leu Phe
465                 470                 475                 480

Glu Arg Asp Trp Ser Ser His Tyr Ala Met Asp Leu Asp Arg Gln Val
                485                 490                 495

Pro Ser Gln Asp Cys Val Trp
            500
```